United States Patent
Boissel et al.

(10) Patent No.: US 11,643,452 B2
(45) Date of Patent: May 9, 2023

(54) FC-EPSILON CAR

(71) Applicant: ImmunityBio, Inc., El Segundo, CA (US)

(72) Inventors: Laurent H. Boissel, El Segundo, CA (US); Hans G. Klingemann, El Segundo, CA (US); Abhijit Dandapat, El Segundo, CA (US); Himani Chinnapen, El Segundo, CA (US)

(73) Assignee: ImmunityBio, Inc., Culver City, CA (US)

( * ) Notice: Subject to any disclaimer, the term of this patent is extended or adjusted under 35 U.S.C. 154(b) by 64 days.

(21) Appl. No.: 17/341,098

(22) Filed: Jun. 7, 2021

(65) Prior Publication Data

US 2021/0347850 A1    Nov. 11, 2021

Related U.S. Application Data

(62) Division of application No. 17/056,385, filed as application No. PCT/US2019/033407 on May 21, 2019.

(60) Provisional application No. 62/674,936, filed on May 22, 2018.

(51) Int. Cl.

| | |
|---|---|
| *C07K 14/735* | (2006.01) |
| *A61K 38/17* | (2006.01) |
| *C07K 16/28* | (2006.01) |
| *A61K 39/395* | (2006.01) |
| *C07K 14/55* | (2006.01) |
| *C07K 14/54* | (2006.01) |
| *C12N 5/0783* | (2010.01) |
| *A61P 35/00* | (2006.01) |
| *A61K 35/17* | (2015.01) |
| *A61K 38/20* | (2006.01) |
| *A61K 45/06* | (2006.01) |
| *C07K 14/705* | (2006.01) |
| *C07K 16/32* | (2006.01) |
| *A61K 39/00* | (2006.01) |

(52) U.S. Cl.
CPC ........ *C07K 14/70535* (2013.01); *A61K 35/17* (2013.01); *A61K 38/1774* (2013.01); *A61K 38/2013* (2013.01); *A61K 38/2086* (2013.01); *A61K 39/3955* (2013.01); *A61K 39/39558* (2013.01); *A61K 45/06* (2013.01); *A61P 35/00* (2018.01); *C07K 14/5443* (2013.01); *C07K 14/55* (2013.01); *C07K 14/70517* (2013.01); *C07K 14/70521* (2013.01); *C07K 16/2803* (2013.01); *C07K 16/2827* (2013.01); *C07K 16/2863* (2013.01); *C07K 16/2866* (2013.01); *C07K 16/2878* (2013.01); *C07K 16/32* (2013.01); *C12N 5/0646* (2013.01); *A61K 2039/505* (2013.01); *A61K 2039/5154* (2013.01); *A61K 2039/5156* (2013.01); *A61K 2039/5158* (2013.01); *C07K 2317/53* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 7,098,008 B2 | 8/2006 | Park et al. | |
| 7,618,817 B2 | 11/2009 | Campbell | |
| 8,034,332 B2 | 10/2011 | Klingemann | |
| 8,313,943 B2 | 11/2012 | Campbell | |
| 9,150,636 B2 | 10/2015 | Campbell | |
| 9,181,322 B2 | 11/2015 | Campbell | |
| 10,023,648 B2 * | 7/2018 | Hombach | A61K 48/00 |
| 10,138,462 B2 | 11/2018 | Klingemann | |
| 10,174,095 B2 * | 1/2019 | Brogdon | C07K 16/2878 |
| 10,765,701 B2 * | 9/2020 | Klingemann | A61K 35/17 |
| 10,960,024 B2 * | 3/2021 | Klingemann | C07K 14/5443 |
| 11,058,723 B2 * | 7/2021 | Klingemann | A61P 1/00 |
| 11,077,143 B2 * | 8/2021 | Klingemann | C07K 14/70535 |

(Continued)

FOREIGN PATENT DOCUMENTS

| | | |
|---|---|---|
| CA | 2 977 106 A1 | 9/2016 |
| CA | 3 097 904 A1 | 11/2019 |

(Continued)

OTHER PUBLICATIONS

Koene et al. Blood 1997; 90(3): 1109-1114.*
Sugita et al. Clin Exp Immunol 1999; 117: 350-354.*
U.S. Appl. No. 17/489,607, filed Sep. 2021, Lee; John H.*
U.S. Appl. No. 17/446,024, filed Aug. 2021, Klingemann; Hans G.*
U.S. Appl. No. 17/438,386, filed Sep. 2021, Soon-Shiong; Patrick.*
U.S. Appl. No. 17/287,462, filed Apr. 2021, Klingemann; Hans G.*

(Continued)

*Primary Examiner* — Ilia I Ouspenski
(74) *Attorney, Agent, or Firm* — Martin Fessenmaier; Umberg Zipser LLP

(57) ABSTRACT

Recombinant NK cells, and especially recombinant NK-92 cells express a chimeric antigen receptor (CAR) having an intracellular domain of FcεRIγ. Notably, CAR constructs with an intracellular domain of FcεRIγ had a substantially prolonged duration of expression and significantly extended cytotoxicity over time. The CAR may be expressed from RNA and DNA, preferably as a tricistronic construct that further encodes CD16 and a cytokine to confer autocrine growth support. Advantageously, such constructs also enable high levels of transfection and expression of the recombinant proteins and provide a convenient selection marker to facilitate rapid production of recombinant NK/NK-92 cells.

8 Claims, 63 Drawing Sheets

Specification includes a Sequence Listing.

(56) References Cited

U.S. PATENT DOCUMENTS

| | | | |
|---|---|---|---|
| 11,129,850 | B2 * | 9/2021 | Klingemann .......... C07K 14/82 |
| 2002/0068044 | A1 | 6/2002 | Klingemann |
| 2008/0247990 | A1 | 10/2008 | Campbell |
| 2013/0189268 | A1 | 7/2013 | Du et al. |
| 2013/0280285 | A1 | 10/2013 | Schonfeld et al. |
| 2014/0242701 | A1 | 8/2014 | Shiku et al. |
| 2014/0274909 | A1 | 9/2014 | Orentas et al. |
| 2018/0360881 | A1 * | 12/2018 | Rabizadeh ......... A61K 39/3955 |
| 2019/0233797 | A1 * | 8/2019 | Navarro ................. A61P 35/00 |
| 2020/0123503 | A1 * | 4/2020 | Navarro ................. C12N 9/22 |
| 2020/0376033 | A1 * | 12/2020 | Klingemann .......... C07K 14/55 |
| 2021/0015870 | A1 * | 1/2021 | Wu .................. C07K 14/70578 |
| 2021/0038645 | A1 * | 2/2021 | Soon-Shiong ......... A61K 35/17 |
| 2021/0145879 | A1 * | 5/2021 | Lee ......................... A61P 35/00 |
| 2021/0169931 | A1 * | 6/2021 | Boissel ................ C12N 5/0636 |
| 2021/0198342 | A1 | 7/2021 | Boissel et al. |
| 2021/0230547 | A1 * | 7/2021 | Lee ......................... A61P 35/00 |
| 2021/0260116 | A1 * | 8/2021 | Boissel ............... C07K 14/7051 |
| 2021/0315934 | A1 * | 10/2021 | Klingemann .......... A61K 35/17 |
| 2021/0322477 | A1 * | 10/2021 | Klingemann .... C07K 14/70535 |

FOREIGN PATENT DOCUMENTS

| | | | |
|---|---|---|---|
| CN | 112534046 | A | 3/2021 |
| EP | 3 797 157 | A1 | 3/2021 |
| JP | 2021-525073 | A | 9/2021 |
| KR | 10-2021-0003292 | A | 1/2021 |
| WO | 98/49268 | A1 | 11/1998 |
| WO | 99/24566 | A1 | 5/1999 |
| WO | 00/20460 | A1 | 4/2000 |
| WO | 2014/039523 | A1 | 3/2014 |
| WO | 2014/099671 | A1 | 6/2014 |
| WO | 2016/201304 | A1 | 12/2016 |
| WO | 2017/100709 | A1 | 6/2017 |
| WO | 2017/112877 | A1 | 6/2017 |
| WO | 2017/192440 | A1 | 11/2017 |
| WO | 2018/064594 | A2 | 4/2018 |
| WO | 2018/076391 | A1 | 5/2018 |
| WO | 2019/177986 | A1 | 9/2019 |
| WO | 2019/226708 | A1 | 11/2019 |
| WO | 2019/226708 | A4 | 12/2019 |
| WO | WO/2021/154263 | * | 8/2021 .......... C12N 5/0787 |

OTHER PUBLICATIONS

Office Action received for Canadian Patent Application Serial No. 3097904 dated Oct. 4, 2021, 3 pages.

Gong et al., "Characterization of a human cell line (NK-92) with phenotypical and functional characteristics of activated natural killer cells", Leukemia, 1994, vol. 8, No. 4, pp. 652-658.

Haynes et al., "Redirecting Mouse CTL Against Colon Carcinoma: Superior Signaling Efficacy of Single-Chain Variable Domain Chimeras Containing TCR-ζ vs FcεRI-γ", The Journal of Immunology, 2001, vol. 166, pp. 182-187.

Cartellier et al., "Chimeric Antigen Receptor-Engineered T Cells for Immunotherapy of Cancer", Journal of Biomedicine and Biotechnology, 2010, No. 956304, pp. 1-13.

Hermanson et al., "Utilizing Chimeric Antigen Receptors to Direct Natural Killer Cell Activity", Frontiers in Immunology, 2015, vol. 6, No. 195, pp. 1-6.

Bollino et al., "Chimeric antigen receptor engineered natural killer and natural killer T cells for cancer immunotherapy", Transl Res, 2017, vol. 187, 21 pages.

Konstantinidis et al., "Targeting IL-2 to the endoplasmic reticulum confines autocrine growth stimulation to NK-92 cells", Experimental Hematology, 2005, vol. 33, pp. 159-164.

Bruhns et al., "Specificity and affinity of human Fcγ receptors and their polymorphic variants for human IgG subclasses", Blood, 2009, vol. 113, No. 16, pp. 3716-3725.

Jochems et al., "An NK cell line (haNK) expressing high levels of granzyme and engineered to express the high affinity CD16 allele", Oncotarget, 2016,vol. 7, No. 2, pp. 86359-86373.

Garcia-Sanchez et al., "Cytosine deaminase adenoviral vector and 5-fluorocytosine selectively reduce breast cancer cells 1 million-fold when they contaminate hematopoietic cells: a potential purging method for autologous transplantation", Blood, 1998, vol. 92, No. 2, pp. 672-682.

Touati et al., "A suicide gene therapy combining the improvement of cyclophosphamide tumor cytotoxicity and the development of an anti tumor immune response", Current Gene Therapy, 2014, vol. 14, pp. 236-246.

Di Stasi et al., "Inducible apoptosis as a safety switch for adoptive cell therapy", N Engl J Med., Nov. 3, 2011, vol. 365, No. 18, pp. 1673-1683.

Morgan Richard A, "Live and Let Die: A New Suicide Gene Therapy Moves to the Clinic", Molecular therapy, Jan. 2012, vol. 20, No. 1, pp. 11-13.

Smith et al., "Comparison of biosequences", Advances in Applied Mathematics, 1981, vol. 2, No. 4, pp. 482-489.

Altschul et al., "Gapped BLAST and PSI-BLAST: a new generation of protein database search programs", Nucleic Acids Research, 1997, vol. 25, No. 17, pp. 3389-3402.

Henikoff et al., "Amino acid substitution matrices from protein blocks", Proc. Natl. Acad., 1992, vol. 89, pp. 10915-10919.

Yazawa et al., "Current progress in suicide gene therapy for cancer", World J. Surg., 2002, vol. 26, pp. 783-789.

International Search Report and Written opinion received for PCT Application Serial No. PCT/US2019/033407 dated Sep. 18, 2019, 12 pages.

Zhang et al., "Chimeric Antigen Receptor-Engineered NK-92 Cells: An Off-the-Shelf Cellular Therapeutic for Targeted Elimination of Cancer Cells and Induction of Protective Antitumor Immunity", Frontiers in Immunology, 2017, vol. 8, No. 533, pp. 1-17.

Rodewald et al., "The high affinity Fc epsilon receptor gamma subunit (Fc epsilon RI gamma) facilitates T cell receptor expression and antigen/major histocompatibility complex-driven signaling in the absence of CD3 zeta and CD3 eta", The Journal of Biological Chemistry, 1991, vol. 266, No. 24, pp. 15974-1978.

International Preliminary Report on Patentability Chapter II received for PCT Application Serial No. PCT/US2019/033407 dated Nov. 23, 2020, 35 pages.

Office Action received for Israel Patent Application Serial No. 278857 dated Feb. 24, 2022, 16 pages. (Including English Translation).

Extended European Search Report received for EP Patent Application Serial No. 19807670.5 dated Feb. 10, 2022, 10 pages.

Clémenceau et al., "In Vitro and In Vivo Comparison of Lymphocytes Transduced with a Human CD16 or with a Chimeric Antigen Receptor Reveals Potential Off-Target Interactions due to the IgG2 CH2-CH3 CAR-Spacer", Hindawi, Journal of Immunology Research, vol. 2015, Article 482089, Jan. 1, 2015, pp. 1-13.

Examination Report No. 2 received for Australian Patent Application Serial No. 2019272608 dated Dec. 14, 2022, 4 pages.

Office Action received for Canadian Patent Application Serial No. 3097904 dated Feb. 1, 2023, 4 pages.

* cited by examiner

SEQUENCE LISTING

<160> NUMBER OF SEQ ID NOS: 85

<210> SEQ ID NO 1
<211> LENGTH: 41
<212> TYPE: PRT
<213> ORGANISM: Artificial Sequence
<220> FEATURE:
<223> OTHER INFORMATION: FceRIgamma intracellular

<400> SEQUENCE: 1

```
Leu Lys Ile Gln Val Arg Lys Ala Ala Ile Thr Ser Tyr Glu Lys Ser
1               5                   10                  15

Asp Gly Val Tyr Thr Gly Leu Ser Thr Arg Asn Gln Glu Thr Tyr Glu
            20                  25                  30

Thr Leu Lys His Glu Lys Pro Pro Gln
        35                  40
```

<210> SEQ ID NO 2
<211> LENGTH: 123
<212> TYPE: DNA
<213> ORGANISM: Artificial Sequence
<220> FEATURE:
<223> OTHER INFORMATION: FceR1gamma for the Intracellular Signaling
      Domain

<400> SEQUENCE: 2

```
ctgaagatcc aggtccgaaa ggccgccatc accagctacg agaagtctga tggcgtgtac        60
accggcctga gcaccagaaa ccaggaaacc tacgagacac tgaagcacga gaagcccccc       120
cag                                                                    123
```

<210> SEQ ID NO 3
<211> LENGTH: 54
<212> TYPE: PRT
<213> ORGANISM: Artificial Sequence
<220> FEATURE:
<223> OTHER INFORMATION: CD8 Hinge

<400> SEQUENCE: 3

```
Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys
    50
```

<210> SEQ ID NO 4
<211> LENGTH: 65
<212> TYPE: PRT
<213> ORGANISM: Artificial Sequence
<220> FEATURE:
<223> OTHER INFORMATION: CD8 Hinge

<400> SEQUENCE: 4

```
Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45
```

```
Arg Pro Ala Ala Gly Gly Ala Val His Thr Arg Gly Leu Asp Phe Ala
    50                  55                  60

Cys
65
```

<210> SEQ ID NO 5
<211> LENGTH: 195
<212> TYPE: DNA
<213> ORGANISM: Artificial Sequence
<220> FEATURE:
<223> OTHER INFORMATION: CD8a Hinge DNA

<400> SEQUENCE: 5

```
gcgctgagca acagcatcat gtacttcagc cacttcgtgc ctgtgttcct gcctgccaag      60
cctacaacaa caccagcccc tagacctcca acccctgccc ctacaattgc ctctcagcct     120
ctgtctctga ggcccgaagc ttgtagacct gctgctggcg gagctgtgca caccagagga     180
ctggatttcg cctgc                                                      195
```

<210> SEQ ID NO 6
<211> LENGTH: 28
<212> TYPE: PRT
<213> ORGANISM: Artificial Sequence
<220> FEATURE:
<223> OTHER INFORMATION: CD28 Transmembrane

<400> SEQUENCE: 6

```
Phe Trp Val Leu Val Val Val Gly Gly Val Leu Ala Cys Tyr Ser Leu
1               5                   10                  15

Leu Val Thr Val Ala Phe Ile Ile Phe Trp Val Arg
            20                  25
```

<210> SEQ ID NO 7
<211> LENGTH: 84
<212> TYPE: DNA
<213> ORGANISM: Artificial Sequence
<220> FEATURE:
<223> OTHER INFORMATION: CD28 for the Transmembrane DNA

<400> SEQUENCE: 7

```
ttttgggtgc tggtggtcgt gggcggagtg ctggcttgtt attctctgct ggtcaccgtg      60
gccttcatca tcttttgggt ccga                                             84
```

<210> SEQ ID NO 8
<211> LENGTH: 134
<212> TYPE: PRT
<213> ORGANISM: Artificial Sequence
<220> FEATURE:
<223> OTHER INFORMATION: CD8 hinge region, CD28 transmembrane, and
      FceRIgamma signaling domain

<400> SEQUENCE: 8

```
Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp Phe Ala
    50                  55                  60

Cys Phe Trp Val Leu Val Val Val Gly Gly Val Leu Ala Cys Tyr Ser
65                  70                  75                  80
```

Leu Leu Val Thr Val Ala Phe Ile Ile Phe Trp Val Arg Leu Lys Ile
            85                  90                  95

Gln Val Arg Lys Ala Ala Ile Thr Ser Tyr Glu Lys Ser Asp Gly Val
        100                 105                 110

Tyr Thr Gly Leu Ser Thr Arg Asn Gln Glu Thr Tyr Glu Thr Leu Lys
    115                 120                 125

His Glu Lys Pro Pro Gln
    130

<210> SEQ ID NO 9
<211> LENGTH: 402
<212> TYPE: DNA
<213> ORGANISM: Artificial Sequence
<220> FEATURE:
<223> OTHER INFORMATION: CD8 hinge, CD28 transmembrane, and FceRIgamma
      signaling domain DNA

<400> SEQUENCE: 9
gcgctgagca acagcatcat gtacttcagc cacttcgtgc ctgtgttcct gcctgccaag      60
cctacaacaa caccagcccc tagacctcca acccctgccc ctacaattgc ctctcagcct     120
ctgtctctga ggcccgaagc ttgtagacct gctgctggcg agctgtgca ccaccagagga    180 ctggatttcg cctgcttttg ggtgctggtg gtcgtgggcg gagtgctggc ttgttattct     240
ctgctggtca ccgtggcctt catcatcttt gggtccgac tgaagatcca ggtccgaaag     300
gccgccatca ccagctacga gaagtctgat ggcgtgtaca ccggcctgag caccagaaac     360
caggaaacct acgagacact gaagcacgag aagcccccc ag                         402

<210> SEQ ID NO 10
<211> LENGTH: 398
<212> TYPE: PRT
<213> ORGANISM: Artificial Sequence
<220> FEATURE:
<223> OTHER INFORMATION: CD19CAR_ FceRIgamma

<400> SEQUENCE: 10

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Leu Lys Arg Gly Gly Gly Gly Ser Gly Gly Gly Gly Ser Gly Gly Gly
    130                 135                 140

Gly Ser Gly Gly Gly Gly Ser Glu Val Gln Leu Gln Gln Ser Gly Pro
145                 150                 155                 160

-continued

```
Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
            180                 185                 190

Arg Lys Gly Leu Glu Trp Leu Gly Val Ile Trp Gly Ser Glu Thr Thr
        195                 200                 205

Tyr Tyr Asn Ser Ala Leu Lys Ser Arg Leu Thr Ile Ile Lys Asp Asn
    210                 215                 220

Ser Lys Ser Gln Val Phe Leu Lys Met Asn Ser Leu Gln Thr Asp Asp
225                 230                 235                 240

Thr Ala Ile Tyr Tyr Cys Ala Lys His Tyr Tyr Gly Gly Ser Tyr
                245                 250                 255

Ala Met Asp Tyr Trp Gly Gln Gly Thr Thr Val Thr Val Ser Ser Ala
            260                 265                 270

Ala Ala Leu Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Phe Trp Val Leu Val Val Val
                325                 330                 335

Gly Gly Val Leu Ala Cys Tyr Ser Leu Leu Val Thr Val Ala Phe Ile
            340                 345                 350

Ile Phe Trp Val Arg Leu Lys Ile Gln Val Arg Lys Ala Ala Ile Thr
        355                 360                 365

Ser Tyr Glu Lys Ser Asp Gly Val Tyr Thr Gly Leu Ser Thr Arg Asn
    370                 375                 380

Gln Glu Thr Tyr Glu Thr Leu Lys His Glu Lys Pro Pro Gln
385                 390                 395

<210> SEQ ID NO 11
<211> LENGTH: 255
<212> TYPE: PRT
<213> ORGANISM: Artificial Sequence
<220> FEATURE:
<223> OTHER INFORMATION: Anti-CD19 scFv

<400> SEQUENCE: 11

Ala Gln Pro Ala Asp Ile Gln Met Thr Gln Thr Thr Ser Ser Leu Ser
1               5                   10                  15

Ala Ser Leu Gly Asp Arg Val Thr Ile Ser Cys Arg Ala Ser Gln Asp
            20                  25                  30

Ile Ser Lys Tyr Leu Asn Trp Tyr Gln Gln Lys Pro Asp Gly Thr Val
        35                  40                  45

Lys Leu Leu Ile Tyr His Thr Ser Arg Leu His Ser Gly Val Pro Ser
    50                  55                  60

Arg Phe Ser Gly Ser Gly Ser Gly Thr Asp Tyr Ser Leu Thr Ile Ser
65                  70                  75                  80

Asn Leu Glu Gln Glu Asp Ile Ala Thr Tyr Phe Cys Gln Gln Gly Asn
                85                  90                  95

Thr Leu Pro Tyr Thr Phe Gly Gly Gly Thr Lys Leu Glu Leu Lys Arg
            100                 105                 110

Gly Gly Gly Gly Ser Gly Gly Gly Ser Gly Gly Gly Gly Ser Gly
        115                 120                 125
```

Gly Gly Gly Ser Glu Val Gln Leu Gln Gln Ser Pro Gly Leu Val
            130             135             140

Ala Pro Ser Gln Ser Leu Ser Val Thr Cys Thr Val Ser Gly Val Ser
145             150             155             160

Leu Pro Asp Tyr Gly Val Ser Trp Ile Arg Gln Pro Pro Arg Lys Gly
                165             170             175

Leu Glu Trp Leu Gly Val Ile Trp Gly Ser Glu Thr Thr Tyr Tyr Asn
            180             185             190

Ser Ala Leu Lys Ser Arg Leu Thr Ile Ile Lys Asp Asn Ser Lys Ser
            195             200             205

Gln Val Phe Leu Lys Met Asn Ser Leu Gln Thr Asp Asp Thr Ala Ile
        210             215             220

Tyr Tyr Cys Ala Lys His Tyr Tyr Tyr Gly Gly Ser Tyr Ala Met Asp
225             230             235             240

Tyr Trp Gly Gln Gly Thr Thr Val Thr Val Ser Ser Ala Ala Ala
                245             250             255

<210> SEQ ID NO 12
<211> LENGTH: 1197
<212> TYPE: DNA
<213> ORGANISM: Artificial Sequence
<220> FEATURE:
<223> OTHER INFORMATION: CD19CAR_ FceRIgamma DNA

<400> SEQUENCE: 12
atggactgga tctggcggat tctgtttctc gtgggagctg ccacaggcgc tcattctgct      60
cagcctgccg atatccagat gacccagaca caagcagcc tgagcgcctc tctgggcgat     120
agagtgacaa tcagctgcag agccagccag gacatcagca gtacctgaa ctggtatcag     180 cagaaacccg acggcaccgt gaagctgctg atctaccaca caagcagact gcacagcggc     240
gtgccaagca gattttctgg cagcggcagc ggcaccgatt acagcctgac catcagcaac     300
ctggaacagg aagatatcgc tacctacttc tgtcagcagg caacaccct gccttacacc     360 tttggcggcg gaacaaagct ggaactgaaa agaggcggcg gaggaagcgg aggcggagga     420 tctggggcg gaggctctgg cggaggggga tctgaagtgc agctgcagca gtctggacct     480
ggactggtgg ctccttctca gtccctgtct gtgacctgta cagtgtctgg cgtgtccctg     540
cctgattacg gcgtgtcctg gatcagacag cctcccagaa aaggcctgga atggctggga     600
gtgatctggg gcagcgagac aacctactac aacagcgccc tgaagtcccg gctgaccatc     660
atcaaggaca cagcaagag ccaggtgttc ctgaagatga cagcctgca gaccgacgac     720 accgccatct actactgcgc caagcactac tactacggcg gcagctacgc catggattat     780
tggggccagg gcaccaccgt gacagtgtca tctgctgctg ctctgttcgt gcctgtgttc     840
ctgcctgcca gcctacaac aacaccagcc ctagacctc aaccctgc ccctacaatt     900 gcctctcagc ctctgtctct gaggcccgaa gcttgtagac tgctgctgg cggagctgtg     960 cacaccagag gactggattt cgcctgctttt gggtgctgg tggtcgtggg cggagtgctg    1020
gcttgttatt ctctgctggt caccgtggcc ttcatcatct tttgggtccg actgaagatc    1080
caggtccgaa aggccgccat caccagctac gagaagtctg atggcgtgta caccggcctg    1140
agcaccagaa accaggaaac ctacgagaca ctgaagcacg agaagccccc ccagtaa      1197

<210> SEQ ID NO 13
<211> LENGTH: 41
<212> TYPE: PRT

```
<213> ORGANISM: Artificial Sequence
<220> FEATURE:
<223> OTHER INFORMATION: CD28 signaling domain

<400> SEQUENCE: 13

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 14
<211> LENGTH: 42
<212> TYPE: PRT
<213> ORGANISM: Artificial Sequence
<220> FEATURE:
<223> OTHER INFORMATION: 4-1BB signaling domain

<400> SEQUENCE: 14

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 15
<211> LENGTH: 113
<212> TYPE: PRT
<213> ORGANISM: Artificial Sequence
<220> FEATURE:
<223> OTHER INFORMATION: CD3 zeta signaling domain

<400> SEQUENCE: 15

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 16
<211> LENGTH: 1410
<212> TYPE: DNA
<213> ORGANISM: Artificial Sequence
<220> FEATURE:
<223> OTHER INFORMATION: CD19CAR_CD3z
```

<400> SEQUENCE: 16

```
atggactgga tctggcggat cctgtttctc gtgggagctg ccacaggcgc tcattctgct    60
cagcctgccg atatccagat gacccagaca caagcagcc tgagcgcctc tctgggcgat   120
agagtgacaa tcagctgcag agccagccag gacatcagca agtacctgaa ctggtatcag   180
cagaaacccg acggcaccgt gaagctgctg atctaccaca agcagact gcacagcggc    240
gtgccaagca gattttctgg cagcggcagc ggcaccgatt acagcctgac catcagcaac   300
ctggaacagg aagatatcgc tacctacttc tgtcagcaag gcaacaccct gccttacacc   360
tttggcggcg aacaaagct ggaactgaaa gaggcggcg gaggaagcgg aggcggagga    420
tctgggggcg aggctctgg cggaggggga tctgaagtgc agctgcagca gtctggacct   480
ggactggtgg ctccttctca gtccctgtct gtgacctgta cagtgtctgg cgtgtccctg   540
cctgattacg gcgtgtcctg gatcagacag cctcccagaa aggcctgga atggctggga   600
gtgatctggg gcagcgagac aacctactac aacagcgccc tgaagtcccg gctgaccatc   660
atcaaggaca acagcaagag ccaggtgttc ctgaagatga cagcctgca gaccgacgac   720
accgccatct actactgcgc caagcactac tactacggcg gcagctacgc catggattat   780
tggggccagg gcaccaccgt gacagtgtca tctgctgctg ctctgttcgt gcctgtgttc   840
ctgcctgcca gcctacaac aacaccagcc ctagacctc aaccccctgc ccctacaatt   900
gcctctcagc ctctgtctct gaggcccgaa gcttgtagac ctgctgctgg cggagctgtg   960
cacaccagag gactggattt cgcctgcttt tgggtgctgg tggtcgtggg cggagtgctg  1020
gcttgttatt ctctgctggt caccgtggcc ttcatcatct tttgggtccg agtgaagttc  1080
agcagatccg ccgatgcccc tgcttaccag cagggccaga atcagctgta caacgagctg  1140
aacctgggca cgggaaga gtacgacgtg ctggataaga gaagaggcag agatcccgag  1200
atgggcggca gccccagag aagaaagaat ccccaggaag gcctgtataa cgaactgcag  1260
aaagacaaga tggccgaggc ctacagcgag atcggcatga agggcgagag aagaagaggc  1320
aagggccacg atggactgta ccagggactg agcacagcca ccaaggatac ctacgatgcc  1380
ctgcacatgc aggccctgcc tccaagataa                                  1410
```

<210> SEQ ID NO 17
<211> LENGTH: 1533
<212> TYPE: DNA
<213> ORGANISM: Artificial Sequence
<220> FEATURE:
<223> OTHER INFORMATION: CD19CAR_CD28/CD3z

<400> SEQUENCE: 17

```
atggactgga tctggcggat cctgtttctc gtgggagctg ccacaggcgc tcattctgct    60
cagcctgccg atatccagat gacccagaca caagcagcc tgagcgcctc tctgggcgat   120
agagtgacaa tcagctgcag agccagccag gacatcagca agtacctgaa ctggtatcag   180
cagaaacccg acggcaccgt gaagctgctg atctaccaca agcagact gcacagcggc    240
gtgccaagca gattttctgg cagcggcagc ggcaccgatt acagcctgac catcagcaac   300
ctggaacagg aagatatcgc tacctacttc tgtcagcagg gcaacaccct gccttacacc   360
tttggcggcg aacaaagct ggaactgaaa gaggcggcg gaggaagcgg aggcggagga    420
tctgggggcg aggctctgg cggaggggga tctgaagtgc agctgcagca gtctggacct   480
ggactggtgg ctccttctca gtccctgtct gtgacctgta cagtgtctgg cgtgtccctg   540
```

```
cctgattacg gcgtgtcctg atcagacag cctcccagaa aaggcctgga atggctggga      600
gtgatctggg gcagcgagac aacctactac aacagcgccc tgaagtcccg gctgaccatc      660
atcaaggaca acagcaagag ccaggtgttc ctgaagatga acagcctgca gaccgacgac      720
accgccatct actactgcgc caagcactac tactacggcg gcagctacgc catggattat      780
tggggccagg gcaccaccgt gacagtgtca tctgctgctg ctctgttcgt gcctgtgttc      840
ctgcctgcca agcctacaac aaccaccagcc ctagacctc caaccccctgc ccctacaatt      900
gcctctcagc tctgtctct gaggcccgaa gcttgtagac ctgctgctgg cggagctgtg      960
cacaccagag gactggattt cgcctgcttt tgggtgctgg tggtcgtggg cggagtgctg     1020
gcttgttatt ctctgctggt caccgtggcc ttcatcatct tttgggtccg aagcaagcgg     1080
agcaggctgc tgcacagcga ctacatgaac atgaccccta aaggcctgg ccccaccaga     1140
aagcactatc agccttacgc ccctcccaga gacttcgccg cctacagatc cagagtgaag     1200
ttcagcagat ctgccgacgc ccctgcttac cagcagggcc agaatcagct gtacaacgag     1260
ctgaacctgg gcagacggga agagtacgac gtgctggata gagaagagg cagagatccc     1320
gagatgggcg gcaagcccca gagaagaaag aatccccagg aaggcctgta taacgaactg     1380
cagaaagaca gatggccga ggcctacagc gagatcggca tgaagggcga gagaagaaga     1440
ggcaagggcc acgatggact gtaccaggga ctgagcacag ccaccaagga tacctacgat     1500
gccctgcaca tgcaggccct gcctccaaga taa                                  1533

<210> SEQ ID NO 18
<211> LENGTH: 1536
<212> TYPE: DNA
<213> ORGANISM: Artificial Sequence
<220> FEATURE:
<223> OTHER INFORMATION: CD19CAR_4-1BB/CD3z

<400> SEQUENCE: 18
atggactgga tctggcggat cctgtttctc gtgggagctg ccacaggcgc tcattctgct       60
cagcctgccg atatccagat gacccagaca caagcagcc tgagcgcctc tctgggcgat      120
agagtgacaa tcagctgcag agccagccag gacatcagca gtacctgaa ctggtatcag      180
cagaaaccg acggcaccgt gaagctgctg atctaccaca caagcagact gcacagcggc      240
gtgccaagca gattttctgg cagcggcagc ggcaccgatt acagcctgac catcagcaac      300
ctggaacagg aagatatcgc tacctacttc tgtcagcagg gcaacaccct gccttacacc      360
tttggcggcg aacaaagct ggaactgaaa agaggcggcg aggaagcgg aggcggagga      420
tctggggcg gaggctctgg cggaggggga tctgaagtgc agctgcagca gtctggacct      480
ggactggtgg ctcctctca gtccctgtct gtgacctgta cagtgtctgg cgtgtccctg      540
cctgattacg gcgtgtcctg atcagacag cctcccagaa aaggcctgga atggctggga      600
gtgatctggg gcagcgagac aacctactac aacagcgccc tgaagtcccg gctgaccatc      660
atcaaggaca acagcaagag ccaggtgttc ctgaagatga acagcctgca gaccgacgac      720
accgccatct actactgcgc caagcactac tactacggcg gcagctacgc catggattat      780
tggggccagg gcaccaccgt gacagtgtca tctgctgctg ctctgttcgt gcctgtgttc      840
ctgcctgcca agcctacaac aaccaccagcc ctagacctc caaccccctgc ccctacaatt      900
gcctctcagc tctgtctct gaggcccgaa gcttgtagac ctgctgctgg cggagctgtg      960
cacaccagag gactggattt cgcctgcttt tgggtgctgg tggtcgtggg cggagtgctg     1020
gcttgttatt ctctgctggt caccgtggcc ttcatcatct tttgggtcaa gcggggcaga     1080
```

| | | |
|---|---|---|
| aagaagctgc tgtacatctt caagcagccc ttcatgaggc ccgtgcagac cacacaggaa | 1140 | |
| gaggacggct gcagctgtag attccctgag gaagaagaag gcggctgcga gctgagagtg | 1200 | |
| aagtttagca gatctgccga cgcccctgcc taccagcagg acagaatca gctgtacaac | 1260 | |
| gagctgaacc tgggcagacg ggaagagtac gacgtgctgg ataagagaag aggcagagat | 1320 | |
| cccgagatgg gcggcaagcc ccagagaaga aagaatcccc aggaaggcct gtataacgaa | 1380 | |
| ctgcagaaag acaagatggc cgaggcctac agcgagatcg gcatgaaggg cgagagaaga | 1440 | |
| agaggcaagg gccacgatgg actgtaccag ggactgagca cagccaccaa ggatacctac | 1500 | |
| gatgccctgc acatgcaggc cctgcctcca agataa | 1536 | |

<210> SEQ ID NO 19
<211> LENGTH: 1659
<212> TYPE: DNA
<213> ORGANISM: Artificial Sequence
<220> FEATURE:
<223> OTHER INFORMATION: CD19CAR_CD28/4-1BB/CD3z

<400> SEQUENCE: 19

| | | |
|---|---|---|
| atggactgga tctggcggat cctgtttctc gtgggagctg ccacaggcgc tcattctgct | 60 | |
| cagcctgccg atatccagat gacccagaca caagcagcc tgagcgcctc tctgggcgat | 120 | |
| agagtgacaa tcagctgcag agccagccag gacatcagca agtacctgaa ctggtatcag | 180 | |
| cagaaacccg acggcaccgt gaagctgctg atctaccaca agcagact gcacagcggc | 240 | |
| gtgccaagca gattttctgg cagcggcagc ggcaccgatt acagcctgac catcagcaac | 300 | |
| ctggaacagg aagatatcgc tacctacttc tgtcagcagg gcaacaccct gccttacacc | 360 | |
| tttggcggcg gaacaaagct ggaactgaaa gaggcggcg gaggaagcgg aggcggagga | 420 | |
| tctgggggcg gaggctctgg cggagggga tctgaagtgc agctgcagca gtctggacct | 480 | |
| ggactggtgg ctccttctca gtccctgtct gtgacctgta cagtgtctgg cgtgtccctg | 540 | |
| cctgattacg gcgtgtcctg gatcagacag cctcccagaa aggcctgga atggctggga | 600 | |
| gtgatctggg gcagcgagac aacctactac aacagcgccc tgaagtcccg gctgaccatc | 660 | |
| atcaaggaca acagcaagag ccaggtgttc ctgaagatga cagcctgca gaccgacgac | 720 | |
| accgccatct actactgcgc caagcactac tactacggcg gcagctacgc catggattat | 780 | |
| tggggccagg gcaccaccgt gacagtgtca tctgctgctg ctctgttcgt gcctgtgttc | 840 | |
| ctgcctgcca gcctacaac aacaccagcc ctagacctc aaccctgc cctacaatt | 900 | |
| gcctctcagc ctctgtctct gaggcccgaa gcttgtagac tgctgctgg cggagctgtg | 960 | |
| cacaccagag actggatttt cgcctgcttt tgggtgctgg tggtcgtggg cggagtgctg | 1020 | |
| gcttgttatt ctctgctggt caccgtggcc ttcatcatct tttgggtccg aagcaagcgg | 1080 | |
| agcaggctgc tgcacagcga ctacatgaac atgacccta aaggcctgg ccccaccaga | 1140 | |
| aagcactatc agcctacgc ccctcccaga gacttcgccg cctatagatc caagcggggc | 1200 | |
| agaaagaagc tgctgtacat cttcaagcag cccttcatga ggcccgtgca gaccacacag | 1260 | |
| gaagaggacg gctgcagctg tagattccct gaggaagaag aaggcggctg cgagctgaga | 1320 | |
| gtgaagtttta gcagatctgc cgacgccct gcctaccagc agggacagaa tcagctgtac | 1380 | |
| aacgagctga acctgggcag acgggaagag tacgacgtgc tggataagag aagaggcaga | 1440 | |
| gatcccgaga tgggcggcaa gccccagaga agaaagaatc cccaggaagg cctgtataac | 1500 | |
| gaactgcaga aagacaagat ggccgaggcc tacagcgaga tcggcatgaa gggcgagaga | 1560 | |

```
agaagaggca agggccacga tggactgtac cagggactga gcacagccac caaggatacc    1620
tacgatgccc tgcacatgca ggccctgcct ccaagataa                           1659
```

<210> SEQ ID NO 20
<211> LENGTH: 1659
<212> TYPE: DNA
<213> ORGANISM: Artificial Sequence
<220> FEATURE:
<223> OTHER INFORMATION: CD19CAR_4-1BB/CD3z/CD28

<400> SEQUENCE: 20

```
atggactgga tctggcggat cctgtttctc gtgggagctg ccacaggcgc tcattctgct     60
cagcctgccg atatccagat gacccagaca acaagcagcc tgagcgcctc tctgggcgat    120
agagtgacaa tcagctgcag agccagccag gacatcagca agtacctgaa ctggtatcag    180
cagaaacccg acggcaccgt gaagctgctg atctaccaca agcagact gcacagcggc     240 gtgccaagca gattttctgg cagcggcagc ggcaccgatt acagcctgac catcagcaac    300
ctggaacagg aagatatcgc tacctacttc tgtcagcagg caacaccct gccttacacc     360 tttggcggcg gaacaaagct ggaactgaaa agaggcggcg gaggaagcgg aggcggagga    420 tctggggggcg gaggctctgg cggaggggga tctgaagtgc agctgcagca gtctggacct    480
ggactggtgg ctccttctca gtccctgtct gtgacctgta cagtgtctgg cgtgtccctg    540
cctgattacg gcgtgtcctg gatcagacag cctcccagaa aggcctgga atggctggga    600 gtgatctggg gcagcgagac aacctactac aacagcgccc tgaagtcccg gctgaccatc    660
atcaaggaca cagcaagag ccaggtgttc ctgaagatga acagcctgca gaccgacgac    720
accgccatct actactgcgc caagcactac tactacggcg gcagctacgc catggattat    780 tgggggccagg gcaccaccgt gacagtgtca tctgctgctg ctctgttcgt gcctgtgttc    840
ctgcctgcca gcctacaac aacaccagcc ctagacctc caaccccctgc cctacaatt     900 gcctctcagc ctctgtctct gaggcccgaa gcttgtagac ctgctgctgg cggagctgtg    960
cacaccagag gactggattt cgcctgcttt tgggtgctgg tggtcgtggg cggagtgctg    1020
gcttgttatt ctctgctggt caccgtggcc ttcatcatct tttgggtcaa gcggggcaga    1080
aagaagctgc tgtacatctt caagcagccc ttcatgaggc ccgtgcagac cacacaggaa    1140
gaggacggct gcagctgtag attccctgag gaagaagaag cgggctgcga gctgagagtg    1200
aagtttagca gatctgccga cgcccctgcc taccagcagg gacagaatca gctgtacaac    1260
gagctgaacc tgggcagacg ggaagagtac gacgtgctgg ataagagaag aggcagagat    1320
cccgagatgg gcggcaagcc ccagagaaga aagaatcccc aggaaggcct gtataacgaa    1380
ctgcagaaag acaagatggc cgaggcctac agcgagatcg gcatgaaggg cgagagaaga    1440
agaggcaagg ccacgatgg actgtaccag ggactgagca cagccaccaa ggatacctac    1500
gatgccctgc acatgcaggc cctgcctcca agaagaagca agagatctag actgctgcac    1560
agcgactaca tgaacatgac ccctagaagg cctggcccca ccagaaagca ctatcagcct    1620
tacgcccctc ccagagactt cgccgcctac agatcttga                           1659
```

<210> SEQ ID NO 21
<211> LENGTH: 153
<212> TYPE: PRT
<213> ORGANISM: Artificial Sequence
<220> FEATURE:
<223> OTHER INFORMATION: Wild-Type IL-2

<400> SEQUENCE: 21

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr
145                 150

<210> SEQ ID NO 22
<211> LENGTH: 160
<212> TYPE: PRT
<213> ORGANISM: Artificial Sequence
<220> FEATURE:
<223> OTHER INFORMATION: IL-2-ER

<400> SEQUENCE: 22

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr Gly Ser Glu Lys Asp Glu Leu
145                 150                 155                 160

<210> SEQ ID NO 23
<211> LENGTH: 220
<212> TYPE: PRT
<213> ORGANISM: Artificial Sequence
<220> FEATURE:

<223> OTHER INFORMATION: NP_006130.1 CD28 Human

<400> SEQUENCE: 23

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

<210> SEQ ID NO 24
<211> LENGTH: 135
<212> TYPE: PRT
<213> ORGANISM: Artificial Sequence
<220> FEATURE:
<223> OTHER INFORMATION: CD19K_ Transmembrane and Signaling domain

<400> SEQUENCE: 24

```
Ala Ala Val Leu Glu Leu Leu Ser Asn Ser Ile Met Tyr Phe Ser His
1               5                   10                  15

Phe Val Pro Val Phe Leu Pro Ala Lys Pro Thr Thr Thr Pro Ala Pro
            20                  25                  30

Arg Pro Pro Thr Pro Ala Pro Thr Ile Ala Ser Gln Pro Leu Ser Leu
        35                  40                  45

Arg Pro Glu Ala Cys Arg Pro Ala Ala Gly Gly Ala Val His Thr Arg
    50                  55                  60

Gly Leu Asp Leu Leu Asp Pro Lys Leu Cys Tyr Leu Leu Asp Gly Ile
65                  70                  75                  80

Leu Phe Ile Tyr Gly Val Ile Leu Thr Ala Leu Phe Leu Arg Leu Lys
                85                  90                  95

Ile Gln Val Arg Lys Ala Ala Ile Thr Ser Tyr Glu Lys Ser Asp Gly
            100                 105                 110

Val Tyr Thr Gly Leu Ser Thr Arg Asn Gln Glu Thr Tyr Glu Thr Leu
        115                 120                 125
```

```
Lys His Glu Lys Pro Gln
    130             135

<210> SEQ ID NO 25
<211> LENGTH: 398
<212> TYPE: PRT
<213> ORGANISM: Artificial Sequence
<220> FEATURE:
<223> OTHER INFORMATION: CD19CAR  FceRIgamma protein

<400> SEQUENCE: 25

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Leu Lys Arg Gly Gly Gly Gly Ser Gly Gly Gly Gly Ser Gly Gly Gly
    130                 135                 140

Gly Ser Gly Gly Gly Gly Ser Glu Val Gln Leu Gln Gln Ser Gly Pro
145                 150                 155                 160

Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
            180                 185                 190

Arg Lys Gly Leu Glu Trp Leu Gly Val Ile Trp Gly Ser Glu Thr Thr
        195                 200                 205

Tyr Tyr Asn Ser Ala Leu Lys Ser Arg Leu Thr Ile Ile Lys Asp Asn
    210                 215                 220

Ser Lys Ser Gln Val Phe Leu Lys Met Asn Ser Leu Gln Thr Asp Asp
225                 230                 235                 240

Thr Ala Ile Tyr Tyr Cys Ala Lys His Tyr Tyr Tyr Gly Gly Ser Tyr
                245                 250                 255

Ala Met Asp Tyr Trp Gly Gln Gly Thr Thr Val Thr Val Ser Ser Ala
            260                 265                 270

Ala Ala Leu Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Phe Trp Val Leu Val Val Val
                325                 330                 335

Gly Gly Val Leu Ala Cys Tyr Ser Leu Leu Val Thr Val Ala Phe Ile
            340                 345                 350
```

Ile Phe Trp Val Arg Leu Lys Ile Gln Val Arg Lys Ala Ala Ile Thr
            355                 360                 365

Ser Tyr Glu Lys Ser Asp Gly Val Tyr Thr Gly Leu Ser Thr Arg Asn
        370                 375                 380

Gln Glu Thr Tyr Glu Thr Leu Lys His Glu Lys Pro Pro Gln
385                 390                 395

<210> SEQ ID NO 26
<211> LENGTH: 441
<212> TYPE: DNA
<213> ORGANISM: Artificial Sequence
<220> FEATURE:
<223> OTHER INFORMATION: 15AD23HC_1805843_CD19K_Eps (879 - 1319)

<400> SEQUENCE: 26
tggggccaag ggaccacggt caccgtctcc tcggccgcgg ttctagagct cttgagcaac      60
tccatcatgt acttcagcca cttcgtgccg gtcttcctgc agcgaagcc caccacgacg     120 ccagcgccgc gaccaccaac accggcgccc accatcgcgt cgcagcccct gtccctgcgc    180
ccagaggcgt gccggccagc ggcgggggc gcagtgcaca cgaggggct ggacctgctg      240 gatcccaaac tctgctacct gctggatgga atcctcttca tctatggtgt cattctcact    300
gccttgttcc tgagactgaa gatccaagtg cgaaaggcag ctataaccag ctatgagaaa    360
tcagatggtg tttacacggg cctgagcacc aggaaccagg agacttacga gactctgaag    420
catgagaaac caccacagta a                                              441

<210> SEQ ID NO 27
<211> LENGTH: 4278
<212> TYPE: DNA
<213> ORGANISM: Artificial Sequence
<220> FEATURE:
<223> OTHER INFORMATION: 15AD23HC_1805843_CD19K_Eps

<400> SEQUENCE: 27
taatacgact cactataggg agacaagctt gcttgttctt tttgcagaag ctcagaataa     60
acgctcaact ttggcagatc ggtaccgaat tcgccaccat ggactggatc tggcgcatcc    120
tcttcctcgt cggcgctgct accggcgctc attcggccca gccggccgac atccagatga    180
cacagactac atcctccctg tctgcctctc tgggagacag agtcaccatc agttgcaggg    240
caagtcagga cattagtaaa tatttaaatt ggtatcagca aaaaccagat ggaactgtta    300
aactcctgat ctaccataca tcaagattac actcaggagt cccatcaagg ttcagtggca    360
gtgggtctgg aacagattat tctctcacca ttagcaacct ggagcaagaa gatattgcca    420
cttacttttg ccaacagggt aatacgcttc cgtacacgtt cggagggggg accaagctgg    480
agctgaaacg tggtggtggt ggttctggtg gtggtggttc tggcggcggc ggctccggtg    540
gtggtggatc cgaggtgcag ctgcagcagt ctggacctgg cctggtggcg ccctcacaga    600
gcctgtccgt cacatgcact gtctcagggg tctcattacc cgactatggt gtaagctgga    660
ttcgccagcc tccacgaaag ggtctggagt ggctgggagt aatatggggt agtgaaacca    720
catactataa ttcagctctc aaatccgac tgaccatcat caaggacaac tccaagagcc    780
aagttttctt aaaaatgaac agtctgcaaa ctgatgacac agccatttac tactgtgcca    840
aacattatta ctacggtggt agctatgcta tggactactg gggccaaggg accacggtca    900
ccgtctcctc ggccgcggtt ctagagctct gagcaactc catcatgtac ttcagccact    960
tcgtgccggt cttcctgcca gcgaagccca ccacgacgcc agcgccgcga ccaccaacac   1020

```
cggcgcccac catcgcgtcg cagcccctgt ccctgcgccc agaggcgtgc cggccagcgg      1080 cgggggggcgc agtgcacacg aggggggctgg acctgctgga tcccaaactc tgctacctgc    1140
tggatggaat cctcttcatc tatggtgtca ttctcactgc cttgttcctg agactgaaga     1200
tccaagtgcg aaaggcagct ataaccagct atgagaaatc agatggtgtt tacacgggcc     1260
tgagcaccag gaaccaggag acttacgaga ctctgaagca tgagaaacca ccacagtaac     1320
agccagggca tttctccctc gagagatctg atatcactag tgactgacta ggatctggtt     1380
accactaaac cagcctcaag aacacccgaa tggagtctct aagctacata ataccaactt     1440
acactttaca aaatgttgtc ccccaaaatg tagccattcg tatctgctcc taataaaaag     1500
aaagtttctt cacattctaa aaaaaaaaaa aaaaaaaaaa aaaaaaaaaa acccccccccc    1560 ccccccccct gcaggtcgac tctagaggat cccgggtac cgagctcgaa ttagtattct     1620
atagtgtcac ctaaatccaa ttcactggcc gtcgttttac aacgtcgtga ctgggaaaac    1680
cctggcgtta cccaacttaa tcgccttgca gcacatcccc ctttcgccag ctggcgtaat    1740
agcgaagagg cccgcaccga tcgcccttcc caacagttgc gcagcctgaa tggcgaatgg    1800
cgcctgatgc ggtattttct ccttacgcat ctgtgcggta tttcacaccg catatggtgc    1860
actctcagta caatctgctc tgatgccgca tagttaagcc agccccgaca cccgccaaca    1920
cccgctgacg cgccctgacg ggcttgtctg ctcccggcat ccgcttacag acaagctgtg    1980
accgtctccg ggagctgcat gtgtcagagg ttttcaccgt catcaccgaa acgcgcgaga    2040
cgaaagggcc tcgtgatacg cctatttta taggttaatg tcatgataat aatggtttct    2100
tagacgtcag gtggcacttt tcggggaaat gtgcgcggaa cccctatttg tttatttttc    2160
taaatacatt caaatatgta tccgctcatg agacaataac cctgataaat gcttcaataa    2220
tattgaaaaa ggaagagtat gagtattcaa catttccgtg tcgcccttat ccctttttt    2280 gcggcatttt gccttcctgt ttttgctcac ccagaaacgc tggtgaaagt aaaagatgct    2340
gaagatcagt tgggtgcacg agtgggttac atcgaactgg atctcaacag cggtaagatc    2400
cttgagagtt ttcgccccga agaacgtttt ccaatgatga gcacttttaa agttctgcta    2460
tgtggcgcgg tattatcccg tattgacgcc gggcaagagc aactcggtcg ccgcatacac    2520
tattctcaga atgacttggt tgagtactca ccagtcacag aaaagcatct tacggatggc    2580
atgacagtaa gagaattatg cagtgctgcc ataaccatga gtgataacac tgcggccaac    2640
ttacttctga caacgatcgg aggaccgaag gagctaaccg cttttttgca acatgggg     2700 gatcatgtaa ctcgccttga tcgttgggaa ccggagctga atgaagccat accaaacgac    2760
gagcgtgaca ccacgatgcc tgtagcaatg gcaacaacgt tgcgcaaact attaactggc    2820
gaactactta ctctagcttc ccggcaacaa ttaatagact ggatggaggc ggataaagtt    2880
gcaggaccac ttctgcgctc ggcccttccg gctggctggt ttattgctga taaatctgga    2940
gccggtgagc gtgggtctcg cggtatcatt gcagcactgg ggccagatgg taagccctcc    3000
cgtatcgtag ttatctacac gacggggagt caggcaacta tggatgaacg aaatagacag    3060
atcgctgaga taggtgcctc actgattaag cattggtaac tgtcagacca agtttactca    3120
tatatacttt agattgattt aaaacttcat ttttaattta aaaggatcta ggtgaagatc    3180 cttttttgata atctcatgac caaaatccct taacgtgagt tttcgttcca ctgagcgtca    3240
gaccccgtag aaaagatcaa aggatcttct tgagatcctt ttttttctgcg cgtaatctgc    3300 tgcttgcaaa caaaaaaacc accgctacca gcggtggttt gtttgccgga tcaagagcta    3360
```

| | |
|---|---|
| ccaactctttt tccgaaggt aactggcttc agcagagcgc agataccaaa tactgttctt | 3420 |
| ctagtgtagc cgtagttagg ccaccacttc aagaactctg tagcaccgcc tacatacctc | 3480 |
| gctctgctaa tcctgttacc agtggctgct gccagtggcg ataagtcgtg tcttaccggg | 3540 |
| ttggactcaa gacgatagtt accggataag cgcagcggt cgggctgaac gggggttcg | 3600 |
| tgcacacagc ccagcttgga gcgaacgacc tacaccgaac tgagatacct acagcgtgag | 3660 |
| ctatgagaaa gcgccacgct tcccgaaggg agaaaggcgg acaggtatcc ggtaagcggc | 3720 |
| agggtcggaa caggagagcg cacgagggag cttccagggg gaaacgcctg gtatctttat | 3780 |
| agtcctgtcg ggtttcgcca cctctgactt gagcgtcgat ttttgtgatg ctcgtcaggg | 3840 |
| gggcggagcc tatggaaaaa cgccagcaac gcggcctttt tacggttcct ggccttttgc | 3900 |
| tggccttttg ctcacatgtt ctttcctgcg ttatcccctg attctgtgga taaccgtatt | 3960 |
| accgcctttg agtgagctga taccgctcgc cgcagccgaa cgaccgagcg cagcgagtca | 4020 |
| gtgagcgagg aagcggaaga gcgcccaata cgcaaaccgc ctctccccgc gcgttggccg | 4080 |
| attcattaat gcagctggca cgacaggttt cccgactgga aagcgggcag tgagcgcaac | 4140 |
| gcaattaatg tgagttagct cactcattag gcaccccagg ctttacactt tatgcttccg | 4200 |
| gctcgtatgt tgtgtggaat tgtgagcgga taacaatttc acacaggaaa cagctatgac | 4260 |
| catgattacg ccaagctc | 4278 |

<210> SEQ ID NO 28
<211> LENGTH: 3136
<212> TYPE: DNA
<213> ORGANISM: Artificial Sequence
<220> FEATURE:
<223> OTHER INFORMATION: pNEUKv1_CD19CAR_CD16(158V)_ERIL-2 vector

<400> SEQUENCE: 28

| | |
|---|---|
| atggactgga tctggcggat tctgtttctc gtgggagctg ccacaggcgc tcattctgct | 60 |
| cagcctgccg atatccagat gacccagaca acaagcagcc tgagcgcctc tctgggcgat | 120 |
| agagtgacaa tcagctgcag agccagccag gacatcagca gtacctgaa ctggtatcag | 180 |
| cagaaacccg acggcaccgt gaagctgctg atctaccaca caagcagact gcacagcggc | 240 |
| gtgccaagca gattttctgg cagcggcagc ggcaccgatt acagcctgac catcagcaac | 300 |
| ctggaacagg aagatatcgc tacctacttc tgtcagcagg gcaacaccct gccttacacc | 360 |
| tttggcggcg gaacaaagct ggaactgaaa agaggcggcg gaggaagcgg aggcggagga | 420 |
| tctggggcg gaggctctgg cggaggggga tctgaagtgc agctgcagca gtctggacct | 480 |
| ggactggtgg ctccttctca gtccctgtct gtgacctgta cagtgtctgg cgtgtccctg | 540 |
| cctgattacg gcgtgtcctg gatcagacag cctcccagaa aaggcctgga atggctggga | 600 |
| gtgatctggg gcagcgagac aacctactac aacagcgccc tgaagtcccg gctgaccatc | 660 |
| atcaaggaca cagcaagag ccaggtgttc ctgaagatga acagcctgca gaccgacgac | 720 |
| accgccatct actactgcgc caagcactac tactacggcg gcagctacgc catggattat | 780 |
| tggggccagg gcaccaccgt gacagtgtca tctgcggccg cgctgagcaa cagcatcatg | 840 |
| tacttcagcc acttcgtgcc tgtgttcctg cctgccaagc ctacaacaac accagccct | 900 |
| agacctccaa cccctgcccc tacaattgcc tctcagcctc tgtctctgag gcccgaagct | 960 |
| tgtagacctg ctgctggcgg agctgtgcac accagaggac tggatttcgc tgcttttggg | 1020 |
| gtgctggtg tcgtgggcgg agtgctggct tgttattctc tgctggtcac cgtggccttc | 1080 |
| atcatctttt gggtccgact gaagatccag gtccgaaagg ccgccatcac cagctacgag | 1140 |

```
aagtctgatg gcgtgtacac cggcctgagc accagaaacc aggaaaccta cgagacactg      1200
aagcacgaga agccccccca gggatctgga gctactaact tcagcctgct gaagcaggct      1260
ggagacgtgg aggagaaccc tggacctatg tggcagctgc tgctgcctac agctctcctg      1320
ctgctggtgt ccgccggcat gagaaccgag gatctgccta aggccgtggt gttcctggaa      1380
ccccagtggt acagagtgct ggaaaaggac agcgtgaccc tgaagtgcca gggcgcctac      1440
agccccgagg acaatagcac ccagtggttc cacaacgaga gcctgatcag cagccaggcc      1500
agcagctact tcatcgacgc cgccaccgtg acgacagcg gcgagtatag atgccagacc      1560
aacctgagca ccctgagcga ccccgtgcag ctggaagtgc acatcggatg gctgctgctg      1620
caggccccca gatgggtgtt caagaagag accccatcc acctgagatg ccactcttgg      1680
aagaacaccg ccctgcacaa agtgacctac ctgcagaacg gcaagggcag aaagtacttc      1740
caccacaaca gcgacttcta catccccaag gccaccctga aggactccgg ctcctacttc      1800
tgcagaggcc tcgtgggcag caagaacgtg tccagcgaga cagtgaacat caccatcacc      1860
cagggcctgg ccgtgtctac catcagcagc ttttttccac ccggctacca ggtgtccttc      1920
tgcctcgtga tggtgctgct gttcgccgtg acaccggcc tgtacttcag cgtgaaaaca      1980
aacatcagaa gcagcacccg ggactggaag gaccacaagt tcaagtggcg gaaggacccc      2040
caggacaagt gaaattccgc ccctctcccc ccccccctc tccctccccc cccctaacg       2100 ttactggccg aagccgcttg aataaggcc ggtgtgcgtt tgtctatatg ttattttcca      2160
ccatattgcc gtcttttggc aatgtgaggg cccggaaacc tggccctgtc ttcttgacga      2220
gcattcctag gggtctttcc cctctcgcca aggaatgca aggtctgttg aatgtcgtga      2280
aggaagcagt tcctctggaa gcttcttgaa gacaaacaac gtctgtagcg acccttgca       2340 ggcagcggaa ccccccacct ggcgacaggt gcctctgcgg ccaaaagcca cgtgtataag      2400
atacacctgc aaaggcggca acccccagt gccacgttgt gagttggata ttgtggaaa       2460 gagtcaaatg gctctcctca agcgtattca acaaggggct gaaggatgcc cagaaggtac      2520
cccattgtat gggatctgat ctggggcctc ggtgcacatg ctttacatgt gtttagtcga      2580
ggttaaaaaa acgtctaggc ccccgaacc acggggacgt ggttttcctt tgaaaacac      2640 gataaccgcc accatgtacc ggatgcagct gctgagctgt atcgccctgt ctctggccct      2700
cgtgaccaac agcgccccta ccagcagcag caccaagaaa acccagctgc agctggaaca      2760
tctgctgctg gacctgcaga tgatcctgaa cggcatcaac aactacaaga accccaagct      2820
gacccggatg ctgaccttca gttctacat gcccaagaag gccaccgaac tgaaacatct      2880
gcagtgcctg gaagaggaac tgaagcccct ggaagaagtg ctgaacctgg cccagagcaa      2940
gaacttccac ctgaggccca gggacctgat cagcaacatc aacgtgatcg tgctggaact      3000
gaaaggcagc gagacaacct tcatgtgcga gtacgccgac gagacagcta ccatcgtgga      3060
atttctgaac cggtggatca ccttctgcca gagcatcatc agcaccctga ccggctccga      3120
gaaggacgag ctgtga                                                       3136
```

<210> SEQ ID NO 29
<211> LENGTH: 683
<212> TYPE: PRT
<213> ORGANISM: Artificial Sequence
<220> FEATURE:
<223> OTHER INFORMATION: CD19CAR_P2A_CD16(158V) protein

<400> SEQUENCE: 29

| | | | | | | | | | | | | | | |
|---|---|---|---|---|---|---|---|---|---|---|---|---|---|---|
|Met|Asp|Trp|Ile|Trp|Arg|Ile|Leu|Phe|Leu|Val|Gly|Ala|Ala|Thr|Gly|
|1| | | |5| | | | |10| | | | |15|

Ala His Ser Ala Gln Pro Ala Asp Ile Gln Met Thr Gln Thr Thr Ser
                  20                      25                    30

Ser Leu Ser Ala Ser Leu Gly Asp Arg Val Thr Ile Ser Cys Arg Ala
                    35                      40                      45

Ser Gln Asp Ile Ser Lys Tyr Leu Asn Trp Tyr Gln Gln Lys Pro Asp
            50                      55                      60

Gly Thr Val Lys Leu Leu Ile Tyr His Thr Ser Arg Leu His Ser Gly
65                      70                      75                      80

Val Pro Ser Arg Phe Ser Gly Ser Gly Ser Gly Thr Asp Tyr Ser Leu
                    85                      90                      95

Thr Ile Ser Asn Leu Glu Gln Glu Asp Ile Ala Thr Tyr Phe Cys Gln
                    100                     105                     110

Gln Gly Asn Thr Leu Pro Tyr Thr Phe Gly Gly Gly Thr Lys Leu Glu
            115                     120                     125

Leu Lys Arg Gly Gly Gly Gly Ser Gly Gly Gly Gly Ser Gly Gly Gly
        130                     135                     140

Gly Ser Gly Gly Gly Gly Ser Glu Val Gln Leu Gln Gln Ser Gly Pro
145                     150                     155                     160

Gly Leu Val Ala Pro Ser Gln Ser Leu Ser Val Thr Cys Thr Val Ser
                    165                     170                     175

Gly Val Ser Leu Pro Asp Tyr Gly Val Ser Trp Ile Arg Gln Pro Pro
                    180                     185                     190

Arg Lys Gly Leu Glu Trp Leu Gly Val Ile Trp Gly Ser Glu Thr Thr
                    195                     200                     205

Tyr Tyr Asn Ser Ala Leu Lys Ser Arg Leu Thr Ile Ile Lys Asp Asn
            210                     215                     220

Ser Lys Ser Gln Val Phe Leu Lys Met Asn Ser Leu Gln Thr Asp Asp
225                     230                     235                     240

Thr Ala Ile Tyr Tyr Cys Ala Lys His Tyr Tyr Gly Gly Ser Tyr
                    245                     250                     255

Ala Met Asp Tyr Trp Gly Gln Gly Thr Thr Val Thr Val Ser Ser Ala
            260                     265                     270

Ala Ala Leu Ser Asn Ser Ile Met Tyr Phe Ser His Phe Val Pro Val
        275                     280                     285

Phe Leu Pro Ala Lys Pro Thr Thr Thr Pro Ala Pro Arg Pro Pro Thr
290                     295                     300

Pro Ala Pro Thr Ile Ala Ser Gln Pro Leu Ser Leu Arg Pro Glu Ala
305                     310                     315                     320

Cys Arg Pro Ala Ala Gly Gly Ala Val His Thr Arg Gly Leu Asp Phe
                    325                     330                     335

Ala Cys Phe Trp Val Leu Val Val Val Gly Gly Val Leu Ala Cys Tyr
                    340                     345                     350

Ser Leu Leu Val Thr Val Ala Phe Ile Ile Phe Trp Val Arg Leu Lys
            355                     360                     365

Ile Gln Val Arg Lys Ala Ala Ile Thr Ser Tyr Glu Lys Ser Asp Gly
        370                     375                     380

Val Tyr Thr Gly Leu Ser Thr Arg Asn Gln Glu Thr Tyr Glu Thr Leu
385                     390                     395                     400

```
Lys His Glu Lys Pro Pro Gln Gly Ser Gly Ala Thr Asn Phe Ser Leu
                405                 410                 415

Leu Lys Gln Ala Gly Asp Val Glu Glu Asn Pro Gly Pro Met Trp Gln
            420                 425                 430

Leu Leu Leu Pro Thr Ala Leu Leu Leu Val Ser Ala Gly Met Arg
            435                 440                 445

Thr Glu Asp Leu Pro Lys Ala Val Val Phe Leu Glu Pro Gln Trp Tyr
450                 455                 460

Arg Val Leu Glu Lys Asp Ser Val Thr Leu Lys Cys Gln Gly Ala Tyr
465                 470                 475                 480

Ser Pro Glu Asp Asn Ser Thr Gln Trp Phe His Asn Glu Ser Leu Ile
                485                 490                 495

Ser Ser Gln Ala Ser Ser Tyr Phe Ile Asp Ala Ala Thr Val Asp Asp
            500                 505                 510

Ser Gly Glu Tyr Arg Cys Gln Thr Asn Leu Ser Thr Leu Ser Asp Pro
        515                 520                 525

Val Gln Leu Glu Val His Ile Gly Trp Leu Leu Leu Gln Ala Pro Arg
530                 535                 540

Trp Val Phe Lys Glu Glu Asp Pro Ile His Leu Arg Cys His Ser Trp
545                 550                 555                 560

Lys Asn Thr Ala Leu His Lys Val Thr Tyr Leu Gln Asn Gly Lys Gly
                565                 570                 575

Arg Lys Tyr Phe His His Asn Ser Asp Phe Tyr Ile Pro Lys Ala Thr
            580                 585                 590

Leu Lys Asp Ser Gly Ser Tyr Phe Cys Arg Gly Leu Val Gly Ser Lys
        595                 600                 605

Asn Val Ser Ser Glu Thr Val Asn Ile Thr Ile Thr Gln Gly Leu Ala
610                 615                 620

Val Ser Thr Ile Ser Ser Phe Phe Pro Pro Gly Tyr Gln Val Ser Phe
625                 630                 635                 640

Cys Leu Val Met Val Leu Leu Phe Ala Val Asp Thr Gly Leu Tyr Phe
                645                 650                 655

Ser Val Lys Thr Asn Ile Arg Ser Ser Thr Arg Asp Trp Lys Asp His
            660                 665                 670

Lys Phe Lys Trp Arg Lys Asp Pro Gln Asp Lys
        675                 680

<210> SEQ ID NO 30
<211> LENGTH: 160
<212> TYPE: PRT
<213> ORGANISM: Artificial Sequence
<220> FEATURE:
<223> OTHER INFORMATION: ERIL-2 protein

<400> SEQUENCE: 30

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80
```

```
Glu Leu Lys Pro Leu Glu Glu Val Leu Asn Leu Ala Gln Ser Lys
            85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr Gly Ser Glu Lys Asp Glu Leu
145                 150                 155                 160

<210> SEQ ID NO 31
<211> LENGTH: 3126
<212> TYPE: DNA
<213> ORGANISM: Artificial Sequence
<220> FEATURE:
<223> OTHER INFORMATION: Codon-optimized CD33ScfV-P2A-CD16-IRES-erIL2

<400> SEQUENCE: 31
atggactgga tctggcgcat cctcttcctc gtcggcgctg ctaccggcgc tcattcggcc      60
cagccggccg acattcaaat gactcagtcc ccttccagct tgtcagcctc agtagggac     120
cgggtcacga tcacctgtcg agcgtctgag tcagtggata actacgggat ttctttcatg    180
aactggttcc agcagaagcc cggcaaagct cctaagctcc ttatatatgc agcctcaaat    240
caggggagcg gtgttcctag tcgcttcagt ggaagcggta gcggtacgga ctttacgttg    300
acgataagta gccttcagcc agatgacttt gccacttatt attgtcagca gtctaaggaa    360
gttccttgga cgtttggcca aggaacgaag gtcgaaatca aggggggagg gggctcagga    420
ggggcggca gtggtggtgg aggctctcaa gtccaactcg tacagtctgg cgcggaggtt    480
aaaaagccgg gaagctccgt gaaagtatcc tgtaaggcaa gcggatacac ctttaccgat    540
tataacatgc actgggttag gcaggcgccc ggccaaggtc tggaatggat cggttatatt    600
tatccataca acggtggtac cggctataat cagaagttta agagtaaggc tactattaca    660
gcggatgagt caaccaatac tgcatacatg gagctctcct cactcaggag cgaagatacc    720
gcagtgtatt actgtgcccg agggagacca gccatggact actggggtca gggtaccctt    780
gtgacagtat ctagcgcggc cgcgctgagc aacagcatca gtacttcag ccacttcgtg    840
cctgtgttcc tgcctgccaa gcctacaaca caccagccc tagacctcc aaccccctgcc    900
cctacaattg cctctcagcc tctgtctctg aggcccgaag cttgtagacc tgctgctggc    960
ggagctgtgc acaccagagg actggatttc gcctgctttt gggtgctggt ggtcgtgggc   1020
ggagtgctgg cttgttattc tctgctggtc accgtggcct tcatcatctt tggtccga    1080
ctgaagatcc aggtccgaaa ggccgccatc accagctacg agaagtctga tggcgtgtac   1140
accggcctga gcaccagaaa ccaggaaacc tacgagacac tgaagcacga aagccccc     1200
cagggaagcg gagctactaa cttcagcctg ctgaagcagg ctggagacgt ggaggagaac   1260
cctggaccta tgtggcagct gctgctgcct acagctctcc tgctgctggt gtccgccggc   1320
atgagaaccg aggatctgcc taaggccgtg gtgttcctgg aaccccagtg gtacagagtg   1380
ctggaaaagg acagcgtgac cctgaagtgc cagggcgcct acagcccga ggacaatagc   1440
acccagtggt tccacaacga gagcctgatc agcagccagg ccagcagcta cttcatcgac   1500
gccgccaccg tggacgacag cggcgagtat agatgccaga ccaacctgag caccctgagc   1560
gaccccgtgc agctggaagt gcacatcgga tggctgctgc tgcaggcccc cagatgggtg   1620
```

```
ttcaaagaag aggacccat ccacctgaga tgccactctt ggaagaacac cgccctgcac    1680
aaagtgacct acctgcagaa cggcaagggc agaaagtact tccaccacaa cagcgacttc    1740
tacatcccca aggccaccct gaaggactcc ggctcctact tctgcagagg cctcgtgggc    1800
agcaagaacg tgtccagcga cagtgaac atcaccatca cccagggcct ggccgtgtct    1860
accatcagca gcttttccc acccggctac caggtgtcct tctgcctcgt gatggtgctg    1920
ctgttcgccg tggacaccgg cctgtacttc agcgtgaaaa caaacatcag aagcagcacc    1980
cgggactgga aggaccacaa gttcaagtgg cggaaggacc cccaggacaa gtgaaattcc    2040
gcccctctcc cccccccc tctccctccc ccccctaa cgttactggc cgaagccgct    2100
tggaataagg ccggtgtgcg tttgtctata tgttattttc caccatattg ccgtcttttg    2160
gcaatgtgag ggcccggaaa cctggccctg tcttcttgac gagcattcct aggggtcttt    2220
cccctctcgc caaaggaatg caaggtctgt tgaatgtcgt gaaggaagca gttcctctgg    2280
aagcttcttg aagacaaaca acgtctgtag cgacccttg caggcagcgg aaccccccac    2340
ctggcgacag gtgcctctgc ggccaaaagc cacgtgtata agatacacct gcaaaggcgg    2400 cacaaccccca gtgccacgtt gtgagttgga tagttgtgga aagagtcaaa tggctctcct    2460
caagcgtatt caacaagggg ctgaaggatg cccagaaggt accccattgt atgggatctg    2520
atctggggcc tcggtgcaca tgctttacat gtgtttagtc gaggttaaaa aaacgtctag    2580
gccccccgaa ccacggggac gtggttttcc tttgaaaaac acgataaccg ccaccatgta    2640
ccggatgcag ctgctgagct gtatcgccct gtctctggcc ctcgtgacca acagcgcccc    2700
taccagcagc agcaccaaga aaacccagct gcagctggaa catctgctgc tggacctgca    2760
gatgatcctg aacggcatca caactacaa gaaccccaag ctgacccgga tgctgacctt    2820
caagttctac atgcccaaga aggccaccga actgaaacat ctgcagtgcc tggaagagga    2880
actgaagccc ctggaagaag tgctgaacct ggcccagagc aagaacttcc acctgaggcc    2940
cagggacctg atcagcaaca tcaacgtgat cgtgctggaa ctgaaaggca gcgagacaac    3000
cttcatgtgc gagtacgccg acgagacagc taccatcgtg gaatttctga accggtggat    3060
caccttctgc cagagcatca tcagcaccct gaccggctcc gagaaggacg agctgtgagc    3120
ggccgc                                                               3126
```

<210> SEQ ID NO 32
<211> LENGTH: 677
<212> TYPE: PRT
<213> ORGANISM: Artificial Sequence
<220> FEATURE:
<223> OTHER INFORMATION: CD33 CAR-P2A-CD16 peptide

<400> SEQUENCE: 32

```
Met Asp Trp Ile Trp Arg Ile Leu Phe Leu Val Gly Ala Ala Thr Gly
  1               5                  10                  15

Ala His Ser Ala Gln Pro Ala Asp Ile Gln Met Thr Gln Ser Pro Ser
             20                  25                  30

Ser Leu Ser Ala Ser Val Gly Asp Arg Val Thr Ile Thr Cys Arg Ala
         35                  40                  45

Ser Glu Ser Val Asp Asn Tyr Gly Ile Ser Phe Met Asn Trp Phe Gln
     50                  55                  60

Gln Lys Pro Gly Lys Ala Pro Lys Leu Leu Ile Tyr Ala Ala Ser Asn
 65                  70                  75                  80
```

```
Gln Gly Ser Gly Val Pro Ser Arg Phe Ser Gly Ser Gly Ser Gly Thr
                    85                  90                  95

Asp Phe Thr Leu Thr Ile Ser Ser Leu Gln Pro Asp Asp Phe Ala Thr
                100                 105                 110

Tyr Tyr Cys Gln Gln Ser Lys Glu Val Pro Trp Thr Phe Gly Gln Gly
            115                 120                 125

Thr Lys Val Glu Ile Lys Gly Gly Gly Ser Gly Gly Gly Gly Ser
        130                 135                 140

Gly Gly Gly Gly Ser Gln Val Gln Leu Val Gln Ser Gly Ala Glu Val
145                 150                 155                 160

Lys Lys Pro Gly Ser Ser Val Lys Val Ser Cys Lys Ala Ser Gly Tyr
                165                 170                 175

Thr Phe Thr Asp Tyr Asn Met His Trp Val Arg Gln Ala Pro Gly Gln
            180                 185                 190

Gly Leu Glu Trp Ile Gly Tyr Ile Tyr Pro Tyr Asn Gly Gly Thr Gly
            195                 200                 205

Tyr Asn Gln Lys Phe Lys Ser Lys Ala Thr Ile Thr Ala Asp Glu Ser
210                 215                 220

Thr Asn Thr Ala Tyr Met Glu Leu Ser Ser Leu Arg Ser Glu Asp Thr
225                 230                 235                 240

Ala Val Tyr Tyr Cys Ala Arg Gly Arg Pro Ala Met Asp Tyr Trp Gly
                245                 250                 255

Gln Gly Thr Leu Val Thr Val Ser Ser Ala Ala Ala Leu Ser Asn Ser
            260                 265                 270

Ile Met Tyr Phe Ser His Phe Val Pro Val Phe Leu Pro Ala Lys Pro
            275                 280                 285

Thr Thr Thr Pro Ala Pro Arg Pro Pro Thr Pro Ala Pro Thr Ile Ala
        290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Phe Ala Cys Phe Trp Val Leu
                325                 330                 335

Val Val Val Gly Gly Val Leu Ala Cys Tyr Ser Leu Leu Val Thr Val
            340                 345                 350

Ala Phe Ile Ile Phe Trp Val Arg Leu Lys Ile Gln Val Arg Lys Ala
            355                 360                 365

Ala Ile Thr Ser Tyr Glu Lys Ser Asp Gly Val Tyr Thr Gly Leu Ser
        370                 375                 380

Thr Arg Asn Gln Glu Thr Tyr Glu Thr Leu Lys His Glu Lys Pro Pro
385                 390                 395                 400

Gln Gly Ser Gly Ala Thr Asn Phe Ser Leu Leu Lys Gln Ala Gly Asp
                405                 410                 415

Val Glu Glu Asn Pro Gly Pro Met Trp Gln Leu Leu Leu Pro Thr Ala
            420                 425                 430

Leu Leu Leu Leu Val Ser Ala Gly Met Arg Thr Glu Asp Leu Pro Lys
            435                 440                 445

Ala Val Val Phe Leu Glu Pro Gln Trp Tyr Arg Val Leu Glu Lys Asp
        450                 455                 460

Ser Val Thr Leu Lys Cys Gln Gly Ala Tyr Ser Pro Glu Asp Asn Ser
465                 470                 475                 480

Thr Gln Trp Phe His Asn Glu Ser Leu Ile Ser Ser Gln Ala Ser Ser
                485                 490                 495
```

```
Tyr Phe Ile Asp Ala Ala Thr Val Asp Ser Gly Glu Tyr Arg Cys
                500                 505                 510

Gln Thr Asn Leu Ser Thr Leu Ser Asp Pro Val Gln Leu Glu Val His
            515                 520                 525

Ile Gly Trp Leu Leu Leu Gln Ala Pro Arg Trp Val Phe Lys Glu Glu
        530                 535                 540

Asp Pro Ile His Leu Arg Cys His Ser Trp Lys Asn Thr Ala Leu His
545                 550                 555                 560

Lys Val Thr Tyr Leu Gln Asn Gly Lys Gly Arg Lys Tyr Phe His His
                565                 570                 575

Asn Ser Asp Phe Tyr Ile Pro Lys Ala Thr Leu Lys Asp Ser Gly Ser
            580                 585                 590

Tyr Phe Cys Arg Gly Leu Val Gly Ser Lys Asn Val Ser Ser Glu Thr
        595                 600                 605

Val Asn Ile Thr Ile Thr Gln Gly Leu Ala Val Ser Thr Ile Ser Ser
    610                 615                 620

Phe Phe Pro Pro Gly Tyr Gln Val Ser Phe Cys Leu Val Met Val Leu
625                 630                 635                 640

Leu Phe Ala Val Asp Thr Gly Leu Tyr Phe Ser Val Lys Thr Asn Ile
                645                 650                 655

Arg Ser Ser Thr Arg Asp Trp Lys Asp His Lys Phe Lys Trp Arg Lys
            660                 665                 670

Asp Pro Gln Asp Lys
            675

<210> SEQ ID NO 33
<211> LENGTH: 192
<212> TYPE: PRT
<213> ORGANISM: Artificial Sequence
<220> FEATURE:
<223> OTHER INFORMATION: erIL2

<400> SEQUENCE: 33

Met Leu Tyr Met Cys Leu Val Glu Val Lys Lys Thr Ser Arg Pro Pro
1               5                   10                  15

Glu Pro Arg Gly Arg Gly Phe Pro Leu Lys Asn Thr Ile Thr Ala Thr
            20                  25                  30

Met Tyr Arg Met Gln Leu Leu Ser Cys Ile Ala Leu Ser Leu Ala Leu
        35                  40                  45

Val Thr Asn Ser Ala Pro Thr Ser Ser Ser Thr Lys Lys Thr Gln Leu
    50                  55                  60

Gln Leu Glu His Leu Leu Leu Asp Leu Gln Met Ile Leu Asn Gly Ile
65                  70                  75                  80

Asn Asn Tyr Lys Asn Pro Lys Leu Thr Arg Met Leu Thr Phe Lys Phe
                85                  90                  95

Tyr Met Pro Lys Lys Ala Thr Glu Leu Lys His Leu Gln Cys Leu Glu
            100                 105                 110

Glu Glu Leu Lys Pro Leu Glu Glu Val Leu Asn Leu Ala Gln Ser Lys
        115                 120                 125

Asn Phe His Leu Arg Pro Arg Asp Leu Ile Ser Asn Ile Asn Val Ile
    130                 135                 140

Val Leu Glu Leu Lys Gly Ser Glu Thr Thr Phe Met Cys Glu Tyr Ala
145                 150                 155                 160

Asp Glu Thr Ala Thr Ile Val Glu Phe Leu Asn Arg Trp Ile Thr Phe
                165                 170                 175
```

Cys Gln Ser Ile Ile Ser Thr Leu Thr Gly Ser Glu Lys Asp Glu Leu
            180                 185                 190

<210> SEQ ID NO 34
<211> LENGTH: 254
<212> TYPE: PRT
<213> ORGANISM: Artificial Sequence
<220> FEATURE:
<223> OTHER INFORMATION: sp.8637|G3A_HUMAN Low affinity IgG gamma
      FcR III-A

<400> SEQUENCE: 34

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 35
<211> LENGTH: 254
<212> TYPE: PRT
<213> ORGANISM: Artificial Sequence
<220> FEATURE:
<223> OTHER INFORMATION: High Affinity Variant Immunoglobulin Gamma
      FcRIII-A

<400> SEQUENCE: 35

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
                20                  25                  30

```
Gln Trp Tyr Arg Val Leu Glu Lys Asp Ser Val Thr Leu Lys Cys Gln
         35                  40                  45

Gly Ala Tyr Ser Pro Glu Asp Asn Ser Thr Gln Trp Phe His Asn Glu
 50                  55                  60

Ser Leu Ile Ser Ser Gln Ala Ser Ser Tyr Phe Ile Asp Ala Ala Thr
 65                  70                  75                  80

Val Asp Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 36
<211> LENGTH: 765
<212> TYPE: DNA
<213> ORGANISM: Artificial Sequence
<220> FEATURE:
<223> OTHER INFORMATION: High Affinity Variant Ig Gamma Fc Region
      Receptor III-A DNA

<400> SEQUENCE: 36
atgtggcagc tgctgctgcc tacagctctc ctgctgctgg tgtccgccgg catgagaacc      60
gaggatctgc ctaaggccgt ggtgttcctg aaccccagt ggtacagagt gctggaaaag     120
gacagcgtga ccctgaagtg ccagggcgcc tacagccccg aggacaatag cacccagtgg     180
ttccacaacg agagcctgat cagcagccag gccagcagct acttcatcga cgccgccacc     240
gtggacgaca gcggcgagta tagatgccag accaacctga gcaccctgag cgaccccgtg     300
cagctggaag tgcacatcgg atggctgctg ctgcaggccc ccagatgggt gttcaaagaa     360
gaggacccca tccacctgag atgccactct tggaagaaca ccgccctgca caaagtgacc     420
tacctgcaga acggcaaggg cagaaagtac ttccaccaca cagcgacttc ctacatcccc     480
aaggccaccc tgaaggactc cggctcctac ttctgcagag gcctcgtggg cagcaagaac     540
gtgtccagcg agacagtgaa catcaccatc acccaggggcc tggccgtgtc taccatcagc     600 agcttttcc cacccggcta ccaggtgtcc ttctgcctcg tgatggtgct gctgttcgcc     660
gtggacaccg gcctgtactt cagcgtgaaa acaaacatca gaagcagcac ccgggactgg     720
aaggaccaca gttcaagtg gcggaaggac ccccaggaca agtga                     765
```

<210> SEQ ID NO 37
<211> LENGTH: 1233
<212> TYPE: DNA
<213> ORGANISM: Artificial Sequence
<220> FEATURE:
<223> OTHER INFORMATION: artificial sequence

<400> SEQUENCE: 37

| | | | | | |
|---|---|---|---|---|---|
| atggactgga | tctggcggat | tctgtttctc | gtgggagctg | ccacaggcgc | tcattctgct | 60 |
| cagcctgccg | acatccagat | gacccagagc | cccagcagcc | tgagcgccag | cgtgggcgac | 120 |
| agagtgacca | tcacctgcag | agccagccag | gacgtgaaca | ccgccgtggc | ctggtaccag | 180 |
| cagaagcccg | gcaaggcccc | caagctgctg | atctacagcg | ccagcttcct | gtacagcggc | 240 |
| gtgcccagca | gattcagcgg | cagcagaagc | ggcaccgact | tcaccctgac | catcagcagc | 300 |
| ctgcagcccg | aggacttcgc | cacctactac | tgccagcagc | actacaccac | ccccccacc | 360 |
| ttcggccagg | gcaccaaggt | ggagatcaag | tcctcagggg | gcgggggaag | tggtgggggc | 420 |
| ggcagcggcg | gagggggctc | aggaggaggc | ggatcaggcg | atcagaggt | gcagctggtg | 480 |
| gagagcggcg | gcggcctggt | gcagcccggc | ggcagcctga | gactgagctg | cgccgccagc | 540 |
| ggcttcaaca | tcaaggacac | ctacatccac | tgggtgagac | aggcccccgg | caagggcctg | 600 |
| gagtgggtgg | ccagaatcta | ccccaccaac | ggctacacca | gatacgccga | cagcgtgaag | 660 |
| ggcagattca | ccatcagcgc | cgacaccagc | aagaacaccg | cctacctgca | gatgaacagc | 720 |
| ctgagagccg | aggacaccgc | cgtgtactac | tgcagcagat | ggggcggcga | cggcttctac | 780 |
| gccatggact | actggggcca | gggcaccctg | gtgaccgtga | gcagcgcggc | cgcgctgagc | 840 |
| aacagcatca | tgtacttcag | ccacttcgtg | cctgtgttcc | tgcctgccaa | gcctacaaca | 900 |
| acaccagccc | ctagacctcc | aaccctgcc | cctacaattg | cctctcagcc | tctgtctctg | 960 |
| aggcccgaag | cttgtagacc | tgctgctggc | ggagctgtgc | acaccagagg | actggatttc | 1020 |
| gcctgctttt | gggtgctggt | ggtcgtgggc | ggagtgctgg | cttgttattc | tctgctggtc | 1080 |
| accgtggcct | tcatcatctt | ttgggtccga | ctgaagatcc | aggtccgaaa | ggccgccatc | 1140 |
| accagctacg | agaagtctga | tggcgtgtac | accggcctga | gcaccagaaa | ccaggaaacc | 1200 |
| tacgagacac | tgaagcacga | gaagcccccc | cag | | | 1233 |

<210> SEQ ID NO 38
<211> LENGTH: 1230
<212> TYPE: DNA
<213> ORGANISM: Artificial Sequence
<220> FEATURE:
<223> OTHER INFORMATION: artificial sequence

<400> SEQUENCE: 38

| | | | | | |
|---|---|---|---|---|---|
| atggactgga | tctggcggat | tctgtttctc | gtgggagctg | ccacaggcgc | tcattctgct | 60 |
| cagcctgccg | atatccaaat | gactcaatct | cctagttcac | tgtcagcctc | tgttggtgat | 120 |
| cgcgtgacca | ttacctgcca | agctagccag | gatattagca | actacttgaa | ctggtatcag | 180 |
| cagaagcctg | gcaaagcccc | aaagctgttg | atctacgatg | taagtaactt | ggaaactggc | 240 |
| gtcccaagcc | gcttctctgg | atctggttca | ggcaccgact | tcactttcac | tatcagcagc | 300 |
| ctgcagcctg | aagatatcgc | aacctactat | tgccagcagg | ttgctaatgt | tcctctgact | 360 |
| ttcggccaag | gcaccaaggt | ggagatcaag | ggcggcggag | gaagcggagg | cggaggatct | 420 |
| ggggcggag | gctctggcgg | aggggatct | gaagttcagc | ttgtagaatc | tggaggtgga | 480 |
| ttggttcaac | tggtggctc | tcttcgcctg | agttgtgcag | cctctggttt | tactttctct | 540 |

```
agttactgga tgcattgggt tcgtcaggct cctgggaaag gcctggaatg ggtttcagct    600
attagttgga gtggagatag tacttactac gcagacagtg tgaaaggtcg cttcaccatc    660
agccgtgata attctaagaa cactttgtac ctgcaaatga actccttgcg cgcagaagac    720
acggctgtgt actattgtgc ccgtgatcgc tctgcgactt ggtattatct ggggcttggt    780
ttcgatgtat ggggacaagg taccctggta acggtttcta gcgcggccgc gctgagcaac    840
agcatcatgt acttcagcca cttcgtgcct gtgttcctgc ctgccaagcc tacaacaaca    900
ccagccccta gacctccaac ccctgcccct acaattgcct ctcagcctct gtctctgagg    960
cccgaagctt gtagacctgc tgctggcgga gctgtgcaca ccagaggact ggatttcgcc   1020
tgcttttggg tgctggtggt cgtgggcgga gtgctggctt gttattctct gctggtcacc   1080
gtggccttca tcatcttttg ggtccgactg aagatccagg tccgaaaggc cgccatcacc   1140
agctacgaga agtctgatgg cgtgtacacc ggcctgagca ccagaaacca ggaaacctac   1200
gagacactga agcacgagaa gccccccag                                     1230

<210> SEQ ID NO 39
<211> LENGTH: 1215
<212> TYPE: DNA
<213> ORGANISM: Artificial Sequence
<220> FEATURE:
<223> OTHER INFORMATION: artificial sequence

<400> SEQUENCE: 39
atggactgga tctggcggat tctgtttctc gtgggagctg ccacaggcgc tcattctgct    60
cagcctgccg atattcttct tactcaatct cccgttattt tgtcagtatc cccaggtgag   120
cgagtcagct tctcttgtcg agcgtcacaa tccattggca ccaacataca ttggtaccaa   180
cagcgcacca acgggtctcc ccggctcttg attaagtacg catcagaaag tatttctggg   240
atacccagta ggttctcagg gagcgggagt ggcactgact ttaccctgtc cataaacagc   300
gttgagtctg aggacatcgc ggactactat tgtcagcaga caacaattg gccgaccacg   360 tttggtgcgg gaacaaaact tgaactcaaa ggcggcggag gaagcggagg cggaggatct   420
gggggcggag gctctggcgg aggggatct caggtgcagc tcaaacagtc aggacctggc   480
ctcgttcagc caagccaatc actgagtata acgtgcacgg tgagcggctt tagcctgaca   540
aactatggtg tccactgggt ccgccaatct cctggaaaag cttggagtg gctcggtgtt   600 atctggtccg gtggtaacac agactacaac acgccattca ccagtcgcct tagtattaac   660
aaggacaact ccaagtctca ggtttttctt aaaatgaact ctctgcagtc taatgatacc   720
gcaatttact actgtgcgag ggcactcacg tactatgact atgagttcgc gtattggggc   780
caagggactc tcgttactgt ctcagcggcg gccgcgctga gcaacagcat catgtacttc   840
agccacttcg tgcctgtgtt cctgcctgcc aagcctacaa caacaccagc cctagacct    900 ccaacccctg cccctacaat tgcctctcag cctctgtctc tgaggcccga agcttgtaga   960
cctgctgctg gcggagctgt gcacaccaga ggactggatt tcgcctgctt ttgggtgctg   1020
gtggtcgtgg gcggagtgct ggcttgttat tctctgctgg tcaccgtggc cttcatcatc   1080
ttttgggtcc gactgaagat ccaggtccga aaggccgcca tcaccagcta cgagaagtct   1140
gatggcgtgt acaccggcct gagcaccaga aaccaggaaa cctacgagac actgaagcac   1200
gagaagcccc ccag                                                     1215

<210> SEQ ID NO 40
```

<211> LENGTH: 1230
<212> TYPE: DNA
<213> ORGANISM: Artificial Sequence
<220> FEATURE:
<223> OTHER INFORMATION: artificial sequence

<400> SEQUENCE: 40

| | | | | | |
|---|---|---|---|---|---|
| atggactgga | tctggcggat | tctgtttctc | gtgggagctg | ccacaggcgc | tcattctgct | 60 |
| cagcctgccg | atgttgtaat | gacgcagtca | cccctgtcac | tcccggtcac | acccggagaa | 120 |
| ccagcgtcaa | ttagctgccg | atctagccaa | agtttgcttc | attccaatgg | ttacaattat | 180 |
| ctcgactggt | acttgcagaa | acccggccaa | tcccctcagc | tgctcatcta | ccttgggtct | 240 |
| aatagggcat | ctggggttcc | cgataggttc | tctggctccg | ggagcggcac | cgactttacg | 300 |
| ttgaaaatct | ctaggggttga | ggcggaagac | gtaggcgttt | actattgcat | gcaggggacc | 360 |
| cactggccgc | tgaccttcgg | ccagggcacc | aaggttgaaa | taaaaggcgg | cggaggaagc | 420 |
| ggaggcggag | gatctggggg | cggaggctct | ggcggagggg | gatctcaggt | acagctccag | 480 |
| gaatcaggac | ccggtttggt | taagccctcc | gggaccctt | ccctcacgtg | tgcagtctca | 540 |
| ggtgggtcaa | ttagttcttc | caattggtgg | tcttgggtgc | ggcaaccacc | tggtaaaggt | 600 |
| ctcgagtgga | taggggaaat | ttatcatagt | ggctccacca | attataaccc | ctcactcaag | 660 |
| tccagggtta | cgatatctgt | ggacaaaagt | aaaaaccaat | tctccctcaa | acttagtagt | 720 |
| gtaacagcgg | cagacaccgc | ggtgtactac | tgcgcacggt | ggacaggccg | aactgatgcc | 780 |
| tttgacattt | ggggacaggg | aactatggtg | actgtgtcat | ccgcggccgc | gctgagcaac | 840 |
| agcatcatgt | acttcagcca | cttcgtgcct | gtgttcctgc | ctgccaagcc | tacaacaaca | 900 |
| ccagccccta | gacctccaac | ccctgcccct | acaattgcct | ctcagcctct | gtctctgagg | 960 |
| cccgaagctt | gtagacctgc | tgctggcgga | gctgtgcaca | ccagaggact | ggatttcgcc | 1020 |
| tgcttttggg | tgctggtggt | cgtgggcgga | gtgctggctt | gttattctct | gctggtcacc | 1080 |
| gtggccttca | tcatcttttg | ggtccgactg | aagatccagg | tccgaaaggc | cgccatcacc | 1140 |
| agctacgaga | agtctgatgg | cgtgtacacc | ggcctgagca | ccagaaacca | ggaaacctac | 1200 |
| gagacactga | agcacgagaa | gccccccag | | | | 1230 |

<210> SEQ ID NO 41
<211> LENGTH: 1203
<212> TYPE: DNA
<213> ORGANISM: Artificial Sequence
<220> FEATURE:
<223> OTHER INFORMATION: artificial sequence

<400> SEQUENCE: 41

| | | | | | |
|---|---|---|---|---|---|
| atggactgga | tctggcgcat | cctcttcctc | gtcggcgctg | ctaccggcgc | tcattcggcc | 60 |
| cagccggccg | acattcaaat | gactcagtcc | ccttccagct | tgtcagcctc | agtaggggac | 120 |
| cgggtcacga | tcacctgtcg | agcgtctgag | tcagtggata | actacgggat | ttctttcatg | 180 |
| aactggttcc | agcagaagcc | cggcaaagct | cctaagctcc | ttatatatgc | agcctcaaat | 240 |
| caggggagcg | gtgttcctag | tcgcttcagt | ggaagcggta | gcggtacgga | ctttacgttg | 300 |
| acgataagta | gccttcagcc | agatgacttt | gccacttatt | attgtcagca | gtctaaggaa | 360 |
| gttccttgga | cgtttggcca | aggaacgaag | gtcgaaatca | aaggggagg | gggctcagga | 420 |
| gggggcggca | gtgtggtggt | ggaggctctcaa | gtccaactcg | tacagtctgg | cgcggaggtt | 480 |
| aaaaagccgg | gaagctccgt | gaaagtatcc | tgtaaggcaa | gcggatacac | ctttaccgat | 540 |
| tataacatgc | actgggttag | gcaggcgccc | ggccaaggtc | tggaatggat | cggttatatt | 600 |

```
tatccataca acggtggtac cggctataat cagaagttta agagtaaggc tactattaca      660
gcggatgagt caaccaatac tgcatacatg gagctctcct cactcaggag cgaagatacc      720
gcagtgtatt actgtgcccg agggagacca gccatggact actggggtca gggtacccct      780
t gtgacagtat ctagcgcggc cgcgctgagc aacagcatca tgtacttcag ccacttcgtg      840
cctgtgttcc tgcctgccaa gcctacaaca caccagccc ctagacctcc aaccctgcc       900 cctacaattg cctctcagcc tctgtctctg aggcccgaag cttgtagacc tgctgctggc      960
ggagctgtgc acaccagagg actggatttc gcctgctttt gggtgctggt ggtcgtgggc     1020
ggagtgctgg cttgttattc tctgctggtc accgtggcct tcatcatctt tgggtccga     1080 ctgaagatcc aggtccgaaa ggccgccatc accagctacg agaagtctga tggcgtgtac     1140
accggcctga gcaccagaaa ccaggaaacc tacgagacac tgaagcacga gaagcccccc     1200
cag                                                                    1203

<210> SEQ ID NO 42
<211> LENGTH: 1215
<212> TYPE: DNA
<213> ORGANISM: Artificial Sequence
<220> FEATURE:
<223> OTHER INFORMATION: artificial sequence

<400> SEQUENCE: 42
atggactgga tctggcggat tctgtttctc gtgggagctg ccacaggcgc tcattctgct       60
cagcctgcca acatccagat gacccagtct ccatcttctg tgtctgcatc tgtaggagac      120
agagtcacca tcacttgtcg ggcgagtcag gatattagcc gctggttagc ctggtatcag      180
cagaaaccag ggaaagcccc taaactcctg atctatgctg catccagttt gcaaagtggg      240
gtcccatcga ggttcagcgg cagtggatct gggacagatt tcgctctcac tatcagcagc      300
ctgcagcctg aagattttgc aacttactat tgtcaacagg ctgacagtcg tttctcgatc      360
accttcggcc aagggacacg actggagatt aaaggcggcg gaggaagcgg aggcggagga      420 tctggggcg gaggctctgg cggagggga tctgaggtgc agctggtgca gtctggggga       480
ggcttggtac agcctggggg gtccctgaga ctctcctgtg cagcctctgg attcaccttc      540
agtagctata gcatgaactg ggtccgccag gctccaggga aggggctgga gtgggtttca     600
tacattagta gtagtagtag taccatacag tacgcagact ctgtgaaggg ccgattcacc     660
atctccagag acaatgccaa gaactcactg tatctgcaaa tgaacagcct gagagacgag     720
gacacggctg tgtattactg tgcgagaggg gactactact acggtatgga cgtctggggc     780
caagggacca cggtcaccgt gagctcagcg gccgcgctga gcaacagcat catgtacttc      840
agccacttcg tgcctgtgtt cctgcctgcc aagcctacaa caccagcc cctagacct       900 ccaaccctg cccctacaat tgcctctcag cctctgtctc tgaggcccga agcttgtaga      960
cctgctgctg gcggagctgt gcacaccaga ggactggatt tcgcctgctt ttgggtgctg    1020
gtggtcgtgg gcggagtgct ggcttgttat tctctgctgg tcaccgtggc cttcatcatc     1080
ttttgggtcc gactgaagat ccaggtccga aaggccgcca tcaccagcta cgagaagtct    1140
gatggcgtgt acaccggcct gagcaccaga accaggaaa cctacgagac actgaagcac    1200
gagaagcccc cccag                                                      1215

<210> SEQ ID NO 43
<211> LENGTH: 1203
<212> TYPE: DNA
```

<213> ORGANISM: Artificial Sequence
<220> FEATURE:
<223> OTHER INFORMATION: artificial sequence

<400> SEQUENCE: 43

```
atggactgga tctggcgcat cctcttcctc gtcggcgctg ctaccggcgc tcattcggcc      60
cagccggccg acattcaaat gactcagtcc ccttccagct tgtcagcctc agtagggac     120
cgggtcacga tcacctgtcg agcgtctgag tcagtggata actacgggat ttctttcatg    180
aactggttcc agcagaagcc cggcaaagct cctaagctcc ttatatatgc agcctcaaat    240
caggggagcg gtgttcctag tcgcttcagt ggaagcggta gcggtacgga ctttacgttg    300
acgataagta gccttcagcc agatgacttt gccacttatt attgtcagca gtctaaggaa    360
gttccttgga cgtttggcca aggaacgaag gtcgaaatca aaggggagg gggctcagga    420
ggggcggca gtggtggtgg aggctctcaa gtccaactcg tacagtctgg cgcggaggtt    480
aaaaagccgg gaagctccgt gaaagtatcc tgtaaggcaa gcggatacac ctttaccgat    540
tataacatgc actgggttag gcaggcgccc ggccaaggtc tggaatggat cggttatatt    600
tatccataca cgtggtac cggctataat cagaagttta agagtaaggc tactattaca    660
gcggatgagt caaccaatac tgcatacatg gagctctcct cactcaggag cgaagatacc    720
gcagtgtatt actgtgcccg agggagacca gccatggact actggggtca gggtacctt    780
gtgacagtat ctagcgcggc cgcgctgagc aacagcatca tgtacttcag ccacttcgtg    840
cctgtgttcc tgcctgccaa gcctacaaca acaccagccc ctagacctcc aacccctgcc    900
cctacaattg cctctcagcc tctgtctctg aggcccgaag cttgtagacc tgctgctggc    960
ggagctgtgc acaccagagg actggatttc gcctgctttt gggtgctggt ggtcgtgggc   1020
ggagtgctgg cttgttattc tctgctggtc accgtggcct tcatcatctt tgggtccga   1080
ctgaagatcc aggtccgaaa ggccgccatc accagctacg agaagtctga tggcgtgtac   1140
accggcctga gcaccagaaa ccaggaaacc tacgagacac tgaagcacga aagcccccc   1200
cag                                                                 1203
```

<210> SEQ ID NO 44
<211> LENGTH: 1596
<212> TYPE: DNA
<213> ORGANISM: Artificial Sequence
<220> FEATURE:
<223> OTHER INFORMATION: artificial sequence

<400> SEQUENCE: 44

```
atgaaccggg gagtcccttt taggcacttg cttctggtgc tgcaactggc gctcctccca     60
gcagccactc agggaaagaa agtggtgctg ggcaaaaaag gggatacagt ggaactgacc    120
tgtacagctt cccagaagaa gagcatacaa ttccactgga aaaactccaa ccagataaag    180
attctgggaa atcagggctc cttcttaact aaaggtccat ccaagctgaa tgatcgcgct    240
gactcaagaa gaagcctttg ggaccaagga aactttcccc tgatcatcaa gaatcttaag    300
atagaagact cagatactta catctgtgaa gtggaggacc agaaggagga ggtgcaattg    360
ctagtgttcg gattgactgc caactctgac acccacctgc ttcaggggca gagcctgacc    420
ctgaccttgg agagcccccc tggtagtagc ccctcagtgc aatgtaggag tccaagggt    480
aaaaacatac aggggggaa gaccctctcc gtgtctcagc tggagctcca ggatagtggc    540
acctggacat gcactgtctt gcagaaccag aagaaggtgg agttcaaaat agacatcgtg    600
gtgctagctt tccagaaggc ctccagcata gtctataaga aagagggga acaggtggag    660
```

```
ttctccttcc cactcgcctt tacagttgaa aagctgacgg gcagtggcga gctgtggtgg    720
caggcggaga gggcttcctc ctccaagtct tggatcacct ttgacctgaa gaacaaggaa    780
gtgtctgtaa acgggttac ccaggaccct aagctccaga tgggcaagaa gctcccgctc    840
cacctcaccc tgcccaggc cttgcctcag tatgctggct ctggaaacct caccctggcc    900
cttgaagcga aaacaggaaa gttgcatcag gaagtgaacc tggtggtgat gagagccact    960
cagctccaga aaaatttgac ctgtgaggtg tggggaccca cctcccctaa gctgatgctg   1020
agtttgaaac tggagaacaa ggaggcaaag gtctcgaagc gggagaaggc ggtgtgggtg   1080
ctgaaccctg aggcggggat gtggcagtgt ctgctgagtg actcgggaca ggtcctgctg   1140
gaatccaaca tcaaggttct gcccacatgg tccaccccgg tgcagccagc ggccgcgctg   1200
agcaacagca tcatgtactt cagccacttc gtgcctgtgt tcctgcctgc caagcctaca   1260
acaacaccag ccctagacc tccaaccct gccctacaa ttgcctctca gcctctgtct   1320
ctgaggcccg aagcttgtag acctgctgct ggcggagctg tgcacaccag aggactggat   1380
ttcgcctgct tttgggtgct ggtggtcgtg gcggagtgc tggcttgtta ttctctgctg   1440
gtcaccgtgg ccttcatcat cttttgggtc cgactgaaga tccaggtccg aaaggccgcc   1500
atcaccagct acgagaagtc tgatggcgtg tacaccggcc tgagcaccag aaaccaggaa   1560
acctacgaga cactgaagca cgagaagccc ccccag                              1596
```

<210> SEQ ID NO 45
<211> LENGTH: 1215
<212> TYPE: DNA
<213> ORGANISM: Artificial Sequence
<220> FEATURE:
<223> OTHER INFORMATION: artificial sequence

<400> SEQUENCE: 45

```
atggactgga tctggcggat tctgtttctc gtgggagctg ccacaggcgc tcattctgct     60
cagcctgccg aagttcagct tgtagaatct ggaggtggat tggttcaacc tggtggctct    120
cttcgcctga gttgtgcagc ctctggtttt acttcaata gttacgctat gcattgggtt    180
cgtcaggctc ctgggaaagg cctggaatgg gtttcagcta ttagtggtaa tggaggtagt    240
actcgttacg cagacagtgt gaaaggtcgc ttcaccatca gccgtgataa ttctaagaac    300
actttgtacc tgcaaatgaa ctccttgcgc gcagaagaca cggctgtgta ctattgtgcc    360
cgtgatcgct ttcggaaggt tcatggtttc gatgtatggg acaaggtac cctggtaacg    420 gtttctagcg gaggtggtgg gagtggtgga ggcggctcgg tgagggtgg ttcaggagga    480 ggcggagata tccaaatgac tcaatctcct agttcactgt cagcctctgt tggtgatcgc    540
gtgaccatta cctgccaagc tagccaggat attagcaact acttgaactg gtatcagcag    600
aagcctggca agcccccaaa gctgttgatc tacgatgcaa gtaacttgga aactggcgtc    660
ccaagccgct ctctggatc tggttcaggc accgacttca ctttcactat cagcagcctg    720
cagcctgaag atatcgcaac ctactattgc cagcaggatg ctacttttcc tttgactttc    780
ggccaaggca ccaaggtgga gatcaaggcg ccgcgctga gcaacagcat catgtacttc    840
agccacttcg tgcctgtgtt cctgcctgcc aagcctacaa caacaccagc cctagacct   900 ccaaccctg ccctacaat tgcctctcag cctctgtctc tgaggcccga agcttgtaga    960
cctgctgctg gcggagctgt gcacaccaga ggactggatt tcgcctgctt tttgggtgctg  1020 gtggtcgtgg gcggagtgct ggcttgttat tctctgctgg tcaccgtggc cttcatcatc  1080
```

| ttttgggtcc gactgaagat ccaggtccga aaggccgcca tcaccagcta cgagaagtct | 1140 |
| gatggcgtgt acaccggcct gagcaccaga accaggaaaa cctacgagac actgaagcac | 1200 |
| gagaagcccc cccag | 1215 |

<210> SEQ ID NO 46
<211> LENGTH: 1194
<212> TYPE: DNA
<213> ORGANISM: Artificial Sequence
<220> FEATURE:
<223> OTHER INFORMATION: artificial sequence

<400> SEQUENCE: 46

| atggactgga tctggcggat tctgtttctc gtgggagctg ccacaggcgc tcattctgct | 60 |
| cagcctgccg tccagctgca gcagtctgga cctgagctgg taaagcctgg ggcttcagtg | 120 |
| aagatgtcct gcaaggcttc tggatacaca ttcactagct atgttatgca ctgggtgaag | 180 |
| cagaagcctg gcagggcct tgagtggatt ggatatatta ttccttacaa tgatgctact | 240 |
| aagtacaatg agaagttcaa aggcaaggcc acactgactt cagacaaatc ctccagcaca | 300 |
| gcctacatgg agctcagcag cctgacctct gaggactctg cggtctatta ctgtgcacgc | 360 |
| tataattacg acgggtactt cgatgtctgg ggcgcaggga ccacggtcac cgtctcctca | 420 |
| ggcggcggag gaagcggagg cggaggatct ggggcggag ctctgacat tgtgatgact | 480 |
| cagtctccag ccaccctgtc tgtgactcca ggagatagag tctctctttc ctgcagggcc | 540 |
| agccagagta ttagcgacta cttacactgg tatcaacaaa aatcacatga gtctccaagg | 600 |
| cttctcatca aatatgcttc caatccatc tctggaatcc cctccaggtt cagtggcagt | 660 |
| ggatcagggt cagatttcac tctcagtatc aacagtgtgg aacctgaaga tgttggagtg | 720 |
| tattactgtc aaaatggtca cagctttcct ccgacgttcg gtggaggcac caagctggaa | 780 |
| atcaaagcgg ccgcgctgag caacagcatc atgtacttca gccacttcgt gcctgtgttc | 840 |
| ctgcctgcca agcctacaac aacaccagcc cctagacctc caaccctgc ccctacaatt | 900 |
| gcctctcagc ctctgtctct gaggcccgaa gcttgtagac ctgctgctgg cggagctgtg | 960 |
| cacaccagag gactggattt cgcctgcttt tgggtgctgg tggtcgtggg cggagtgctg | 1020 |
| gcttgttatt ctctgctggt caccgtggcc ttcatcatct ttggtccga ctgaagatc | 1080 |
| caggtccgaa aggccgccat caccagctac gagaagtctg atggcgtgta caccggcctg | 1140 |
| agcaccagaa accaggaaac ctacgagaca ctgaagcacg agaagccccc ccag | 1194 |

<210> SEQ ID NO 47
<211> LENGTH: 1206
<212> TYPE: DNA
<213> ORGANISM: Artificial Sequence
<220> FEATURE:
<223> OTHER INFORMATION: artificial sequence

<400> SEQUENCE: 47

| atggactgga tctggcggat tctgtttctc gtgggagctg ccacaggcgc tcattctgct | 60 |
| cagcctgccc aggtgcaagt gaaagagtct ggccctggac tggtggcccc aagccagtct | 120 |
| ctgagcatca catgtaccgt gtccggcttc agcctgacca actatggcgt gcactgggtc | 180 |
| cgacagcctc caggcaaagg actggaatgg ctgggagtga tttggctgg cggcagcacc | 240 |
| aactacaaca gcccctgat gagcggctg agcatctcca aggacaacag caagagccag | 300 |
| gtgttcctga gatgaacag cctgcagacc gacgacaccg ccatgtacta ctgtgctagc | 360 |
| agaggcggca actacggcta cgccctggat tattggggcc agggcacaag cgtgaccgtg | 420 |

```
tcatctggcg gcggaggaag cggaggcgga ggatctgggg gcggaggctc tggcggaggg      480
ggatctagca tcgtgatgac ccagactcct aagttcctgc tggtgtctgc cggcgacaga      540
gtgaccatca cctgtaaagc cagccagagc gtgtccaacg acgtggcctg gtatcagcag      600
aagcctggac agagccccaa gctgctgatc tacagcgcca gcaacagata caccggcgtg      660
cccgatagat tcaccggctc tggctacggc accgacttca cctttaccat cagcaccgtg      720
caggccgagg atctggccgt gtacttctgc cagcaagact acagctctct cggcggaggc      780
accaagctgg aaatcaaagc ggccgcgctg agcaacagca tcatgtactt cagccacttc      840
gtgcctgtgt tcctgcctgc caagcctaca acaacaccag cccctagacc tccaacccct      900
gcccctacaa ttgcctctca gcctctgtct ctgaggcccg aagcttgtag acctgctgct      960
ggcggagctg tgcacaccag aggactggat ttcgcctgct tttgggtgct ggtggtcgtg      1020
ggcggagtgc tggcttgtta ttctctgctg gtcaccgtgg ccttcatcat cttttgggtc      1080
cgactgaaga tccaggtccg aaaggccgcc atcaccagct acgagaagtc tgatggcgtg      1140
tacaccggcc tgagcaccag aaaccaggaa acctacgaga cactgaagca cgagaagccc      1200
ccccag                                                                 1206

<210> SEQ ID NO 48
<211> LENGTH: 1248
<212> TYPE: DNA
<213> ORGANISM: Artificial Sequence
<220> FEATURE:
<223> OTHER INFORMATION: artificial sequence

<400> SEQUENCE: 48
atggactgga tctggcggat tctgtttctc gtgggagctg ccacaggcgc tcattctgct       60
cagcctgccc aggttcagct gcagcagtct ggacctgagc tggttaagcc tggcgcctcc      120
gtgaagatga gctgcaagac cagccggtac accttcaccg agtacaccat ccactgggtc      180
cgacagagcc acggcaagag cctggaatgg atcggcggca tcaaccccaa caacggcatc      240
cccaactaca ccagaagtt caagggcaga gccacactga ccgtgggcaa gtctagcagc      300
accgcctaca tggaactgcg gagcctgaca agcgaggaca cgccgtgta cttctgcgcc      360 agaagaagaa tcgcctacgg ctacgatgag ggccacgcca tggattattg gggccaggga      420
acaagcgtga ccgtgtctag tggcggcgga ggaagcggag cggaggatc tggggcgga       480 ggctctggcg gagggatc tgacatcgtg atgacacaga gcccttctag cctggccgtg      540
tccgtgggag agaaagtgac catgagctgc aagagcagcc agagcctgct gtactcccgg      600
aaccagaaga actacctggc ctggttccag cagaagcccg gccagtctcc taagctgctg      660
atcttctggg ccagcaccag agaaagcggc gtgcccgata gattcaccgg cagcggcttt      720
ggcaccgact tcaacctgac aatcagcagc gtgcaggccg aggacctggc tgtgtacgat      780
tgccagcagt acttcagcta ccctctgacc tttggagccg gcaccaagct ggaactgaga      840
gcggccgcgc tgagcaacag catcatgtac ttcagccact cgtgcctgt gttcctgcct      900 gccaagccta caacaacacc agcccctaga cctccaaccc ctgcccctac aattgcctct      960
cagcctctgt ctctgaggcc cgaagcttgt agacctgctg ctggcggagc tgtgcacacc     1020
agaggactga atttcgcctg cttttgggtg ctggtggtcg tgggcggagt gctggcttgt     1080
tattctctgc tggtcaccgt ggccttcatc atcttttggg tccgactgaa gatccaggtc     1140
```

```
cgaaaggccg ccatcaccag ctacgagaag tctgatggcg tgtacaccgg cctgagcacc    1200
agaaaccagg aaacctacga gacactgaag cacgagaagc cccccag                  1248

<210> SEQ ID NO 49
<211> LENGTH: 510
<212> TYPE: DNA
<213> ORGANISM: Artificial Sequence
<220> FEATURE:
<223> OTHER INFORMATION: artificial sequence

<400> SEQUENCE: 49
atgcgcatca gcaagcccca cctgcgcagc atcagcatcc agtgctacct gtgcctgctg      60
ctgaacagcc acttcctgac cgaggccggc atccacgtgt tcatcctggg ctgcttcagc     120
gccggcctgc ccaagaccga ggccaactgg gtgaacgtga tcagcgacct gaagaagatc     180
gaggacctga tccagagcat gcacatcgac gccaccctgt acaccgagag cgacgtgcac     240
cccagctgca aggtgaccgc catgaagtgc ttcctgctgg agctgcaggt gatcagcctg     300
gagagcggcg acgccagcat ccacgacacc gtggagaacc tgatcatcct ggccaacaac     360
agcctgagca gcaacggcaa cgtgaccgag agcggctgca aggagtgcga ggagctggag     420
gagaagaaca tcaaggagtt cctgcagagc ttcgtgcaca tcgtgcagat gttcatcaac     480
accagcggct ccgagaagga cgagctgtaa                                      510

<210> SEQ ID NO 50
<211> LENGTH: 169
<212> TYPE: PRT
<213> ORGANISM: Artificial Sequence
<220> FEATURE:
<223> OTHER INFORMATION: artificial sequence

<400> SEQUENCE: 50

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser Gly Ser Glu Lys Asp Glu Leu
                165

<210> SEQ ID NO 51
<211> LENGTH: 1215
```

<212> TYPE: DNA
<213> ORGANISM: Artificial Sequence
<220> FEATURE:
<223> OTHER INFORMATION: artificial sequence

<400> SEQUENCE: 51

```
atggactgga tctggcgcat cctcttcctc gtcggcgctg ctaccggcgc tcattcggcc     60
cagccggcca tggcgcaagt aaaactccaa gaatctgggg cggagctggt gaaaccgggg    120
gcgtctgtga agatgagctg taaagcatca ggctacacct tcacctccta taatatgcac    180
tgggtgaaac aaacacccgg acagggcctc gaatggattg gtgccatcta tcctggaaat    240
ggtgatacct catataatca gaagtttaag ggcaaggcta cgcttactgc ggataaaagc    300
tcttccactg cttacatgca actgagcagt ctcacttcag aggactcagc cgattattat    360
tgtgcccgca gcaactacta tggtagttca tactggtttt tcgacgtttg ggggcaaggt    420
accaccgtca cggtttcttc tggtgggggc ggaagcgggg gtggaggatc tgggggcggt    480
ggttcagaca ttgaactcac ccagagccct actattctga gcgcgtctcc aggtgaaaaa    540
gttacgatga cgtgcagagc atcaagtagt gtgaattata tggattggta tcaaaagaag    600
ccaggctcat ccccaaaacc gtggatctat gcaactagca acctcgcgtc aggggtgcca    660
gcaaggtttt ccggaagtgg ttctggcaca tcttatagtc tcaccatttc ccgagtggag    720
gctgaggatg cggccactta ttactgccag caatggtcat tcaatccccc aacatttggt    780
ggcggaacaa aactcgaaat taaacgggcg ccgcgctga gcaacagcat catgtacttc    840
agccacttcg tgcctgtgtt cctgcctgcc aagcctacaa caacaccagc ccctagacct    900
ccaaccectg ccctacaat tgcctctcag cctctgtctc tgaggcccga agcttgtaga    960
cctgctgctg gcggagctgt gcacaccaga ggactggatt tcgcctgctt ttgggtgctg   1020
gtggtcgtgg gcggagtgct ggcttgttat tctctgctgg tcaccgtggc cttcatcatc   1080
ttttgggtcc gactgaagat ccaggtccga aaggccgcca tcaccagcta cgagaagtct   1140
gatggcgtgt acaccggcct gagcaccaga aaccaggaaa cctacgagac actgaagcac   1200
gagaagcccc cccag                                                    1215
```

<210> SEQ ID NO 52
<211> LENGTH: 1248
<212> TYPE: DNA
<213> ORGANISM: Artificial Sequence
<220> FEATURE:
<223> OTHER INFORMATION: artificial sequence

<400> SEQUENCE: 52

```
atggactgga tctggcgcat cctcttcctc gtcggcgctg ctaccggcgc tcattcggcc     60
cagccggccg atatcgagct cacccaatct ccaaaattca tgtccacatc agtaggagac    120
agggtcagcg tcacctgcaa ggccagtcag aatgtggata ctaatgtagc gtggtatcaa    180
caaaaaccag gcaatctcc tgaaccactg cttttctcgg catcctaccg ttacactgga    240
gtccctgatc gcttcacagg cagtggatct gggacagatt tcactctcac catcagcaat    300
gtgcagtctg aagacttggc agagtatttc tgtcagcaat ataacagcta tcctctgacg    360
ttcggtggcg gcaccaagct ggaaatcaaa cgggctgccg cagaaggtgg aggcggttca    420
ggtggcggag gttccggcgg aggtggctct ggcggtggcg gatcggccat ggcccaggtg    480
aagctgcagc agtcaggagg gggcttggtg caacctggag ctccatgaa actctcctgt    540
gttgtctctg gattcacttt cagtaattac tggatgaact gggtccgcca gtctccagag    600
```

| | | | | |
|---|---|---|---|---|
| aaggggcttg | agtggattgc | agaaattaga | ttgaaatcca | ataattttgg | aagatattat | 660 |
| gcggagtctg | tgaaagggag | gttcaccatc | tcaagagatg | attccaaaag | tagtgcctac | 720 |
| ctgcaaatga | tcaacctaag | agctgaagat | actggcattt | attactgtac | cagttatggt | 780 |
| aactacgttg | ggcactattt | tgaccactgg | ggccaaggga | ccacggtcac | cgtatcgagt | 840 |
| gcggccgcgc | tgagcaacag | catcatgtac | ttcagccact | tcgtgcctgt | gttcctgcct | 900 |
| gccaagccta | caacaacacc | agcccctaga | cctccaaccc | ctgcccctac | aattgcctct | 960 |
| cagcctctgt | ctctgaggcc | cgaagcttgt | agacctgctg | ctggcggagc | tgtgcacacc | 1020 |
| agaggactgg | atttcgcctg | cttttgggtg | ctggtggtcg | tgggcggagt | gctggcttgt | 1080 |
| tattctctgc | tggtcaccgt | ggccttcatc | atcttttggg | tccgactgaa | gatccaggtc | 1140 |
| cgaaaggccg | ccatcaccag | ctacgagaag | tctgatggcg | tgtacaccgg | cctgagcacc | 1200 |
| agaaaccagg | aaacctacga | gacactgaag | cacgagaagc | ccccccag | | 1248 |

<210> SEQ ID NO 53
<211> LENGTH: 6787
<212> TYPE: DNA
<213> ORGANISM: Artificial Sequence
<220> FEATURE:
<223> OTHER INFORMATION: artificial sequence

<400> SEQUENCE: 53

| | | | | | | |
|---|---|---|---|---|---|---|
| tgtatttaga | aaaataaaca | aatagggggtt | ccgcgcacat | ttccccgaaa | agtgccacct | 60 |
| gacgtcgacg | gatcgggaga | tctcccgatc | ccctatggtg | cactctcagt | acaatctgct | 120 |
| ctgatgccgc | atagttaagc | cagtatctgc | tccctgcttg | tgtgttggag | gtcgctgagt | 180 |
| agtgcgcgag | caaaatttaa | gctacaacaa | ggcaaggctt | gaccgacaat | tgcatgaaga | 240 |
| atctgcttag | ggttaggcgt | tttgcgctgc | ttcgggatcc | gctgaccaaa | agagcaccaa | 300 |
| aggcgccctg | accttcagcc | cctacctgcg | ctccggtgcc | cgtcagtggg | cagagcgcac | 360 |
| atcgcccaca | gtccccgaga | agttgggggg | agggggtcggc | aattgaaccg | gtgcctagag | 420 |
| aaggtggcgc | ggggtaaact | gggaaagtga | tgtcgtgtac | tggctccgcc | ttttcccga | 480 |
| gggtgggggga | gaaccgtata | taagtgcagt | agtcgccgtg | aacgttcttt | ttcgcaacgg | 540 |
| gtttgccgcc | agaacacagg | taagtgccgt | gtgtggttcc | cgcgggcctg | gcctctttac | 600 |
| gggttatggc | ccttgcgtgc | cttgaattac | ttccacctgg | ctgcagtacg | tgattcttga | 660 |
| tcccgagctt | cgggttggaa | gtgggtggga | gagttcgagg | ccttgcgctt | aaggagcccc | 720 |
| ttcgcctcgt | gcttgagttg | aggcctggcc | tgggcgctgg | ggccgccgcg | tgcgaatctg | 780 |
| gtggcacctt | cgcgcctgtc | tcgctgcttt | cgataagtct | ctagccattt | aaaattttg | 840 |
| atgacctgct | gcgacgcttt | ttttctggca | agatagtctt | gtaaatgcgg | gccaagatct | 900 |
| gcacactggt | atttcggttt | ttggggccgc | gggcggcgac | ggggcccgtg | cgtcccagcg | 960 |
| cacatgttcg | gcgaggcggg | gcctgcgagc | gcggccaccg | agaatcggac | ggggggtagtc | 1020 |
| tcaagctggc | cggcctgctc | tggtgcctgg | cctcgcgccg | ccgtgtatcg | ccccgccctg | 1080 |
| ggcggcaagg | ctggcccggt | cggcaccagt | tgcgtgagcg | gaaagatggc | cgcttcccgg | 1140 |
| ccctgctgca | gggagctcaa | aatggaggac | gcggcgctcg | ggagagcggg | cgggtgagtc | 1200 |
| acccacacaa | aggaaaaggg | cctttccgtc | ctcagccgtc | gcttcatgtg | actccacgga | 1260 |
| gtaccgggcg | ccgtccaggc | acctcgatta | gttctcgagc | ttttggagta | cgtcgtcttt | 1320 |
| aggttggggg | gaggggttt | atgcgatgga | gtttccccac | actgagtggg | tggagactga | 1380 |
| agttaggcca | gcttggcact | tgatgtaatt | ctccttggaa | tttgcccttt | ttgagtttgg | 1440 |

| | |
|---|---|
| atcttggttc attctcaagc ctcagacagt ggttcaaagt ttttttcttc catttcaggt | 1500 |
| gtcgtgataa tacgactcac tatagggaga cccaagctgg aattcgccac catggactgg | 1560 |
| atctggcgga ttctgtttct cgtgggagct gccacaggcg ctcattctgc tcagcctgcc | 1620 |
| gatgttgtaa tgacgcagtc acccctgtca ctcccggtca cacccggaga accagcgtca | 1680 |
| attagctgcc gatctagcca aagtttgctt cattccaatg gttacaatta tctcgactgg | 1740 |
| tacttgcaga aacccggcca atcccctcag ctgctcatct accttgggtc taatagggca | 1800 |
| tctggggttc ccgataggtt ctctggctcc gggagcggca ccgactttac gttgaaaatc | 1860 |
| tctaggggttg aggcggaaga cgtaggcgtt tactattgca tgcaggggac ccactggccg | 1920 |
| ctgaccttcg gccagggcac caaggttgaa ataaaaggcg gcggaggaag cggaggcgga | 1980 |
| ggatctgggg gcggaggctc tggcggaggg ggatctcagg tacagctcca ggaatcagga | 2040 |
| cccggtttgg ttaagccctc cgggacccctt tccctcacgt gtgcagtctc aggtgggtca | 2100 |
| attagttctt ccaattggtg gtcttgggtg cggcaaccac ctggtaaagg tctcgagtgg | 2160 |
| atagggaaa tttatcatag tggctccacc aattataacc cctcactcaa gtccagggtt | 2220 |
| acgatatctg tggacaaaag taaaaaccaa ttctccctca aacttagtag tgtaacagcg | 2280 |
| gcagacaccg cggtgtacta ctgcgcacgg tggacaggcc gaactgatgc ctttgacatt | 2340 |
| tggggacagg gaactatggt gactgtgtca tccgcggccg cgctgagcaa cagcatcatg | 2400 |
| tacttcagcc acttcgtgcc tgtgttcctg cctgccaagc ctacaacaac accagcccct | 2460 |
| agacctccaa cccctgcccc tacaattgcc tctcagcctc tgtctctgag gcccgaagct | 2520 |
| tgtagacctg ctgctggcgg agctgtgcac accagaggac tggatttcgc ctgcttttgg | 2580 |
| gtgctggtgg tcgtgggcgg agtgctggct tgttattctc tgctggtcac cgtggccttc | 2640 |
| atcatctttt gggtccgact gaagatccag gtccgaaagg ccgccatcac cagctacgag | 2700 |
| aagtctgatg gcgtgtacac cggcctgagc accagaaacc aggaaaccta cgagacactg | 2760 |
| aagcacgaga agccccccca gggatctgga gctactaact tcagcctgct gaagcaggct | 2820 |
| ggagacgtgg aggagaaccc tggacctatg tggcagctgc tgctgcctac agctctcctg | 2880 |
| ctgctggtgt ccgccggcat gagaaccgag gatctgccta aggccgtggt gttcctggaa | 2940 |
| ccccagtggt acagagtgct ggaaaaggac agcgtgaccc tgaagtgcca gggcgcctac | 3000 |
| agccccgagg acaatagcac ccagtggttc cacaacgaga gcctgatcag cagccaggcc | 3060 |
| agcagctact tcatcgacgc cgccaccgtg gacgacagcg gcgagtatag atgccagacc | 3120 |
| aacctgagca ccctgagcga ccccgtgcag ctggaagtgc acatcggatg gctgctgctg | 3180 |
| caggccccca gatgggtgtt caaagaagag gaccccatcc acctgagatg ccactcttgg | 3240 |
| aagaacaccg ccctgcacaa agtgacctac ctgcagaacg gcaagggcag aaagtacttc | 3300 |
| caccacaaca gcgacttcta catccccaag gccaccctga aggactccgg ctcctacttc | 3360 |
| tgcagaggcc tcgtgggcag caagaacgtg tccagcgaga cagtgaacat caccatcacc | 3420 |
| cagggcctgg ccgtgtctac catcagcagc ttttttccac ccggctacca ggtgtccttc | 3480 |
| tgcctcgtga tggtgctgct gttcgccgtg gacaccggcc tgtacttcag cgtgaaaaca | 3540 |
| aacatcagaa gcagcacccg ggactggaag gaccacaagt caagtggcg gaaggacccc | 3600 |
| caggacaagt gaaattccgc ccctctcccc cccccccctc tccctccccc cccctaacg | 3660 |
| ttactggccg aagccgcttg gaataaggcc ggtgtgcgtt tgtctatatg ttatttccca | 3720 |
| ccatattgcc gtcttttggc aatgtgaggg cccggaaacc tggccctgtc ttcttgacga | 3780 |

```
gcattcctag gggtctttcc cctctcgcca aaggaatgca aggtctgttg aatgtcgtga    3840
aggaagcagt tcctctggaa gcttcttgaa gacaaacaac gtctgtagcg acccttttgca   3900 ggcagcggaa ccccccacct ggcgacaggt gcctctgcgg ccaaaagcca cgtgtataag    3960
atacacctgc aaaggcggca aaccccagt gccacgttgt gagttggata gttgtggaaa     4020
gagtcaaatg gctctcctca agcgtattca acaaggggct gaaggatgcc cagaaggtac    4080
cccattgtat gggatctgat ctggggcctc ggtgcacatg ctttacatgt gtttagtcga    4140
ggttaaaaaa acgtctaggc cccccgaacc acggggacgt ggttttcctt tgaaaaacac    4200
gataaccgcc accatgtacc ggatgcagct gctgagctgt atcgccctgt ctctggccct    4260
cgtgaccaac agcgccccta ccagcagcag caccaagaaa acccagctgc agctggaaca    4320
tctgctgctg gacctgcaga tgatcctgaa cggcatcaac aactacaaga accccaagct    4380
gacccggatg ctgaccttca gttctacat gcccaagaag gccaccgaac tgaaacatct     4440
gcagtgcctg gaagaggaac tgaagcccct ggaagaagtg ctgaacctgg cccagagcaa    4500
gaacttccac ctgaggccca gggacctgat cagcaacatc aacgtgatcg tgctggaact    4560
gaaaggcagc gagacaacct tcatgtgcga gtacgccgac gagacagcta ccatcgtgga    4620
atttctgaac cggtggatca ccttctgcca gagcatcatc agcaccctga ccggctccga    4680
gaaggacgag ctgtgagcgg ccgcccgctg atcagcctcg aacgagattt cgattccacc    4740
gccgccttct atgaaaggtt gggcttcgga atcgttttcc gggacgccgg ctggatgatc    4800
ctccagcgcg gggatctcat gctggagttc ttcgcccacc ccaacttgtt tattgcagct    4860
tataatggtt acaaataaag caatagcatc acaaatttca caaataaagc atttttttca    4920
ctgcattcta gttgtggttt gtccaaactc atcaatgtat cttatcatgt ctgtgcggtg    4980
ggctctatgg cttctgaggc ggaaagaacc agctggggct ctaggggta tccccggatc     5040 ctgagcaaaa ggccagcaaa aggccaggaa ccgtaaaaag gccgcgttgc tggcgttttt    5100
ccataggctc cgccccctg acgagcatca caaaaatcga cgctcaagtc agaggtggcg     5160
aaacccgaca ggactataaa gataccaggc gtttccccct ggaagctccc tcgtgcgctc    5220
tcctgttccg accctgccgc ttaccggata cctgtccgcc tttctccctt cgggaagcgt    5280
ggcgctttct catagctcac gctgtaggta tctcagttcg gtgtaggtcg ttcgctccaa    5340
gctgggctgt gtgcacgaac ccccgttca gcccgaccgc tgcgccttat ccggtaacta    5400
tcgtcttgag tccaacccgg taagacacga cttatcgcca ctggcagcag ccactggtaa    5460
caggattagc agagcgaggt atgtaggcgg tgctacagag ttcttgaagt ggtggcctaa    5520
ctacggctac actagaagaa cagtatttgg tatctgcgct ctgctgaagc cagttacctt    5580
cggaaaaaga gttggtagct cttgatccgg caaacaaacc accgctggta gcggtggttt    5640
ttttgtttgc aagcagcaga ttacgcgcag aaaaaaagga tctcaagaag atcctttgat    5700
cttttctacg gggtctgacg ctcagtggaa cgaaaactca cgttaaggga ttttggtcat    5760
gagattatca aaaaggatct tcacctagat ccttttaaat taaaaatgaa gttttaaatc    5820
aatctaaagt atatatgagt aaacttggtc tgacagttac caatgcttaa tcagtgaggc    5880
acctatctca gcgatctgtc tatttcgttc atccatagtt gcctgactcc ccgtcgtgta    5940
gataactacg atacgggagg gcttaccatc tggccccagt gctgcaatga taccgcgaga    6000
accacgctca ccggctccag atttatcagc aataaaccag ccagccggaa gggccgagcg    6060
cagaagtggt cctgcaactt tatccgcctc catccagtct attaattgtt gccgggaagc    6120
tagagtaagt agttcgccag ttaatagttt cgcaacgtt gttgccattg ctacaggcat    6180
```

-continued

```
cgtggtgtca cgctcgtcgt ttggtatggc ttcattcagc tccggttccc aacgatcaag    6240
gcgagttaca tgatccccca tgttgtgcaa aaaagcggtt agctccttcg gtcctccgat    6300
cgttgtcaga agtaagttgg ccgcagtgtt atcactcatg gttatggcag cactgcataa    6360
ttctcttact gtcatgccat ccgtaagatg ctttctgtg actggtgagt actcaaccaa     6420
gtcattctga gaatagtgta tgcggcgacc gagttgctct tgcccggcgt caatacggga    6480
taataccgcg ccacatagca gaactttaaa agtgctcatc attggaaaac gttcttcggg    6540
gcgaaaactc tcaaggatct taccgctgtt gagatccagt tcgatgtaac ccactcgtgc    6600
acccaactga tcttcagcat cttttacttt caccagcgtt tctgggtgag caaaaacagg    6660
aaggcaaaat gccgcaaaaa agggaataag ggcgacacgg aaatgttgaa tactcatact    6720 cttcctttt caatattatt gaagcattta tcagggttat tgtctcatga gcggatacat     6780
atttgaa                                                              6787
```

<210> SEQ ID NO 54
<211> LENGTH: 411
<212> TYPE: PRT
<213> ORGANISM: Artificial Sequence
<220> FEATURE:
<223> OTHER INFORMATION: HER2-CAR

<400> SEQUENCE: 54

```
Met Asp Trp Ile Trp Arg Ile Leu Phe Leu Val Gly Ala Ala Thr Gly
 1               5                  10                  15

Ala His Ser Ala Gln Pro Ala Asp Ile Gln Met Thr Gln Ser Pro Ser
             20                  25                  30

Ser Leu Ser Ala Ser Val Gly Asp Arg Val Thr Ile Thr Cys Arg Ala
         35                  40                  45

Ser Gln Asp Val Asn Thr Ala Val Ala Trp Tyr Gln Gln Lys Pro Gly
     50                  55                  60

Lys Ala Pro Lys Leu Leu Ile Tyr Ser Ala Ser Phe Leu Tyr Ser Gly
 65                  70                  75                  80

Val Pro Ser Arg Phe Ser Gly Ser Arg Ser Gly Thr Asp Phe Thr Leu
                 85                  90                  95

Thr Ile Ser Ser Leu Gln Pro Glu Asp Phe Ala Thr Tyr Tyr Cys Gln
            100                 105                 110

Gln His Tyr Thr Thr Pro Pro Thr Phe Gly Gln Gly Thr Lys Val Glu
        115                 120                 125

Ile Lys Ser Ser Gly Gly Gly Ser Gly Gly Gly Ser Gly Gly
    130                 135                 140

Gly Gly Ser Gly Gly Gly Ser Gly Gly Ser Glu Val Gln Leu Val
145                 150                 155                 160

Glu Ser Gly Gly Gly Leu Val Gln Pro Gly Gly Ser Leu Arg Leu Ser
                165                 170                 175

Cys Ala Ala Ser Gly Phe Asn Ile Lys Asp Thr Tyr Ile His Trp Val
            180                 185                 190

Arg Gln Ala Pro Gly Lys Gly Leu Glu Trp Val Ala Arg Ile Tyr Pro
        195                 200                 205

Thr Asn Gly Tyr Thr Arg Tyr Ala Asp Ser Val Lys Gly Arg Phe Thr
    210                 215                 220

Ile Ser Ala Asp Thr Ser Lys Asn Thr Ala Tyr Leu Gln Met Asn Ser
225                 230                 235                 240
```

```
Leu Arg Ala Glu Asp Thr Ala Val Tyr Tyr Cys Ser Arg Trp Gly Gly
                245                 250                 255

Asp Gly Phe Tyr Ala Met Asp Tyr Trp Gly Gln Gly Thr Leu Val Thr
            260                 265                 270

Val Ser Ser Ala Ala Ala Leu Ser Asn Ser Ile Met Tyr Phe Ser His
        275                 280                 285

Phe Val Pro Val Phe Leu Pro Ala Lys Pro Thr Thr Thr Pro Ala Pro
    290                 295                 300

Arg Pro Pro Thr Pro Ala Pro Thr Ile Ala Ser Gln Pro Leu Ser Leu
305                 310                 315                 320

Arg Pro Glu Ala Cys Arg Pro Ala Ala Gly Gly Ala Val His Thr Arg
                325                 330                 335

Gly Leu Asp Phe Ala Cys Phe Trp Val Leu Val Val Gly Gly Val
            340                 345                 350

Leu Ala Cys Tyr Ser Leu Leu Val Thr Val Ala Phe Ile Ile Phe Trp
        355                 360                 365

Val Arg Leu Lys Ile Gln Val Arg Lys Ala Ala Ile Thr Ser Tyr Glu
    370                 375                 380

Lys Ser Asp Gly Val Tyr Thr Gly Leu Ser Thr Arg Asn Gln Glu Thr
385                 390                 395                 400

Tyr Glu Thr Leu Lys His Glu Lys Pro Pro Gln
                405                 410

<210> SEQ ID NO 55
<211> LENGTH: 410
<212> TYPE: PRT
<213> ORGANISM: Artificial Sequence
<220> FEATURE:
<223> OTHER INFORMATION: CD30-CAR

<400> SEQUENCE: 55

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Ser Pro Ser
                20                  25                  30

Ser Leu Ser Ala Ser Val Gly Asp Arg Val Thr Ile Thr Cys Gln Ala
            35                  40                  45

Ser Gln Asp Ile Ser Asn Tyr Leu Asn Trp Tyr Gln Gln Lys Pro Gly
        50                  55                  60

Lys Ala Pro Lys Leu Leu Ile Tyr Asp Val Ser Asn Leu Glu Thr Gly
65                  70                  75                  80

Val Pro Ser Arg Phe Ser Gly Ser Gly Ser Gly Thr Asp Phe Thr Phe
                85                  90                  95

Thr Ile Ser Ser Leu Gln Pro Glu Asp Ile Ala Thr Tyr Tyr Cys Gln
                100                 105                 110

Gln Val Ala Asn Val Pro Leu Thr Phe Gly Gln Gly Thr Lys Val Glu
            115                 120                 125

Ile Lys Gly Gly Gly Gly Ser Gly Gly Gly Gly Ser Gly Gly Gly Gly
        130                 135                 140

Ser Gly Gly Gly Gly Ser Glu Val Gln Leu Val Glu Ser Gly Gly Gly
145                 150                 155                 160

Leu Val Gln Pro Gly Gly Ser Leu Arg Leu Ser Cys Ala Ala Ser Gly
                165                 170                 175

Phe Thr Phe Ser Ser Tyr Trp Met His Trp Val Arg Gln Ala Pro Gly
            180                 185                 190
```

Lys Gly Leu Glu Trp Val Ser Ala Ile Ser Trp Ser Gly Asp Ser Thr
            195                 200                 205

Tyr Tyr Ala Asp Ser Val Lys Gly Arg Phe Thr Ile Ser Arg Asp Asn
    210                 215                 220

Ser Lys Asn Thr Leu Tyr Leu Gln Met Asn Ser Leu Arg Ala Glu Asp
225                 230                 235                 240

Thr Ala Val Tyr Tyr Cys Ala Arg Asp Arg Ser Ala Thr Trp Tyr Tyr
                245                 250                 255

Leu Gly Leu Gly Phe Asp Val Trp Gly Gln Gly Thr Leu Val Thr Val
            260                 265                 270

Ser Ser Ala Ala Ala Leu Ser Asn Ser Ile Met Tyr Phe Ser His Phe
        275                 280                 285

Val Pro Val Phe Leu Pro Ala Lys Pro Thr Thr Thr Pro Ala Pro Arg
    290                 295                 300

Pro Pro Thr Pro Ala Pro Thr Ile Ala Ser Gln Pro Leu Ser Leu Arg
305                 310                 315                 320

Pro Glu Ala Cys Arg Pro Ala Ala Gly Gly Ala Val His Thr Arg Gly
                325                 330                 335

Leu Asp Phe Ala Cys Phe Trp Val Leu Val Val Val Gly Gly Val Leu
            340                 345                 350

Ala Cys Tyr Ser Leu Leu Val Thr Val Ala Phe Ile Ile Phe Trp Val
        355                 360                 365

Arg Leu Lys Ile Gln Val Arg Lys Ala Ala Ile Thr Ser Tyr Glu Lys
    370                 375                 380

Ser Asp Gly Val Tyr Thr Gly Leu Ser Thr Arg Asn Gln Glu Thr Tyr
385                 390                 395                 400

Glu Thr Leu Lys His Glu Lys Pro Pro Gln
                405                 410

<210> SEQ ID NO 56
<211> LENGTH: 405
<212> TYPE: PRT
<213> ORGANISM: Artificial Sequence
<220> FEATURE:
<223> OTHER INFORMATION: EGFR-CAR

<400> SEQUENCE: 56

Met Asp Trp Ile Trp Arg Ile Leu Phe Leu Val Gly Ala Ala Thr Gly
1               5                   10                  15

Ala His Ser Ala Gln Pro Ala Asp Ile Leu Leu Thr Gln Ser Pro Val
            20                  25                  30

Ile Leu Ser Val Ser Pro Gly Glu Arg Val Ser Phe Ser Cys Arg Ala
        35                  40                  45

Ser Gln Ser Ile Gly Thr Asn Ile His Trp Tyr Gln Gln Arg Thr Asn
    50                  55                  60

Gly Ser Pro Arg Leu Leu Ile Lys Tyr Ala Ser Glu Ser Ile Ser Gly
65                  70                  75                  80

Ile Pro Ser Arg Phe Ser Gly Ser Gly Ser Gly Thr Asp Phe Thr Leu
                85                  90                  95

Ser Ile Asn Ser Val Glu Ser Glu Asp Ile Ala Asp Tyr Tyr Cys Gln
            100                 105                 110

Gln Asn Asn Asn Trp Pro Thr Thr Phe Gly Ala Gly Thr Lys Leu Glu
        115                 120                 125

Leu Lys Gly Gly Gly Gly Ser Gly Gly Gly Gly Ser Gly Gly Gly Gly
    130                 135                 140

-continued

Ser Gly Gly Gly Gly Ser Gln Val Gln Leu Lys Gln Ser Gly Pro Gly
145                 150                 155                 160

Leu Val Gln Pro Ser Gln Ser Leu Ser Ile Thr Cys Thr Val Ser Gly
            165                 170                 175

Phe Ser Leu Thr Asn Tyr Gly Val His Trp Val Arg Gln Ser Pro Gly
        180                 185                 190

Lys Gly Leu Glu Trp Leu Gly Val Ile Trp Ser Gly Gly Asn Thr Asp
    195                 200                 205

Tyr Asn Thr Pro Phe Thr Ser Arg Leu Ser Ile Asn Lys Asp Asn Ser
210                 215                 220

Lys Ser Gln Val Phe Phe Lys Met Asn Ser Leu Gln Ser Asn Asp Thr
225                 230                 235                 240

Ala Ile Tyr Tyr Cys Ala Arg Ala Leu Thr Tyr Tyr Asp Tyr Glu Phe
            245                 250                 255

Ala Tyr Trp Gly Gln Gly Thr Leu Val Thr Val Ser Ala Ala Ala Ala
        260                 265                 270

Leu Ser Asn Ser Ile Met Tyr Phe Ser His Phe Val Pro Val Phe Leu
    275                 280                 285

Pro Ala Lys Pro Thr Thr Thr Pro Ala Pro Arg Pro Pro Thr Pro Ala
290                 295                 300

Pro Thr Ile Ala Ser Gln Pro Leu Ser Leu Arg Pro Glu Ala Cys Arg
305                 310                 315                 320

Pro Ala Ala Gly Gly Ala Val His Thr Arg Gly Leu Asp Phe Ala Cys
            325                 330                 335

Phe Trp Val Leu Val Val Val Gly Gly Val Leu Ala Cys Tyr Ser Leu
        340                 345                 350

Leu Val Thr Val Ala Phe Ile Ile Phe Trp Val Arg Leu Lys Ile Gln
    355                 360                 365

Val Arg Lys Ala Ala Ile Thr Ser Tyr Glu Lys Ser Asp Gly Val Tyr
370                 375                 380

Thr Gly Leu Ser Thr Arg Asn Gln Glu Thr Tyr Glu Thr Leu Lys His
385                 390                 395                 400

Glu Lys Pro Pro Gln
            405

<210> SEQ ID NO 57
<211> LENGTH: 410
<212> TYPE: PRT
<213> ORGANISM: Artificial Sequence
<220> FEATURE:
<223> OTHER INFORMATION: IGF1R-CAR

<400> SEQUENCE: 57

Met Asp Trp Ile Trp Arg Ile Leu Phe Leu Val Gly Ala Ala Thr Gly
1               5                   10                  15

Ala His Ser Ala Gln Pro Ala Asp Val Val Met Thr Gln Ser Pro Leu
            20                  25                  30

Ser Leu Pro Val Thr Pro Gly Glu Pro Ala Ser Ile Ser Cys Arg Ser
        35                  40                  45

Ser Gln Ser Leu Leu His Ser Asn Gly Tyr Asn Tyr Leu Asp Trp Tyr
    50                  55                  60

Leu Gln Lys Pro Gly Gln Ser Pro Gln Leu Leu Ile Tyr Leu Gly Ser
65                  70                  75                  80

Asn Arg Ala Ser Gly Val Pro Asp Arg Phe Ser Gly Ser Gly Ser Gly
            85                  90                  95

```
Thr Asp Phe Thr Leu Lys Ile Ser Arg Val Glu Ala Glu Asp Val Gly
                100                 105                 110

Val Tyr Tyr Cys Met Gln Gly Thr His Trp Pro Leu Thr Phe Gly Gln
                115                 120                 125

Gly Thr Lys Val Glu Ile Lys Gly Gly Gly Ser Gly Gly Gly Gly
                130                 135                 140

Ser Gly Gly Gly Gly Ser Gly Gly Gly Gly Ser Gln Val Gln Leu Gln
145                 150                 155                 160

Glu Ser Gly Pro Gly Leu Val Lys Pro Ser Gly Thr Leu Ser Leu Thr
                165                 170                 175

Cys Ala Val Ser Gly Gly Ser Ile Ser Ser Asn Trp Trp Ser Trp
                180                 185                 190

Val Arg Gln Pro Pro Gly Lys Gly Leu Glu Trp Ile Gly Glu Ile Tyr
                195                 200                 205

His Ser Gly Ser Thr Asn Tyr Asn Pro Ser Leu Lys Ser Arg Val Thr
                210                 215                 220

Ile Ser Val Asp Lys Ser Lys Asn Gln Phe Ser Leu Lys Leu Ser Ser
225                 230                 235                 240

Val Thr Ala Ala Asp Thr Ala Val Tyr Tyr Cys Ala Arg Trp Thr Gly
                245                 250                 255

Arg Thr Asp Ala Phe Asp Ile Trp Gly Gln Gly Thr Met Val Thr Val
                260                 265                 270

Ser Ser Ala Ala Ala Leu Ser Asn Ser Ile Met Tyr Phe Ser His Phe
                275                 280                 285

Val Pro Val Phe Leu Pro Ala Lys Pro Thr Thr Thr Pro Ala Pro Arg
                290                 295                 300

Pro Pro Thr Pro Ala Pro Thr Ile Ala Ser Gln Pro Leu Ser Leu Arg
305                 310                 315                 320

Pro Glu Ala Cys Arg Pro Ala Ala Gly Gly Ala Val His Thr Arg Gly
                325                 330                 335

Leu Asp Phe Ala Cys Phe Trp Val Leu Val Val Val Gly Gly Val Leu
                340                 345                 350

Ala Cys Tyr Ser Leu Leu Val Thr Val Ala Phe Ile Ile Phe Trp Val
                355                 360                 365

Arg Leu Lys Ile Gln Val Arg Lys Ala Ala Ile Thr Ser Tyr Glu Lys
                370                 375                 380

Ser Asp Gly Val Tyr Thr Gly Leu Ser Thr Arg Asn Gln Glu Thr Tyr
385                 390                 395                 400

Glu Thr Leu Lys His Glu Lys Pro Pro Gln
                405                 410

<210> SEQ ID NO 58
<211> LENGTH: 401
<212> TYPE: PRT
<213> ORGANISM: Artificial Sequence
<220> FEATURE:
<223> OTHER INFORMATION: CD123-CAR

<400> SEQUENCE: 58

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Ser Pro Ser
                20                  25                  30

Ser Leu Ser Ala Ser Val Gly Asp Arg Val Thr Ile Thr Cys Arg Ala
                35                  40                  45
```

```
Ser Glu Ser Val Asp Asn Tyr Gly Ile Ser Phe Met Asn Trp Phe Gln
 50                  55                  60

Gln Lys Pro Gly Lys Ala Pro Lys Leu Leu Ile Tyr Ala Ala Ser Asn
 65                  70                  75                  80

Gln Gly Ser Gly Val Pro Ser Arg Phe Ser Gly Ser Gly Ser Gly Thr
                 85                  90                  95

Asp Phe Thr Leu Thr Ile Ser Ser Leu Gln Pro Asp Asp Phe Ala Thr
            100                 105                 110

Tyr Tyr Cys Gln Gln Ser Lys Glu Val Pro Trp Thr Phe Gly Gln Gly
        115                 120                 125

Thr Lys Val Glu Ile Lys Gly Gly Gly Ser Gly Gly Gly Gly Ser
    130                 135                 140

Gly Gly Gly Gly Ser Gln Val Gln Leu Val Gln Ser Gly Ala Glu Val
145                 150                 155                 160

Lys Lys Pro Gly Ser Ser Val Lys Val Ser Cys Lys Ala Ser Gly Tyr
                165                 170                 175

Thr Phe Thr Asp Tyr Asn Met His Trp Val Arg Gln Ala Pro Gly Gln
            180                 185                 190

Gly Leu Glu Trp Ile Gly Tyr Ile Tyr Pro Tyr Asn Gly Gly Thr Gly
        195                 200                 205

Tyr Asn Gln Lys Phe Lys Ser Lys Ala Thr Ile Thr Ala Asp Glu Ser
210                 215                 220

Thr Asn Thr Ala Tyr Met Glu Leu Ser Ser Leu Arg Ser Glu Asp Thr
225                 230                 235                 240

Ala Val Tyr Tyr Cys Ala Arg Gly Arg Pro Ala Met Asp Tyr Trp Gly
                245                 250                 255

Gln Gly Thr Leu Val Thr Val Ser Ser Ala Ala Ala Leu Ser Asn Ser
            260                 265                 270

Ile Met Tyr Phe Ser His Phe Val Pro Val Phe Leu Pro Ala Lys Pro
        275                 280                 285

Thr Thr Thr Pro Ala Pro Arg Pro Pro Thr Pro Ala Pro Thr Ile Ala
    290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Phe Ala Cys Asp Phe Trp Val Leu
                325                 330                 335

Val Val Val Gly Gly Val Leu Ala Cys Tyr Ser Leu Leu Val Thr Val
            340                 345                 350

Ala Phe Ile Ile Phe Trp Val Arg Leu Lys Ile Gln Val Arg Lys Ala
        355                 360                 365

Ala Ile Thr Ser Tyr Glu Lys Ser Asp Gly Val Tyr Thr Gly Leu Ser
    370                 375                 380

Thr Arg Asn Gln Glu Thr Tyr Glu Thr Leu Lys His Glu Lys Pro Pro
385                 390                 395                 400

Gln

<210> SEQ ID NO 59
<211> LENGTH: 405
<212> TYPE: PRT
<213> ORGANISM: Artificial Sequence
<220> FEATURE:
<223> OTHER INFORMATION: PD-L1-CAR
```

<400> SEQUENCE: 59

```
Met Asp Trp Ile Trp Arg Ile Leu Phe Leu Val Gly Ala Ala Thr Gly
1               5                   10                  15

Ala His Ser Ala Gln Pro Ala Asn Ile Gln Met Thr Gln Ser Pro Ser
            20                  25                  30

Ser Val Ser Ala Ser Val Gly Asp Arg Val Thr Ile Thr Cys Arg Ala
        35                  40                  45

Ser Gln Asp Ile Ser Arg Trp Leu Ala Trp Tyr Gln Gln Lys Pro Gly
    50                  55                  60

Lys Ala Pro Lys Leu Leu Ile Tyr Ala Ala Ser Ser Leu Gln Ser Gly
65                  70                  75                  80

Val Pro Ser Arg Phe Ser Gly Ser Gly Ser Gly Thr Asp Phe Ala Leu
                85                  90                  95

Thr Ile Ser Ser Leu Gln Pro Glu Asp Phe Ala Thr Tyr Tyr Cys Gln
            100                 105                 110

Gln Ala Asp Ser Arg Phe Ser Ile Thr Phe Gly Gln Gly Thr Arg Leu
        115                 120                 125

Glu Ile Lys Gly Gly Gly Gly Ser Gly Gly Gly Gly Ser Gly Gly Gly
130                 135                 140

Gly Ser Gly Gly Gly Ser Glu Val Gln Leu Val Gln Ser Gly Gly
145                 150                 155                 160

Gly Leu Val Gln Pro Gly Gly Ser Leu Arg Leu Ser Cys Ala Ala Ser
                165                 170                 175

Gly Phe Thr Phe Ser Ser Tyr Ser Met Asn Trp Val Arg Gln Ala Pro
            180                 185                 190

Gly Lys Gly Leu Glu Trp Val Ser Tyr Ile Ser Ser Ser Ser Ser Thr
        195                 200                 205

Ile Gln Tyr Ala Asp Ser Val Lys Gly Arg Phe Thr Ile Ser Arg Asp
    210                 215                 220

Asn Ala Lys Asn Ser Leu Tyr Leu Gln Met Asn Ser Leu Arg Asp Glu
225                 230                 235                 240

Asp Thr Ala Val Tyr Tyr Cys Ala Arg Gly Asp Tyr Tyr Gly Met
                245                 250                 255

Asp Val Trp Gly Gln Gly Thr Thr Val Thr Val Ser Ser Ala Ala Ala
            260                 265                 270

Leu Ser Asn Ser Ile Met Tyr Phe Ser His Phe Val Pro Val Phe Leu
        275                 280                 285

Pro Ala Lys Pro Thr Thr Thr Pro Ala Pro Arg Pro Pro Thr Pro Ala
    290                 295                 300

Pro Thr Ile Ala Ser Gln Pro Leu Ser Leu Arg Pro Glu Ala Cys Arg
305                 310                 315                 320

Pro Ala Ala Gly Gly Ala Val His Thr Arg Gly Leu Asp Phe Ala Cys
                325                 330                 335

Phe Trp Val Leu Val Val Val Gly Gly Val Leu Ala Cys Tyr Ser Leu
            340                 345                 350

Leu Val Thr Val Ala Phe Ile Ile Phe Trp Val Arg Leu Lys Ile Gln
        355                 360                 365

Val Arg Lys Ala Ala Ile Thr Ser Tyr Glu Lys Ser Asp Gly Val Tyr
    370                 375                 380
```

Thr Gly Leu Ser Thr Arg Asn Gln Glu Thr Tyr Glu Thr Leu Lys His
385                 390                 395                 400

Glu Lys Pro Pro Gln
            405

<210> SEQ ID NO 60
<211> LENGTH: 401
<212> TYPE: PRT
<213> ORGANISM: Artificial Sequence
<220> FEATURE:
<223> OTHER INFORMATION: CD33-CAR

<400> SEQUENCE: 60

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Glu Ser Val Asp Asn Tyr Gly Ile Ser Phe Met Asn Trp Phe Gln
    50                  55                  60

Gln Lys Pro Gly Lys Ala Pro Lys Leu Leu Ile Tyr Ala Ala Ser Asn
65                  70                  75                  80

Gln Gly Ser Gly Val Pro Ser Arg Phe Ser Gly Ser Gly Ser Gly Thr
                85                  90                  95

Asp Phe Thr Leu Thr Ile Ser Ser Leu Gln Pro Asp Asp Phe Ala Thr
            100                 105                 110

Tyr Tyr Cys Gln Gln Ser Lys Glu Val Pro Trp Thr Phe Gly Gln Gly
        115                 120                 125

Thr Lys Val Glu Ile Lys Gly Gly Gly Ser Gly Gly Gly Gly Ser
    130                 135                 140

Gly Gly Gly Gly Ser Gln Val Gln Leu Val Gln Ser Gly Ala Glu Val
145                 150                 155                 160

Lys Lys Pro Gly Ser Ser Val Lys Val Ser Cys Lys Ala Ser Gly Tyr
                165                 170                 175

Thr Phe Thr Asp Tyr Asn Met His Trp Val Arg Gln Ala Pro Gly Gln
            180                 185                 190

Gly Leu Glu Trp Ile Gly Tyr Ile Tyr Pro Tyr Asn Gly Gly Thr Gly
        195                 200                 205

Tyr Asn Gln Lys Phe Lys Ser Lys Ala Thr Ile Thr Ala Asp Glu Ser
    210                 215                 220

Thr Asn Thr Ala Tyr Met Glu Leu Ser Ser Leu Arg Ser Glu Asp Thr
225                 230                 235                 240

Ala Val Tyr Tyr Cys Ala Arg Gly Arg Pro Ala Met Asp Tyr Trp Gly
                245                 250                 255

Gln Gly Thr Leu Val Thr Val Ser Ser Ala Ala Ala Leu Ser Asn Ser
            260                 265                 270

Ile Met Tyr Phe Ser His Phe Val Pro Val Phe Leu Pro Ala Lys Pro
        275                 280                 285

Thr Thr Thr Pro Ala Pro Arg Pro Pro Thr Pro Ala Pro Thr Ile Ala
    290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Phe Ala Cys Phe Trp Val Leu
                325                 330                 335

-continued

Val Val Val Gly Gly Val Leu Ala Cys Tyr Ser Leu Leu Val Thr Val
                340                 345                 350

Ala Phe Ile Ile Phe Trp Val Arg Leu Lys Ile Gln Val Arg Lys Ala
                355                 360                 365

Ala Ile Thr Ser Tyr Glu Lys Ser Asp Gly Val Tyr Thr Gly Leu Ser
370                 375                 380

Thr Arg Asn Gln Glu Thr Tyr Glu Thr Leu Lys His Glu Lys Pro Pro
385                 390                 395                 400

Gln

<210> SEQ ID NO 61
<211> LENGTH: 532
<212> TYPE: PRT
<213> ORGANISM: Artificial Sequence
<220> FEATURE:
<223> OTHER INFORMATION: gp120-CAR

<400> SEQUENCE: 61

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
        130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
        210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

```
Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Glu Ser Asn Ile
    370                 375                 380

Lys Val Leu Pro Thr Trp Ser Thr Pro Val Gln Pro Ala Ala Ala Leu
385                 390                 395                 400

Ser Asn Ser Ile Met Tyr Phe Ser His Phe Val Pro Val Phe Leu Pro
                405                 410                 415

Ala Lys Pro Thr Thr Thr Pro Ala Pro Arg Pro Pro Thr Pro Ala Pro
            420                 425                 430

Thr Ile Ala Ser Gln Pro Leu Ser Leu Arg Pro Glu Ala Cys Arg Pro
        435                 440                 445

Ala Ala Gly Gly Ala Val His Thr Arg Gly Leu Asp Phe Ala Cys Phe
    450                 455                 460

Trp Val Leu Val Val Val Gly Gly Val Leu Ala Cys Tyr Ser Leu Leu
465                 470                 475                 480

Val Thr Val Ala Phe Ile Ile Phe Trp Val Arg Leu Lys Ile Gln Val
                485                 490                 495

Arg Lys Ala Ala Ile Thr Ser Tyr Glu Lys Ser Asp Gly Val Tyr Thr
            500                 505                 510

Gly Leu Ser Thr Arg Asn Gln Glu Thr Tyr Glu Thr Leu Lys His Glu
        515                 520                 525

Lys Pro Pro Gln
    530

<210> SEQ ID NO 62
<211> LENGTH: 405
<212> TYPE: PRT
<213> ORGANISM: Artificial Sequence
<220> FEATURE:
<223> OTHER INFORMATION: B7-H4-CAR

<400> SEQUENCE: 62

Met Asp Trp Ile Trp Arg Ile Leu Phe Leu Val Gly Ala Ala Thr Gly
1               5                   10                  15

Ala His Ser Ala Gln Pro Ala Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Thr Phe Asn Ser Tyr Ala Met His Trp Val Arg Gln Ala Pro
    50                  55                  60

Gly Lys Gly Leu Glu Trp Val Ser Ala Ile Ser Gly Asn Gly Gly Ser
65                  70                  75                  80

Thr Arg Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110
```

```
Asp Thr Ala Val Tyr Tyr Cys Ala Arg Asp Arg Phe Arg Lys Val His
            115                 120                 125

Gly Phe Asp Val Trp Gly Gln Gly Thr Leu Val Thr Val Ser Ser Gly
130                 135                 140

Gly Gly Gly Ser Gly Gly Gly Ser Gly Gly Gly Ser Gly Gly
145                 150                 155                 160

Gly Gly Asp Ile Gln Met Thr Gln Ser Pro Ser Ser Leu Ser Ala Ser
                165                 170                 175

Val Gly Asp Arg Val Thr Ile Thr Cys Gln Ala Ser Gln Asp Ile Ser
            180                 185                 190

Asn Tyr Leu Asn Trp Tyr Gln Gln Lys Pro Gly Lys Ala Pro Lys Leu
            195                 200                 205

Leu Ile Tyr Asp Ala Ser Asn Leu Glu Thr Gly Val Pro Ser Arg Phe
210                 215                 220

Ser Gly Ser Gly Ser Gly Thr Asp Phe Thr Phe Thr Ile Ser Ser Leu
225                 230                 235                 240

Gln Pro Glu Asp Ile Ala Thr Tyr Tyr Cys Gln Gln Asp Ala Thr Phe
                245                 250                 255

Pro Leu Thr Phe Gly Gln Gly Thr Lys Val Glu Ile Lys Ala Ala Ala
            260                 265                 270

Leu Ser Asn Ser Ile Met Tyr Phe Ser His Phe Val Pro Val Phe Leu
            275                 280                 285

Pro Ala Lys Pro Thr Thr Thr Pro Ala Pro Arg Pro Pro Thr Pro Ala
290                 295                 300

Pro Thr Ile Ala Ser Gln Pro Leu Ser Leu Arg Pro Glu Ala Cys Arg
305                 310                 315                 320

Pro Ala Ala Gly Gly Ala Val His Thr Arg Gly Leu Asp Phe Ala Cys
                325                 330                 335

Phe Trp Val Leu Val Val Val Gly Gly Val Leu Ala Cys Tyr Ser Leu
            340                 345                 350

Leu Val Thr Val Ala Phe Ile Ile Phe Trp Val Arg Leu Lys Ile Gln
            355                 360                 365

Val Arg Lys Ala Ala Ile Thr Ser Tyr Glu Lys Ser Asp Gly Val Tyr
370                 375                 380

Thr Gly Leu Ser Thr Arg Asn Gln Glu Thr Tyr Glu Thr Leu Lys His
385                 390                 395                 400

Glu Lys Pro Pro Gln
                405

<210> SEQ ID NO 63
<211> LENGTH: 398
<212> TYPE: PRT
<213> ORGANISM: Artificial Sequence
<220> FEATURE:
<223> OTHER INFORMATION: BCMA-CAR

<400> SEQUENCE: 63

Met Asp Trp Ile Trp Arg Ile Leu Phe Leu Val Gly Ala Ala Thr Gly
1               5                   10                  15

Ala His Ser Ala Gln Pro Ala Val Gln Leu Gln Gln Ser Gly Pro Glu
                20                  25                  30

Leu Val Lys Pro Gly Ala Ser Val Lys Met Ser Cys Lys Ala Ser Gly
            35                  40                  45

Tyr Thr Phe Thr Ser Tyr Val Met His Trp Val Lys Gln Lys Pro Gly
        50                  55                  60
```

```
Gln Gly Leu Glu Trp Ile Gly Tyr Ile Ile Pro Tyr Asn Asp Ala Thr
 65                  70                  75                  80
Lys Tyr Asn Glu Lys Phe Lys Gly Lys Ala Thr Leu Thr Ser Asp Lys
                 85                  90                  95
Ser Ser Ser Thr Ala Tyr Met Glu Leu Ser Ser Leu Thr Ser Glu Asp
            100                 105                 110
Ser Ala Val Tyr Tyr Cys Ala Arg Tyr Asn Tyr Asp Gly Tyr Phe Asp
            115                 120                 125
Val Trp Gly Ala Gly Thr Thr Val Thr Val Ser Ser Gly Gly Gly Gly
    130                 135                 140
Ser Gly Gly Gly Gly Ser Gly Gly Gly Gly Ser Asp Ile Val Met Thr
145                 150                 155                 160
Gln Ser Pro Ala Thr Leu Ser Val Thr Pro Gly Asp Arg Val Ser Leu
                165                 170                 175
Ser Cys Arg Ala Ser Gln Ser Ile Ser Asp Tyr Leu His Trp Tyr Gln
            180                 185                 190
Gln Lys Ser His Glu Ser Pro Arg Leu Leu Ile Lys Tyr Ala Ser Gln
            195                 200                 205
Ser Ile Ser Gly Ile Pro Ser Arg Phe Ser Gly Ser Gly Ser Gly Ser
    210                 215                 220
Asp Phe Thr Leu Ser Ile Asn Ser Val Glu Pro Glu Asp Val Gly Val
225                 230                 235                 240
Tyr Tyr Cys Gln Asn Gly His Ser Phe Pro Pro Thr Phe Gly Gly Gly
                245                 250                 255
Thr Lys Leu Glu Ile Lys Ala Ala Ala Leu Ser Asn Ser Ile Met Tyr
            260                 265                 270
Phe Ser His Phe Val Pro Val Phe Leu Pro Ala Lys Pro Thr Thr Thr
            275                 280                 285
Pro Ala Pro Arg Pro Pro Thr Pro Ala Pro Thr Ile Ala Ser Gln Pro
    290                 295                 300
Leu Ser Leu Arg Pro Glu Ala Cys Arg Pro Ala Ala Gly Gly Ala Val
305                 310                 315                 320
His Thr Arg Gly Leu Asp Phe Ala Cys Phe Trp Val Leu Val Val Val
                325                 330                 335
Gly Gly Val Leu Ala Cys Tyr Ser Leu Leu Val Thr Val Ala Phe Ile
            340                 345                 350
Ile Phe Trp Val Arg Leu Lys Ile Gln Val Arg Lys Ala Ala Ile Thr
            355                 360                 365
Ser Tyr Glu Lys Ser Asp Gly Val Tyr Thr Gly Leu Ser Thr Arg Asn
    370                 375                 380
Gln Glu Thr Tyr Glu Thr Leu Lys His Glu Lys Pro Pro Gln
385                 390                 395

<210> SEQ ID NO 64
<211> LENGTH: 402
<212> TYPE: PRT
<213> ORGANISM: Artificial Sequence
<220> FEATURE:
<223> OTHER INFORMATION: GD2-CAR

<400> SEQUENCE: 64

Met Asp Trp Ile Trp Arg Ile Leu Phe Leu Val Gly Ala Ala Thr Gly
1               5                   10                  15
Ala His Ser Ala Gln Pro Ala Gln Val Gln Val Lys Glu Ser Gly Pro
            20                  25                  30
```

```
Gly Leu Val Ala Pro Ser Gln Ser Leu Ser Ile Thr Cys Thr Val Ser
             35                  40                  45

Gly Phe Ser Leu Thr Asn Tyr Gly Val His Trp Val Arg Gln Pro Pro
 50                  55                  60

Gly Lys Gly Leu Glu Trp Leu Gly Val Ile Trp Ala Gly Gly Ser Thr
 65                  70                  75                  80

Asn Tyr Asn Ser Ala Leu Met Ser Arg Leu Ser Ile Ser Lys Asp Asn
                 85                  90                  95

Ser Lys Ser Gln Val Phe Leu Lys Met Asn Ser Leu Gln Thr Asp Asp
            100                 105                 110

Thr Ala Met Tyr Tyr Cys Ala Ser Arg Gly Gly Asn Tyr Gly Tyr Ala
            115                 120                 125

Leu Asp Tyr Trp Gly Gln Gly Thr Ser Val Thr Val Ser Ser Gly Gly
130                 135                 140

Gly Gly Ser Gly Gly Gly Ser Gly Gly Gly Ser Gly Gly Gly
145                 150                 155                 160

Gly Ser Ser Ile Val Met Thr Gln Thr Pro Lys Phe Leu Leu Val Ser
                165                 170                 175

Ala Gly Asp Arg Val Thr Ile Thr Cys Lys Ala Ser Gln Ser Val Ser
            180                 185                 190

Asn Asp Val Ala Trp Tyr Gln Gln Lys Pro Gly Gln Ser Pro Lys Leu
            195                 200                 205

Leu Ile Tyr Ser Ala Ser Asn Arg Tyr Thr Gly Val Pro Asp Arg Phe
210                 215                 220

Thr Gly Ser Gly Tyr Gly Thr Asp Phe Thr Phe Thr Ile Ser Thr Val
225                 230                 235                 240

Gln Ala Glu Asp Leu Ala Val Tyr Phe Cys Gln Gln Asp Tyr Ser Ser
            245                 250                 255

Leu Gly Gly Gly Thr Lys Leu Glu Ile Lys Ala Ala Ala Leu Ser Asn
            260                 265                 270

Ser Ile Met Tyr Phe Ser His Phe Val Pro Val Phe Leu Pro Ala Lys
            275                 280                 285

Pro Thr Thr Thr Pro Ala Pro Arg Pro Pro Thr Pro Ala Pro Thr Ile
            290                 295                 300

Ala Ser Gln Pro Leu Ser Leu Arg Pro Glu Ala Cys Arg Pro Ala Ala
305                 310                 315                 320

Gly Gly Ala Val His Thr Arg Gly Leu Asp Phe Ala Cys Phe Trp Val
            325                 330                 335

Leu Val Val Val Gly Gly Val Leu Ala Cys Tyr Ser Leu Leu Val Thr
            340                 345                 350

Val Ala Phe Ile Ile Phe Trp Val Arg Leu Lys Ile Gln Val Arg Lys
            355                 360                 365

Ala Ala Ile Thr Ser Tyr Glu Lys Ser Asp Gly Val Tyr Thr Gly Leu
            370                 375                 380

Ser Thr Arg Asn Gln Glu Thr Tyr Glu Thr Leu Lys His Glu Lys Pro
385                 390                 395                 400

Pro Gln
```

<210> SEQ ID NO 65
<211> LENGTH: 416
<212> TYPE: PRT
<213> ORGANISM: Artificial Sequence
<220> FEATURE:
<223> OTHER INFORMATION: FAP-CAR

<400> SEQUENCE: 65

```
Met Asp Trp Ile Trp Arg Ile Leu Phe Leu Val Gly Ala Ala Thr Gly
1               5                   10                  15

Ala His Ser Ala Gln Pro Ala Gln Val Gln Leu Gln Gln Ser Gly Pro
            20                  25                  30

Glu Leu Val Lys Pro Gly Ala Ser Val Lys Met Ser Cys Lys Thr Ser
        35                  40                  45

Arg Tyr Thr Phe Thr Glu Tyr Thr Ile His Trp Val Arg Gln Ser His
    50                  55                  60

Gly Lys Ser Leu Glu Trp Ile Gly Gly Ile Asn Pro Asn Asn Gly Ile
65                  70                  75                  80

Pro Asn Tyr Asn Gln Lys Phe Lys Gly Arg Ala Thr Leu Thr Val Gly
                85                  90                  95

Lys Ser Ser Ser Thr Ala Tyr Met Glu Leu Arg Ser Leu Thr Ser Glu
            100                 105                 110

Asp Ser Ala Val Tyr Phe Cys Ala Arg Arg Ile Ala Tyr Gly Tyr
        115                 120                 125

Asp Glu Gly His Ala Met Asp Tyr Trp Gly Gln Gly Thr Ser Val Thr
    130                 135                 140

Val Ser Ser Gly Gly Gly Gly Ser Gly Gly Gly Gly Ser Gly Gly Gly
145                 150                 155                 160

Gly Ser Gly Gly Gly Gly Ser Asp Ile Val Met Thr Gln Ser Pro Ser
                165                 170                 175

Ser Leu Ala Val Ser Val Gly Glu Lys Val Thr Met Ser Cys Lys Ser
            180                 185                 190

Ser Gln Ser Leu Leu Tyr Ser Arg Asn Gln Lys Asn Tyr Leu Ala Trp
        195                 200                 205

Phe Gln Gln Lys Pro Gly Gln Ser Pro Lys Leu Leu Ile Phe Trp Ala
    210                 215                 220

Ser Thr Arg Glu Ser Gly Val Pro Asp Arg Phe Thr Gly Ser Gly Phe
225                 230                 235                 240

Gly Thr Asp Phe Asn Leu Thr Ile Ser Ser Val Gln Ala Glu Asp Leu
                245                 250                 255

Ala Val Tyr Asp Cys Gln Gln Tyr Phe Ser Tyr Pro Leu Thr Phe Gly
            260                 265                 270

Ala Gly Thr Lys Leu Glu Leu Arg Ala Ala Leu Ser Asn Ser Ile
        275                 280                 285

Met Tyr Phe Ser His Phe Val Pro Val Phe Leu Pro Ala Lys Pro Thr
    290                 295                 300

Thr Thr Pro Ala Pro Arg Pro Pro Thr Pro Ala Pro Thr Ile Ala Ser
305                 310                 315                 320

Gln Pro Leu Ser Leu Arg Pro Glu Ala Cys Arg Pro Ala Ala Gly Gly
                325                 330                 335

Ala Val His Thr Arg Gly Leu Asp Phe Ala Cys Phe Trp Val Leu Val
            340                 345                 350

Val Val Gly Gly Val Leu Ala Cys Tyr Ser Leu Leu Val Thr Val Ala
        355                 360                 365

Phe Ile Ile Phe Trp Val Arg Leu Lys Ile Gln Val Arg Lys Ala Ala
    370                 375                 380

Ile Thr Ser Tyr Glu Lys Ser Asp Gly Val Tyr Thr Gly Leu Ser Thr
385                 390                 395                 400

Arg Asn Gln Glu Thr Tyr Glu Thr Leu Lys His Glu Lys Pro Pro Gln
                405                 410                 415
```

<210> SEQ ID NO 66
<211> LENGTH: 416
<212> TYPE: PRT
<213> ORGANISM: Artificial Sequence
<220> FEATURE:
<223> OTHER INFORMATION: CSPG-4-CAR

<400> SEQUENCE: 66

```
Met Asp Trp Ile Trp Arg Ile Leu Phe Leu Val Gly Ala Ala Thr Gly
1               5                   10                  15

Ala His Ser Ala Gln Pro Ala Asp Ile Glu Leu Thr Gln Ser Pro Lys
            20                  25                  30

Phe Met Ser Thr Ser Val Gly Asp Arg Val Ser Val Thr Cys Lys Ala
        35                  40                  45

Ser Gln Asn Val Asp Thr Asn Val Ala Trp Tyr Gln Lys Pro Gly
    50                  55                  60

Gln Ser Pro Glu Pro Leu Leu Phe Ser Ala Ser Tyr Arg Tyr Thr Gly
65                  70                  75                  80

Val Pro Asp Arg Phe Thr Gly Ser Gly Ser Gly Thr Asp Phe Thr Leu
                85                  90                  95

Thr Ile Ser Asn Val Gln Ser Glu Asp Leu Ala Glu Tyr Phe Cys Gln
            100                 105                 110

Gln Tyr Asn Ser Tyr Pro Leu Thr Phe Gly Gly Gly Thr Lys Leu Glu
        115                 120                 125

Ile Lys Arg Ala Ala Ala Glu Gly Gly Gly Ser Gly Gly Gly Gly
    130                 135                 140

Ser Gly Gly Gly Gly Ser Gly Gly Gly Ser Ala Met Ala Gln Val
145                 150                 155                 160

Lys Leu Gln Gln Ser Gly Gly Gly Leu Val Gln Pro Gly Gly Ser Met
                165                 170                 175

Lys Leu Ser Cys Val Val Ser Gly Phe Thr Phe Ser Asn Tyr Trp Met
            180                 185                 190

Asn Trp Val Arg Gln Ser Pro Glu Lys Gly Leu Glu Trp Ile Ala Glu
        195                 200                 205

Ile Arg Leu Lys Ser Asn Asn Phe Gly Arg Tyr Tyr Ala Glu Ser Val
    210                 215                 220

Lys Gly Arg Phe Thr Ile Ser Arg Asp Ser Lys Ser Ser Ala Tyr
225                 230                 235                 240

Leu Gln Met Ile Asn Leu Arg Ala Glu Asp Thr Gly Ile Tyr Tyr Cys
                245                 250                 255

Thr Ser Tyr Gly Asn Tyr Val Gly His Tyr Phe Asp His Trp Gly Gln
            260                 265                 270

Gly Thr Thr Val Thr Val Ser Ser Ala Ala Ala Leu Ser Asn Ser Ile
        275                 280                 285

Met Tyr Phe Ser His Phe Val Pro Val Phe Leu Pro Ala Lys Pro Thr
    290                 295                 300

Thr Thr Pro Ala Pro Arg Pro Pro Thr Pro Ala Pro Thr Ile Ala Ser
305                 310                 315                 320

Gln Pro Leu Ser Leu Arg Pro Glu Ala Cys Arg Pro Ala Ala Gly Gly
                325                 330                 335

Ala Val His Thr Arg Gly Leu Asp Phe Ala Cys Phe Trp Val Leu Val
            340                 345                 350

Val Val Gly Gly Val Leu Ala Cys Tyr Ser Leu Leu Val Thr Val Ala
        355                 360                 365
```

```
Phe Ile Ile Phe Trp Val Arg Leu Lys Ile Gln Val Arg Lys Ala Ala
        370                 375                 380
Ile Thr Ser Tyr Glu Lys Ser Asp Gly Val Tyr Thr Gly Leu Ser Thr
385                 390                 395                 400
Arg Asn Gln Glu Thr Tyr Glu Thr Leu Lys His Glu Lys Pro Pro Gln
                405                 410                 415
```

<210> SEQ ID NO 67
<211> LENGTH: 405
<212> TYPE: PRT
<213> ORGANISM: Artificial Sequence
<220> FEATURE:
<223> OTHER INFORMATION: CD20-CAR

<400> SEQUENCE: 67

```
Met Asp Trp Ile Trp Arg Ile Leu Phe Leu Val Gly Ala Ala Thr Gly
1               5                   10                  15
Ala His Ser Ala Gln Pro Ala Met Ala Gln Val Lys Leu Gln Glu Ser
                20                  25                  30
Gly Ala Glu Leu Val Lys Pro Gly Ala Ser Val Lys Met Ser Cys Lys
            35                  40                  45
Ala Ser Gly Tyr Thr Phe Thr Ser Tyr Asn Met His Trp Val Lys Gln
    50                  55                  60
Thr Pro Gly Gln Gly Leu Glu Trp Ile Gly Ala Ile Tyr Pro Gly Asn
65                  70                  75                  80
Gly Asp Thr Ser Tyr Asn Gln Lys Phe Lys Gly Lys Ala Thr Leu Thr
                85                  90                  95
Ala Asp Lys Ser Ser Ser Thr Ala Tyr Met Gln Leu Ser Ser Leu Thr
            100                 105                 110
Ser Glu Asp Ser Ala Asp Tyr Tyr Cys Ala Arg Ser Asn Tyr Tyr Gly
    115                 120                 125
Ser Ser Tyr Trp Phe Phe Asp Val Trp Gly Gln Gly Thr Thr Val Thr
130                 135                 140
Val Ser Ser Gly Gly Gly Gly Ser Gly Gly Gly Gly Ser Gly Gly Gly
145                 150                 155                 160
Gly Ser Asp Ile Glu Leu Thr Gln Ser Pro Thr Ile Leu Ser Ala Ser
                165                 170                 175
Pro Gly Glu Lys Val Thr Met Thr Cys Arg Ala Ser Ser Ser Val Asn
            180                 185                 190
Tyr Met Asp Trp Tyr Gln Lys Lys Pro Gly Ser Ser Pro Lys Pro Trp
    195                 200                 205
Ile Tyr Ala Thr Ser Asn Leu Ala Ser Gly Val Pro Ala Arg Phe Ser
210                 215                 220
Gly Ser Gly Ser Gly Thr Ser Tyr Ser Leu Thr Ile Ser Arg Val Glu
225                 230                 235                 240
Ala Glu Asp Ala Ala Thr Tyr Tyr Cys Gln Gln Trp Ser Phe Asn Pro
                245                 250                 255
Pro Thr Phe Gly Gly Gly Thr Lys Leu Glu Ile Lys Arg Ala Ala Ala
            260                 265                 270
Leu Ser Asn Ser Ile Met Tyr Phe Ser His Phe Val Pro Val Phe Leu
    275                 280                 285
Pro Ala Lys Pro Thr Thr Thr Pro Ala Pro Arg Pro Pro Thr Pro Ala
290                 295                 300
Pro Thr Ile Ala Ser Gln Pro Leu Ser Leu Arg Pro Glu Ala Cys Arg
305                 310                 315                 320
```

```
Pro Ala Ala Gly Gly Ala Val His Thr Arg Gly Leu Asp Phe Ala Cys
            325                 330                 335

Phe Trp Val Leu Val Val Val Gly Gly Val Leu Ala Cys Tyr Ser Leu
            340                 345                 350

Leu Val Thr Val Ala Phe Ile Ile Phe Trp Val Arg Leu Lys Ile Gln
            355                 360                 365

Val Arg Lys Ala Ala Ile Thr Ser Tyr Glu Lys Ser Asp Gly Val Tyr
        370                 375                 380

Thr Gly Leu Ser Thr Arg Asn Gln Glu Thr Tyr Glu Thr Leu Lys His
385                 390                 395                 400

Glu Lys Pro Pro Gln
            405

<210> SEQ ID NO 68
<211> LENGTH: 510
<212> TYPE: PRT
<213> ORGANISM: Artificial Sequence
<220> FEATURE:
<223> OTHER INFORMATION: 2nd generation CAR with CD28/CD3zeta

<400> SEQUENCE: 68

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Leu Lys Arg Gly Gly Gly Ser Gly Gly Gly Ser Gly Gly Gly
    130                 135                 140

Gly Ser Gly Gly Gly Ser Glu Val Gln Leu Gln Gln Ser Gly Pro
145                 150                 155                 160

Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
            180                 185                 190

Arg Lys Gly Leu Glu Trp Leu Gly Val Ile Trp Gly Ser Glu Thr Thr
        195                 200                 205

Tyr Tyr Asn Ser Ala Leu Lys Ser Arg Leu Thr Ile Ile Lys Asp Asn
    210                 215                 220

Ser Lys Ser Gln Val Phe Leu Lys Met Asn Ser Leu Gln Thr Asp Asp
225                 230                 235                 240

Thr Ala Ile Tyr Tyr Cys Ala Lys His Tyr Tyr Gly Gly Ser Tyr
                245                 250                 255

Ala Met Asp Tyr Trp Gly Gln Gly Thr Thr Val Thr Val Ser Ser Ala
            260                 265                 270
```

```
Ala Ala Leu Phe Val Pro Val Phe Leu Pro Ala Lys Pro Thr Thr Thr
            275                 280                 285

Pro Ala Pro Arg Pro Pro Thr Pro Ala Pro Thr Ile Ala Ser Gln Pro
290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Phe Trp Val Leu Val Val Val
            325                 330                 335

Gly Gly Val Leu Ala Cys Tyr Ser Leu Leu Val Thr Val Ala Phe Ile
            340                 345                 350

Ile Phe Trp Val Arg Ser Lys Arg Ser Arg Leu Leu His Ser Asp Tyr
            355                 360                 365

Met Asn Met Thr Pro Arg Arg Pro Gly Pro Thr Arg Lys His Tyr Gln
            370                 375                 380

Pro Tyr Ala Pro Pro Arg Asp Phe Ala Ala Tyr Arg Ser Arg Val Lys
385                 390                 395                 400

Phe Ser Arg Ser Ala Asp Ala Pro Ala Tyr Gln Gln Gly Gln Asn Gln
            405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Gln Arg
            435                 440                 445

Arg Lys Asn Pro Gln Glu Gly Leu Tyr Asn Glu Leu Gln Lys Asp Lys
            450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
            485                 490                 495

Asp Thr Tyr Asp Ala Leu His Met Gln Ala Leu Pro Pro Arg
            500                 505                 510

<210> SEQ ID NO 69
<211> LENGTH: 511
<212> TYPE: PRT
<213> ORGANISM: Artificial Sequence
<220> FEATURE:
<223> OTHER INFORMATION: 2nd generation CAR with 4-1BB/CD3zeta signaling
      domain

<400> SEQUENCE: 69

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
            85                  90                  95

Thr Ile Ser Asn Leu Glu Gln Glu Asp Ile Ala Thr Tyr Phe Cys Gln
            100                 105                 110
```

```
Gln Gly Asn Thr Leu Pro Tyr Thr Phe Gly Gly Gly Thr Lys Leu Glu
        115                 120                 125

Leu Lys Arg Gly Gly Gly Gly Ser Gly Gly Gly Ser Gly Gly Gly
    130                 135                 140

Gly Ser Gly Gly Gly Ser Glu Val Gln Leu Gln Gln Ser Gly Pro
145                 150                 155                 160

Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
                180                 185                 190

Arg Lys Gly Leu Glu Trp Leu Gly Val Ile Trp Gly Ser Glu Thr Thr
            195                 200                 205

Tyr Tyr Asn Ser Ala Leu Lys Ser Arg Leu Thr Ile Ile Lys Asp Asn
        210                 215                 220

Ser Lys Ser Gln Val Phe Leu Lys Met Asn Ser Leu Gln Thr Asp Asp
225                 230                 235                 240

Thr Ala Ile Tyr Tyr Cys Ala Lys His Tyr Tyr Gly Gly Ser Tyr
                245                 250                 255

Ala Met Asp Tyr Trp Gly Gln Gly Thr Thr Val Thr Val Ser Ser Ala
            260                 265                 270

Ala Ala Leu Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Phe Trp Val Leu Val Val Val
                325                 330                 335

Gly Gly Val Leu Ala Cys Tyr Ser Leu Leu Val Thr Val Ala Phe Ile
            340                 345                 350

Ile Phe Trp Val Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Gln
        435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg
            500                 505                 510

<210> SEQ ID NO 70
<211> LENGTH: 552
```

<212> TYPE: PRT
<213> ORGANISM: Artificial Sequence
<220> FEATURE:
<223> OTHER INFORMATION: 3rd generation CAR with CD28/4-1BB/CD3zeta
      signaling domain

<400> SEQUENCE: 70

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Leu Lys Arg Gly Gly Gly Gly Ser Gly Gly Gly Gly Ser Gly Gly Gly
    130                 135                 140

Gly Ser Gly Gly Gly Gly Ser Glu Val Gln Leu Gln Gln Ser Gly Pro
145                 150                 155                 160

Gly Leu Val Ala Pro Ser Gln Ser Leu Ser Val Thr Cys Thr Val Ser
                165                 170                 175

Gly Val Ser Leu Pro Asp Tyr Gly Val Ser Trp Ile Arg Gln Pro Pro
            180                 185                 190

Arg Lys Gly Leu Glu Trp Leu Gly Val Ile Trp Gly Ser Glu Thr Thr
        195                 200                 205

Tyr Tyr Asn Ser Ala Leu Lys Ser Arg Leu Thr Ile Ile Lys Asp Asn
    210                 215                 220

Ser Lys Ser Gln Val Phe Leu Lys Met Asn Ser Leu Gln Thr Asp Asp
225                 230                 235                 240

Thr Ala Ile Tyr Tyr Cys Ala Lys His Tyr Tyr Tyr Gly Gly Ser Tyr
                245                 250                 255

Ala Met Asp Tyr Trp Gly Gln Gly Thr Thr Val Thr Val Ser Ser Ala
            260                 265                 270

Ala Ala Leu Phe Val Pro Val Phe Leu Pro Ala Lys Pro Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Phe Trp Val Leu Val Val Val
                325                 330                 335

Gly Gly Val Leu Ala Cys Tyr Ser Leu Leu Val Thr Val Ala Phe Ile
            340                 345                 350

Ile Phe Trp Val Arg Ser Lys Arg Ser Arg Leu Leu His Ser Asp Tyr
        355                 360                 365

Met Asn Met Thr Pro Arg Arg Pro Gly Pro Thr Arg Lys His Tyr Gln
    370                 375                 380

```
Pro Tyr Ala Pro Pro Arg Asp Phe Ala Ala Tyr Arg Ser Lys Arg Gly
385                 390                 395                 400

Arg Lys Lys Leu Leu Tyr Ile Phe Lys Gln Pro Phe Met Arg Pro Val
            405                 410                 415

Gln Thr Thr Gln Glu Glu Asp Gly Cys Ser Cys Arg Phe Pro Glu Glu
        420                 425                 430

Glu Glu Gly Gly Cys Glu Leu Arg Val Lys Phe Ser Arg Ser Ala Asp
            435                 440                 445

Ala Pro Ala Tyr Gln Gln Gly Gln Asn Gln Leu Tyr Asn Glu Leu Asn
450                 455                 460

Leu Gly Arg Arg Glu Glu Tyr Asp Val Leu Asp Lys Arg Arg Gly Arg
465                 470                 475                 480

Asp Pro Glu Met Gly Gly Lys Pro Gln Arg Arg Lys Asn Pro Gln Glu
            485                 490                 495

Gly Leu Tyr Asn Glu Leu Gln Lys Asp Lys Met Ala Glu Ala Tyr Ser
            500                 505                 510

Glu Ile Gly Met Lys Gly Glu Arg Arg Gly Lys Gly His Asp Gly
            515                 520                 525

Leu Tyr Gln Gly Leu Ser Thr Ala Thr Lys Asp Thr Tyr Asp Ala Leu
530                 535                 540

His Met Gln Ala Leu Pro Pro Arg
545                 550

<210> SEQ ID NO 71
<211> LENGTH: 552
<212> TYPE: PRT
<213> ORGANISM: Artificial Sequence
<220> FEATURE:
<223> OTHER INFORMATION: 3rd generation CAR with 4-1BB/CD3zeta/
      CD28signaling domain

<400> SEQUENCE: 71

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45

Ser Gln Asp Ile Ser Lys Tyr Leu Asn Trp Tyr Gln Gln Lys Pro Asp
    50                  55                  60

Gly Thr Val Lys Leu Leu Ile Tyr His Thr Ser Arg Leu His Ser Gly
65                  70                  75                  80

Val Pro Ser Arg Phe Ser Gly Ser Gly Ser Gly Thr Asp Tyr Ser Leu
                85                  90                  95

Thr Ile Ser Asn Leu Glu Gln Glu Asp Ile Ala Thr Tyr Phe Cys Gln
            100                 105                 110

Gln Gly Asn Thr Leu Pro Tyr Thr Phe Gly Gly Gly Thr Lys Leu Glu
        115                 120                 125

Leu Lys Arg Gly Gly Gly Ser Gly Gly Gly Ser Gly Gly Gly
    130                 135                 140

Gly Ser Gly Gly Gly Ser Glu Val Gln Leu Gln Gln Ser Gly Pro
145                 150                 155                 160

Gly Leu Val Ala Pro Ser Gln Ser Leu Ser Val Thr Cys Thr Val Ser
                165                 170                 175
```

Gly Val Ser Leu Pro Asp Tyr Val Ser Trp Ile Arg Gln Pro Pro
            180             185             190

Arg Lys Gly Leu Glu Trp Leu Gly Val Ile Trp Gly Ser Glu Thr Thr
        195             200             205

Tyr Tyr Asn Ser Ala Leu Lys Ser Arg Leu Thr Ile Ile Lys Asp Asn
    210             215             220

Ser Lys Ser Gln Val Phe Leu Lys Met Asn Ser Leu Gln Thr Asp Asp
225             230             235             240

Thr Ala Ile Tyr Tyr Cys Ala Lys His Tyr Tyr Gly Gly Ser Tyr
            245             250             255

Ala Met Asp Tyr Trp Gly Gln Gly Thr Thr Val Thr Val Ser Ser Ala
            260             265             270

Ala Ala Leu Phe Val Pro Val Phe Leu Pro Ala Lys Pro Thr Thr Thr
            275             280             285

Pro Ala Pro Arg Pro Pro Thr Pro Ala Pro Thr Ile Ala Ser Gln Pro
    290             295             300

Leu Ser Leu Arg Pro Glu Ala Cys Arg Pro Ala Ala Gly Gly Ala Val
305             310             315             320

His Thr Arg Gly Leu Asp Phe Ala Cys Phe Trp Val Leu Val Val Val
            325             330             335

Gly Gly Val Leu Ala Cys Tyr Ser Leu Leu Val Thr Val Ala Phe Ile
            340             345             350

Ile Phe Trp Val Lys Arg Gly Arg Lys Lys Leu Leu Tyr Ile Phe Lys
            355             360             365

Gln Pro Phe Met Arg Pro Val Gln Thr Thr Gln Glu Glu Asp Gly Cys
    370             375             380

Ser Cys Arg Phe Pro Glu Glu Glu Gly Gly Cys Glu Leu Arg Val
385             390             395             400

Lys Phe Ser Arg Ser Ala Asp Ala Pro Ala Tyr Gln Gln Gly Gln Asn
            405             410             415

Gln Leu Tyr Asn Glu Leu Asn Leu Gly Arg Arg Glu Glu Tyr Asp Val
            420             425             430

Leu Asp Lys Arg Arg Gly Arg Asp Pro Glu Met Gly Gly Lys Pro Gln
            435             440             445

Arg Arg Lys Asn Pro Gln Glu Gly Leu Tyr Asn Glu Leu Gln Lys Asp
            450             455             460

Lys Met Ala Glu Ala Tyr Ser Glu Ile Gly Met Lys Gly Glu Arg Arg
465             470             475             480

Arg Gly Lys Gly His Asp Gly Leu Tyr Gln Gly Leu Ser Thr Ala Thr
            485             490             495

Lys Asp Thr Tyr Asp Ala Leu His Met Gln Ala Leu Pro Pro Arg Arg
            500             505             510

Ser Lys Arg Ser Arg Leu Leu His Ser Asp Tyr Met Asn Met Thr Pro
            515             520             525

Arg Arg Pro Gly Pro Thr Arg Lys His Tyr Gln Pro Tyr Ala Pro Pro
            530             535             540

Arg Asp Phe Ala Ala Tyr Arg Ser
545             550

<210> SEQ ID NO 72
<211> LENGTH: 256
<212> TYPE: PRT
<213> ORGANISM: Artificial Sequence
<220> FEATURE:

<223> OTHER INFORMATION: HER2-CAR binding domain

<400> SEQUENCE: 72

```
Ala Gln Pro Ala Asp Ile Gln Met Thr Gln Ser Pro Ser Ser Leu Ser
1               5                   10                  15
Ala Ser Val Gly Asp Arg Val Thr Ile Thr Cys Arg Ala Ser Gln Asp
            20                  25                  30
Val Asn Thr Ala Val Ala Trp Tyr Gln Gln Lys Pro Gly Lys Ala Pro
        35                  40                  45
Lys Leu Leu Ile Tyr Ser Ala Ser Phe Leu Tyr Ser Gly Val Pro Ser
    50                  55                  60
Arg Phe Ser Gly Ser Arg Ser Gly Thr Asp Phe Thr Leu Thr Ile Ser
65                  70                  75                  80
Ser Leu Gln Pro Glu Asp Phe Ala Thr Tyr Tyr Cys Gln Gln His Tyr
                85                  90                  95
Thr Thr Pro Pro Thr Phe Gly Gln Gly Thr Lys Val Glu Ile Lys Ser
            100                 105                 110
Ser Gly Gly Gly Gly Ser Gly Gly Gly Gly Ser Gly Gly Gly Gly Ser
        115                 120                 125
Gly Gly Gly Gly Ser Gly Gly Ser Glu Val Gln Leu Val Glu Ser Gly
    130                 135                 140
Gly Gly Leu Val Gln Pro Gly Gly Ser Leu Arg Leu Ser Cys Ala Ala
145                 150                 155                 160
Ser Gly Phe Asn Ile Lys Asp Thr Tyr Ile His Trp Val Arg Gln Ala
                165                 170                 175
Pro Gly Lys Gly Leu Glu Trp Val Ala Arg Ile Tyr Pro Thr Asn Gly
            180                 185                 190
Tyr Thr Arg Tyr Ala Asp Ser Val Lys Gly Arg Phe Thr Ile Ser Ala
        195                 200                 205
Asp Thr Ser Lys Asn Thr Ala Tyr Leu Gln Met Asn Ser Leu Arg Ala
    210                 215                 220
Glu Asp Thr Ala Val Tyr Tyr Cys Ser Arg Trp Gly Gly Asp Gly Phe
225                 230                 235                 240
Tyr Ala Met Asp Tyr Trp Gly Gln Gly Thr Leu Val Thr Val Ser Ser
                245                 250                 255
```

<210> SEQ ID NO 73
<211> LENGTH: 255
<212> TYPE: PRT
<213> ORGANISM: Artificial Sequence
<220> FEATURE:
<223> OTHER INFORMATION: CD30-CAR binding domain

<400> SEQUENCE: 73

```
Ala Gln Pro Ala Asp Ile Gln Met Thr Gln Ser Pro Ser Ser Leu Ser
1               5                   10                  15
Ala Ser Val Gly Asp Arg Val Thr Ile Thr Cys Gln Ala Ser Gln Asp
            20                  25                  30
Ile Ser Asn Tyr Leu Asn Trp Tyr Gln Gln Lys Pro Gly Lys Ala Pro
        35                  40                  45
Lys Leu Leu Ile Tyr Asp Val Ser Asn Leu Glu Thr Gly Val Pro Ser
    50                  55                  60
Arg Phe Ser Gly Ser Gly Ser Gly Thr Asp Phe Thr Phe Thr Ile Ser
65                  70                  75                  80
Ser Leu Gln Pro Glu Asp Ile Ala Thr Tyr Tyr Cys Gln Gln Val Ala
                85                  90                  95
```

```
Asn Val Pro Leu Thr Phe Gly Gln Gly Thr Lys Val Glu Ile Lys Gly
                100                 105                 110

Gly Gly Gly Ser Gly Gly Gly Ser Gly Gly Gly Ser Gly Gly
            115                 120                 125

Gly Gly Ser Glu Val Gln Leu Val Glu Ser Gly Gly Gly Leu Val Gln
        130                 135                 140

Pro Gly Gly Ser Leu Arg Leu Ser Cys Ala Ala Ser Gly Phe Thr Phe
145                 150                 155                 160

Ser Ser Tyr Trp Met His Trp Val Arg Gln Ala Pro Gly Lys Gly Leu
                165                 170                 175

Glu Trp Val Ser Ala Ile Ser Trp Ser Gly Asp Ser Thr Tyr Tyr Ala
            180                 185                 190

Asp Ser Val Lys Gly Arg Phe Thr Ile Ser Arg Asp Asn Ser Lys Asn
            195                 200                 205

Thr Leu Tyr Leu Gln Met Asn Ser Leu Arg Ala Glu Asp Thr Ala Val
        210                 215                 220

Tyr Tyr Cys Ala Arg Asp Arg Ser Ala Thr Trp Tyr Tyr Leu Gly Leu
225                 230                 235                 240

Gly Phe Asp Val Trp Gly Gln Gly Thr Leu Val Thr Val Ser Ser
                245                 250                 255

<210> SEQ ID NO 74
<211> LENGTH: 250
<212> TYPE: PRT
<213> ORGANISM: Artificial Sequence
<220> FEATURE:
<223> OTHER INFORMATION: EGFR-CAR binding domain

<400> SEQUENCE: 74

Ala Gln Pro Ala Asp Ile Leu Leu Thr Gln Ser Pro Val Ile Leu Ser
1               5                   10                  15

Val Ser Pro Gly Glu Arg Val Ser Phe Ser Cys Arg Ala Ser Gln Ser
            20                  25                  30

Ile Gly Thr Asn Ile His Trp Tyr Gln Gln Arg Thr Asn Gly Ser Pro
        35                  40                  45

Arg Leu Leu Ile Lys Tyr Ala Ser Glu Ser Ile Ser Gly Ile Pro Ser
50                  55                  60

Arg Phe Ser Gly Ser Gly Ser Gly Thr Asp Phe Thr Leu Ser Ile Asn
65                  70                  75                  80

Ser Val Glu Ser Glu Asp Ile Ala Asp Tyr Tyr Cys Gln Gln Asn Asn
                85                  90                  95

Asn Trp Pro Thr Thr Phe Gly Ala Gly Thr Lys Leu Glu Leu Lys Gly
            100                 105                 110

Gly Gly Gly Ser Gly Gly Gly Ser Gly Gly Gly Ser Gly Gly
        115                 120                 125

Gly Gly Ser Gln Val Gln Leu Lys Gln Ser Gly Pro Gly Leu Val Gln
        130                 135                 140

Pro Ser Gln Ser Leu Ser Ile Thr Cys Thr Val Ser Gly Phe Ser Leu
145                 150                 155                 160

Thr Asn Tyr Gly Val His Trp Val Arg Gln Ser Pro Gly Lys Gly Leu
                165                 170                 175

Glu Trp Leu Gly Val Ile Trp Ser Gly Gly Asn Thr Asp Tyr Asn Thr
            180                 185                 190

Pro Phe Thr Ser Arg Leu Ser Ile Asn Lys Asp Asn Ser Lys Ser Gln
            195                 200                 205
```

```
Val Phe Phe Lys Met Asn Ser Leu Gln Ser Asn Asp Thr Ala Ile Tyr
            210                 215                 220

Tyr Cys Ala Arg Ala Leu Thr Tyr Tyr Asp Tyr Glu Phe Ala Tyr Trp
225                 230                 235                 240

Gly Gln Gly Thr Leu Val Thr Val Ser Ala
                245                 250

<210> SEQ ID NO 75
<211> LENGTH: 255
<212> TYPE: PRT
<213> ORGANISM: Artificial Sequence
<220> FEATURE:
<223> OTHER INFORMATION: IGF1R-CAR binding domain

<400> SEQUENCE: 75

Ala Gln Pro Ala Asp Val Val Met Thr Gln Ser Pro Leu Ser Leu Pro
1               5                   10                  15

Val Thr Pro Gly Glu Pro Ala Ser Ile Ser Cys Arg Ser Ser Gln Ser
            20                  25                  30

Leu Leu His Ser Asn Gly Tyr Asn Tyr Leu Asp Trp Tyr Leu Gln Lys
        35                  40                  45

Pro Gly Gln Ser Pro Gln Leu Leu Ile Tyr Leu Gly Ser Asn Arg Ala
    50                  55                  60

Ser Gly Val Pro Asp Arg Phe Ser Gly Ser Gly Ser Gly Thr Asp Phe
65                  70                  75                  80

Thr Leu Lys Ile Ser Arg Val Glu Ala Glu Asp Val Gly Val Tyr Tyr
                85                  90                  95

Cys Met Gln Gly Thr His Trp Pro Leu Thr Phe Gly Gln Gly Thr Lys
            100                 105                 110

Val Glu Ile Lys Gly Gly Gly Gly Ser Gly Gly Gly Gly Ser Gly Gly
        115                 120                 125

Gly Gly Ser Gly Gly Gly Gly Ser Gln Val Gln Leu Gln Glu Ser Gly
    130                 135                 140

Pro Gly Leu Val Lys Pro Ser Gly Thr Leu Ser Leu Thr Cys Ala Val
145                 150                 155                 160

Ser Gly Gly Ser Ile Ser Ser Ser Asn Trp Trp Ser Trp Val Arg Gln
                165                 170                 175

Pro Pro Gly Lys Gly Leu Glu Trp Ile Gly Glu Ile Tyr His Ser Gly
            180                 185                 190

Ser Thr Asn Tyr Asn Pro Ser Leu Lys Ser Arg Val Thr Ile Ser Val
        195                 200                 205

Asp Lys Ser Lys Asn Gln Phe Ser Leu Lys Leu Ser Ser Val Thr Ala
    210                 215                 220

Ala Asp Thr Ala Val Tyr Tyr Cys Ala Arg Trp Thr Gly Arg Thr Asp
225                 230                 235                 240

Ala Phe Asp Ile Trp Gly Gln Gly Thr Met Val Thr Val Ser Ser
                245                 250                 255

<210> SEQ ID NO 76
<211> LENGTH: 246
<212> TYPE: PRT
<213> ORGANISM: Artificial Sequence
<220> FEATURE:
<223> OTHER INFORMATION: CD123-CAR binding domain
```

<400> SEQUENCE: 76

Ala Gln Pro Ala Asp Ile Gln Met Thr Gln Ser Pro Ser Ser Leu Ser
1               5                   10                  15

Ala Ser Val Gly Asp Arg Val Thr Ile Thr Cys Arg Ala Ser Glu Ser
            20                  25                  30

Val Asp Asn Tyr Gly Ile Ser Phe Met Asn Trp Phe Gln Gln Lys Pro
        35                  40                  45

Gly Lys Ala Pro Lys Leu Leu Ile Tyr Ala Ala Ser Asn Gln Gly Ser
    50                  55                  60

Gly Val Pro Ser Arg Phe Ser Gly Ser Gly Ser Gly Thr Asp Phe Thr
65                  70                  75                  80

Leu Thr Ile Ser Ser Leu Gln Pro Asp Asp Phe Ala Thr Tyr Tyr Cys
                85                  90                  95

Gln Gln Ser Lys Glu Val Pro Trp Thr Phe Gly Gln Gly Thr Lys Val
            100                 105                 110

Glu Ile Lys Gly Gly Gly Gly Ser Gly Gly Gly Gly Ser Gly Gly Gly
        115                 120                 125

Gly Ser Gln Val Gln Leu Val Gln Ser Gly Ala Glu Val Lys Lys Pro
    130                 135                 140

Gly Ser Ser Val Lys Val Ser Cys Lys Ala Ser Gly Tyr Thr Phe Thr
145                 150                 155                 160

Asp Tyr Asn Met His Trp Val Arg Gln Ala Pro Gly Gln Gly Leu Glu
                165                 170                 175

Trp Ile Gly Tyr Ile Tyr Pro Tyr Asn Gly Gly Thr Gly Tyr Asn Gln
            180                 185                 190

Lys Phe Lys Ser Lys Ala Thr Ile Thr Ala Asp Glu Ser Thr Asn Thr
        195                 200                 205

Ala Tyr Met Glu Leu Ser Ser Leu Arg Ser Glu Asp Thr Ala Val Tyr
    210                 215                 220

Tyr Cys Ala Arg Gly Arg Pro Ala Met Asp Tyr Trp Gly Gln Gly Thr
225                 230                 235                 240

Leu Val Thr Val Ser Ser
                245

<210> SEQ ID NO 77
<211> LENGTH: 250
<212> TYPE: PRT
<213> ORGANISM: Artificial Sequence
<220> FEATURE:
<223> OTHER INFORMATION: PD-L1-CAR binding domain

<400> SEQUENCE: 77

Ala Gln Pro Ala Asn Ile Gln Met Thr Gln Ser Pro Ser Ser Val Ser
1               5                   10                  15

Ala Ser Val Gly Asp Arg Val Thr Ile Thr Cys Arg Ala Ser Gln Asp
            20                  25                  30

Ile Ser Arg Trp Leu Ala Trp Tyr Gln Gln Lys Pro Gly Lys Ala Pro
        35                  40                  45

Lys Leu Leu Ile Tyr Ala Ala Ser Ser Leu Gln Ser Gly Val Pro Ser
    50                  55                  60

Arg Phe Ser Gly Ser Gly Ser Gly Thr Asp Phe Ala Leu Thr Ile Ser
65                  70                  75                  80

Ser Leu Gln Pro Glu Asp Phe Ala Thr Tyr Tyr Cys Gln Gln Ala Asp
                85                  90                  95

```
Ser Arg Phe Ser Ile Thr Phe Gly Gln Gly Thr Arg Leu Glu Ile Lys
            100                 105                 110

Gly Gly Gly Gly Ser Gly Gly Gly Gly Ser Gly Gly Gly Ser Gly
        115                 120                 125

Gly Gly Gly Ser Glu Val Gln Leu Val Gln Ser Gly Gly Gly Leu Val
        130                 135                 140

Gln Pro Gly Gly Ser Leu Arg Leu Ser Cys Ala Ala Ser Gly Phe Thr
145                 150                 155                 160

Phe Ser Ser Tyr Ser Met Asn Trp Val Arg Gln Ala Pro Gly Lys Gly
                165                 170                 175

Leu Glu Trp Val Ser Tyr Ile Ser Ser Ser Ser Thr Ile Gln Tyr
            180                 185                 190

Ala Asp Ser Val Lys Gly Arg Phe Thr Ile Ser Arg Asp Asn Ala Lys
            195                 200                 205

Asn Ser Leu Tyr Leu Gln Met Asn Ser Leu Arg Asp Glu Asp Thr Ala
        210                 215                 220

Val Tyr Tyr Cys Ala Arg Gly Asp Tyr Tyr Gly Met Asp Val Trp
225                 230                 235                 240

Gly Gln Gly Thr Thr Val Thr Val Ser Ser
            245                 250

<210> SEQ ID NO 78
<211> LENGTH: 246
<212> TYPE: PRT
<213> ORGANISM: Artificial Sequence
<220> FEATURE:
<223> OTHER INFORMATION: CD33-CAR binding domain

<400> SEQUENCE: 78

Ala Gln Pro Ala Asp Ile Gln Met Thr Gln Ser Pro Ser Ser Leu Ser
1               5                   10                  15

Ala Ser Val Gly Asp Arg Val Thr Ile Thr Cys Arg Ala Ser Glu Ser
            20                  25                  30

Val Asp Asn Tyr Gly Ile Ser Phe Met Asn Trp Phe Gln Gln Lys Pro
        35                  40                  45

Gly Lys Ala Pro Lys Leu Leu Ile Tyr Ala Ala Ser Asn Gln Gly Ser
    50                  55                  60

Gly Val Pro Ser Arg Phe Ser Gly Ser Gly Ser Gly Thr Asp Phe Thr
65                  70                  75                  80

Leu Thr Ile Ser Ser Leu Gln Pro Asp Asp Phe Ala Thr Tyr Tyr Cys
                85                  90                  95

Gln Gln Ser Lys Glu Val Pro Trp Thr Phe Gly Gln Gly Thr Lys Val
            100                 105                 110

Glu Ile Lys Gly Gly Gly Gly Ser Gly Gly Gly Gly Ser Gly Gly Gly
        115                 120                 125

Gly Ser Gln Val Gln Leu Val Gln Ser Gly Ala Glu Val Lys Lys Pro
    130                 135                 140

Gly Ser Ser Val Lys Val Ser Cys Lys Ala Ser Gly Tyr Thr Phe Thr
145                 150                 155                 160

Asp Tyr Asn Met His Trp Val Arg Gln Ala Pro Gly Gln Gly Leu Glu
                165                 170                 175

Trp Ile Gly Tyr Ile Tyr Pro Tyr Asn Gly Gly Thr Gly Tyr Asn Gln
            180                 185                 190

Lys Phe Lys Ser Lys Ala Thr Ile Thr Ala Asp Glu Ser Thr Asn Thr
        195                 200                 205
```

```
Ala Tyr Met Glu Leu Ser Ser Leu Arg Ser Glu Asp Thr Ala Val Tyr
    210                 215                 220

Tyr Cys Ala Arg Gly Arg Pro Ala Met Asp Tyr Trp Gly Gln Gly Thr
225                 230                 235                 240

Leu Val Thr Val Ser Ser
                245
```

<210> SEQ ID NO 79
<211> LENGTH: 396
<212> TYPE: PRT
<213> ORGANISM: Artificial Sequence
<220> FEATURE:
<223> OTHER INFORMATION: gp120-CAR binding domain

<400> SEQUENCE: 79

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320
```

```
Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro
385                 390                 395

<210> SEQ ID NO 80
<211> LENGTH: 250
<212> TYPE: PRT
<213> ORGANISM: Artificial Sequence
<220> FEATURE:
<223> OTHER INFORMATION: B7-H4-CAR binding domain

<400> SEQUENCE: 80

Ala Gln Pro Ala Glu Val Gln Leu Val Glu Ser Gly Gly Gly Leu Val
1               5                   10                  15

Gln Pro Gly Gly Ser Leu Arg Leu Ser Cys Ala Ala Ser Gly Phe Thr
            20                  25                  30

Phe Asn Ser Tyr Ala Met His Trp Val Arg Gln Ala Pro Gly Lys Gly
        35                  40                  45

Leu Glu Trp Val Ser Ala Ile Ser Gly Asn Gly Gly Ser Thr Arg Tyr
    50                  55                  60

Ala Asp Ser Val Lys Gly Arg Phe Thr Ile Ser Arg Asp Asn Ser Lys
65                  70                  75                  80

Asn Thr Leu Tyr Leu Gln Met Asn Ser Leu Arg Ala Glu Asp Thr Ala
                85                  90                  95

Val Tyr Tyr Cys Ala Arg Asp Arg Phe Arg Lys Val His Gly Phe Asp
            100                 105                 110

Val Trp Gly Gln Gly Thr Leu Val Thr Val Ser Ser Gly Gly Gly Gly
        115                 120                 125

Ser Gly Gly Gly Gly Ser Gly Gly Gly Ser Gly Gly Gly Gly Asp
    130                 135                 140

Ile Gln Met Thr Gln Ser Pro Ser Ser Leu Ser Ala Ser Val Gly Asp
145                 150                 155                 160

Arg Val Thr Ile Thr Cys Gln Ala Ser Gln Asp Ile Ser Asn Tyr Leu
                165                 170                 175

Asn Trp Tyr Gln Gln Lys Pro Gly Lys Ala Pro Lys Leu Leu Ile Tyr
            180                 185                 190

Asp Ala Ser Asn Leu Glu Thr Gly Val Pro Ser Arg Phe Ser Gly Ser
        195                 200                 205

Gly Ser Gly Thr Asp Phe Thr Phe Thr Ile Ser Ser Leu Gln Pro Glu
    210                 215                 220

Asp Ile Ala Thr Tyr Tyr Cys Gln Gln Asp Ala Thr Phe Pro Leu Thr
225                 230                 235                 240

Phe Gly Gln Gly Thr Lys Val Glu Ile Lys
                245                 250

<210> SEQ ID NO 81
<211> LENGTH: 243
<212> TYPE: PRT
<213> ORGANISM: Artificial Sequence
<220> FEATURE:
```

<223> OTHER INFORMATION: BCMA-CAR binding domain

<400> SEQUENCE: 81

```
Ala Gln Pro Ala Val Gln Leu Gln Gln Ser Gly Pro Glu Leu Val Lys
 1               5                  10                  15
Pro Gly Ala Ser Val Lys Met Ser Cys Lys Ala Ser Gly Tyr Thr Phe
            20                  25                  30
Thr Ser Tyr Val Met His Trp Val Lys Gln Lys Pro Gly Gln Gly Leu
        35                  40                  45
Glu Trp Ile Gly Tyr Ile Ile Pro Tyr Asn Asp Ala Thr Lys Tyr Asn
    50                  55                  60
Glu Lys Phe Lys Gly Lys Ala Thr Leu Thr Ser Asp Lys Ser Ser Ser
65                  70                  75                  80
Thr Ala Tyr Met Glu Leu Ser Ser Leu Thr Ser Glu Asp Ser Ala Val
                85                  90                  95
Tyr Tyr Cys Ala Arg Tyr Asn Tyr Asp Gly Tyr Phe Asp Val Trp Gly
            100                 105                 110
Ala Gly Thr Thr Val Thr Val Ser Gly Gly Gly Gly Ser Gly Gly
        115                 120                 125
Gly Gly Ser Gly Gly Gly Gly Ser Asp Ile Val Met Thr Gln Ser Pro
130                 135                 140
Ala Thr Leu Ser Val Thr Pro Gly Asp Arg Val Ser Leu Ser Cys Arg
145                 150                 155                 160
Ala Ser Gln Ser Ile Ser Asp Tyr Leu His Trp Tyr Gln Gln Lys Ser
                165                 170                 175
His Glu Ser Pro Arg Leu Leu Ile Lys Tyr Ala Ser Gln Ser Ile Ser
            180                 185                 190
Gly Ile Pro Ser Arg Phe Ser Gly Ser Gly Ser Gly Ser Asp Phe Thr
        195                 200                 205
Leu Ser Ile Asn Ser Val Glu Pro Glu Asp Val Gly Val Tyr Tyr Cys
    210                 215                 220
Gln Asn Gly His Ser Phe Pro Pro Thr Phe Gly Gly Gly Thr Lys Leu
225                 230                 235                 240
Glu Ile Lys
```

<210> SEQ ID NO 82
<211> LENGTH: 247
<212> TYPE: PRT
<213> ORGANISM: Artificial Sequence
<220> FEATURE:
<223> OTHER INFORMATION: GD2-CAR binding domain

<400> SEQUENCE: 82

```
Ala Gln Pro Ala Gln Val Gln Val Lys Glu Ser Gly Pro Gly Leu Val
 1               5                  10                  15
Ala Pro Ser Gln Ser Leu Ser Ile Thr Cys Thr Val Ser Gly Phe Ser
            20                  25                  30
Leu Thr Asn Tyr Gly Val His Trp Val Arg Gln Pro Pro Gly Lys Gly
        35                  40                  45
Leu Glu Trp Leu Gly Val Ile Trp Ala Gly Gly Ser Thr Asn Tyr Asn
    50                  55                  60
Ser Ala Leu Met Ser Arg Leu Ser Ile Ser Lys Asp Asn Ser Lys Ser
65                  70                  75                  80
Gln Val Phe Leu Lys Met Asn Ser Leu Gln Thr Asp Asp Thr Ala Met
                85                  90                  95
```

```
Tyr Tyr Cys Ala Ser Arg Gly Gly Asn Tyr Gly Tyr Ala Leu Asp Tyr
                100                 105                 110

Trp Gly Gln Gly Thr Ser Val Thr Val Ser Ser Gly Gly Gly Ser
        115                 120                 125

Gly Gly Gly Gly Ser Gly Gly Gly Ser Gly Gly Gly Ser Ser
    130                 135                 140

Ile Val Met Thr Gln Thr Pro Lys Phe Leu Leu Val Ser Ala Gly Asp
145                 150                 155                 160

Arg Val Thr Ile Thr Cys Lys Ala Ser Gln Ser Val Ser Asn Asp Val
                165                 170                 175

Ala Trp Tyr Gln Gln Lys Pro Gly Gln Ser Pro Lys Leu Leu Ile Tyr
            180                 185                 190

Ser Ala Ser Asn Arg Tyr Thr Gly Val Pro Asp Arg Phe Thr Gly Ser
        195                 200                 205

Gly Tyr Gly Thr Asp Phe Thr Phe Thr Ile Ser Thr Val Gln Ala Glu
    210                 215                 220

Asp Leu Ala Val Tyr Phe Cys Gln Gln Asp Tyr Ser Ser Leu Gly Gly
225                 230                 235                 240

Gly Thr Lys Leu Glu Ile Lys
                245

<210> SEQ ID NO 83
<211> LENGTH: 261
<212> TYPE: PRT
<213> ORGANISM: Artificial Sequence
<220> FEATURE:
<223> OTHER INFORMATION: FAP-CAR binding domain

<400> SEQUENCE: 83

Ala Gln Pro Ala Gln Val Gln Leu Gln Gln Ser Gly Pro Glu Leu Val
1               5                   10                  15

Lys Pro Gly Ala Ser Val Lys Met Ser Cys Lys Thr Ser Arg Tyr Thr
            20                  25                  30

Phe Thr Glu Tyr Thr Ile His Trp Val Arg Gln Ser His Gly Lys Ser
        35                  40                  45

Leu Glu Trp Ile Gly Gly Ile Asn Pro Asn Asn Gly Ile Pro Asn Tyr
    50                  55                  60

Asn Gln Lys Phe Lys Gly Arg Ala Thr Leu Thr Val Gly Lys Ser Ser
65                  70                  75                  80

Ser Thr Ala Tyr Met Glu Leu Arg Ser Leu Thr Ser Glu Asp Ser Ala
                85                  90                  95

Val Tyr Phe Cys Ala Arg Arg Ile Ala Tyr Gly Tyr Asp Glu Gly
            100                 105                 110

His Ala Met Asp Tyr Trp Gly Gln Gly Thr Ser Val Thr Val Ser Ser
        115                 120                 125

Gly Gly Gly Gly Ser Gly Gly Gly Gly Ser Gly Gly Gly Ser Gly
    130                 135                 140

Gly Gly Gly Ser Asp Ile Val Met Thr Gln Ser Pro Ser Ser Leu Ala
145                 150                 155                 160

Val Ser Val Gly Glu Lys Val Thr Met Ser Cys Lys Ser Ser Gln Ser
                165                 170                 175

Leu Leu Tyr Ser Arg Asn Gln Lys Asn Tyr Leu Ala Trp Phe Gln Gln
            180                 185                 190

Lys Pro Gly Gln Ser Pro Lys Leu Leu Ile Phe Trp Ala Ser Thr Arg
        195                 200                 205
```

-continued

Glu Ser Gly Val Pro Asp Arg Phe Thr Gly Ser Gly Phe Gly Thr Asp
210                 215                 220

Phe Asn Leu Thr Ile Ser Ser Val Gln Ala Glu Asp Leu Ala Val Tyr
225                 230                 235                 240

Asp Cys Gln Gln Tyr Phe Ser Tyr Pro Leu Thr Phe Gly Ala Gly Thr
            245                 250                 255

Lys Leu Glu Leu Arg
            260

<210> SEQ ID NO 84
<211> LENGTH: 261
<212> TYPE: PRT
<213> ORGANISM: Artificial Sequence
<220> FEATURE:
<223> OTHER INFORMATION: CSPG-4-CAR binding domain

<400> SEQUENCE: 84

Ala Gln Pro Ala Asp Ile Glu Leu Thr Gln Ser Pro Lys Phe Met Ser
1               5                   10                  15

Thr Ser Val Gly Asp Arg Val Ser Val Thr Cys Lys Ala Ser Gln Asn
            20                  25                  30

Val Asp Thr Asn Val Ala Trp Tyr Gln Gln Lys Pro Gly Gln Ser Pro
        35                  40                  45

Glu Pro Leu Leu Phe Ser Ala Ser Tyr Arg Tyr Thr Gly Val Pro Asp
50                  55                  60

Arg Phe Thr Gly Ser Gly Ser Gly Thr Asp Phe Thr Leu Thr Ile Ser
65                  70                  75                  80

Asn Val Gln Ser Glu Asp Leu Ala Glu Tyr Phe Cys Gln Gln Tyr Asn
                85                  90                  95

Ser Tyr Pro Leu Thr Phe Gly Gly Gly Thr Lys Leu Glu Ile Lys Arg
            100                 105                 110

Ala Ala Ala Glu Gly Gly Gly Gly Ser Gly Gly Gly Gly Ser Gly Gly
        115                 120                 125

Gly Gly Ser Gly Gly Gly Gly Ser Ala Met Ala Gln Val Lys Leu Gln
    130                 135                 140

Gln Ser Gly Gly Gly Leu Val Gln Pro Gly Gly Ser Met Lys Leu Ser
145                 150                 155                 160

Cys Val Val Ser Gly Phe Thr Phe Ser Asn Tyr Trp Met Asn Trp Val
                165                 170                 175

Arg Gln Ser Pro Glu Lys Gly Leu Glu Trp Ile Ala Glu Ile Arg Leu
            180                 185                 190

Lys Ser Asn Asn Phe Gly Arg Tyr Tyr Ala Glu Ser Val Lys Gly Arg
        195                 200                 205

Phe Thr Ile Ser Arg Asp Asp Ser Lys Ser Ser Ala Tyr Leu Gln Met
    210                 215                 220

Ile Asn Leu Arg Ala Glu Asp Thr Gly Ile Tyr Tyr Cys Thr Ser Tyr
225                 230                 235                 240

Gly Asn Tyr Val Gly His Tyr Phe Asp His Trp Gly Gln Gly Thr Thr
                245                 250                 255

Val Thr Val Ser Ser
            260

<210> SEQ ID NO 85
<211> LENGTH: 250
<212> TYPE: PRT
<213> ORGANISM: Artificial Sequence
<220> FEATURE:

<223> OTHER INFORMATION: CD20-CAR binding domain

<400> SEQUENCE: 85

```
Ala Gln Pro Ala Met Ala Gln Val Lys Leu Gln Glu Ser Gly Ala Glu
1               5                   10                  15
Leu Val Lys Pro Gly Ala Ser Val Lys Met Ser Cys Lys Ala Ser Gly
            20                  25                  30
Tyr Thr Phe Thr Ser Tyr Asn Met His Trp Val Lys Gln Thr Pro Gly
        35                  40                  45
Gln Gly Leu Glu Trp Ile Gly Ala Ile Tyr Pro Gly Asn Gly Asp Thr
    50                  55                  60
Ser Tyr Asn Gln Lys Phe Lys Gly Lys Ala Thr Leu Thr Ala Asp Lys
65                  70                  75                  80
Ser Ser Ser Thr Ala Tyr Met Gln Leu Ser Ser Leu Thr Ser Glu Asp
                85                  90                  95
Ser Ala Asp Tyr Tyr Cys Ala Arg Ser Asn Tyr Tyr Gly Ser Ser Tyr
            100                 105                 110
Trp Phe Phe Asp Val Trp Gly Gln Gly Thr Thr Val Thr Val Ser Ser
        115                 120                 125
Gly Gly Gly Gly Ser Gly Gly Gly Gly Ser Gly Gly Gly Gly Ser Asp
    130                 135                 140
Ile Glu Leu Thr Gln Ser Pro Thr Ile Leu Ser Ala Ser Pro Gly Glu
145                 150                 155                 160
Lys Val Thr Met Thr Cys Arg Ala Ser Ser Ser Val Asn Tyr Met Asp
                165                 170                 175
Trp Tyr Gln Lys Lys Pro Gly Ser Ser Pro Lys Pro Trp Ile Tyr Ala
            180                 185                 190
Thr Ser Asn Leu Ala Ser Gly Val Pro Ala Arg Phe Ser Gly Ser Gly
        195                 200                 205
Ser Gly Thr Ser Tyr Ser Leu Thr Ile Ser Arg Val Glu Ala Glu Asp
    210                 215                 220
Ala Ala Thr Tyr Tyr Cys Gln Gln Trp Ser Phe Asn Pro Pro Thr Phe
225                 230                 235                 240
Gly Gly Gly Thr Lys Leu Glu Ile Lys Arg
                245                 250
```

FC-EPSILON CAR

This application claims the benefit of priority to U.S. patent application with the Ser. No. 17/056,385, which was filed Nov. 17, 2020, which is a 371 application of International application with the serial number PCT/US2019/033407, which was filed May 21, 2019, which claims priority to U.S. patent application with the Ser. No. 62/674,936, which was filed May 22, 2018.

SEQUENCE LISTING

The content of the ASCII text file of the sequence listing named 104077-0004US2_03282002_ST25, which is 206 kb in size was created on Mar. 28, 2022 and electronically submitted via EFS-Web along with the present application is incorporated by reference in its entirety.

FIELD OF THE INVENTION

The field of the invention is recombinant nucleic acids and cells containing same to generate genetically modified cells that express a chimeric antigen receptor (CAR), and particularly modified NK and NK-92 cells expressing a CAR having an Fc epsilon receptor gamma (FcεRIγ) signaling domain.

BACKGROUND OF THE INVENTION

Natural killer (NK) cells are cytotoxic lymphocytes that constitute a significant component of the innate immune system. In most cases, NK cells represent about 10-15% of circulating lymphocytes, and bind and kill targeted cells, including virus-infected cells and many malignant cells. NK cell killing is non-specific with regard to particular antigens and can occur without prior immune sensitization. Killing of targeted cells is typically mediated by cytolytic proteins, including perforin, granzyme, and granulysin.

Autologous NK cells have been used as therapeutic entities. To that end, NK cells are isolated from the peripheral blood lymphocyte fraction of whole blood, expanded in cell culture to obtain sufficient numbers of cells, and then re-infused into a subject. Autologous NK cells have shown in at least some cases moderate effectiveness in both ex vivo therapy and in vivo treatment. However, isolation and growth of autologous NK cell is time and cost intensive. Moreover, autologous NK cell therapy is further limited by the fact that not all NK cells are cytolytic.

At least some of these difficulties can be overcome by use of NK-92 cells, which are a cytolytic cancer cell line which was discovered in the blood of a subject suffering from a non-Hodgkins lymphoma and then immortalized in vitro (Gong et al., *Leukemia* 8:652-658 (1994)). While NK-92 cells are NK cell derivatives, NK-92 cells lack the major of inhibitory receptors that are otherwise displayed by normal NK cells, and retain the majority of the activating receptors. NK-92 cells do not, however, attack normal cells nor do they elicit an unacceptable immune rejection response in humans. Due to these desirable characteristics, NK-92 cells were characterized in detail and explored as therapeutic agent in the treatment of certain cancers as is described, for example, in WO 1998/049268 or US 2002/068044.

Phenotypic changes distinguishing a tumor cell from normal cells derived from the same tissue are often associated with one or more changes in the expression of specific gene products, including the loss of normal cell surface components or the gain of others (i.e., antigens not detectable in corresponding normal, non-cancerous tissue). The antigens which are expressed in neoplastic or tumor cells, but not in normal cells, or which are expressed in neoplastic cells at levels substantially above those found in normal cells, have been termed "tumor-specific antigens" or "tumor-associated antigens." Such tumor-specific antigens may serve as markers for tumor phenotype. Tumor-specific antigens include cancer/testis-specific antigen (e.g. MAGE, BAGE, GAGE, PRAME and NY-ESO-1), melanocyte differentiation antigens (e.g. tyrosinase, Melan-A/MART, gp100, TRP-1 and TRP-2), mutated or aberrantly expressed antigens (e.g. MUM-1, CDK4, beta-catenin, gp100-in4, p15 and N-acetylglucos-aminyltransferase V), and antigens that are expressed at higher levels in tumors (e.g., CD19 and CD20).

Tumor-specific antigens have been used as targets for cancer immunotherapies. One such therapy utilizes chimeric antigen receptors (CARs) expressed on the surface of immune cells, including T cells and NK cells, to improve cytotoxicity against cancer cells. CARs comprise a single-chain variable fragment (scFv) linked to at least one intracellular signaling domain. The scFv recognizes and binds an antigen on the target cell (e.g., a cancer cell) and triggers effector cell activation. The signaling domains contain immunoreceptor tyrosine-based activation domains (ITAMs) that are important for intracellular signaling by the receptor.

The first generation of CARs used in T-cells contained one cytoplasmic signaling domain. For example, one version of a first-generation CAR in T-cells included a signaling domain from the Fc epsilon receptor gamma (FcεRIγ) which contained one ITAM, while another version contained the signaling domain from CD3ζ which contained three ITAMs. In vivo and in vitro studies showed that the CD3ζ CAR T-cells were more efficient at tumor eradication than FcεRIγ CAR T-cells (e.g., Haynes, et al. 2001, *J. Immunology* 166:182-187; Cartellieri, et al. 2010, *J Biomed and Biotech*, Vol. 2010, Article ID 956304). Additional studies then revealed that certain costimulatory signals were required for full activation and proliferation of such recombinant T-cells, and second and third generation CARs combined multiple signaling domains in to a single CAR to enhance efficacy of the recombinant CAR T-cells. Due to their less desirable philological effects in the tested T-cells, first generation CARs and the FcεRIγ signaling domains were largely discarded in favor of the new, more efficient CARs using CD3ζ in combination with one or more additional signaling domains (e.g., Hermanson and Kaufman 2015, *Frontiers in Immunol.*, Vol. 6, Article 195).

More recently, selected CARs have also been expressed in NK cells. For example, CAR-modified NK-92 cells have used first generation CARs with only a CD3ζ intracellular signaling domain. Several antigens have been targeted by these first generation CAR-NK cells, including CD19 and CD20 for B cell lymphoma, ErbB2 for breast, ovarian, and squamous cell carcinoma, GD2 for neuroblastoma, and CD138 for multiple myeloma. Second generation CAR-NK cells from the NK-92 line have also been created for several antigens, including EpCAM for multiple carcinomas HLA-A2 EBNA3 complex for Epstein-Barr virus, CS1 for multiple myeloma, and ErbB2 for HER2 positive epithelial cancers. The most common intracellular costimulatory domain used alongside CD3ζ in second generation NK-92 CARs is CD28. However, the potential effect of the CD28 domain is unclear since NK cells do not naturally express CD28. Additional second generation CARs have incorporated the 4-1BB intracellular signaling domain along with CD3ζ to improve NK cell persistence. Others compared functionality of different intracellular domains using an ErbB2 scFv fused with CD3ζ alone, CD28 and CD3ζ, or 4-1BB and CD3ζ tested against breast cancer cells. They found that both of the second generation constructs improved killing compared to the first generation CARs and the CD28 and CD3ζ had 65% target lysis, the 4-1BB and CD3ζ lysed 62%, and CD3ζ alone killed 51% of targets. 4-1BB and CD28 intracellular domains were also compared in a recent study using anti-CD19 CARs expressed on NK-92 cells for B cell malignances. Still others found that CD3ζ/4-1BB constructs were less effective than CD3ζ/CD28 in cell killing and cytokine production, highlighting differential effects of CD28 and 4-1BB costimulatory domains.

Third generation NK-92 CARs were constructed of an anti-CD5 scFv with CD3ζ, CD28, and 4-1BB intracellular signaling domains and demonstrated specific and potent anti-tumor activity against a variety of T-cell leukemia and lymphoma cell lines and primary tumor cells. Such cells were also able to inhibit disease progression in xenograft mouse models of T cell Acute lymphoblastic leukemia (ALL) cell lines as well as primary tumor cells (*Transl Res.* 2017 September; 187: 32-43). In further examples, WO 2016/201304 and WO 2018/076391 teach use of third generation CD3ζ CARs expressed in NK cells and NK-92 cells.

Autologous NK cells and NK-92 cells require exogenous IL-2 as a survival factor and enhancer of cytotoxic potential. Unfortunately, systemic administration of IL-2 is often associated with significant undesirable side effects and toxicity. To overcome such issues, the cells can be cultivated and expanded in vitro prior to administration to a patient. While IL-2 will allow generation of sufficient quantities of NK cells or NK-92 cells, use of exogenous IL-2 in large scale production of NK cells is typically cost-prohibitive. The requirement for exogenous IL-2 was resolved by recombinant expression of IL-2 confined to the endoplasmic reticulum from a retroviral vector (see *Exp Hematol.* 2005 February; 33(2):159-64). Such approach eliminated the requirement for exogenous IL-2. However, retroviral transfection efficiency is often less than desirable and will be even more inefficient where multiple recombinant genes are to be expressed.

In addition, NK cells and particularly NK-92 cells are often difficult to genetically modify as evidenced by numerous failures to engineer NK-92 cells to express an Fc receptor. Such difficulties are further compounded where NK-92 cells are transfected with multiple recombinant genes or relatively large recombinant nucleic acid payload for heterologous expression. Additionally, NK-92 cells also exhibit a significant lack of predictability with respect to recombinant expression of exogenous proteins (e.g., CD16). On a functional level, most if not all CAR NK-92 cells require a relatively high effector to target cell ratio, likely due to relatively low expression of the CAR construct. Moreover, such CAR NK-92 cells will also experience a fast decline in cytotoxicity over time, thus rendering such cells clinically less attractive.

Therefore, even though numerous recombinant NK-92 cells are known in the art, all or almost all of them suffer from various difficulties. Consequently, there remains a need for CAR-expressing NK-92 cells that express a high-activity CAR in significant quantities with attendant persistent cytotoxicity, and that are easily cultivated in a simple and effective manner.

SUMMARY OF THE INVENTION

The inventors have discovered that NK-92 cells can be efficiently transfected with a recombinant nucleic acid to express an FcεRIγ-containing CAR. Unexpectedly, CARs with a FcεRIγ signaling domain significantly increased expression levels of the CAR and further conveyed extended cytotoxicity over time. Contemplated recombinant nucleic acids that encode a CAR are preferably in a tricistronic arrangement that also includes a sequence portion that encodes CD16 or CD16 variant, and/or IL-2 or an IL-2 variant. Advantageously, such recombinant nucleic acids not only provide an efficient manner of selecting transfected cells (as the IL-2 not only imparts autocrine growth stimulation but also acts as a selection marker for the co-expressed proteins), but also yield CAR NK cells with superior cytolytic activity (e.g., at a relatively low effector to target cell ratio as compared to other constructs) and high levels of expression of the CD16 and the FcεRIγ-containing CAR.

Therefore, in one aspect of the inventive subject matter, the inventors contemplate a genetically modified NK cell that recombinantly expresses a cytokine, CD16, and a membrane bound chimeric antigen receptor (CAR). The CAR will typically comprise in a single polypeptide chain (i) an extracellular binding domain, (ii) a hinge domain, (iii) a transmembrane domain, and (iv) a FcεRIγ signaling domain (e.g., having the amino acid sequence of SEQ ID NO:1).

In many embodiments, the NK cell is an NK-92 cell, and/or the recombinantly expressed cytokine is or comprises IL-2 or IL-15 (which may further include an endoplasmic retention sequence). In further embodiments, the CD16 may be a high-affinity CD16 variant (e.g., $CD16_{158V}$).

Preferably, but not necessarily, the extracellular binding domain will comprise a scFv that may specifically bind to a tumor-specific antigen (e.g., CD19, CD20, NKG2D ligands, CS1, GD2, CD138, EpCAM, HER-2, EBNA3C, GPA7, CD244, CA-125, MUC-1, ETA, MAGE, CEA, CD52, CD30, MUC5AC, c-Met, EGFR, FAP, WT-1, PSMA, NY-ESO1, CSPG-4, IGF1-R, Flt-3, CD276, CD123, PD-L1, BCMA, or CD33), a tumor associated antigen, or a patient- and tumor-specific antigen, or that may specifically bind to a virus-specific antigen (e.g., antigen of an HIV virus, an HPV virus, an RSV virus, an influenza virus, an ebolavirus, or an HCV virus).

In some embodiments, the cytokine, the CD16, and the CAR are expressed from a tricistronic recombinant nucleic acid, while in other embodiments the cytokine and/or the CD16 is expressed from a recombinant nucleic acid that is integrated into the genome of the NK cell.

Therefore, the inventors also contemplate a recombinant nucleic acid that includes a first sequence portion encoding a cytokine, a second sequence portion encoding a CD16, and a third sequence portion encoding a chimeric antigen receptor (CAR) that comprises in a single polypeptide chain an extracellular binding domain, a hinge domain, a transmembrane domain, and an FcεRIγ signaling domain. Most typically, the first, the second, and the third sequence portions are on the same nucleic acid.

While in some embodiments the nucleic acid is a tricistronic RNA, in other embodiments the nucleic acid is a tricistronic DNA.

Moreover, it is typically preferred that the cytokine is IL-2 or IL15 (which may or may not comprise an endoplasmic retention sequence), that the CD16 is a high-affinity CD16 variant having a 158V mutation, and/or that the extracellular binding domain comprises a scFv. As noted before, the extracellular binding domain may specifically bind to a tumor-specific antigen, a tumor associated antigen, or a patient- and tumor-specific antigen, or the extracellular binding domain may specifically bind to a virus-specific antigen.

In further contemplated aspects, the hinge domain and/or the transmembrane domain comprise a CD8 hinge domain and/or a CD28 transmembrane domain, while the FcεRIγ signaling domain may have a nucleic acid sequence of SEQ ID NO:2.

In still further aspects of the inventive subject matter, the inventors also contemplate a recombinant cell comprising the recombinant nucleic acid described above and herein. Where the nucleic acid is prepared and/or amplified, the recombinant cell may be a bacterial cell. On the other hand, where the recombinant nucleic acid is to be expressed, the cell will typically be an autologous NK cell or an NK cell (which may also be an NK-92 cell that is optionally genetically modified).

Consequently, the inventors also contemplate a method of treating cancer in a patient in need thereof. In such method, a therapeutically effective amount of any one of the genetically modified NK cells is administered to the patient, thereby treating the cancer. In addition, and where desired, contemplated methods may include a further step of administering at least one additional therapeutic entity selected from the group consisting of a viral cancer vaccine, a bacterial cancer vaccine, a yeast cancer vaccine, N-803, an antibody, a stem cell transplant, and a tumor targeted cytokine.

Among other cancers, contemplated cancers include leukemia, acute lymphocytic leukemia, acute myelocytic leukemia, chronic leukemias, chronic myelocytic (granulocytic) leukemia, chronic lymphocytic leukemia, polycythemia vera, lymphomas, Hodgkin's disease, non-Hodgkin's disease, multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Likewise, the inventors also contemplate a method of treating a viral infection in a patient in need thereof. In such method, a therapeutically effective amount of any one of the genetically modified NK cells is administered to the patient, thereby treating the viral infection. Where desired or needed, an antiviral drug may also be administered.

Regardless of the type of treatment, it is generally contemplated that $1 \times 10^8$ to about $1 \times 10^{11}$ cells per m2 of body surface area of the patient are administered to the patient. Viewed from a different perspective, use of a genetically modified NK cell as presented herein is contemplated in the treatment of cancer or a viral infection.

Various objects, features, aspects and advantages of the inventive subject matter will become more apparent from the following detailed description of preferred embodiments along with the accompanying drawing figures in which like numerals represent like components.

DETAILED DESCRIPTION OF THE INVENTION

Figure 1:
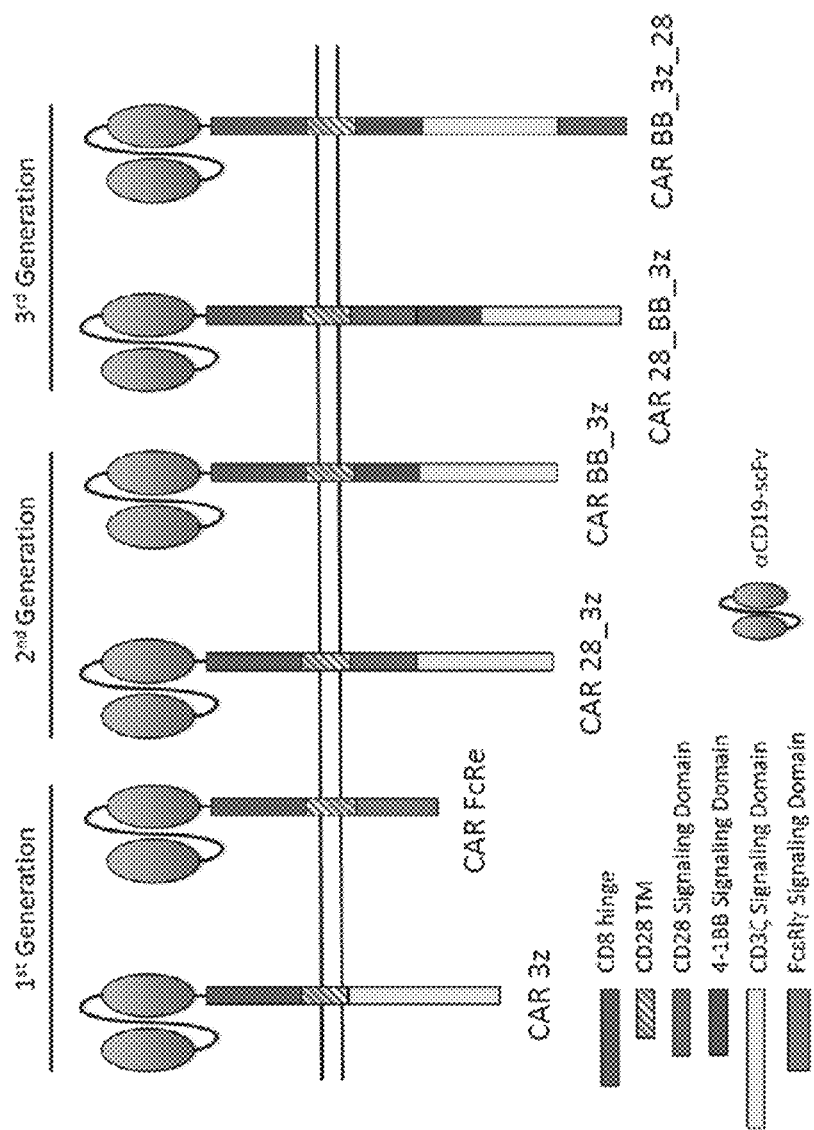
FIG. 1 is a schematic representation of exemplary CD19-CARs tested. All of the CD19-CAR variants contained an extracellular domain comprising an anti-CD19 scFv region (αCD19-scFv), a hinge region from CD8 (CD8 hinge), and a transmembrane domain from CD28 (CD28 TM). The intracellular domains of the CD19CARs were varied as indicated.

The inventors have unexpectedly discovered that CAR mediated cytotoxicity and CAR expression in recombinant NK cells (e.g. NK-92 cells) is substantially increased where the recombinant CAR includes an FcεRIγ signaling domain as is described in more detail below. The finding that a CAR with an FcεRIγ signaling domain has superior properties in NK cells is especially unexpected as such CARs in T cells have performed relatively poorly as compared to CARs that had a CD3ζ, a 4-1BB, or a CD28 signaling domain and optionally additional signaling domains as commonly found in second and third generation CARs.

Therefore, in some embodiments recombinant nucleic acids are contemplated that encode a CAR with an FcεRIγ signaling domain, preferably but not necessarily in a tricistronic arrangement that also includes a sequence portion that encodes CD16 or a CD16 variant, and/or IL-2 or an IL-2 variant. In still further advantageous aspects of the inventive subject matter, such recombinant nucleic acid will not only provide an efficient manner of selecting transfected cells (as the IL-2 not only imparts autocrine growth stimulation) but also acts as a selection marker for the co-expressed proteins.

Consequently, the inventive subject matter is directed to genetically modified NK cells, NK-92 cells, and derivatives thereof that express a chimeric antigen receptor (CAR) on the cell surface where the CAR preferably comprises an intracellular signaling domain from the Fc epsilon receptor gamma (FcεRIγ). For example, the cytoplasmic domain of FcεRIγ may have an amino acid sequence having at least 95% sequence identity to SEQ ID NO:1, or comprises, consists of, or essentially consists of an amino acid sequence having the sequence as noted in SEQ ID NO:1. In some embodiments, the cytoplasmic domain of FcεRIγ is encoded by a nucleic acid having at least 95% sequence identity to SEQ ID NO:2. Contemplated recombinant cells may further express various other proteins, including one or more cytokines and CD16. As will be readily appreciated, the CAR and/or other proteins may be transiently expressed by the recombinant cell, or stably expressed.

In some embodiments, the CAR comprises a hinge region from CD8 and/or in some embodiments, the CAR comprises a transmembrane domain from CD28 having an amino acid sequence as in SEQ ID NO:6 (encoded by a nucleic acid as in SEQ ID NO:7). The full length amino acid sequence of CD28 is shown in SEQ ID NO:23. In further embodiments, the recombinant cell is genetically modified with a nucleic acid having a sequence of SEQ ID NO:9 that encodes a hybrid protein having a sequence of SEQ ID NO:8 comprising a CD8 hinge region that is coupled to a CD28 transmembrane domain that is coupled to an FcεRIγ signaling domain. As will be appreciated, addition of a binding domain to the hinge region will form a functional CAR. For example, binding domain targets or specifically may bind a tumor-associated antigen, and suitable antigens include CD19, CD20, NKG2D ligands, CS1, GD2, CD138, EpCAM, HER-2, EBNA3C, GPA7, CD244, CA-125, MUC-1, ETA, MAGE, CEA, CD52, CD30, MUC5AC, c-Met, EGFR, FAP, WT-1, PSMA, NY-ESO1, CSPG-4, IGF1-R, Flt-3, CD276, CD123, PD-L1, BCMA, and CD33.

In some embodiments, the nucleic acid construct further comprises a (inducible) promoter that promotes transcription of the nucleic acid sequences. Preferably, but not necessarily, the nucleic acid construct is a multi-cistronic vector or RNA comprising one or more Internal Ribosome Entry Site (IRES) to allow for initiation of translation from an internal region of an mRNA transcribed from the nucleic acid sequences. Alternatively, or additionally, the nucleic acid construct comprises a sequence that encodes a 2A peptide, such as a T2A, P2A, E2A, or F2A peptide, in order to produce equimolar levels of polypeptides encoded by the same mRNA. In some embodiments, the nucleic acid construct further comprises a nucleic acid sequence that encodes an antigen binding protein (ABP). In some embodiments, the ABP is an scFv or a codon optimized scFv. In some embodiments, the ABP specifically binds an antigen expressed by a tumor cell. In some embodiments, the ABP is part of a chimeric antigen receptor (CAR). In further embodiments, the construct comprises a nucleic acid that encodes a cytokine, such IL-2 or IL-15, which may be targeted to the endoplasmic reticulum. In some embodiments, the NK-92 cell or cell line is also genetically modified to express CD16 on the cell surface. In one embodiment, the NK-92 cell or cell line is genetically modified to express a high affinity CD16 (F158V) on the cell surface.

With respect to suitable NK cells, it should be noted that all NK cells are deemed suitable for use herein and therefore include primary NK cells (preserved, expanded, and/or fresh cells), secondary NK cells that have been immortalized, autologous or heterologous NK cells (banked, preserved, fresh, etc.), and modified NK cells as described in more detail below. In some embodiments, it is preferred that the NK cells are NK-92 cells. The NK-92 cell line is a unique cell line that was discovered to proliferate in the presence of interleukin 2 (IL-2) (see e.g., Gong et al., Leukemia 8:652-658 (1994)). NK-92 cells are cancerous NK cells with broad anti-tumor cytotoxicity and predictable yield after expansion in suitable culture media. Advantageously, NK-92 cells have high cytolytic activity against a variety of cancers.

The original NK-92 cell line expressed the CD56bright, CD2, CD7, CD11a, CD28, CD45, and CD54 surface markers and did not display the CD1, CD3, CD4, CD5, CD8, CD10, CD14, CD16, CD19, CD20, CD23, and CD34 markers. Growth of such NK-92 cells in culture is dependent upon the presence of interleukin 2 (e.g., rIL-2), with a dose as low as 1 IU/mL being sufficient to maintain proliferation. IL-7 and IL-12 do not support long-term growth, nor have various other cytokines tested, including IL-la, IL-6, tumor necrosis factor α, interferon α, and interferon γ. Compared to primary NK cells, NK-92 typically have a high cytotoxicity even at relatively low effector:target (E:T) ratios, e.g. 1:1. Representative NK-92 cells are deposited with the American Type Culture Collection (ATCC), designation CRL-2407.

Therefore, suitable NK cells may have one or more modified KIR that are mutated such as to reduce or abolish interaction with MHC class I molecules. Of course, it should be noted that one or more KIRs may also be deleted or expression may be suppressed (e.g., via miRNA, siRNA, etc.). Most typically, more than one KIR will be mutated, deleted, or silenced, and especially contemplated KIR include those with two or three domains, with short or long cytoplasmic tail. Viewed from a different perspective, modified, silenced, or deleted KIRs will include KIR2DL1, KIR2DL2, KIR2DL3, KIR2DL4, KIR2DL5A, KIR2DL5B, KIR2DS1, KIR2DS2, KIR2DS3, KIR2DS4, KIR2DS5, KIR3DL1, KIR3DL2, KIR3DL3, and KIR3DS1. Such modified cells may be prepared using protocols well known in the art. Alternatively, such cells may also be commercially obtained from NantKwest (see URL www.nantkwest.com) as aNK cells ('activated natural killer cells). Such cells may then be additionally genetically modified to a CAR as further described in more detail below.

In another aspect of the inventive subject matter, the genetically engineered NK cell may also be an NK-92 derivative that is modified to express the high-affinity Fcγ receptor (CD16). Sequences for high-affinity variants of the Fcγ receptor are well known in the art (see e.g., Blood 2009 113:3716-3725), and all manners of generating and expression are deemed suitable for use herein. Expression of such receptor is believed to allow specific targeting of tumor cells using antibodies that are specific to a patient's tumor cells (e.g., neoepitopes), a particular tumor type (e.g., her2neu, PSA, PSMA, etc.), or that are associated with cancer (e.g., CEA-CAM). Advantageously, such antibodies are commercially available and can be used in conjunction with the cells (e.g., bound to the Fcγ receptor). Alternatively, such cells may also be commercially obtained from NantKwest as haNK cells. Such cells may then be additionally genetically modified to a CAR as further described in more detail below.

Genetic modification of the NK cells contemplated herein can be performed in numerous manners, and all known manners are deemed suitable for use hereon. Moreover, it should be recognized that NK cells can be transfected with DNA or RNA, and the particular choice of transfection will at least in part depend on the type of desired recombinant cell and transfection efficiency. For example, where it is desired that NK cells are stably transfected, linearized DNA may be introduced into the cells for integration into the genome. On the other hand, where transient transfection is desired, circular DNA or linear RNA (e.g., mRNA with polyA+ tail) may be used.

For example, where the NK cell is an autologous NK cell or an NK-92 cell it is contemplated that the recombinant nucleic acid will include a segment that encodes a CAR that includes FcεRIγ signaling domain, and preferably also a segment that encodes a cytokine to provide autocrine growth stimulation (e.g., IL-2, IL-2 that is modified with an ER retention sequence, IL-15, or IL-15 that is modified with an ER retention sequence) and/or a segment that encodes a CD16 or high affinity $CD16^{158V}$. As will be readily appreciated, inclusion of a cytokine that provides autocrine growth stimulation will render the modified recombinant independent of exogenous cytokine addition, which will render large scale production of such cells economically feasible. Likewise, where the modified recombinant also expresses CD16 or a high affinity $CD16^{158V}$, such cells will have further enhanced ADCC characteristics and with that further improved targeted cytotoxicity.

Of course, it should be recognized that the recombinant nucleic acid that encodes that cytokine and/or the CD16 or high affinity $CD16^{158V}$ can be integrated in to the genome of the NK cell, or can be supplied as an extrachromosomal unit (which may be a linear or circular DNA, or a linear RNA, virally delivered or via chemical, mechanical, or electrical transfection). For example, recombinant NK-92 cells expressing IL-2ER and CD16158V are known as haNK cells (Oncotarget 2016 Dec. 27; 7(52): 86359-86373) and can be transfected with a recombinant nucleic acid that includes a segment that encodes a CAR that includes FcεRIγ signaling domain. Once more, such recombinant nucleic acid may comprise further segments that may encode additional immunotherapeutic proteins, such as N-803, TxM-type compounds, IL-8 traps, TGF-β traps, etc. Likewise, NK-92 cells may already be transfected with a cDNA that encodes IL-2 (e.g., NK-92MI, ATCC CRL-2408). Such cells can then be further transfected with a recombinant nucleic acid that includes a segment that encodes a CAR that includes FcεRIγ signaling domain along with a segment that encodes a CD16 or high affinity $CD16^{158V}$.

On the other hand, (autologous, fresh, cultivated, or previously frozen) NK cells or NK-92 cells may also be transfected with a recombinant nucleic acid that includes a segment that encodes a CAR with a FcεRIγ signaling domain, a segment that encodes a cytokine to provide autocrine growth stimulation (e.g., IL-2, IL-2 that is modified with an ER retention sequence, IL-15, or IL-15 that is modified with an ER retention sequence) and a segment that encodes a CD16 (SEQ ID NO:34) or high affinity $CD16^{158V}$ (SEQ ID NO:35, encoded by SEQ ID NO:36). Most typically, such recombinant nucleic acid will be arranged as a tricistronic construct. As noted before, such constructed can be an extrachromosomal circular plasmid, a linear DNA (which may be integrated into the genome of the NK cell), or a linear RNA. Such nucleic acids will typically be transfected into the cells in a manner well known in the art (e.g., electroporation, lipofection, ballistic gene transfer, etc.). Similarly, the nucleic acid may be delivered to the cell via a recombinant virus. Therefore, NK cells suitable for use herein include NK-92 cells (which may be transfected with a tricistronic construct encoding a CAR, a CD16 or variant thereof, and a cytokine or variant thereof), a genetically modified NK cell or NK-92 cell that expresses a CD16 or variant thereof or a cytokine or variant thereof (which may be transfected with a nucleic acid encoding a CAR and a CD16 or variant thereof or a cytokine or variant thereof), and a genetically modified NK cell or NK-92 cell that expresses a CD16 or variant thereof and a cytokine or variant thereof (which may be transfected with a nucleic acid encoding a CAR).

In preferred embodiments, it should therefore be noted that the genetically modified NK cell (especially where the cell expresses a CAR and CD16 or variant thereof) will exhibit three distinct modes of cell killing: General cytotoxicity which is mediated by activating receptors (e.g., an NKG2D receptor), ADCC which is mediated by antibodies bound to a target cell, and CAR mediated cytotoxicity.

Consequently, it should be appreciated that the manner of transfection will at least in part depend on the type of nucleic acid employed. Therefore, viral transfection, chemical transfection, mechanical transfection methods are all deemed suitable for use herein. For example, in one embodiment, the vectors described herein are transient expression vectors. Exogenous transgenes introduced using such vectors are not integrated in the nuclear genome of the cell; therefore, in the absence of vector replication, the foreign transgenes will be degraded or diluted over time.

In another embodiment, the vectors described herein allow for stable transfection of cells. In one embodiment, the vector allows incorporation of the transgene(s) into the genome of the cell. Preferably, such vectors have a positive selection marker and suitable positive selection markers include any genes that allow the cell to grow under conditions that would kill a cell not expressing the gene. Non-limiting examples include antibiotic resistance, e.g. geneticin (Neo gene from Tn5).

Alternatively, or additionally, the vector is a plasmid vector. In one embodiment, the vector is a viral vector. As would be understood by one of skill in the art, any suitable vector can be used, and suitable vectors are well-known in the art.

In still other embodiments, the cells are transfected with mRNA encoding the protein of interest (e.g., the CAR). Transfection of mRNA results in transient expression of the protein. In one embodiment, transfection of mRNA into NK-92 cells is performed immediately prior to administration of the cells. In one embodiment, "immediately prior" to administration of the cells refers to between about 15 minutes and about 48 hours prior to administration. Preferably, mRNA transfection is performed about 5 hours to about 24 hours prior to administration. In at least some embodiments as described in more detail below, NK cell transfection with mRNA resulted in unexpectedly consistent and strong expression of the CAR at a high faction of transfected cells. Moreover, such transfected cells also exhibited a high specific cytotoxicity at comparably low effector to target cell ratios.

With respect to contemplated CARs it is noted that the NK or NK-92 cells will be genetically modified to express the CAR as a membrane bound protein exposing a portion of the CAR on the cell surface while maintaining the signaling domain in the intracellular space. Most typically, the CAR will include at least the following elements (in order): an extracellular binding domain, a hinge domain, a transmembrane domain, and an FcεRIγ signaling domain.

In preferred embodiments, the cytoplasmic domain of the CAR comprises or consists of a signaling domain of FcεRIγ. Notably, and as described in more detail below, the FcεRIγ signaling domain provide for substantially increased expression levels of the CAR as much as for significantly extended cytotoxicity over time. For example, the FcεRIγ signaling domain comprises or consists of or consists essentially of the amino acid sequence of SEQ ID NO:1. In some embodiments, the FcεRIγ cytoplasmic domain is the sole signaling domain. However, it should be appreciated that additional elements may also be included, such as other signaling domains (e.g., CD28 signaling domain, CD3ζ signaling domain, 4-1BB signaling domain, etc.). These additional signaling domains may be positioned downstream of the FcεRIγ cytoplasmic domain and/or upstream of the FcεRIγ cytoplasmic domain.

In some embodiments, the FcεRIγ signaling domain comprises or consists of or consists essentially of an amino acid sequence having at least about 85%, 90%, 95%, 96%, 97%, 98%, or 99% sequence homology to the amino acid sequence of SEQ ID NO:1.

In alternative embodiments, the cytoplasmic domain of the CAR may also comprise a signaling domain of CD3 zeta (CD3ζ). In one embodiment, the cytoplasmic domain of the CAR consists of a signaling domain of CD3 zeta. In one embodiment, the CD3 zeta signaling domain comprises or consists of or consists essentially of the amino acid sequence of SEQ ID NO:15. In some embodiments, the CD3 zeta signaling domain comprises or consists of or consists essentially of an amino acid sequence having at least about 85%, 90%, 95%, 96%, 97%, 98%, or 99% sequence homology to the amino acid sequence of SEQ ID NO:15.

The CAR may comprise any suitable transmembrane domain. In one aspect, the CAR comprises a transmembrane domain of CD28. In one embodiment, the CD28 transmembrane domain comprises or consists of or consists essentially of the amino acid sequence of SEQ ID NO:6 (encoded by nucleic acid with the SEQ ID NO:7). In one embodiment, the CD28 transmembrane domain comprises or consists of or consists essentially of an amino acid sequence having at least about 85%, 90%, 95%, 96%, 97%, 98%, or 99% sequence homology to the amino acid sequence of SEQ ID NO:6. In other embodiments, the transmembrane domain may also be a 4-1BB transmembrane domain.

The CAR may comprise any suitable hinge region. In one aspect, the CAR comprises a hinge region of CD8. In one embodiment, the CD8 hinge region comprises or consists of or consists essentially of the amino acid sequence of SEQ ID NO:3 or SEQ ID NO:4. In one embodiment, the CD8 hinge region comprises or consists of or consists essentially of an amino acid sequence having at least about 85%, 90%, 95%, 96%, 97%, 98%, or 99% sequence homology to the amino acid sequence of SEQ ID NO:3 or SEQ ID NO:4. Such region may be encoded by a nucleic acid having the sequence of SEQ ID NO: 5.

Therefore, contemplated CARs will include a general structure of a desired antigen binding domain that is coupled to a hinge domain, which is coupled to a transmembrane domain, which is coupled to a signaling domain. Viewed from another perspective, contemplated CARs may have a desired binding domain that is then coupled to a hybrid protein that comprises, consists of, or essentially consists of a hinge domain, which is coupled to a transmembrane domain, which is coupled to a signaling domain. For example, such hybrid protein may have an amino acid sequence having at least about 85%, 90%, 95%, 96%, 97%, 98%, or 99% sequence homology to the amino acid sequence of SEQ ID NO:8 (encoded by nucleic acid sequence SEQ ID NO:9).

Most typically, but not necessarily, the extracellular binding domain of the CAR will be a scFv or other natural or synthetic binding portion that specifically binds an antigen of interest. Especially suitable binding portions include small antibody fragments with single, dual, or multiple target specificities, beta barrel domain binders, phage display fusion proteins, etc. Among other suitable extracellular binding domains, preferred domains will specifically bind to a tumor-specific antigen, a tumor associated antigen, or a patient- and tumor-specific antigen. Tumor-specific antigens include, without limitation, NKG2D ligands, CS1, GD2, CD138, EpCAM, EBNA3C, GPA7, CD244, CA-125, ETA, MAGE, CAGE, BAGE, HAGE, LAGE, PAGE, NY-SEO-1, GAGE, CEA, CD52, CD30, MUC5AC, c-Met, EGFR, FAP, WT-1, PSMA, NY-ESO1, AFP, CEA, CTAGIB, and CD33. Additional non-limiting tumor-associated antigens, and the malignancies associated therewith, can be found in Table 1. Still further tumor-specific antigens are described, by way of non-limiting example, in US2013/0189268; WO 1999024566 A1; U.S. Pat. No. 7,098,008; and WO 2000020460, each of which is incorporated herein by reference in its entirety. Likewise, other preferred domains will specifically bind to a (pathogenic) virus-specific antigen, such as an antigen of an HIV virus (e.g., gp120), an HPV virus, an RSV virus, an influenza virus, an ebolavirus, or an HCV virus.

TABLE 1

| Target antigen | Associated malignancy |
|---|---|
| α-Folate receptor | Ovarian cancer |
| CAIX | Renal cell carcinoma |
| CD19 | B-cell malignancies |
| | CLL |
| | B-ALL |
| | ALL; ALL post-HSCT |
| | Lymphoma; Refractory Follicular |
| | Lymphoma; B-NHL |
| | Leukemia |
| | B-cell malignancies; B-cell malignancies post-HSCT |
| | B-lineage lymphoid malignancies post-UCBT |
| | B-cell malignancies, CLL, B-NHL |
| CD19/CD20 | Lymphoblastic leukemia |
| CD20 | Lymphomas |
| | B-cell malignancies |
| | B-cell lymphomas |
| | Mantle cell lymphoma |
| | indolent B-NHL |
| | Leukemia |
| CD22 | B-cell malignancies |
| CD30 | Lymphomas; Hodgkin lymphoma |
| CD33 | AML |
| CD44v7/8 | Cervical carcinoma |
| CD138 | Multiple myeloma |
| CD244 | Neuroblastoma |
| CEA | Breast cancer |
| | Colorectal cancer |
| CS1 | Multiple myeloma |
| EBNA3C | EBV positive T cells |
| EGP-2 | Multiple malignancies |
| EGP-40 | Colorectal cancer |
| EpCAM | Breast carcinoma |
| erb-B2 | Colorectal cancer |
| | Breast and others |
| | Prostate cancer |
| erb-B 2,3,4 | Breast and others |
| FBP | Ovarian cancer |
| Fetal acetylcholine receptor | Rhabdomyosarcoma |
| GD2 | Neuroblastoma |
| GD3 | Melanoma |
| GPA7 | Melanoma |
| Her2 | Breast carcinoma |
| | Ovarian cancer |
| | Tumors of epithelial origin |

TABLE 1-continued

| Target antigen | Associated malignancy |
|---|---|
| Her2/neu | Medulloblastoma |
| | Lung malignancy |
| | Advanced osteosarcoma |
| | Glioblastoma |
| IL-13R-a2 | Glioma |
| | Glioblastoma |
| | Medulloblastoma |
| KDR | Tumor neovasculature |
| k-light chain | B-cell malignancies |
| | (B-NHL, CLL) |
| LeY | Carcinomas |
| | Epithelial derived tumors |
| L1 cell adhesion molecule | Neuroblastoma |
| MAGE-A1 | Melanoma |
| Mesothelin | Various tumors |
| MUC1 | Breast, Ovary |
| NKG2D ligands | Various tumors |
| Oncofetal antigen (h5T4) | Various tumors |
| PSCA | Prostate carcinoma |
| PSMA | Prostate/tumor vasculature |
| TAA targeted by mAb IgE | Various tumors |
| TAG-72 | Adenocarcinomas |
| VEGF-R2 | Tumor neovasculature |

For example, the CAR may comprise an anti-CD19 extracellular domain. In one embodiment, the anti-CD19 extracellular domain comprises, consists of, or consists essentially of the amino acid sequence of SEQ ID NO:11. In one embodiment, the anti-CD19 extracellular domain comprises or consists of or consists essentially of an amino acid sequence having at least about 85%, 90%, 95%, 96%, 97%, 98%, or 99% sequence homology to the amino acid sequence of SEQ ID NO:11.

Consequently, contemplated CARs will target antigens associated with a specific cancer type. For example, targeted cancers include leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Therefore, contemplated CARs will generally have a structure of an extracellular binding domain that is (directly) coupled to a hinge domain, which is (directly) coupled to a transmembrane domain, which is (directly) coupled to an FcεRIγ signaling domain. In still further contemplated aspects, contemplated CARs may also include one or more signaling domains in addition to or replacing the FcεRIγ signaling domain, and especially contemplated signaling domains include CD3ζ signaling domains, 4-1BB signaling domains, and CD28 signaling domains. For example, contemplated CARs may therefore include any binding domain (e.g., having SEQ ID NO:11) that is coupled to a hinge domain (e.g., CD8 hinge as in SEQ ID NO:3 or SEQ ID NO:4, encoded by SEQ ID NO:5), which is in turn coupled to a transmembrane domain (e.g., CD28 TM as in SEQ ID NO:6, encoded by SEQ ID NO:7), which is coupled to a signaling domain (e.g., FcεRIγ signaling domain as in SEQ ID NO:1, encoded by SEQ ID NO:1, or CD28 signaling domain as in SEQ ID NO:13, or 4-1BB signaling domain as in SEQ ID NO:14, or CD3ζ signaling domain as in SEQ ID NO:15)

With respect to the construction of contemplated CARs it should be recognized that CARs can be engineered in numerous manners as described, for example, in WO 2014/039523; US 2014/0242701; US 2014/0274909; US 2013/0280285 and WO 2014/099671, each of which is incorporated herein by reference in its entirety.

In still further contemplated aspects, and as noted above, NK cells may be further genetically modified to express one or more cytokines to so provide a selection marker where the cytokine and the CAR are encoded on the same recombinant nucleic acid, and/or to render the recombinant cells independent of exogenous IL-2. Therefore, in some aspects of the inventive subject matter, NK-92 cells are modified to express at least one cytokine. In particular, the at least one cytokine is IL-2, IL-12, IL-15, IL-18, IL-21, or a variant thereof. In preferred embodiments, the cytokine is IL-2 or a variant thereof and especially preferred variants include endoplasmic retention signals (e.g., human IL-2 as in SEQ ID NO:21, or with ER retention signal as in SEQ ID NO:22, SEQ ID NO:30, or SEQ ID NO:33). For example, the IL-2 gene is cloned and expressed with a signal sequence that directs the IL-2 to the endoplasmic reticulum. This permits expression of IL-2 at levels sufficient for autocrine activation, but without releasing IL-2 extracellularly (e.g., *Exp Hematol.* 2005 February; 33(2):159-64.) Alternatively, expression of a cytokine (and especially IL-15) may also be such that the cytokine will be expressed in sufficient quantities to provide an autocrine growth signal to the recombinant cells, but also to allow at least some of the expressed IL-15 to be released from the cell, which will so provide an immune stimulatory signal. For example, such expression may be achieved using a human IL-15 sequence that includes both the signal peptide and an endoplasmic retention sequence. An exemplary DNA and protein sequence for an endoplasmic retained IL-15 is shown in SEQ ID NO:49 and SEQ ID NO:50, respectively.

Where desired, contemplated cells may also express a suicide gene. The term "suicide gene" refers to a transgene that allows for the negative selection of cells expressing the suicide gene. A suicide gene is used as a safety system, allowing cells expressing the gene to be killed by introduction of a selective agent. This is desirable in case the recombinant gene causes a mutation leading to uncontrolled cell growth, or the cells themselves are capable of such growth. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene. Typically, the suicide gene encodes for a protein that has no ill effect on the cell but, in the presence of a specific compound, will kill the cell. Thus, the suicide gene is typically part of a system.

In one embodiment, the suicide gene is active in NK-92 cells. In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir. In another embodiment, the suicide gene is cytosine deaminase, which is toxic to cells in the presence of 5-fluorocytosine. Garcia-Sanchez et al. "Cytosine deaminase adenoviral vector and 5-fluorocytosine selectively reduce breast cancer cells 1 million-fold when they contaminate hematopoietic cells: a potential purging method for autologous transplantation." Blood. 1998 Jul. 15; 92(2):672-82. In a further embodiment, the suicide gene is cytochrome P450, which is toxic in the presence of ifosfamide or cyclophosphamide. See, e.g. Touati et al. "A suicide gene therapy combining the improvement of cyclophosphamide tumor cytotoxicity and the development of an anti-tumor immune response." *Curr Gene Ther.* 2014; 14(3):236-46. In yet another embodiment, the suicide gene is iCasp9. Di Stasi, (2011) "Inducible apoptosis as a safety switch for adoptive cell therapy." *N Engl J Med* 365: 1673-1683. See also Morgan, "Live and Let Die: A New Suicide Gene Therapy Moves to the Clinic" *Molecular Therapy* (2012); 20: 11-13. iCasp9 induces apoptosis in the presence of a small molecule, AP1903. AP1903 is biologically inert small molecule, that has been shown in clinical studies to be well tolerated, and has been used in the context of adoptive cell therapy.

Of course, it should be noted that all of the recombinant proteins can be expressed from individual recombinant sequences. However, it is generally preferred that where multiple recombinant sequences are expressed (e.g., CAR, CD16, cytokine), coding regions may be arranged in a polycistronic unit with at least two or at least three coding regions encoding the recombinant proteins. For example, a tricistronic DNA or RNA construct (e.g., encoding a CAR with an FcεRIγ signaling domain, a $CD16^{158V}$, and $IL-2^{ER}$ or $IL15^{ER}$) may be transfected into an NK or NK-92 cell. Therefore, transgenes can be engineered into an expression vector by any mechanism known to those of skill in the art. Where multiple transgenes are to be inserted into a cell, transgenes may be engineered into the same expression vector or a different expression vector. In some embodiments, the cells are transfected with mRNA encoding the transgenic protein to be expressed. In some embodiments, the cells are transfected with DNA encoding the transgenic protein to be expressed. Transgenes, mRNA and DNA can be introduced into the NK-92 cells using any transfection method known in the art, including, by way of non-limiting example, infection, viral vectors, electroporation, lipofection, nucleofection, or "gene-gun."

As will be readily apparent, contemplated genetically modified cells can be used for treatment of various diseases, and especially of various cancers and viral infections where a diseased cell presents a disease-specific or disease-associated antigen. Consequently, the inventors contemplate methods of treating patients with modified NK or NK-92 cells as described herein. In one embodiment, the patient is suffering from cancer (e.g., a tumor) and the modified NK-92 cell or cell line expresses a CAR specific for an antigen expressed on the surface of a cell from the cancer or tumor. In one embodiment, the patient is suffering from a viral infection and the modified NK-92 cell or cell line expresses a CAR specific for an antigen expressed on the surface of a cell that has been infected by the virus. In one embodiment, the patient is suffering from a bacterial infection and the modified NK-92 cell or cell line expresses a CAR specific for an antigen expressed on the surface of a bacterial cell causing the infection.

Contemplated modified NK or NK-92 cells can be administered to an individual by absolute numbers of cells. For example, the individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) modified NK-92 cells per injection, or any ranges between any two of the numbers, end points inclusive. In other embodiments, modified NK-92 cells can be administered to an individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) modified NK-92 cells per kilogram of the individual, or any ranges between any two of the numbers, end points inclusive. In other embodiments, the total dose may calculated by $m^2$ of body surface area, including about $1\times10^{11}$, $1\times10^{10}$, $1\times10^9$, $1\times10^8$, $1\times10^7$, per $m^2$, or any ranges between any two of the numbers, end points inclusive. The average person is about 1.6 to about 1.8 $m^2$. In a preferred embodiment, between about 1 billion and about 3 billion NK-92 cells are administered to a patient.

The modified NK-92 cells, and optionally other anti-cancer or anti-viral agents can be administered once to a patient with cancer or infected with a virus or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

In one embodiment, where the modified NK-92 cells express a suicide gene, the patient is administered an agent to trigger modified NK-92 cell death. In one embodiment, the agent is administered at a time point after administration of the modified NK-92 cells that is sufficient for the NK-92 cells to kill target cells.

In one embodiment, the modified NK-92 cells are irradiated prior to administration to the patient. Irradiation of NK-92 cells is described, for example, in U.S. Pat. No. 8,034,332, which is incorporated herein by reference in its entirety. In one embodiment, modified NK-92 cells that have not been engineered to express a suicide gene are irradiated.

Furthermore, it should be appreciated that contemplated treatments will also include administration of other immune therapeutic entities, and especially preferred immune therapeutic entities include a viral cancer vaccine (e.g., adenoviral vector encoding cancer specific antigens), a bacterial cancer vaccine (e.g., non-pyrogenic *E. coli* expressing one or more cancer specific antigens), a yeast cancer vaccine, N-803 (also known as ALT-803, ALTOR Biosciences), an antibody (e.g., binding to a tumor associated antigen or patient specific tumor neoantigen), a stem cell transplant (e.g., allogeneic or autologous), and a tumor targeted cytokine (e.g., NHS-IL12, IL-12 coupled to a tumor targeting antibody or fragment thereof).

EXAMPLES

The following examples are for illustrative purposes only and should not be interpreted as limitations of the claimed invention. There are a variety of alternative techniques and procedures available to those of skill in the art which would similarly permit one to successfully perform the intended invention.

Example 1: CAR mRNA Preparation

DNA sequences encoding each variant of CD19CAR schematically depicted in FIG. 1 were designed in silico, synthesized de novo, and subcloned into the mRNA expression vector, pXT7 (GeneArt, Life Technologies). Ten micrograms (μg) of plasmid were linearized by digestion with the SalIrestriction enzyme (New England Biolabs) and purified using a QIAgen gel purification kit (QIAgen) according to manufacturer's instructions.

The linearized DNA was used as template for in vitro synthesis of mRNA using a T7 mMessage mMachine Ultra transcription kit (ThermoFisher Scientific, Waltham, Mass.) according to the manufacturer's instructions. This kit includes a polyadenylation extension step that increases the length of the polyA tail of the mRNA and thus enhances stability in vivo.

mRNA for six CD19CAR variants were prepared, with a green fluorescent protein (GFP) mRNA prepared as a negative control. All of the CD19CAR variants contained an extracellular domain comprising an anti-CD19 scFv region (αCD19-scFv) (SEQ ID NO:11), a hinge region from CD8 (SEQ ID NO:3 or NO:4), and a transmembrane domain from CD28 (SEQ ID NO:6 encoded by SEQ ID NO:7) The intracellular domains of the CD19CARs were as follows and schematically shown in FIG. 1: CAR 3z contained a CD3ζ signaling domain; CAR FcRe contained a FcεRIγ signaling domain (SEQ ID NO:1); CAR 28_3z contained a CD28 signaling domain fused to a CD3ζ signaling domain; CAR BB_3z contained a 4-1BB signaling domain fused to a CD3ζ signaling domain; CAR 28_BB_3z contained a CD28 signaling domain fused to a 4-1BB signaling domain fused to a CD3ζ signaling domain; CAR BB_3z_28 contained a 4-1BB signaling domain fused to a CD3ζ signaling domain fused to a CD28 signaling domain.

More particularly, the 1$^{st}$ generation CAR with CD3ζ signaling domain of FIG. 1 had a nucleic acid sequence of SEQ ID NO:16 (human). The 1$^{st}$ generation CAR with a FcεRIγ signaling domain nucleic had a nucleic acid sequence of SEQ ID NO:12 and an amino acid sequence of SEQ ID NO:10. The 2$^{nd}$ generation CAR with CD28/CD3ζ signaling domain had a nucleic acid sequence of SEQ ID NO:17 and an amino acid sequence of SEQ ID NO:68. The 2$^{nd}$ generation CAR with 4-1BB/CD3ζ signaling domain had a nucleic acid sequence of SEQ ID NO:18 and an amino acid sequence of SEQ ID NO:69. The 3$^{rd}$ generation CAR with CD28/4-1BB/CD3ζ signaling domain had a nucleic acid sequence of SEQ ID NO:19 and an amino acid sequence of SEQ ID NO:70. The 3$^{rd}$ generation CAR with 4-1BB/CD3ζ/CD28signaling domain had a nucleic acid sequence of SEQ ID NO:20 and an amino acid sequence of SEQ ID NO:71. A further 1$^{st}$ generation CAR with a FcεRIγ signaling domain nucleic had an amino acid sequence of SEQ ID NO:25.

Example 2: Electroporation of NK-92 Cells with CD19CAR mRNA

NK-92 cells were grown in X-Vivo10 medium (Lonza, Basel, Switzerland) supplemented with 5% Human AB Serum (Valley Biomedical, Winchester, Va.) and 500 IU/mL IL-2 (Prospec, Rehovot, Israel). Cells were electroporated with mRNA using the Neon™ electroporation device (Life Technologies, Carlsbad, Calif.), following the manufacturer's parameters for NK-92 cells (1250 V, 10 ms, 3 pulses) and using 5 μg of mRNA per $10^6$ cells in a volume of 100 μl. Electroporated cells were maintained in medium (same as above) for 20 hours (h).

Figure 2A:
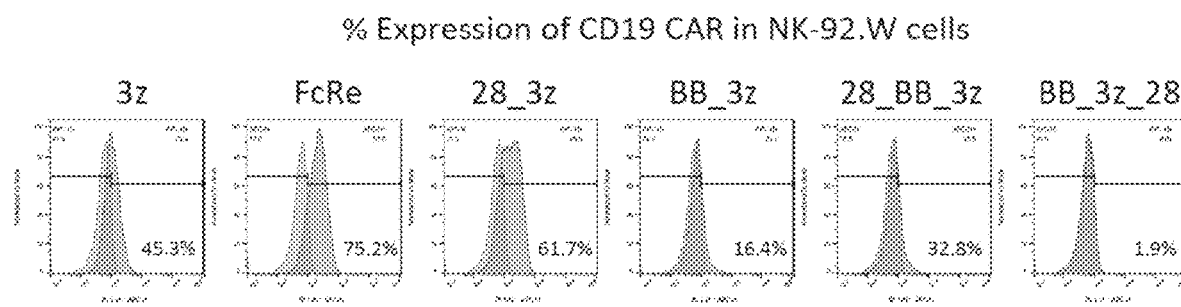
FIG. 2A are exemplary results for the percentage of NK-92 cells expressing the CD19-CAR of FIG. 1 after transfection with CD19-CAR mRNA as determined by flow cytometry with an anti-scFv antibody labeled with eF660.
Figure 2B:
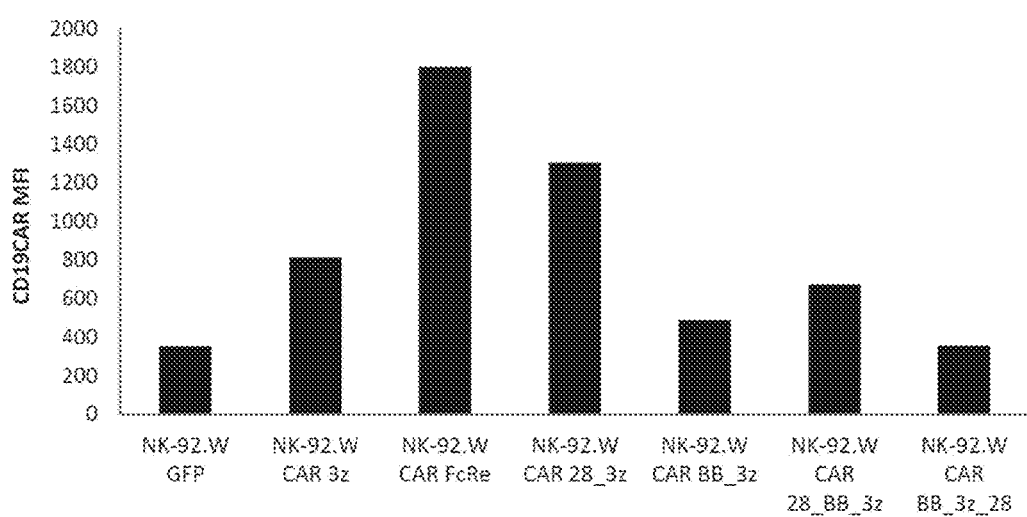
FIG. 2B are exemplary results for the median fluorescent intensity (MFI) minus background for CD19-CAR-expressing NK-92 cells labeled with an anti-scFv antibody labeled with eF660.

The CD19CAR expression on the NK-92 cell surface was determined by flow cytometry using anti-scFv antibody labeled with eF660 (eBioscience, San Diego, Calif.). FIG. 2A shows the % expression of the indicated CD19CAR in the NK-92 cell population. FIG. 2B shows the median fluorescence intensity (MFI, minus background) of cells electroporated with the indicated CD19CAR. As can be taken from FIGS. 2A and 2B, CAR FcRe unexpectedly had the highest percentage of cells (75.2%) expressing CD19CAR at the cell surface, as well as the highest MFI (quantity of expressed CAR on a recombinant cell), followed by 28_3z (61.7%).

Example 3: Cytotoxicity of NK-92 Cells Expressing CD19CAR Against Cancer Cell Lines The efficacy of CAR-expressing NK-92 cells to target cancer cells in vitro was tested 20 hours post-electroporation using a flow-based in vitro cytotoxicity assay. Effector cells (NK-92 expressing CD19CAR or GFP) were mixed with PKHGL67-labeled (Sigma-Aldrich, St. Louis, Mo.) target cells (K562; or SUPB15, B-ALL, CD19+) at different effector to target ratios (5:1 to 0.3:1) in a 96-well plate and incubated 4 h at 37° C. Propidium Iodide (PI) (Sigma Aldrich, St. Louis, Mo.) was added to the cells and samples were analyzed within 2 h using an Attune flow cytometer (Life Technologies, Carlsbad, Calif.). The cytotoxicity was determined by the % of PI-positive cells within the PKH-positive target population.

Figure 3A:
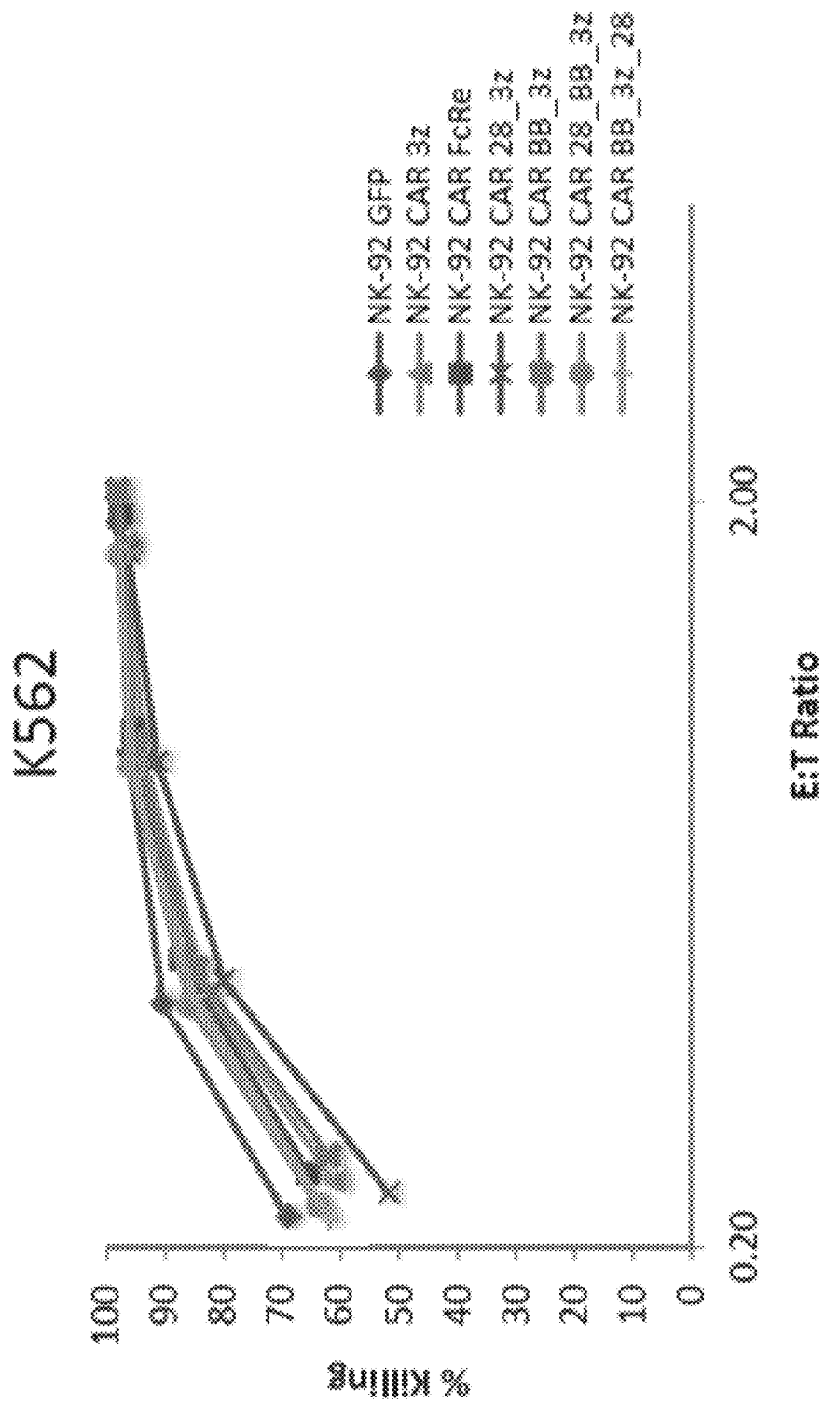
FIG. 3A shows exemplary results for the percentage of NK-92 cell-sensitive target cancer cells (K562) that were killed by NK-92 cells (effector) expressing the CD19CARs at effector:target ratios of from 5:1 to 0.3:1.
Figure 3B:
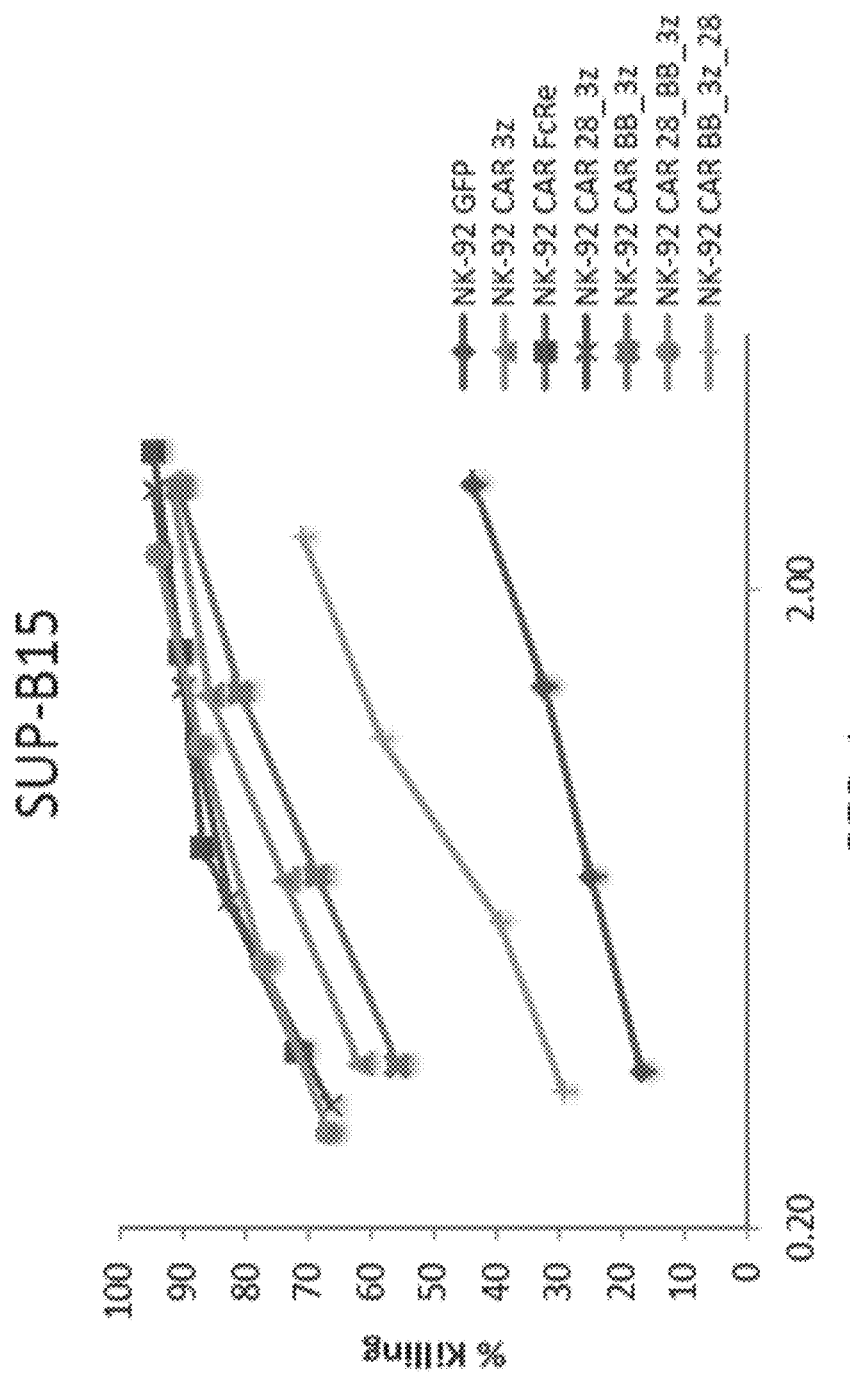
FIG. 3B shows exemplary results for the percentage of NK-92 cell-resistant, CD19-positive target cancer cells (SUP-B15) that were killed by NK-92 cells (effector) expressing the CD19CARs at effector:target ratios of from 5:1 to 0.3:1.

Exemplary results are provided in FIGS. 3A and 3B. NK-92 cells are effective at killing K562 cells regardless of CD19CAR expression as can be seen from FIG. 3A. Thus, it should be noted that recombinant cells will not lose cytotoxicity. In contrast, GFP-expressing NK-92 cells were inefficient at killing the cancer cell line SUP-B15. SUP-B15 is an acute lymphoblastic leukemia cell line that is CD19-positive and resistant to NK-92-mediated cytotoxicity. Expression of any CD19CAR tested provided increased cytotoxic activity against the SUP-B15 cell line compared to control (GFP-expressing NK-92 cells) as can be readily taken from FIG. 3B. Surprisingly, CARs with the FcεRIγ signaling domain exhibited cytotoxicity similar or even superior to the 2$^{nd}$ and 3$^{rd}$ generation CARs. Such finding is particularly unexpected as the FcεRIγ signaling domain was present only as a single unit and not combined with other signaling domains. Such arrangement, when used in CAR T-cells failed to provide desirable targeted cytotoxicity.

Degranulation is a critical step required for the release of the lytic proteins (e.g., perforin and granzyme) from secretory granules in the NK-92 cells. Degranulation is initiated by recognition of a target cell by NK-92. To test degranulation in the constructs, effector cells (NK-92) were mixed with unlabeled target cells (SUP-B15) at different effector to target ratios (5:1 to 0.3:1) in a 96-well plate, and anti-CD107a (FITC-conjugated, BD Pharmingen, San Jose, Calif.) was added to each well. Plates were incubated at 37° C. in a $CO_2$ incubator and after 1 h monensin (Golgi-stop) was added to the wells. The plates were incubated for another 3 h at 37° C. and the samples were analyzed by flow cytometry (Attune, Life technologies, Carlsbad, Calif.). Percentage degranulation was determined by subtracting the %

Figure 4:
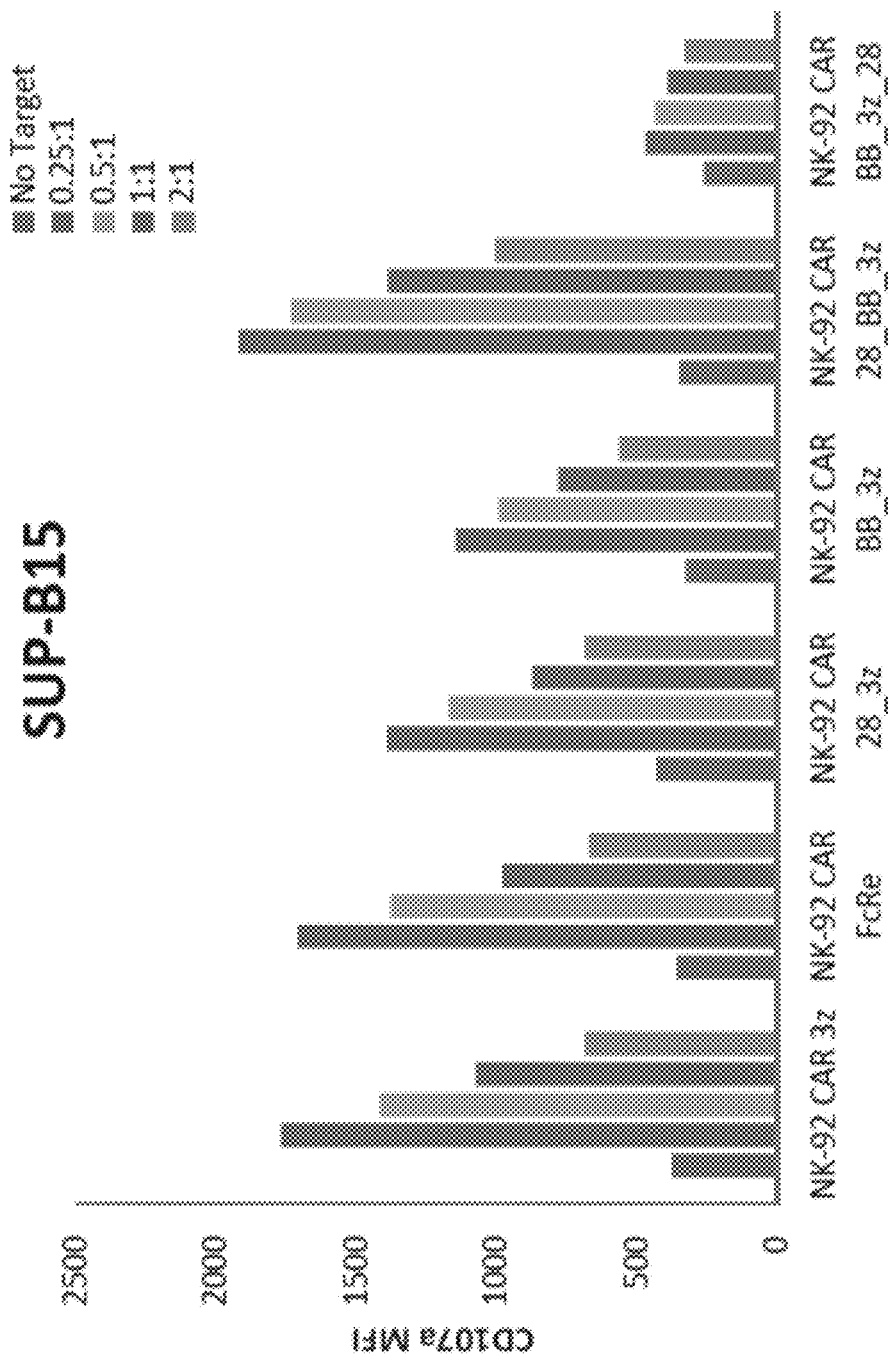
FIG. 4 shows exemplary results for the MFI of CD19-CAR-expressing NK-92 cells (effector) labeled with anti-CD107a antibody in a degranulation assay with SUP-B15 target cells at effector:target ratios of from 2:1 to 0.25:1.

CD107a positive in NK-92 cells alone to the % CD107a positive in the effector+target samples, and exemplary results are provided in FIG. 4.

Example 4. Surface Expression and Cytotoxicity of NK-92 Cells Expressing CD19CAR Against Cancer Cell Lines The inventors quantified expression levels for the various CAR constructs to investigate durability of expression over time. As can be seen from the results in FIG. 5, NK-92 cells transfected with the different CD19 CAR constructs expressed detectable levels of the respective CARs on the cell surface for up to 72 hours. Unexpectedly, and as can be readily seen from FIG. 5, the CAR constructs that comprised the Fc-epsilon cytoplasmic signaling domain had substantially higher durations of expression. Notably, it was also observed that addition of one or more signaling domains in addition to the FcεRIγ signaling domain (e.g., CD28 signaling domain in the example presented here) would not adversely affect the duration of expression. Indeed, in the CAR having the FcεRIγ signaling domain and the CD28 signaling domain duration of expression was even further increased over time, whereas CAR constructs with a CD3-zeta signaling domain had a dramatic reduction in expression at the 72 hour mark, and even before then.

Figure 5:
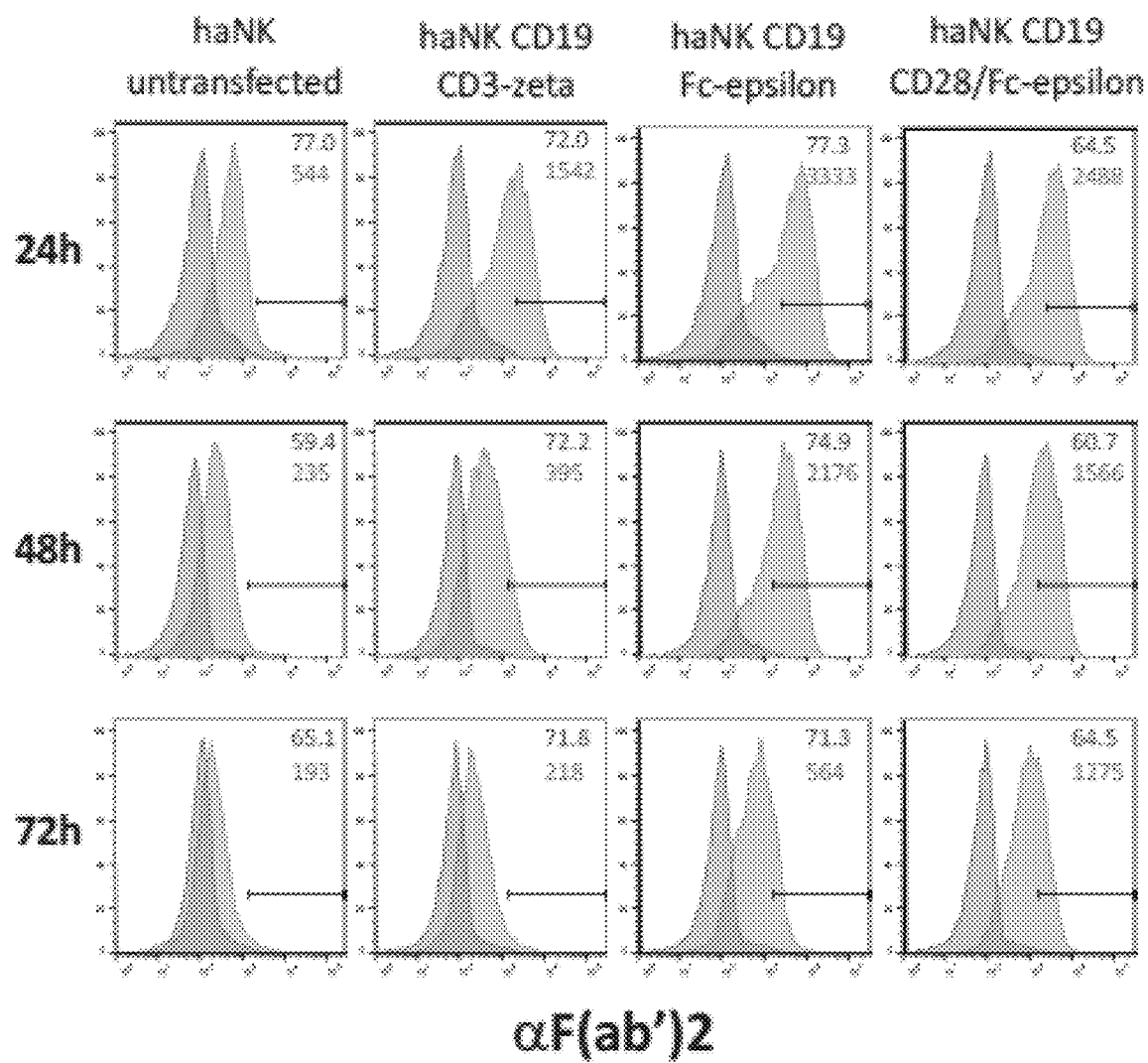
FIG. 5 shows exemplary results for surface expression of CD19 CAR on haNK cells transfected with CD19 CAR mRNA constructs at various time points. All CAR constructs tested show detectable expression for up to 72 h under the conditions used with CD19/CD28-Fc-epsilon CAR having the longest duration of expression.

Moreover, as can also be seen from the results in FIG. 5, the quantity of expression of CAR constructs having the FcεRIγ signaling domain was also initially significantly higher than corresponding constructs with a CD3-zeta signaling domain.

Figure 6:
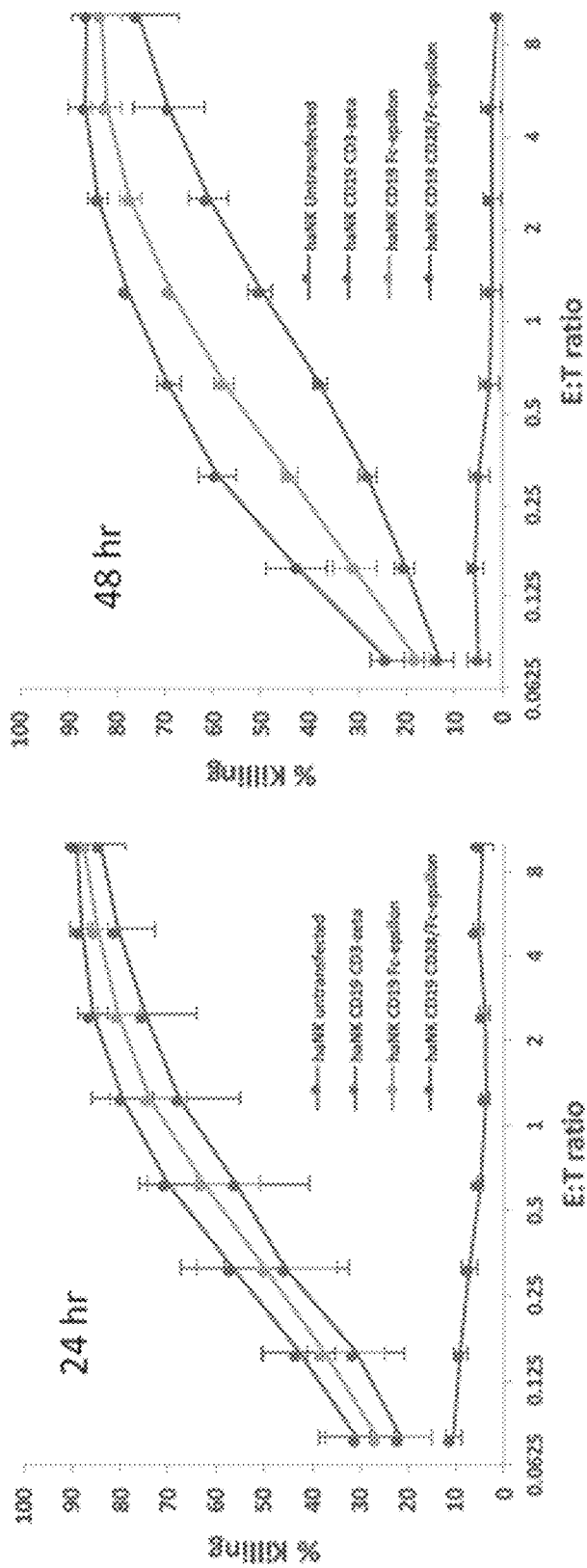
FIG. 6 shows exemplary results for cytotoxicity of CD19.taNK on SUPB15 CD19+ cells (an aNK resistant cell line). All CAR constructs tested show comparable (maximum) cytotoxic properties at 24 h. However, at 48 h, CD19/CD3-zeta shows a marked decrease in cytotoxic properties while Fc-epsilon based CARs show only minimal decrease 48 hours post-electroporation.

The inventors then set out to test whether the extended and stronger expression of the CAR constructs having the FcεRIγ signaling domain would also translate into a higher rate of cytotoxicity. Exemplary results for tests on SUPB15 CD19+ cells at 24 hours and 48 hours are depicted in FIG. 6. As can be taken from the results, all CAR constructs tested showed somewhat comparable (maximum) cytotoxic properties at 24 hours. However, at 48 hours, CD19/CD3-zeta showed a marked decrease in cytotoxic properties. Remarkably, the Fc-epsilon based CARs showed only minimal decrease in cytotoxic activity 48 hours post-electroporation, which paralleled the extended expression results from FIG. 5. Thus, it should be recognized that the CAR constructs with an FcεRIγ signaling domain exhibited extended cytotoxicity, which is believed to be of substantial clinical benefit.

Advantageously, tricistronic mRNA constructs were able to produce substantial quantities of desired CARs with excellent functional activity. Such constructs are especially beneficial where the CAR expression should be transient. In contrast, the following examples for targeted CAR constructs and associated functional data were from linearized DNA vector constructs, which allowed transfected cells to integrate the linearized DNA into the genome and to so provide an avenue for non-transient expression of the specific CARs.

Example 5. Map of Tricistronic Expression Cassette

Figure 7:
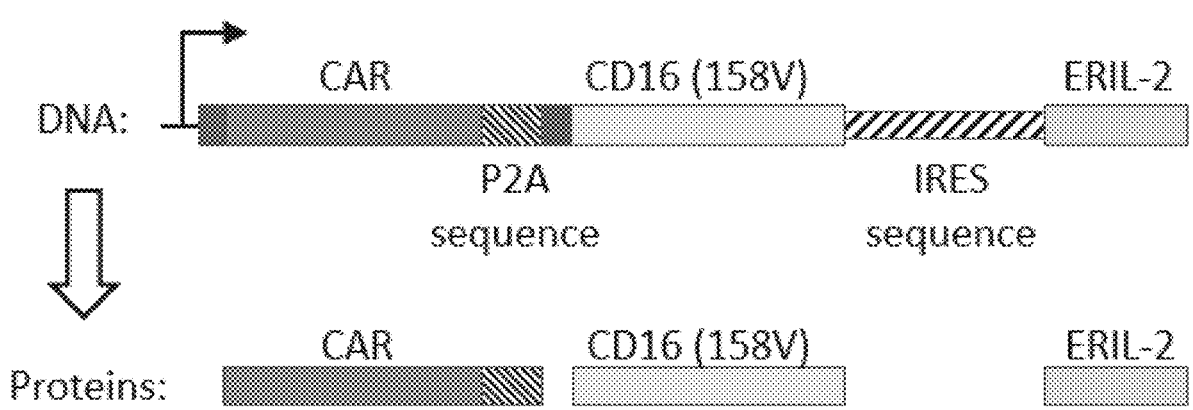
FIG. 7 is an exemplary schematic of a recombinant tricistronic DNA construct and corresponding protein products.
Figure 8:
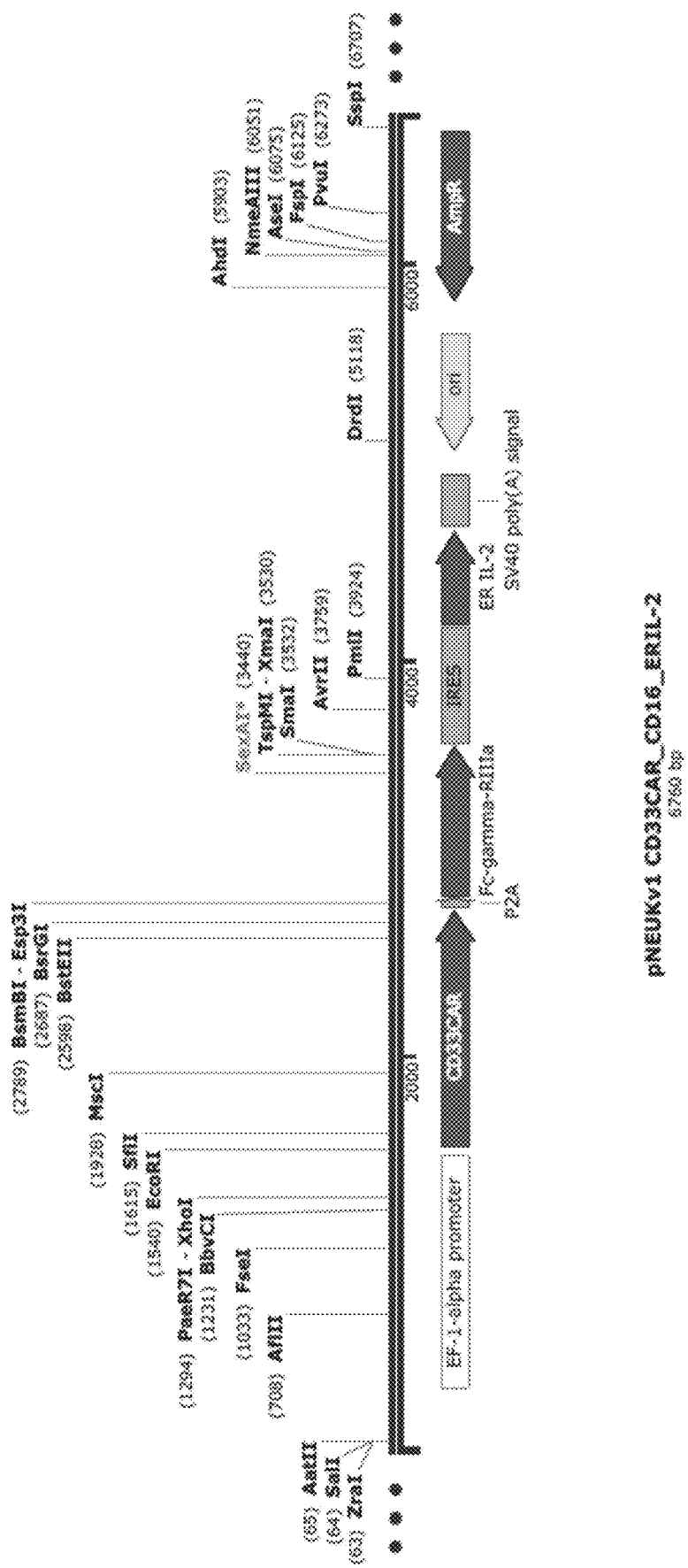
FIG. 8 shows an exemplary linearized version of the plasmid shown in FIG. 8.

FIG. 7 shows diagrammatically the DNA and protein products produced by a representative tricistronic expression cassette. FIG. 8 shows the linearized version of the plasmid with the expression cassette.

SEQ ID NO:28 is an exemplary nucleic acid sequence for part of the pNEUKv1_CD19CAR_CD16(158V)_ERIL-2 vector, which is a construct similar to FIG. 8. SEQ ID NO:29 is an exemplary tricistronic protein (similar to FIG. 7) that represents a CD19CAR_P2A_CD16(158V) protein. Similarly SEQ ID NO:31 is an exemplary nucleic acid sequence for the Codon-optimized CD33ScfV-P2A-CD16-IRES-erIL2 tricistronic sequence, while SEQ ID NO:32 shows a CD33 CAR-P2A-CD16 peptide.

Still further constructs made include SEQ ID NO:24 is an exemplary amino acid sequence for CD19K_Transmembrane and Signaling domain, while SEQ ID NO.:26 is an exemplary nucleic acid sequence for 15AD23HC_1805843_CD19K_Eps (879-1319), and SEQ ID NO: 27 is an exemplary nucleic acid sequence for 15AD23HC_1805843_CD19K_Eps, which did not include a CD28 transmembrane domain.

Example 6. Cytotoxicity of NK-92 Cells Expressing CD33-CAR Against Cancer Cell Lines The following example is provided to demonstrate that cells that are resistant to specific lysis (cytotoxicity) by control (unmodified) NK-92 cells can be efficiently killed by NK-92 cells that express a CAR. In this example, the cells were THP-1 cells expressing CD33. NK-92 cell were modified to express a CAR with an extracellular binding domain specifically binds to CD33, and that an FcεRIγ signaling domain as shown in FIGS. 8 and 9.

Figure 9A:
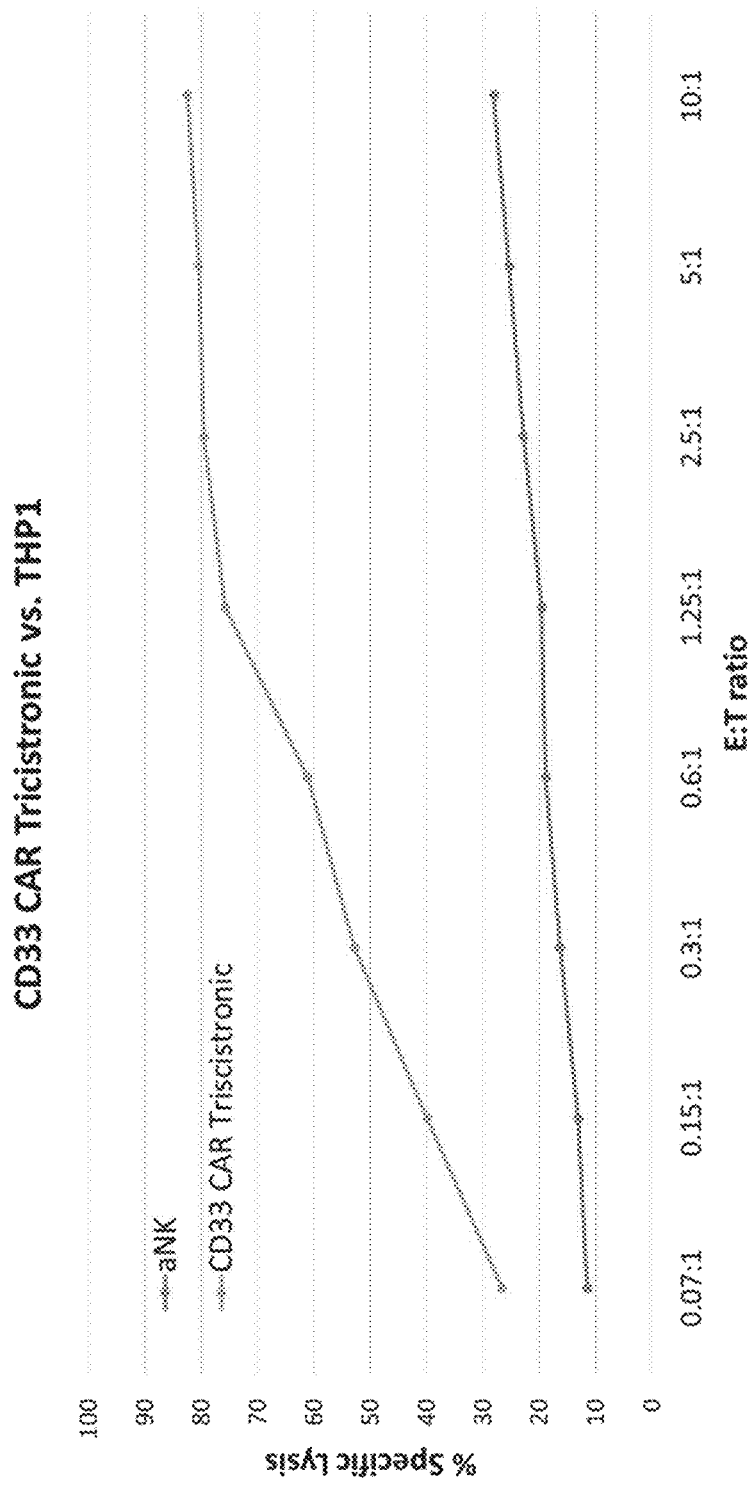
FIG. 9A shows exemplary results for in vitro data showing that CD33 positive (CD33+) THP-1 cells are relatively resistant to cytotoxicity (specific lysis) by control NK-92 (aNK) cells, whereas there is a high percentage of specific lysis when THP-1 cells are cultured with NK-92 cells that express a CAR that specifically binds CD33 (CD33-CAR/NK-92 cells).
Figure 9B:
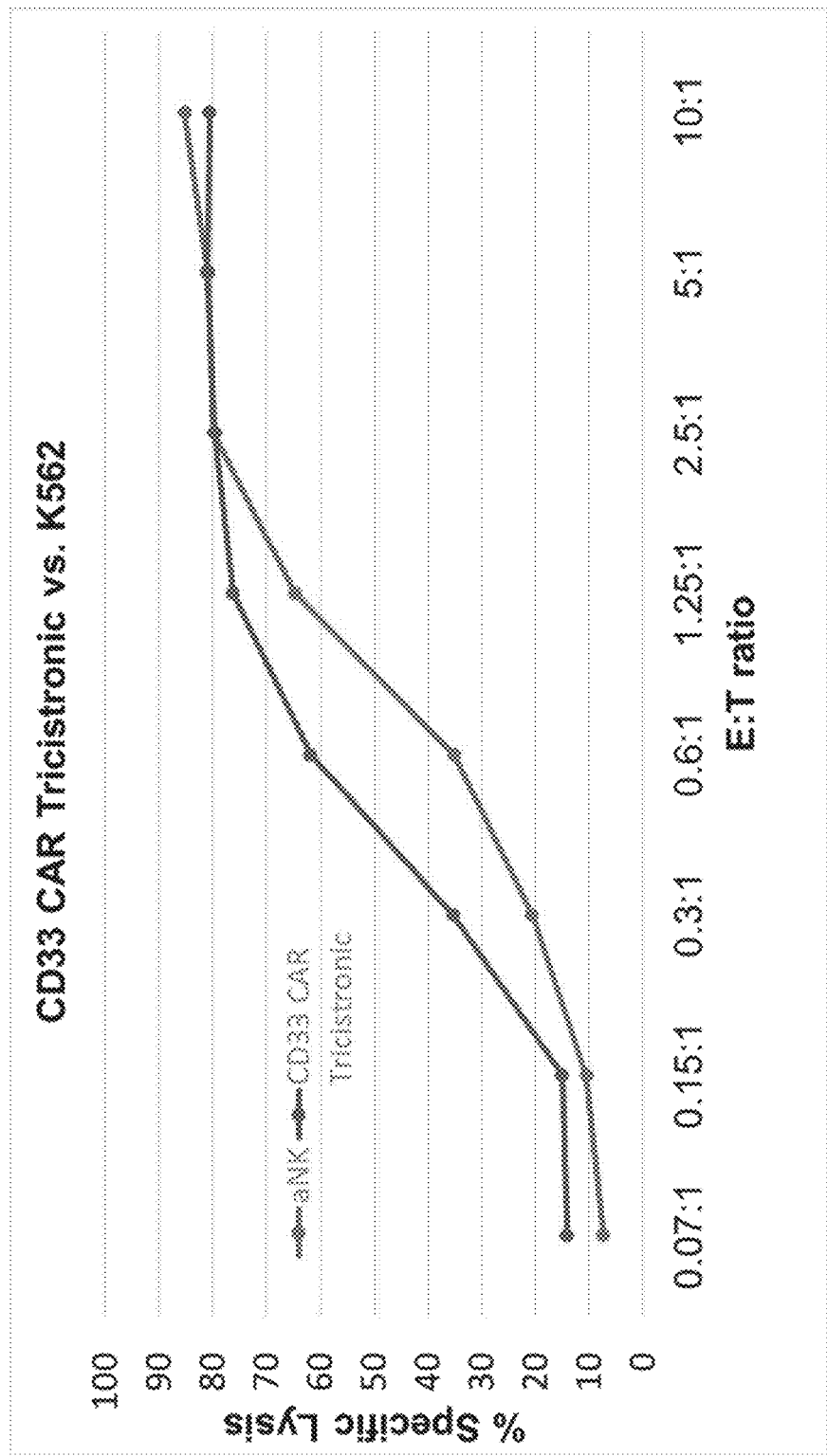
FIG. 9B shows exemplary results for in vitro data showing that K562 cells are killed by both control aNK cells and CD33-CAR/NK-92 cells.

FIG. 9A provides in vitro data showing that CD33 positive (CD33+) THP-1 cells are relatively resistant to cytotoxicity (specific lysis) by control NK-92 (aNK) cells, whereas there is a high percentage of specific lysis when THP-1 cells are cultured with NK-92 cells that express a CAR that specifically binds CD33 (CD33-CAR/NK-92 cells). Moreover, it should be noted that the modified NK-92 cells expressing the CAR exhibited killing at a relatively low effector:target ratio. FIG. 9B provides in vitro data showing that K562 cells are efficiently killed by both control aNK cells and CD33-CAR/NK-92 cells.

Example 7: HER2-CAR with FcεRIγ Signaling Domain

In this example, the inventors constructed a 1$^{st}$ generation CARs with a FcεRIγ signaling domain that included an anti-HER2 scFv coupled to a CD8 hinge, that in turn was coupled to a CD28 transmembrane domain, which was coupled to a FcεRIγ signaling domain. The so constructed HER2-CAR had a nucleic acid sequence of SEQ ID NO:37 and an amino acid sequence of SEQ ID NO:54.

Figure 10:
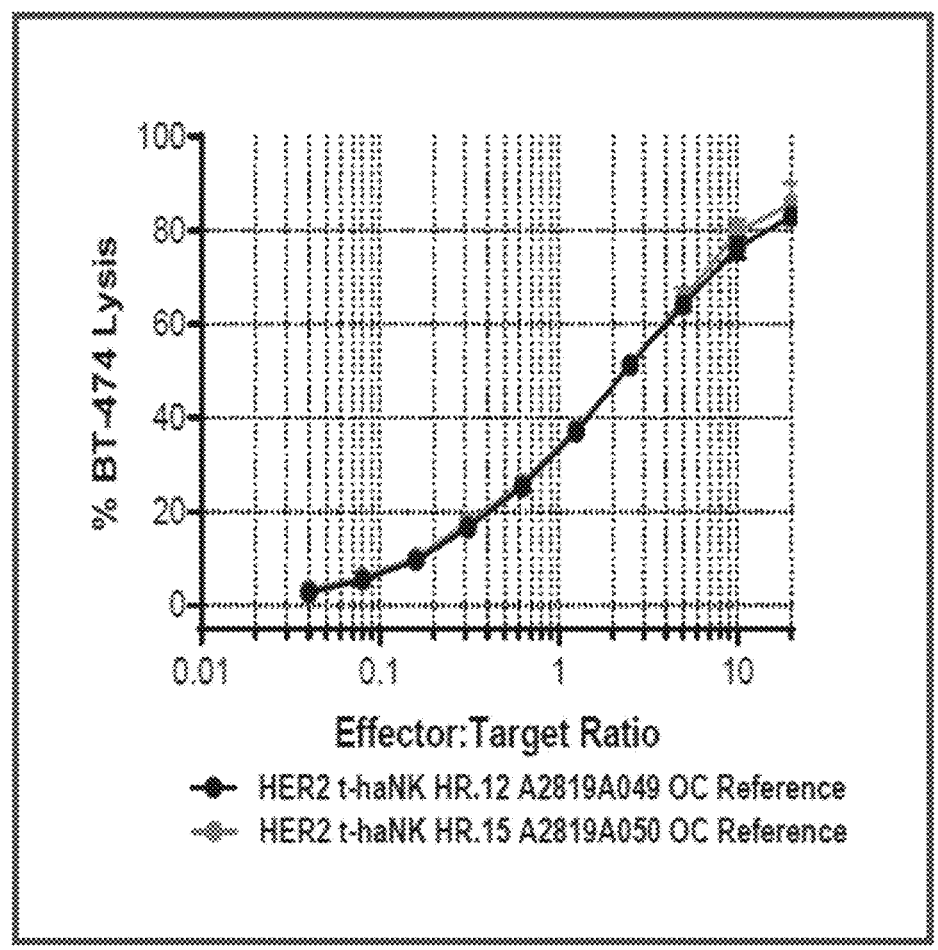
FIG. 10 shows exemplary results for cytotoxicity of HER2.CAR-t-haNK cells against BT-474 cells.

Functionality of the so constructed HER2.CAR-t-haNK cells was tested against BT-474 cells using a standard CalceinAM-based cytotoxicity assay and exemplary results are shown in FIG. 10. As can be readily seen from the data, the HER2.CAR-t-haNK cells expressing the CAR with the FcεRIγ signaling domain exhibited significant cytotoxicity against the BT-474 target cells.

Figure 36:
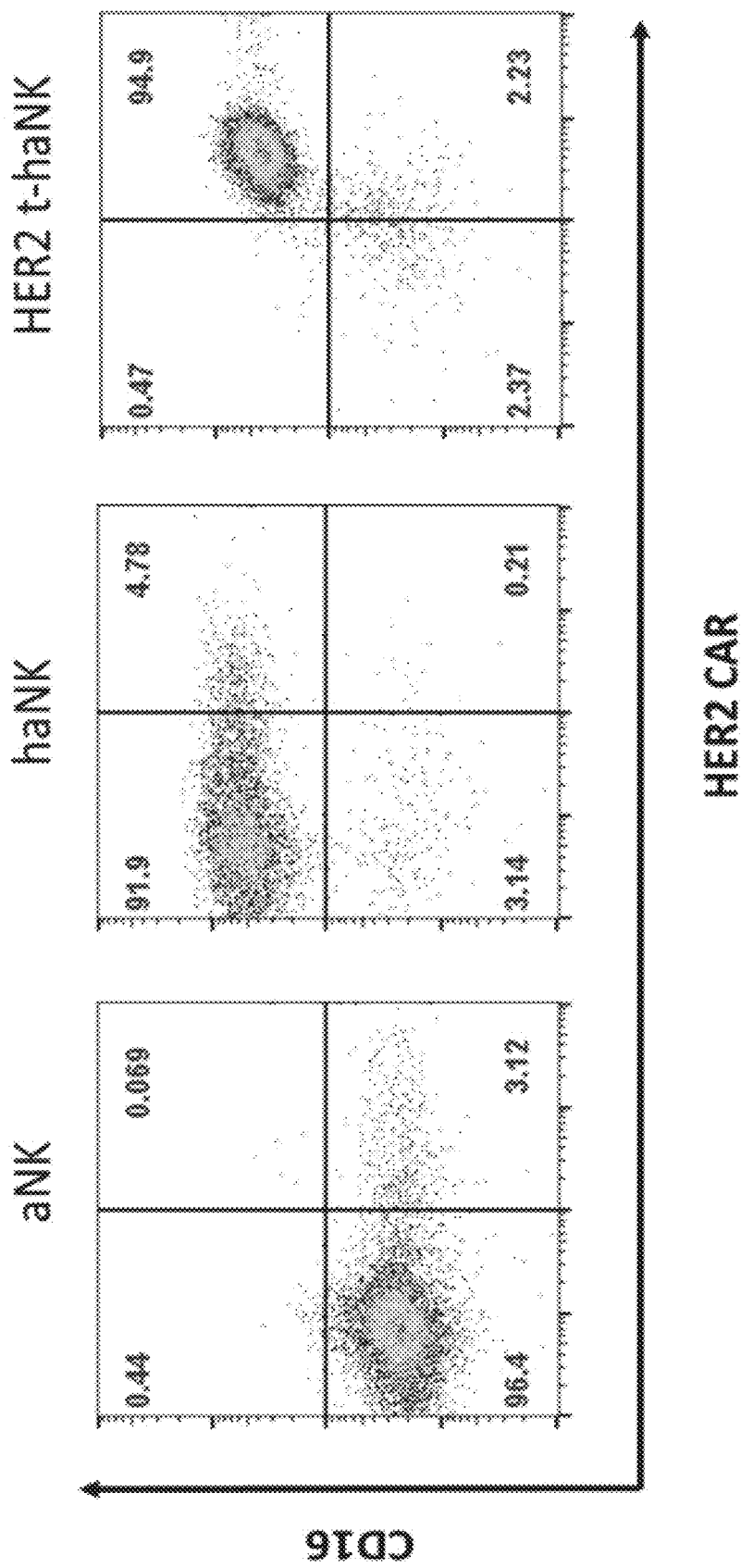
FIG. 36 shows exemplary results for expression of CD16 and HER2.CAR.
Figure 37:
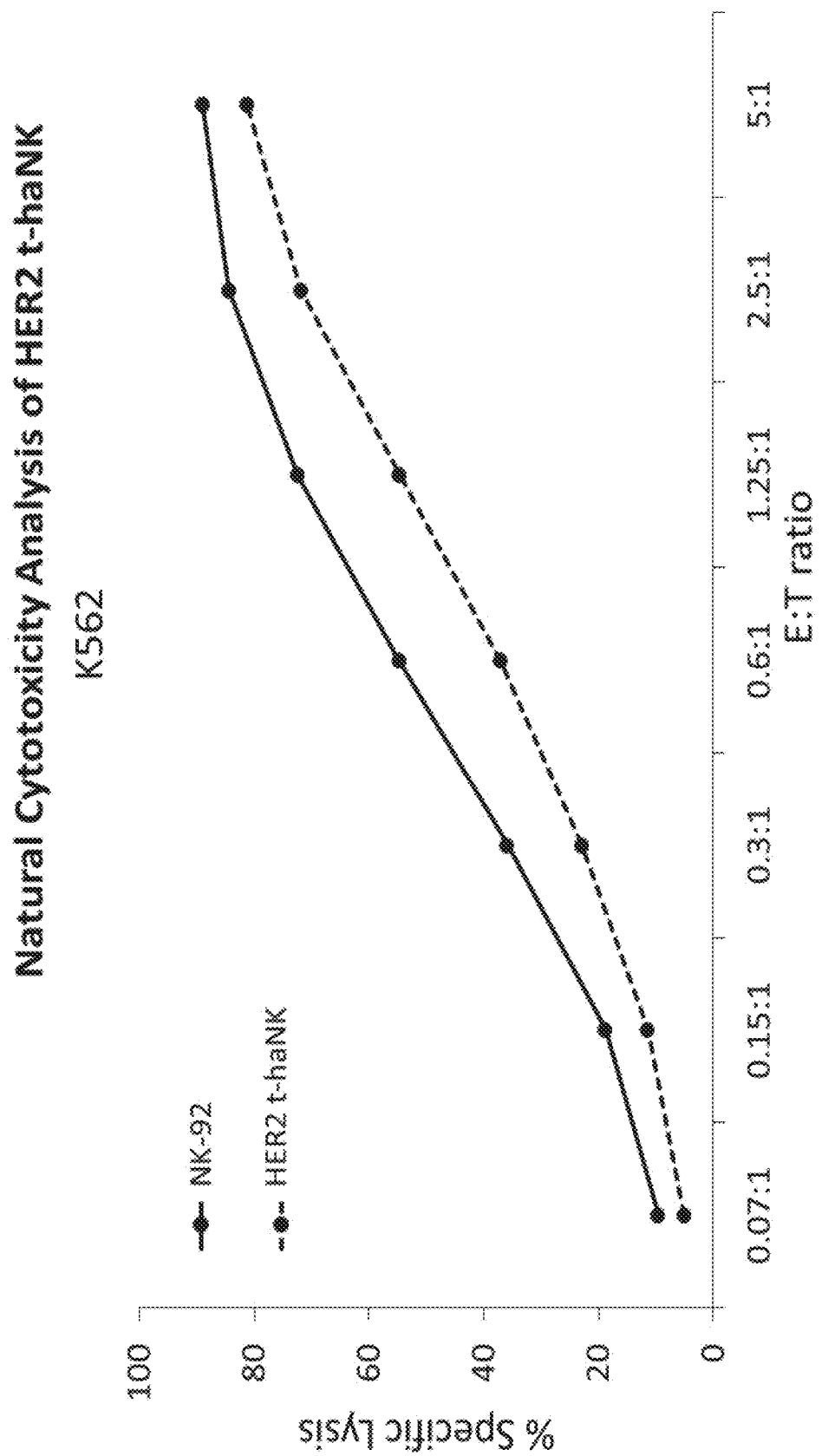
FIG. 37 shows exemplary results for natural cytotoxicity of HER2.CAR-t-haNK cells against K562 cells.
Figure 38:
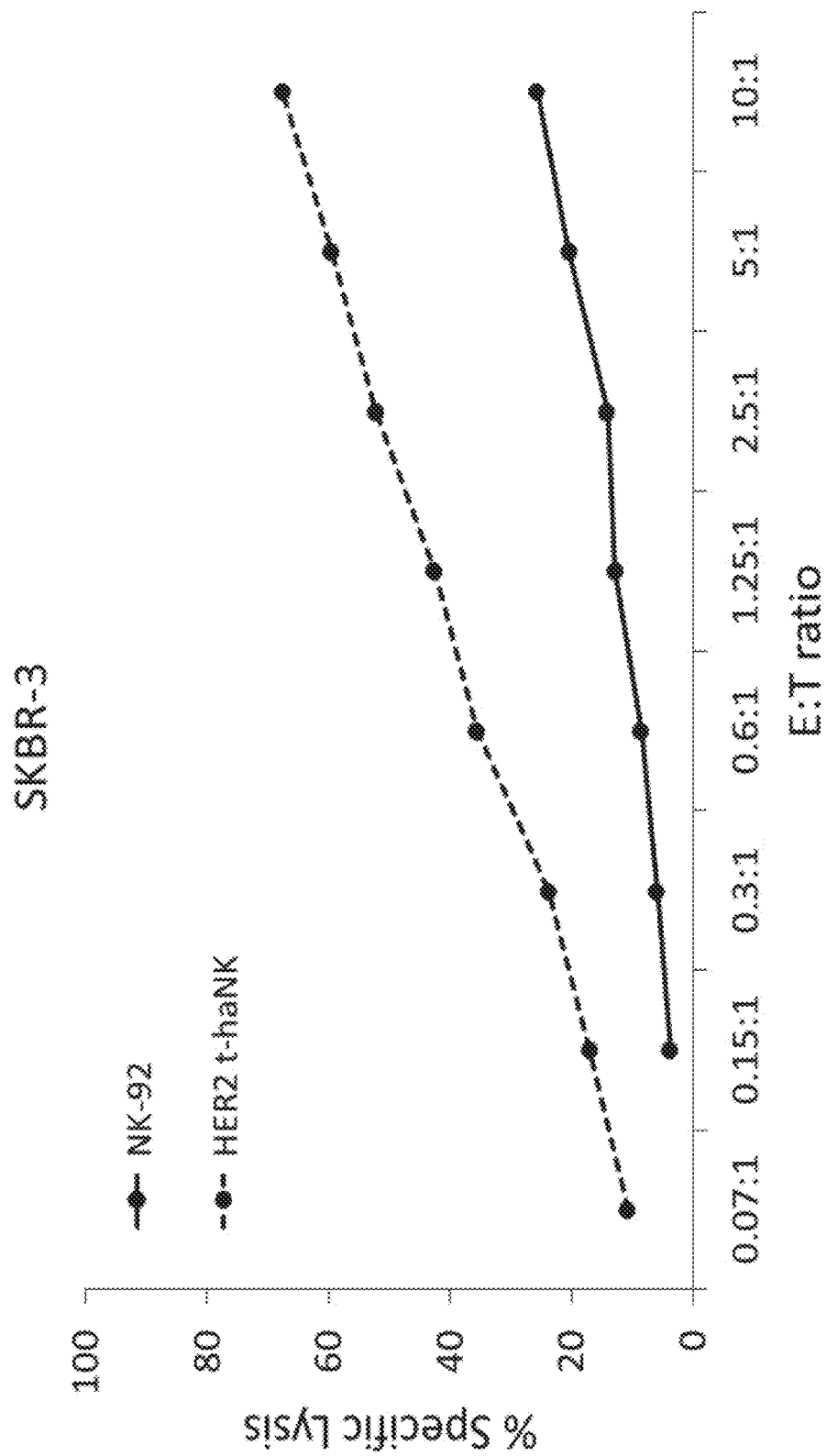
FIG. 38 shows exemplary results for CAR mediated cytotoxicity of HER2.CAR-t-haNK cells against SKBR-3 cells.
Figure 39:
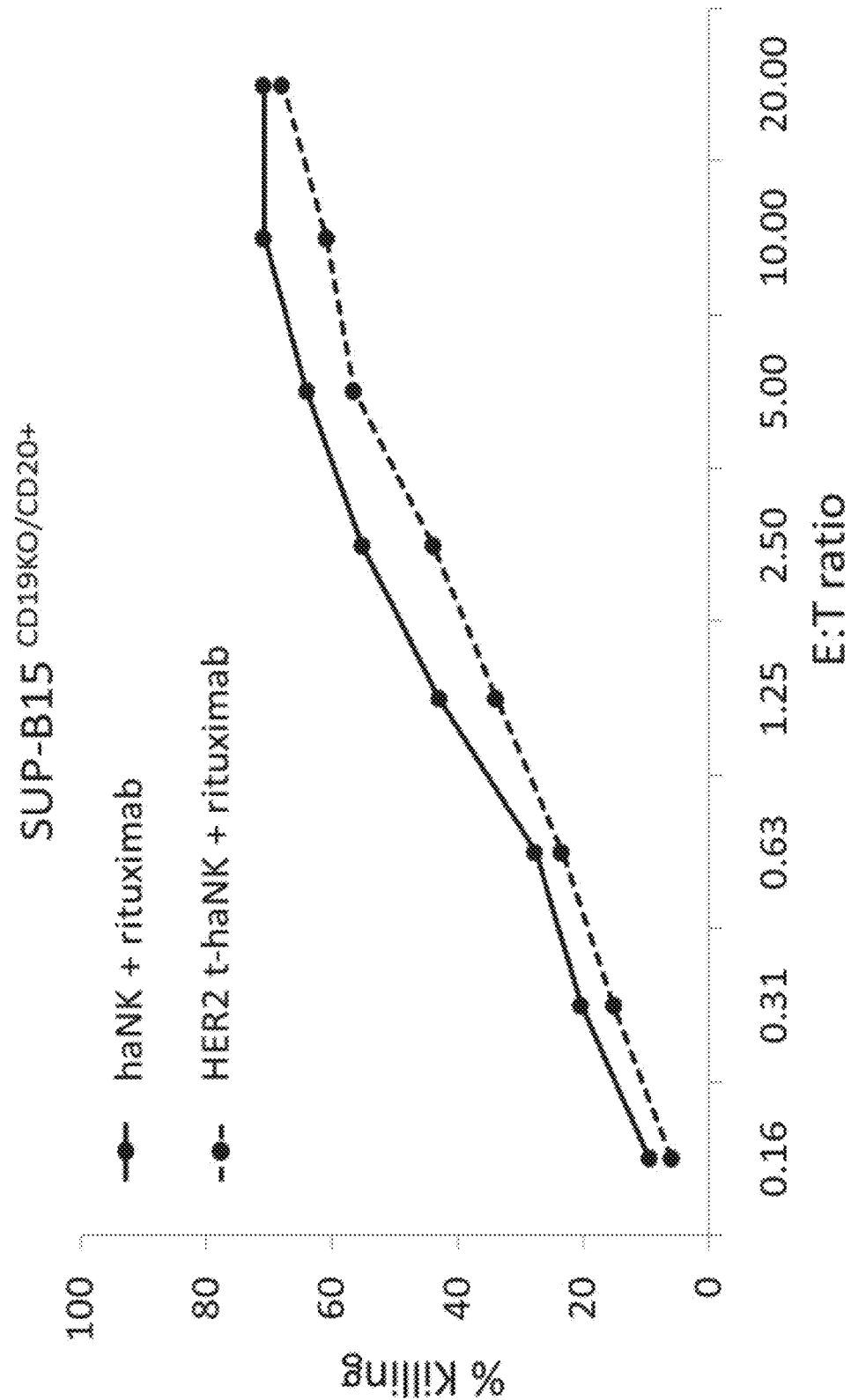
FIG. 39 shows exemplary results for ADCC of HER2.CAR-t-haNK cells.

In further experiments, the inventor demonstrated expression of the HER2.CAR in HER2.CAR-t-haNK cells as is illustrated in FIG. 36. Natural cytotoxicity of the HER2.CAR-t-haNK cells is shown in the results of FIG. 37, while results for CAR mediated cytotoxicity are shown in FIG. 38. Exemplary data for ADCC of HER2.CAR-t-haNK cells are shown in the graph of FIG. 39.

Example 8: CD30-CAR with FcεRIγ Signaling Domain

In this example, the inventors constructed a 1$^{st}$ generation CARs with a FcεRIγ signaling domain that included an anti-CD30 scFv coupled to a CD8 hinge, that in turn was coupled to a CD28 transmembrane domain, which was coupled to a FcεRIγ signaling domain. The so constructed CD30-CAR had a nucleic acid sequence of SEQ ID NO:38 and an amino acid sequence of SEQ ID:55.

Figure 46:
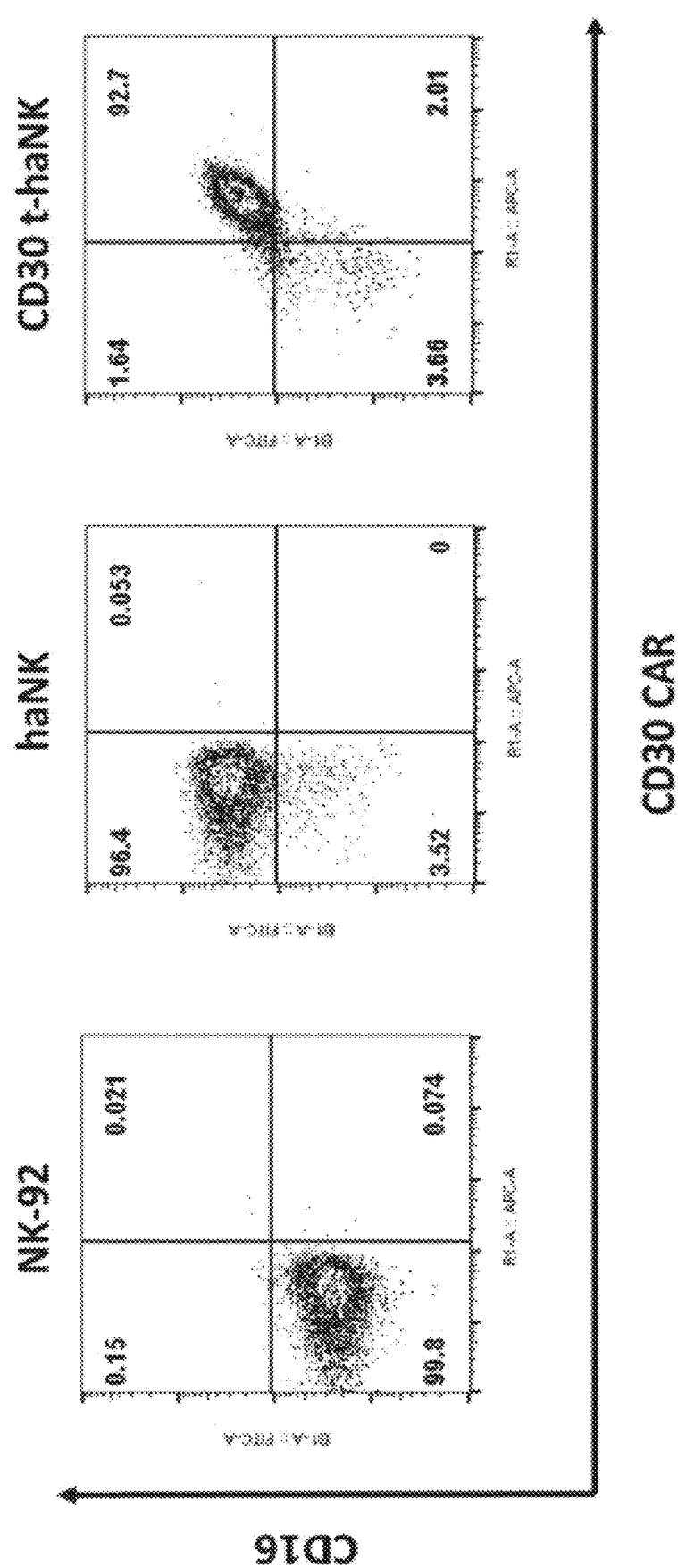
FIG. 46 shows exemplary results for expression of CD16 and CD30.CAR.
Figure 47:
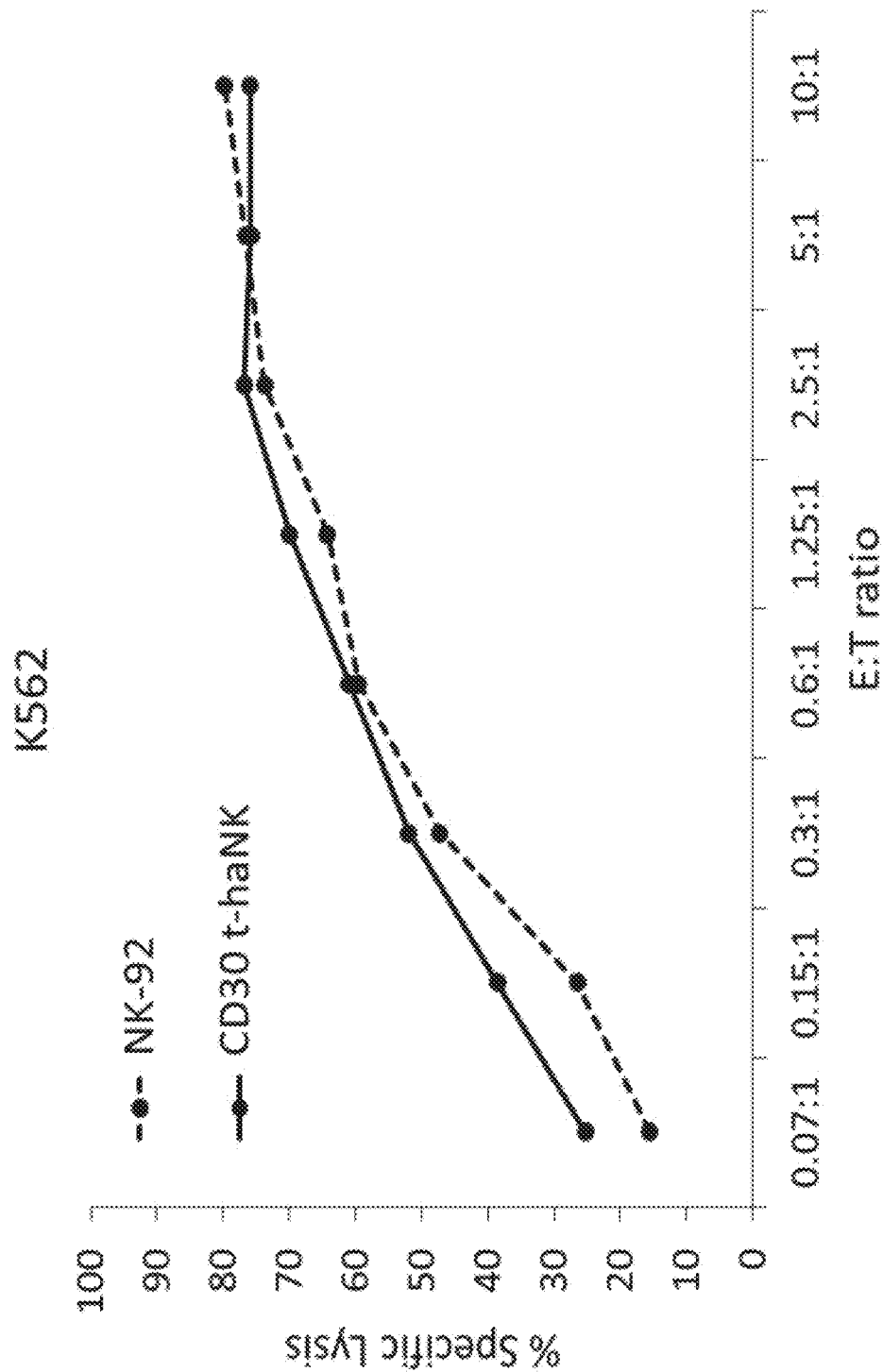
FIG. 47 shows exemplary results for natural cytotoxicity of CD30.CAR-t-haNK cells against K562 cells.
Figure 48:
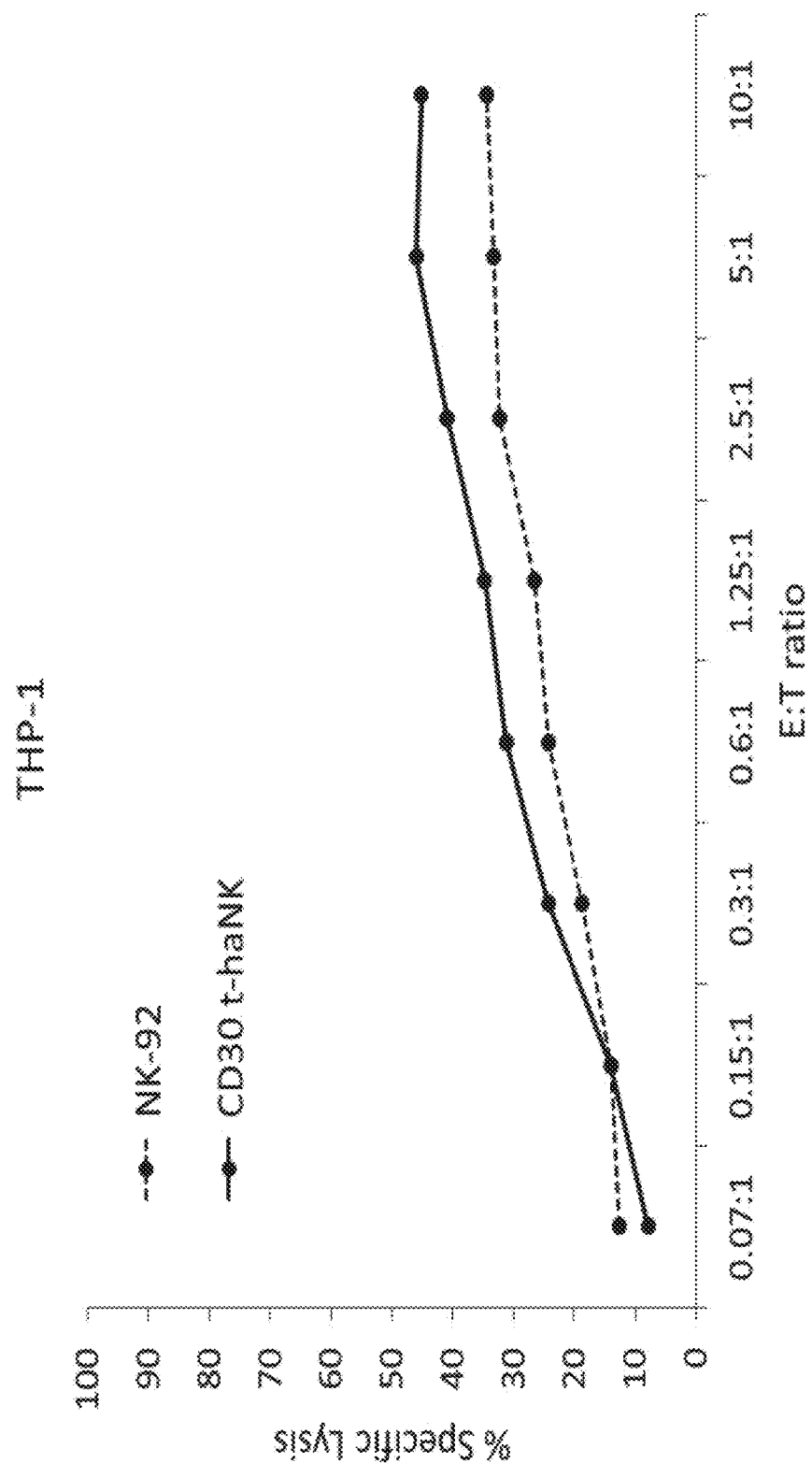
FIG. 48 shows exemplary results for CAR mediated cytotoxicity of CD30.CAR-t-haNK cells against THP-1 cells.
Figure 49:
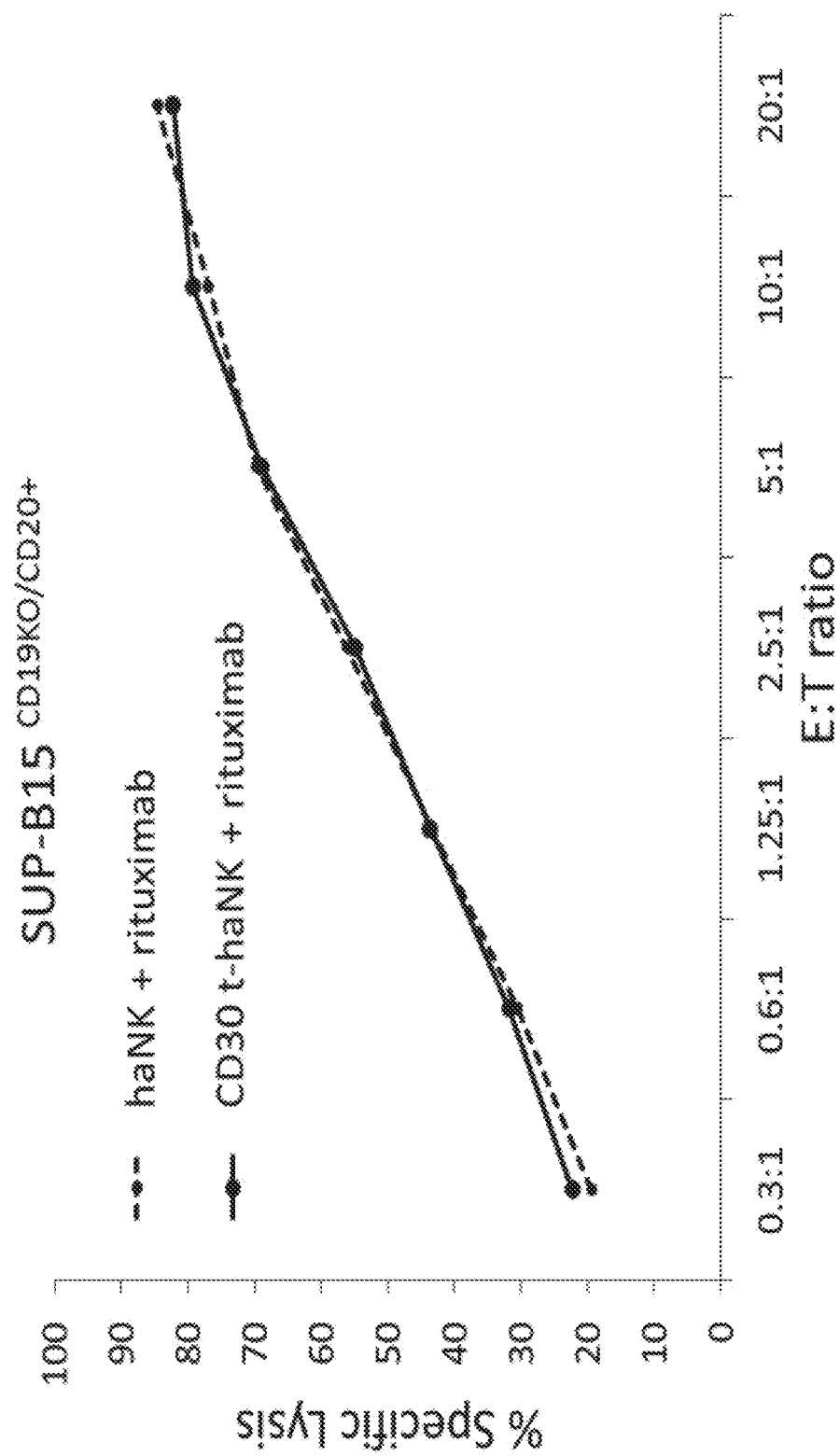
FIG. 49 shows exemplary results for ADCC of CD30.CAR-t-haNK cells.

Expression of the CD30-CAR is demonstrated in the results of FIG. 46, while the results for natural cytotoxicity of the recombinant cells are shown in FIG. 47. CAR mediated cytotoxicity was demonstrated in the results of FIG. 48, while exemplary results for ADCC are shown in the data of FIG. 49.

Example 9: EGFR-CAR with FcεRIγ Signaling Domain

In this example, the inventors constructed a $1^{st}$ generation CARs with a FcεRIγ signaling domain that included an anti-EGFR scFv coupled to a CD8 hinge, that in turn was coupled to a CD28 transmembrane domain, which was coupled to a FcεRIγ signaling domain. The so constructed EGFR-CAR had a nucleic acid sequence of SEQ ID NO:39 and an amino acid sequence of SEQ ID NO:56.

Figure 14:
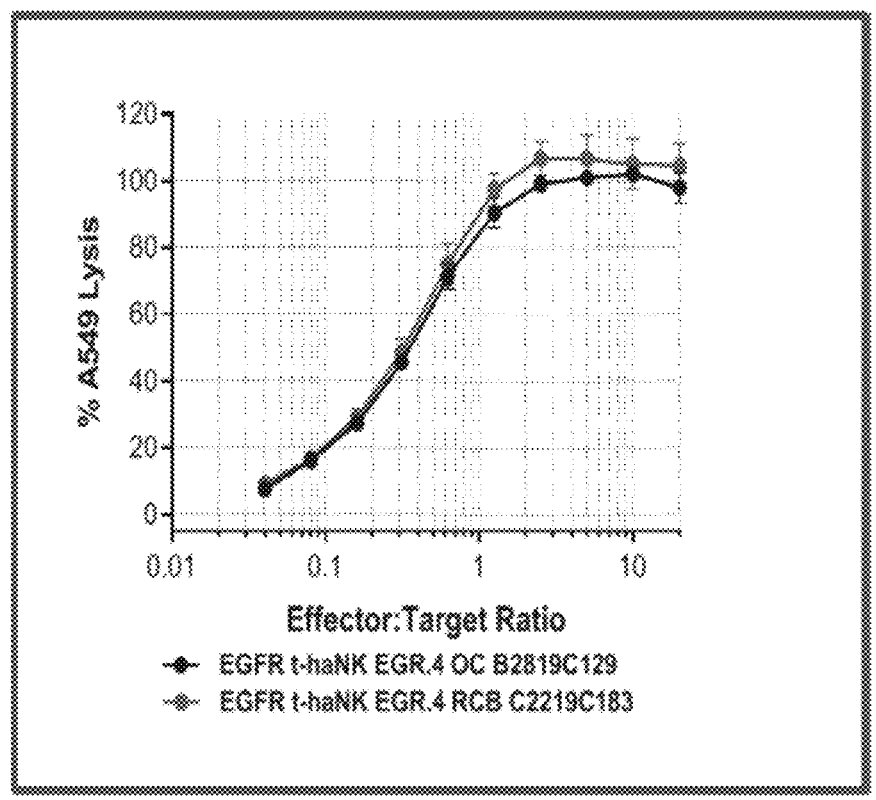
FIG. 14 shows exemplary results for cytotoxicity of EGFR.CAR-t-haNK cells against A-549 cells.
Figure 31:
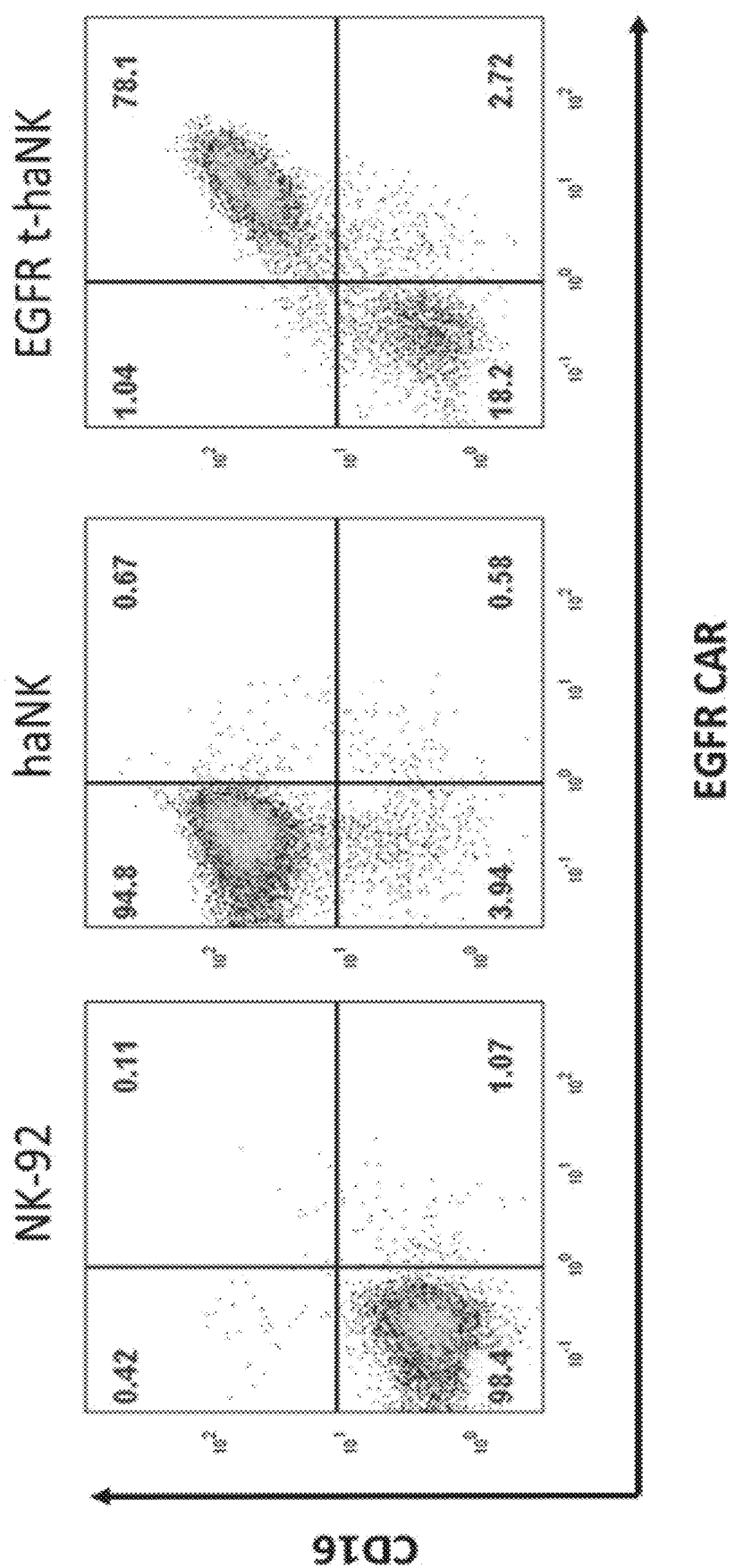
FIG. 31 shows exemplary results for expression of CD16 and EGFR.CAR.
Figure 32:
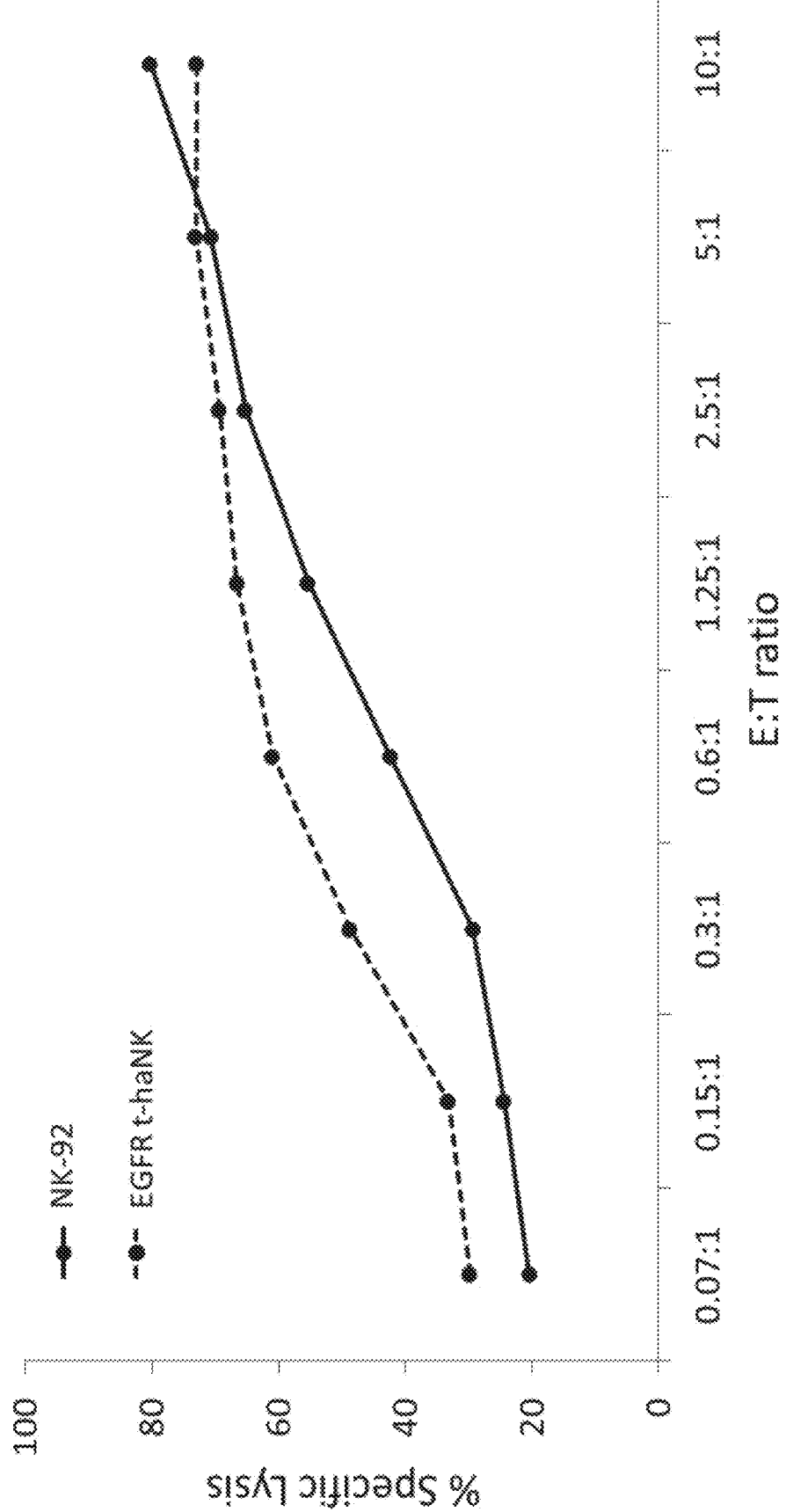
FIG. 32 shows exemplary results for natural cytotoxicity of EGFR.CAR-t-haNK cells against K562 cells.
Figure 33:
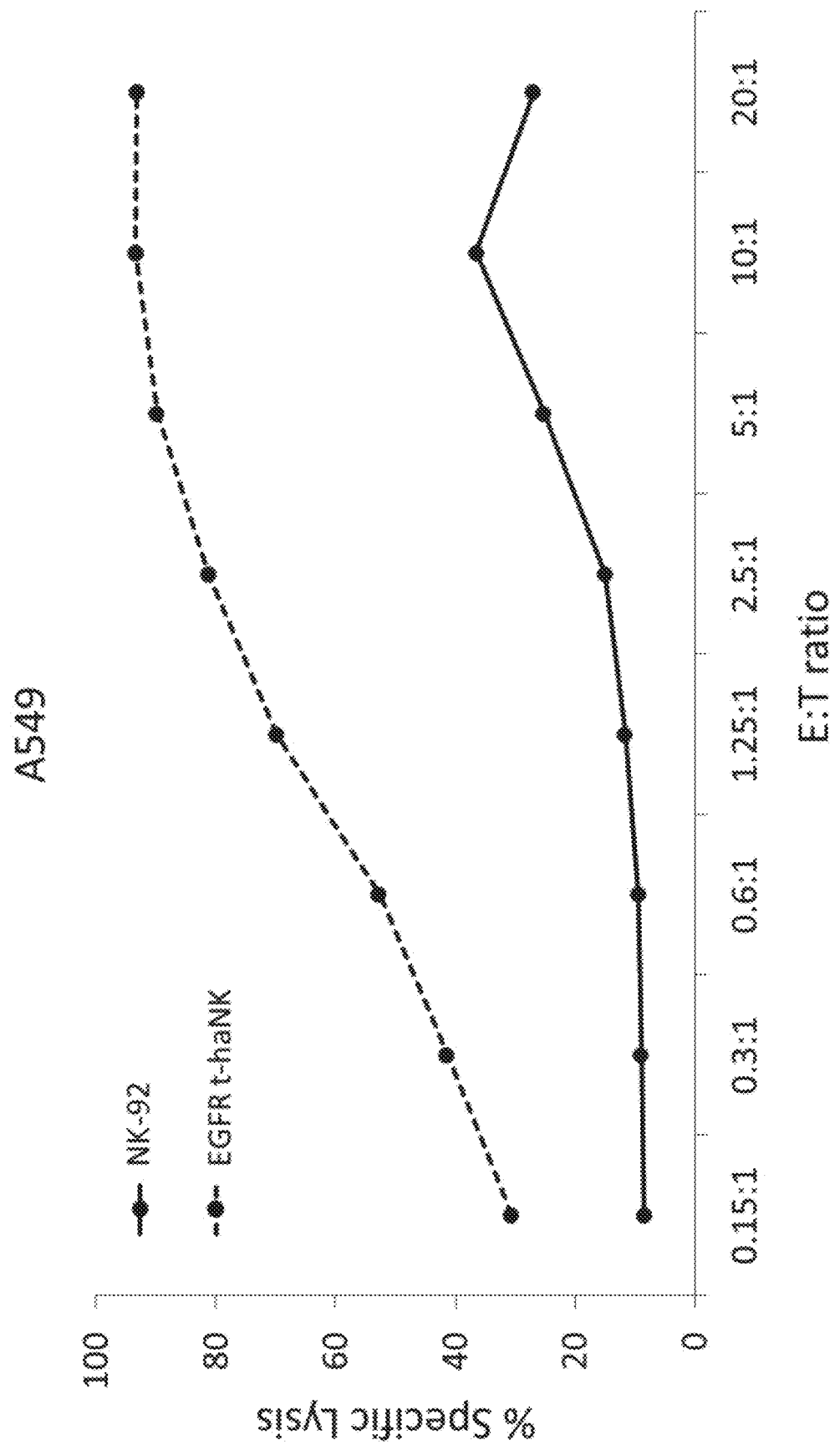
FIG. 33 shows exemplary results for CAR mediated cytotoxicity of EGFR.CAR-t-haNK cells against A549 cells.
Figure 34:
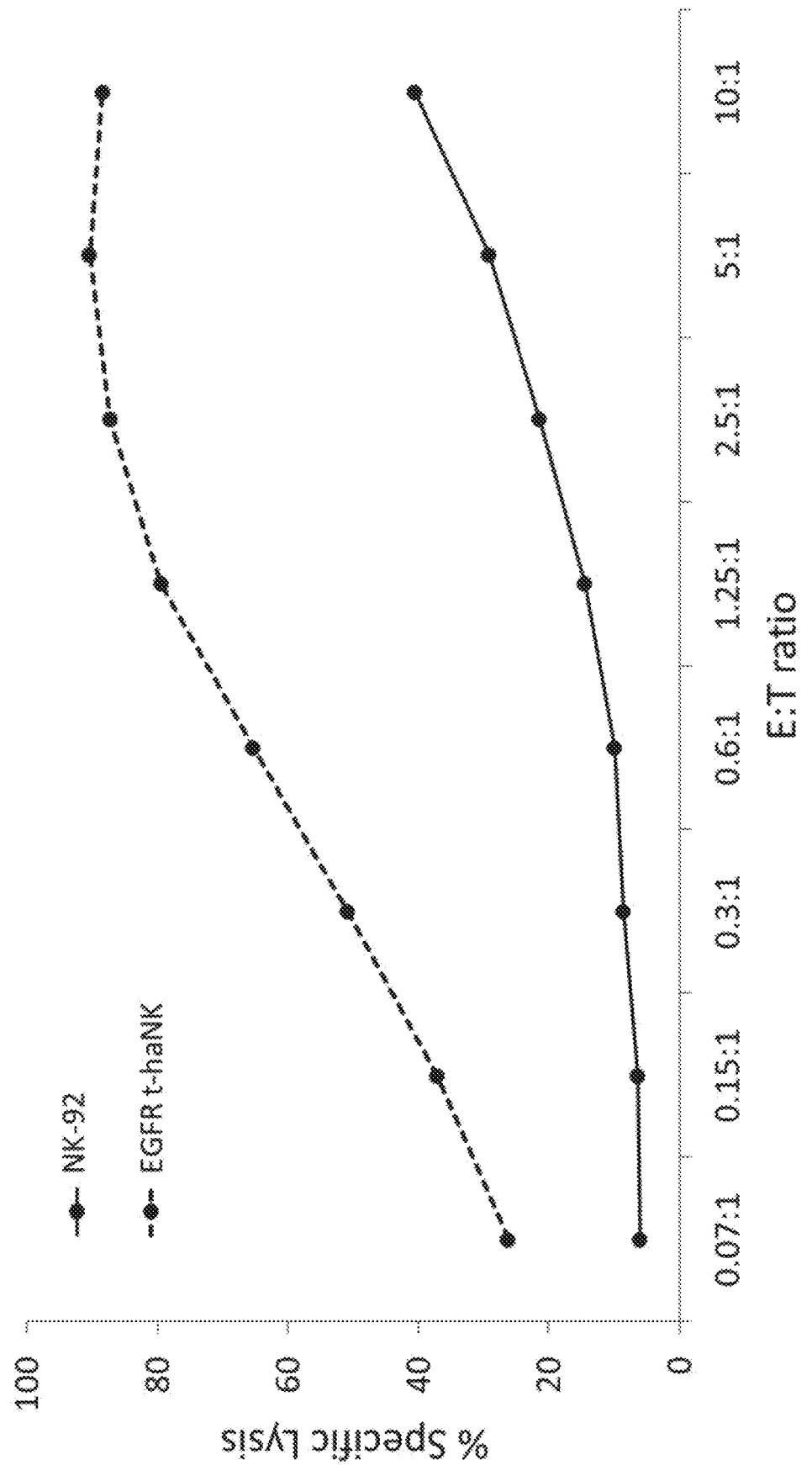
FIG. 34 shows exemplary results for CAR mediated cytotoxicity of EGFR.CAR-t-haNK cells against HCT 116 cells.
Figure 35:
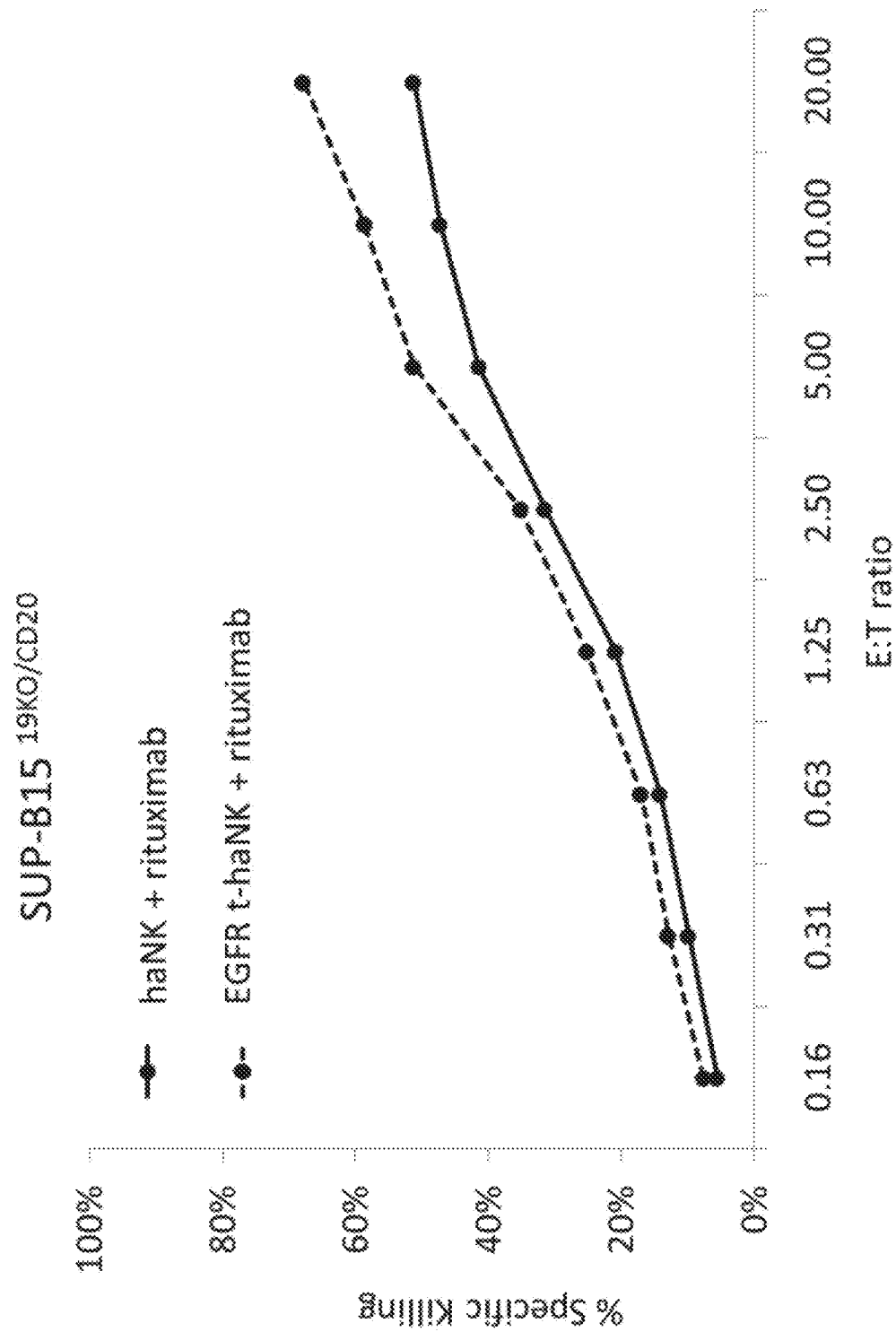
FIG. 35 shows exemplary results for ADCC of EGFR-.CAR-t-haNK cells.

Functionality of the so constructed EGFR.CAR-t-haNK cells was tested against A-549 cells using a standard cytotoxicity assay and exemplary results are shown in FIG. 14. As can be readily seen from the data, the EGFR.CAR-t-haNK cells expressing the CAR with the FcεRIγ signaling domain exhibited significant cytotoxicity against the A-549 target cells. Expression of the EGFR-CAR in the EGFR-.CAR-t-haNK cells is shown in FIG. 31, while natural cytotoxicity results are shown in FIG. 32. Exemplary results for CAR mediated cytotoxicity of EGFR.CAR-t-haNK cells are shown in FIG. 33 and FIG. 34, while results for ADCC of EGFR.CAR-t-haNK cells are shown in FIG. 35.

Example 10: IGF1R-CAR with FcεRIγ Signaling Domain

Figure 61:
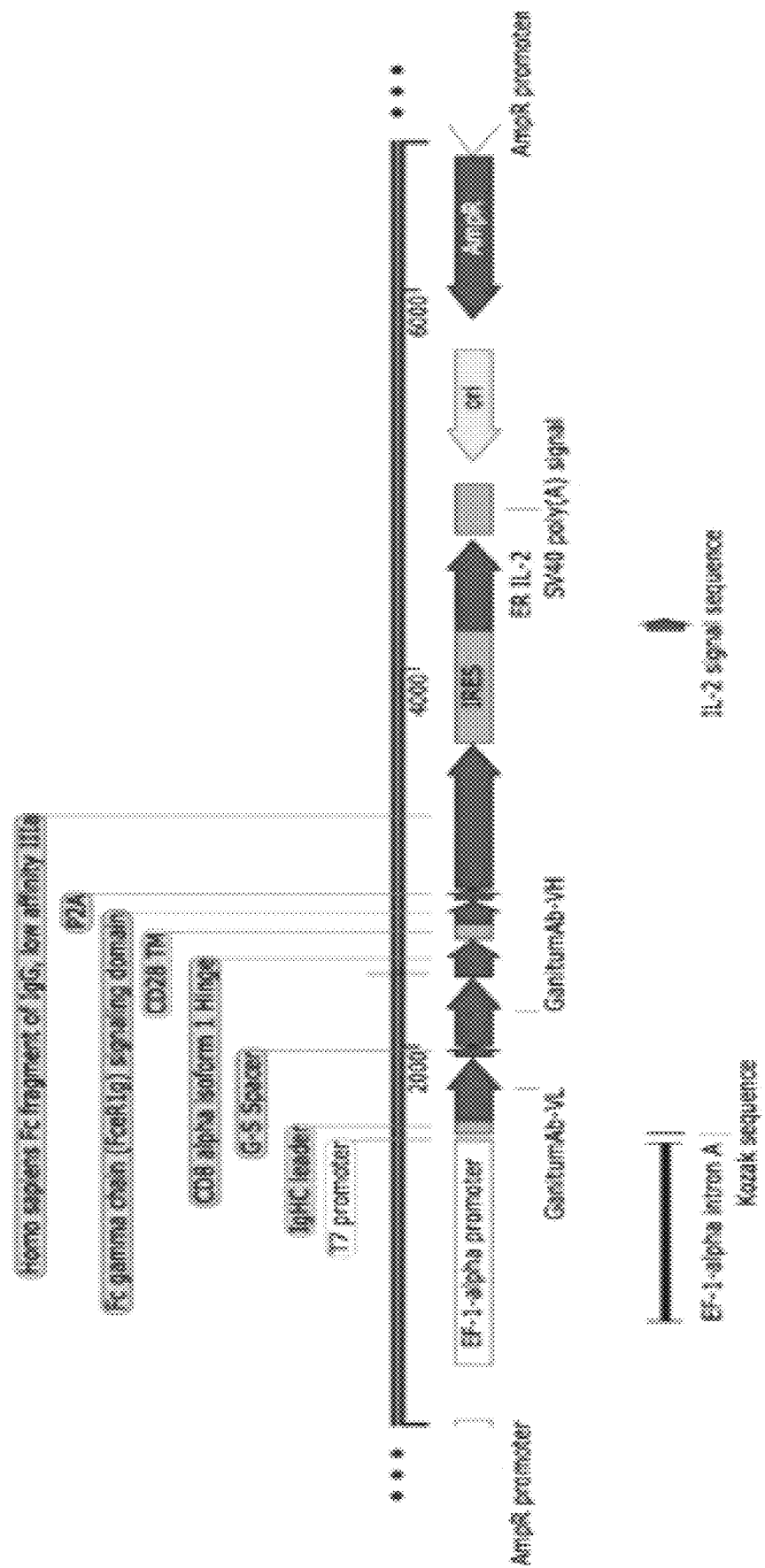
FIG. 61 depicts an exemplary tricistronic construct encoding IGF1R-CAR, CD16, and IL-$2^{ER}$.

In this example, the inventors constructed a $1^{st}$ generation CARs with a FcεRIγ signaling domain that included an anti-IGF1R scFv coupled to a CD8 hinge, that in turn was coupled to a CD28 transmembrane domain, which was coupled to a FcεRIγ signaling domain. The so constructed IGF1R-CAR had a nucleic acid sequence of SEQ ID NO:40, and an amino acid sequence of SEQ ID NO:57. A tricistronic construct encoding IGF1R-CAR, CD16, and IL-$2^{ER}$ had a nucleic acid sequence of SEQ ID NO:53, which is also schematically illustrated in FIG. 61.

Figure 18:
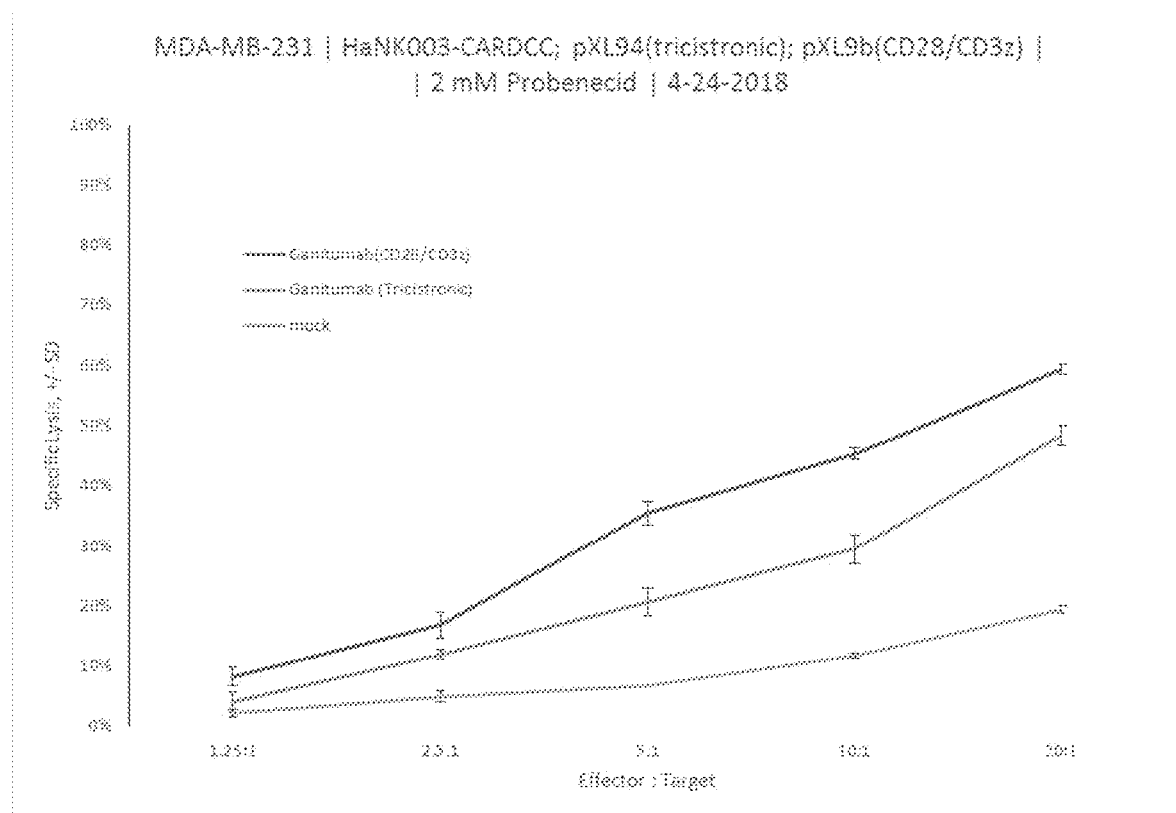
FIG. 18 shows exemplary results for cytotoxicity of IGF1R.CAR-t-haNK cells against MDA-MB-231 cells.

Functionality of the so constructed IGF1R.CAR-t-haNK cells was tested against MDA-MB-231 cells using a standard cytotoxicity assay in comparison with a $2^{nd}$ generation CAR (CD28/CD3z) and exemplary results are shown in FIG. 18. As can be readily seen from the data, the IGF1R.CAR-t-haNK cells expressing the CAR with the FcεRIγ signaling domain exhibited significant and target specific cytotoxicity against the MDA-MB-231 target cells, which was comparable with the cytotoxicity of the $2^{nd}$ generation CAR.

Example 11: CD123-CAR with FcεRIγ Signaling Domain

Figure 44:
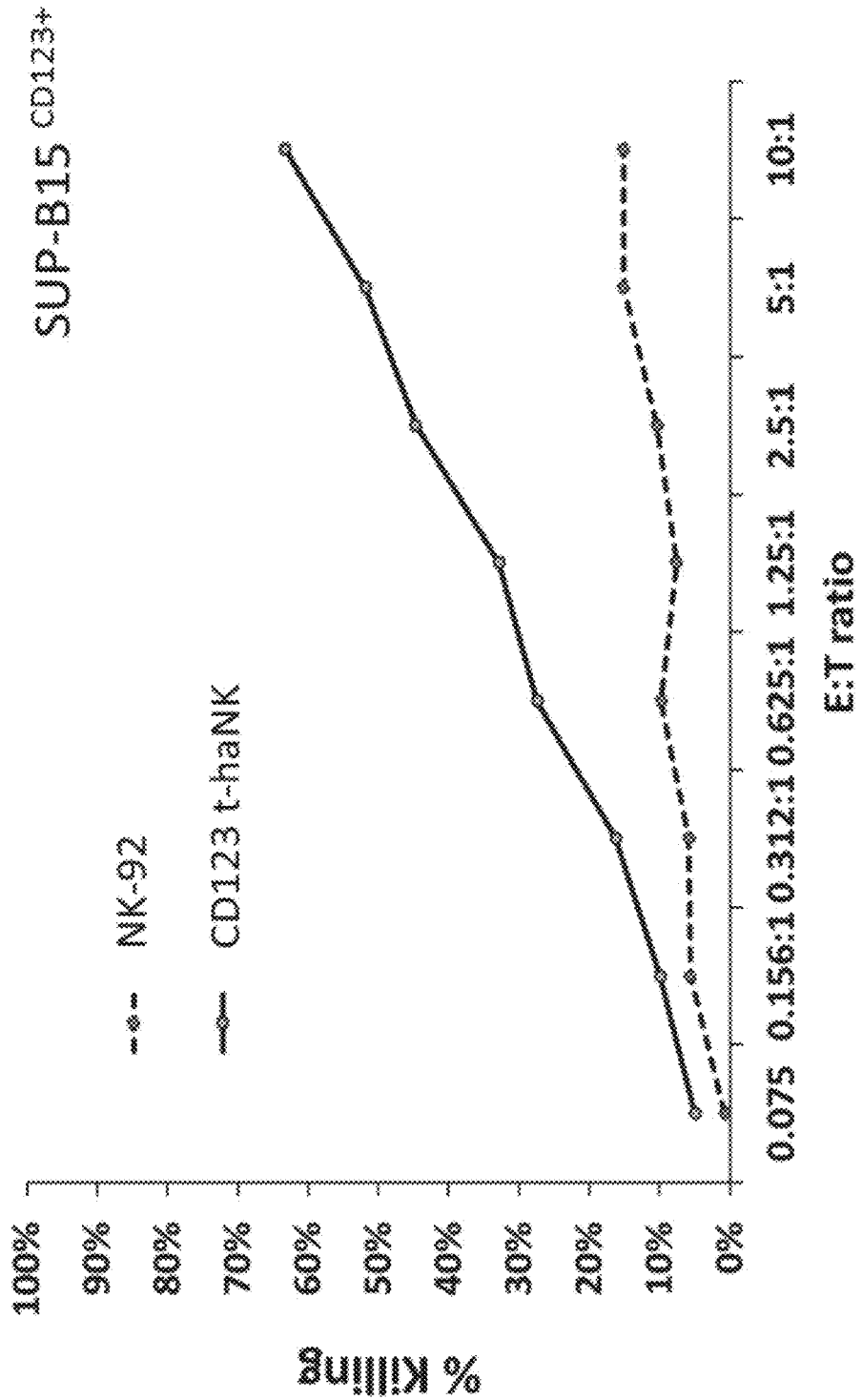
FIG. 44 shows exemplary results for CAR mediated cytotoxicity of CD123.CAR-t-haNK cells.
Figure 45:
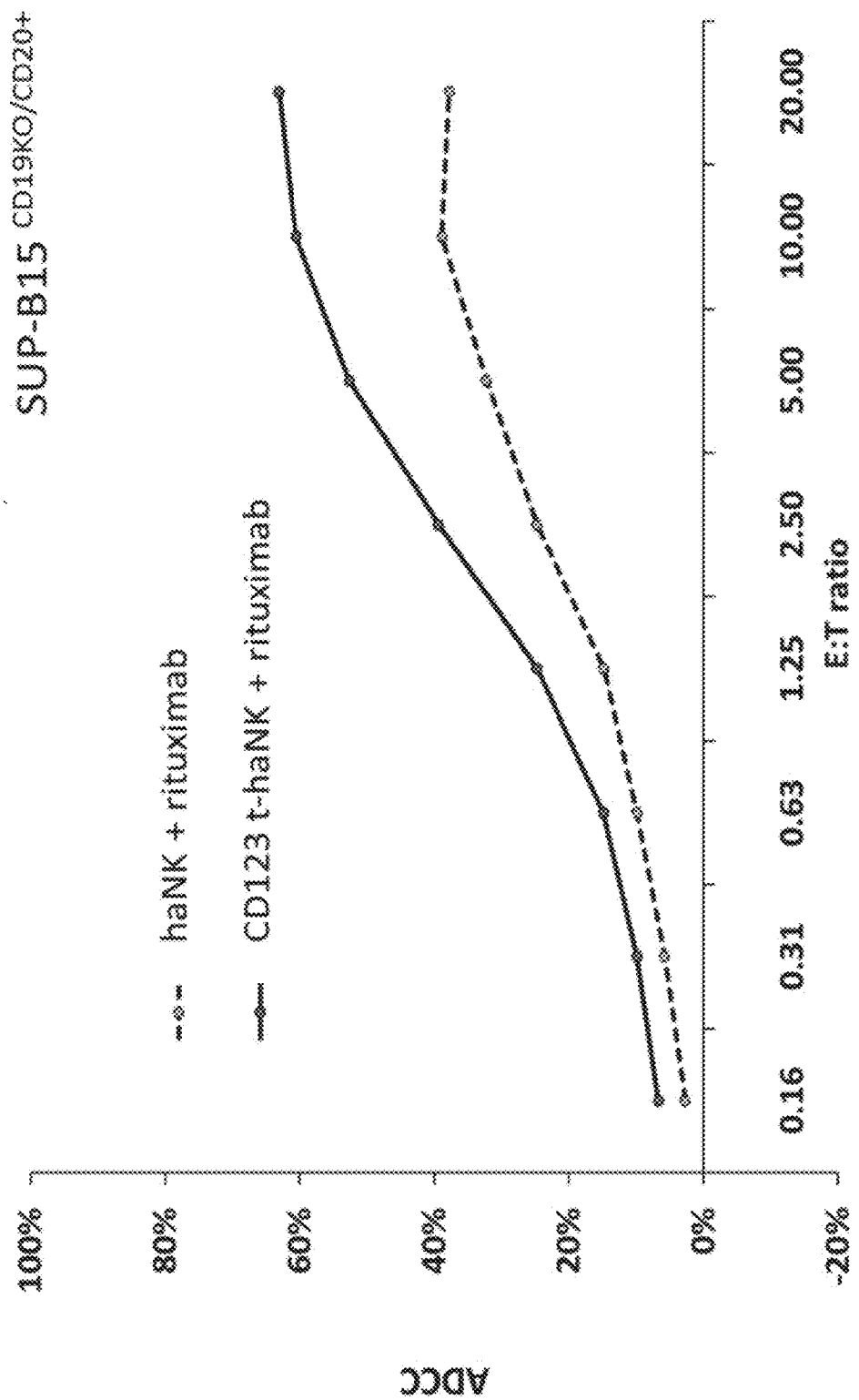
FIG. 45 shows exemplary results for ADCC of CD123.CAR-t-haNK cells.

In this example, the inventors constructed a $1^{st}$ generation CARs with a FcεRIγ signaling domain that included an anti-CD123 scFv coupled to a CD8 hinge, that in turn was coupled to a CD28 transmembrane domain, which was coupled to a FcεRIγ signaling domain. The so constructed CD123-CAR had a nucleic acid sequence of SEQ ID NO.41 and an amino acid sequence of SEQ ID NO:58. Data for the CAR mediated cytotoxicity of the CD123-CAR expressing recombinant NK cells is shown in FIG. 44, and FIG. 45 shows exemplary data for ADCC of CD123-CAR expressing recombinant NK cells.

Example 12: PD-L1-CAR with FcεRIγ Signaling Domain

In this example, the inventors constructed a $1^{st}$ generation CARs with a FcεRIγ signaling domain that included an anti-PD-L1 scFv coupled to a CD8 hinge, that in turn was coupled to a CD28 transmembrane domain, which was coupled to a FcεRIγ signaling domain. The so constructed PD-L1-CAR had a nucleic acid sequence of SEQ ID NO.42 and an amino acid sequence of SEQ ID NO:59.

Figure 12:
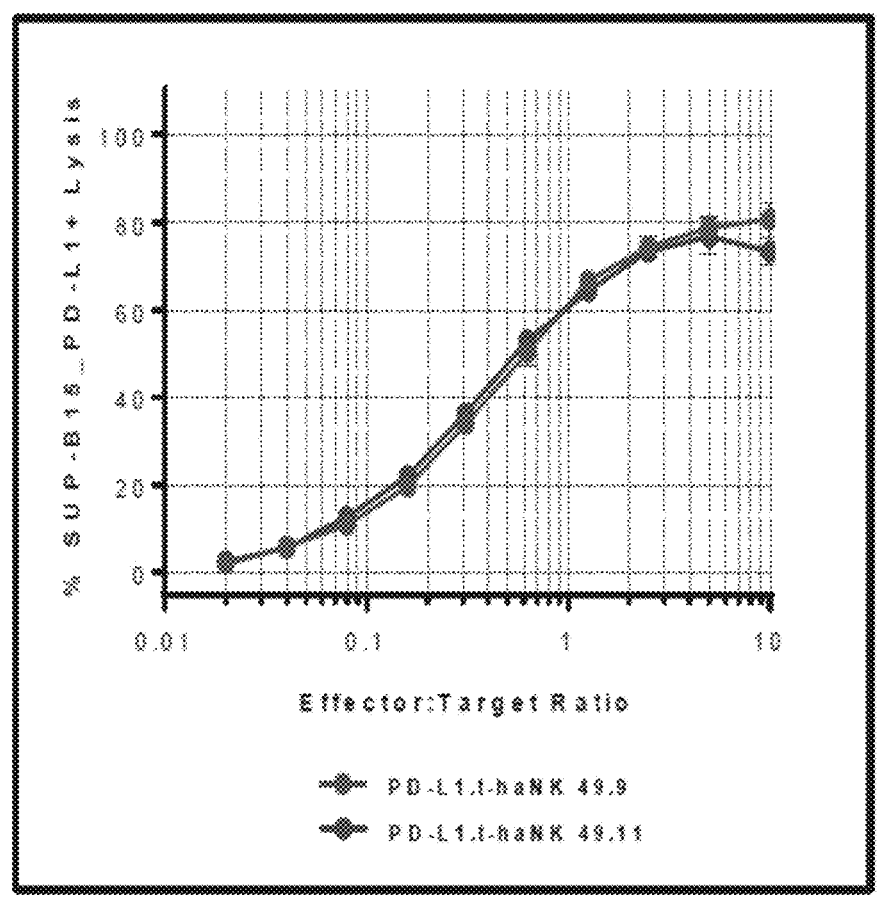
FIG. 12 shows exemplary results for cytotoxicity of PD-L1.CAR-t-haNK cells against SUP-B15.PD-L1+ cells.

Functionality of the so constructed PD-L1.CAR-t-haNK cells was tested against SUP-B15.PD-L1V cells using a standard cytotoxicity assay and exemplary results are shown in FIG. 12. As can be readily seen from the data, the PD-L1.CAR-t-haNK cells expressing the CAR with the FcεRIγ signaling domain exhibited significant cytotoxicity against the SUP-B15.PD-LV1 target cells.

Figure 13:
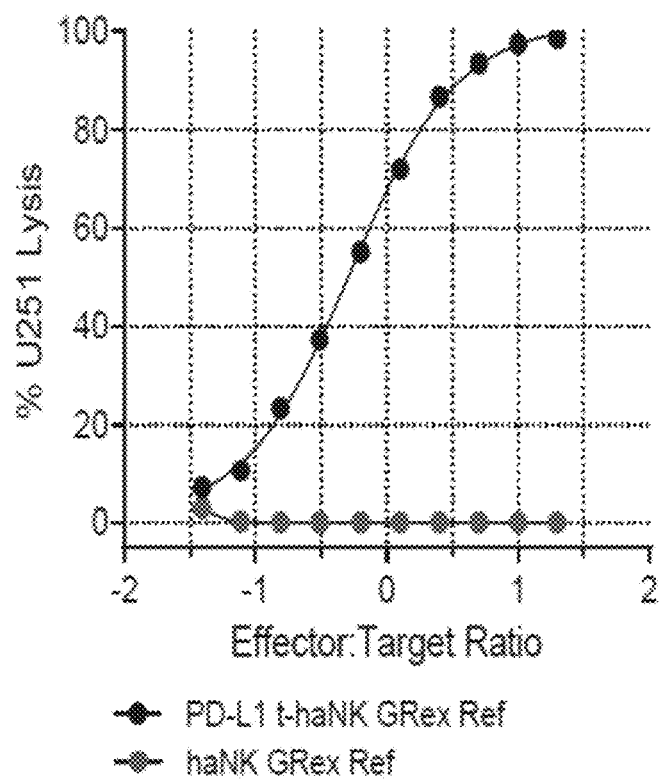
FIG. 13 shows exemplary results for cytotoxicity of PD-L1.CAR-t-haNK cells against U251 cells.

Functionality of the so constructed PD-L1.CAR-t-haNK cells was also tested against U251 cells using a standard cytotoxicity assay and exemplary results are shown in FIG. 13 along with non-transfected haNK cells. As can be readily seen from the data, the PD-L1.CAR-t-haNK cells expressing the CAR with the FcεRIγ signaling domain exhibited target specific and significant cytotoxicity against the U251 target cells, whereas the haNK control cells had substantially no cytotoxicity against the same U251 cells.

Figure 19:
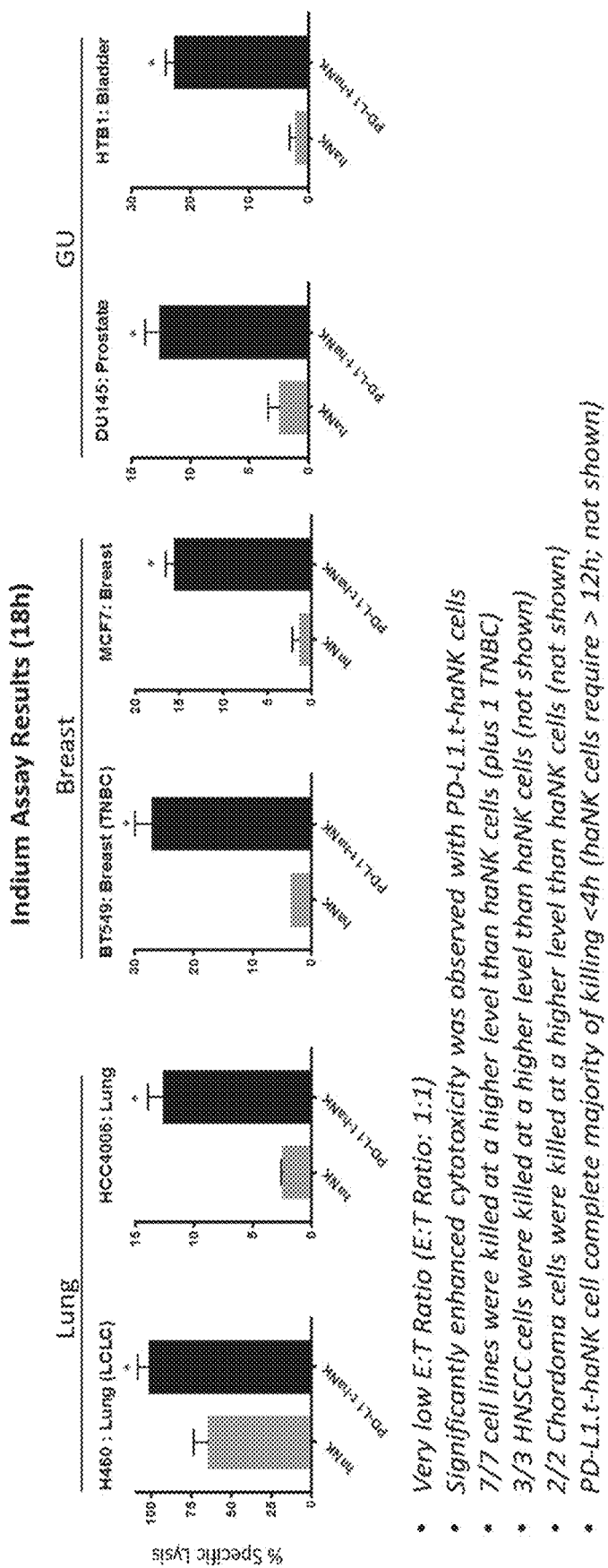
FIG. 19 shows exemplary results for cytotoxicity of PD-L1.CAR-t-haNK cells against a variety of cancer cells.

In still further experiments on target cell specificity with respect to PD-L1, the inventors tested several PD-L1 positive tumor cell lines using the PD-L1.CAR-t-haNK cells along with haNK cells as control for general cytotoxicity. As can be readily seen from FIG. 19, the PD-L1.CAR-t-haNK cells had superior cytotoxicity across a wide variety of tumor cells (lung, breast, genitourinary tumor cells, and additionally, head and neck small cell cancer, chordoma). Notably, the PD-L1.CAR-t-haNK cells required less than 4 hours for the majority (>85%) of cell killing whereas the control haNK cells required more than 12 hours.

Figure 20:
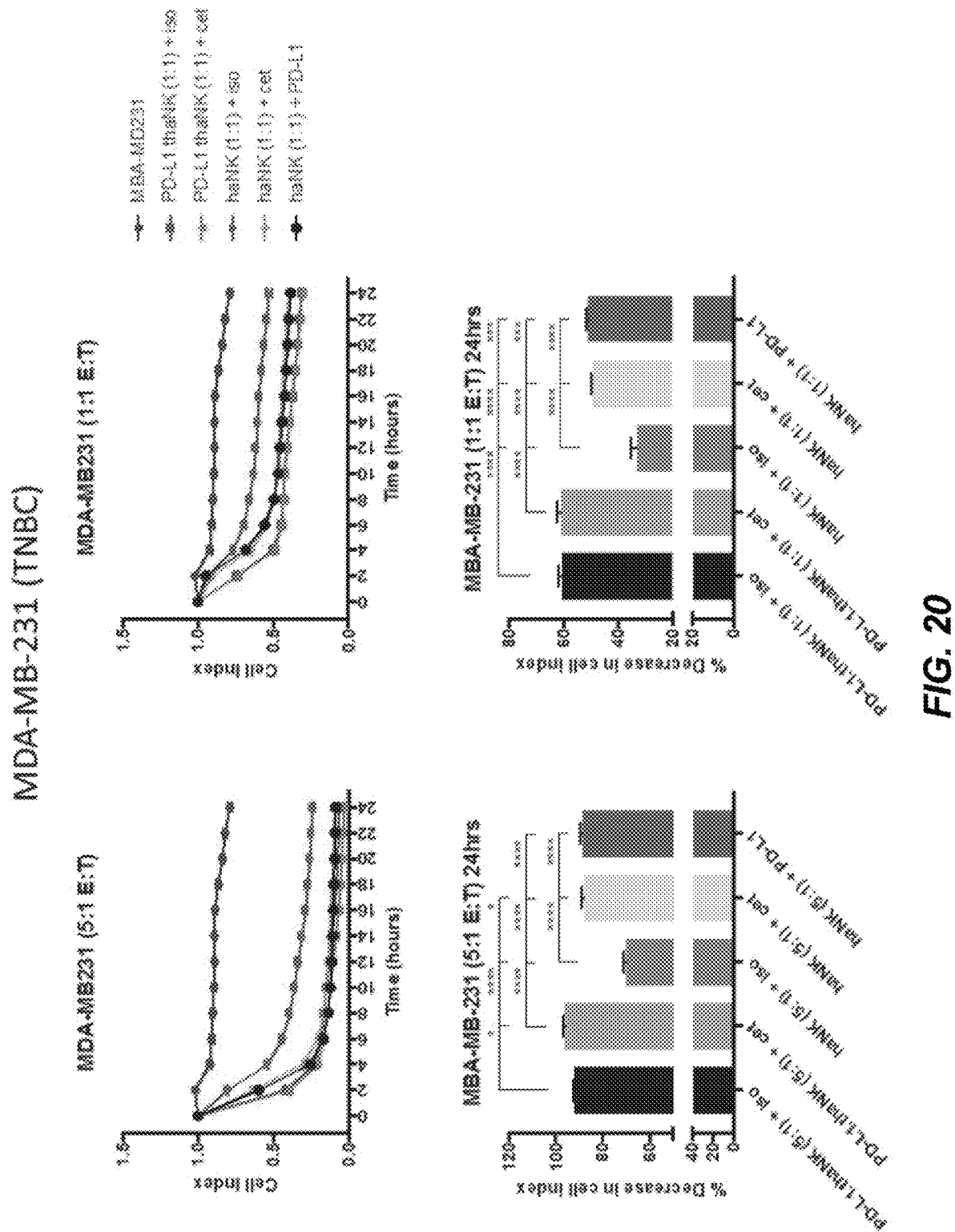
FIG. 20 shows exemplary comparative results for cytotoxicity of PD-L1.CAR-t-haNK cells against MDA-MB-231 cells.

FIG. 20 further illustrates cytotoxicity of the PD-L1.CAR-t-haNK cells against MDA-MB-231 cells as compared to various other control cells (haNK cells as indicated). As can be taken from the data, at a 5:1 E:T ratio, MDA-MB-231 lysis by PD-L1.thaNK was improved by cetuximab, and haNK activity was improved by the addition of cetuximab and a-PD-L1. Plain PD-L1.thank had improved cytotoxic activity compared to haNK and haNK+cetuximab, and plain PD-L1.thank killing was comparable to that of haNK+PD-L1 antibody but PD-L1.thank+cetuximab outperformed haNK+cetuximab and haNK+PD-L1. At a 1:1 E:T ratio, PD-L1.thaNK activity was the same with or without cetuximab, and PD-L1.thaNK significantly outperformed intrinsic and ADCC-mediated killing by hank. haNK activity was improved by the addition of cetuximab and a-PD-L1.

Figure 40:
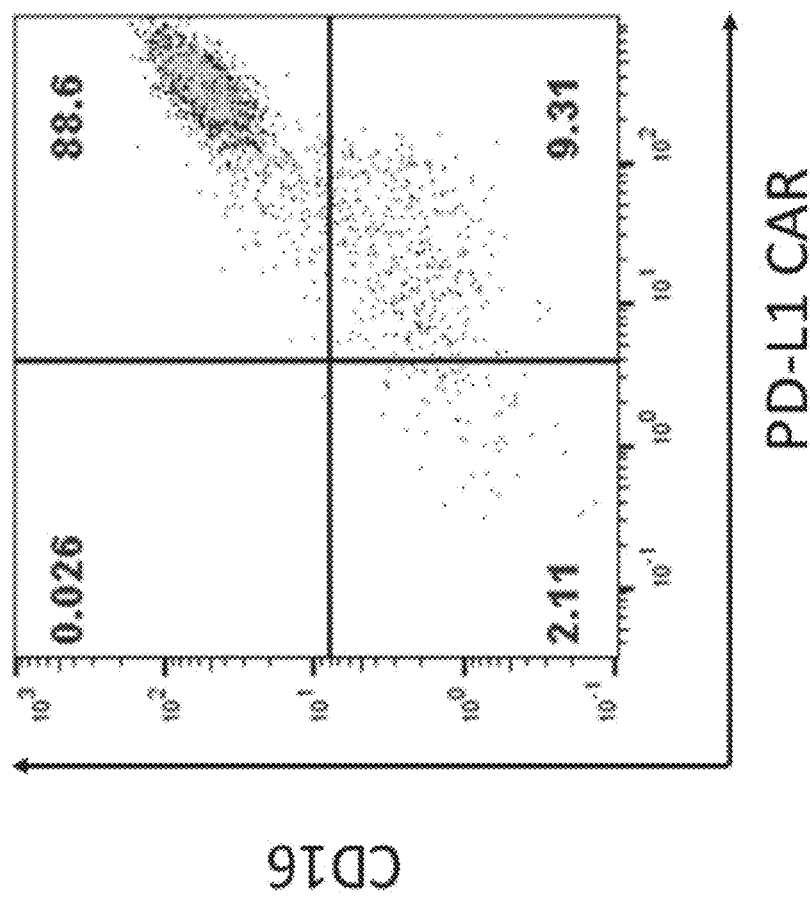
FIG. 40 shows exemplary results expression of CD16 and PD-L1.CAR.
Figure 41:
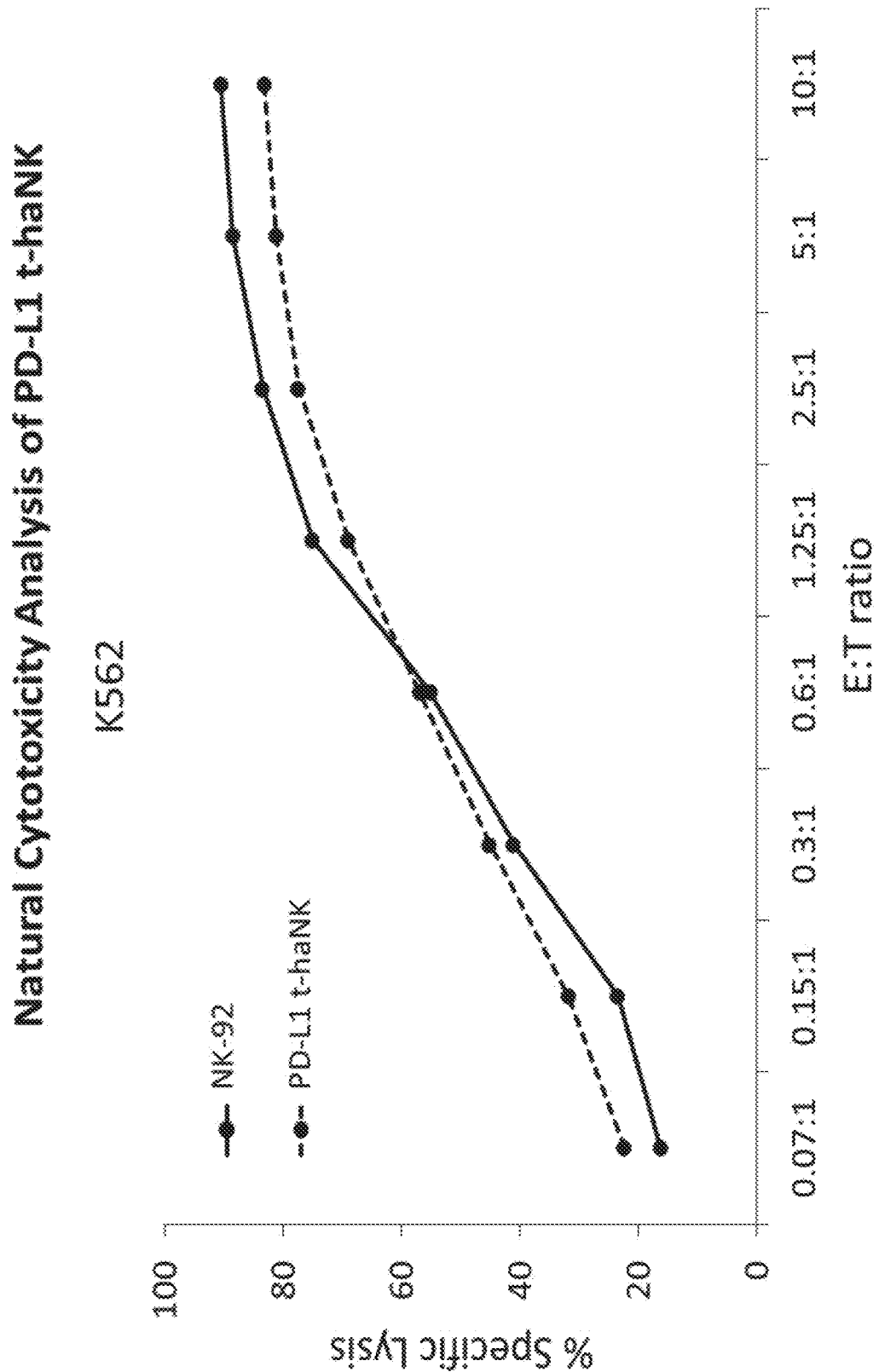
FIG. 41 shows exemplary results for natural cytotoxicity of PD-L1.CAR-t-haNK cells against K562 cells.
Figure 42:
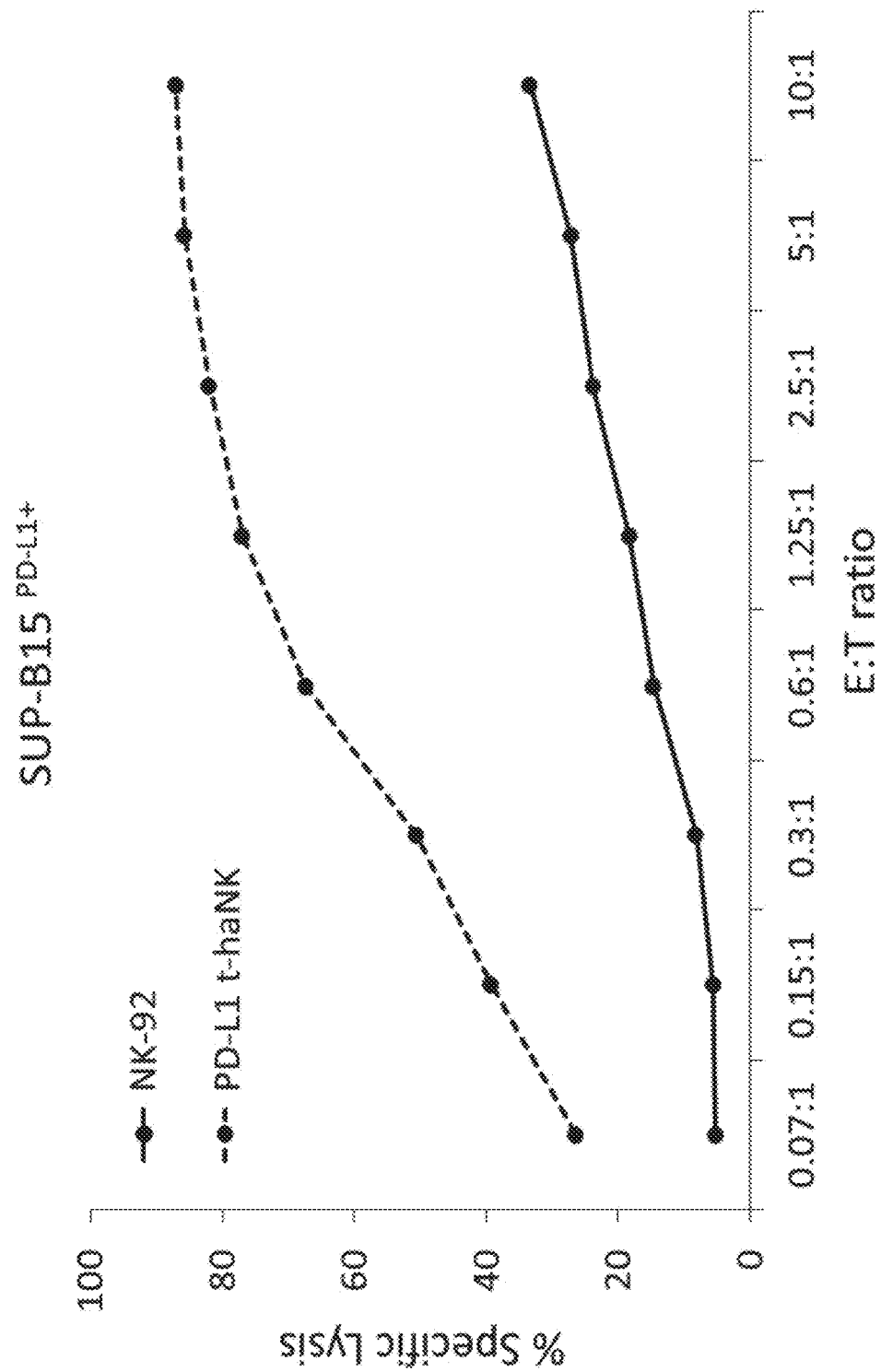
FIG. 42 shows exemplary results for CAR mediated cytotoxicity of PD-L1.CAR-t-haNK cells.
Figure 43:
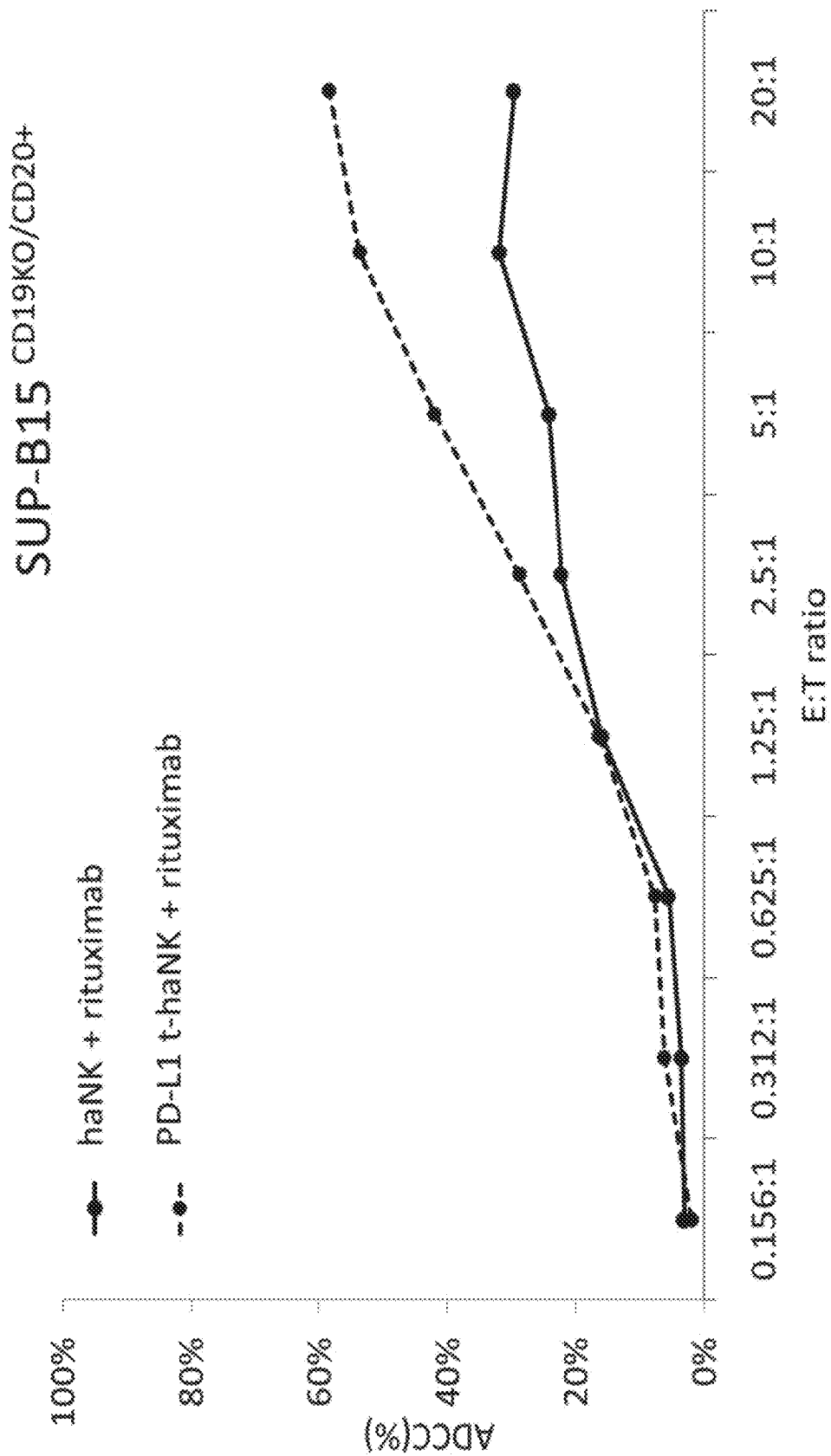
FIG. 43 shows exemplary results for ADCC of PD-L1.CAR-t-haNK cells.

In further experiments, the inventors demonstrated expression of the PD-L1.CAR in PD-L1.CAR-t-haNK cells as is illustrated in FIG. 40. Natural cytotoxicity of the PD-L1.CAR-t-haNK cells is shown in the results of FIG. 41, while results for CAR mediated cytotoxicity are shown in FIG. 42. Exemplary data for ADCC of PD-L1.CAR-t-haNK cells are shown in the graph of FIG. 43.

Example 13: CD33-CAR with FcεRIγ Signaling Domain

In this example, the inventors constructed a 1$^{st}$ generation CARs with a FcεRIγ signaling domain that included an anti-HER2 scFv coupled to a CD8 hinge, that in turn was coupled to a CD28 transmembrane domain, which was coupled to a FcεRIγ signaling domain. The so constructed CD33-CAR had a nucleic acid sequence of SEQ ID NO:43 and an amino acid sequence of SEQ ID NO:60.

Figure 11:
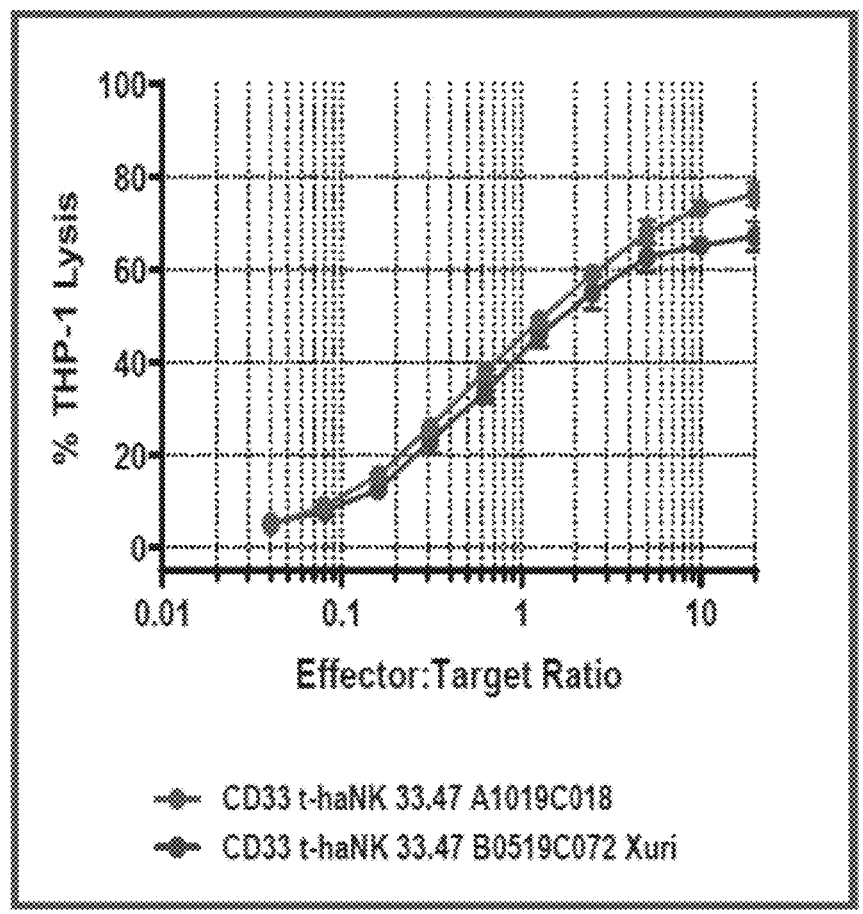
FIG. 11 shows exemplary results for cytotoxicity of CD33.CAR-t-haNK cells against THP-1 cells.
Figure 27:
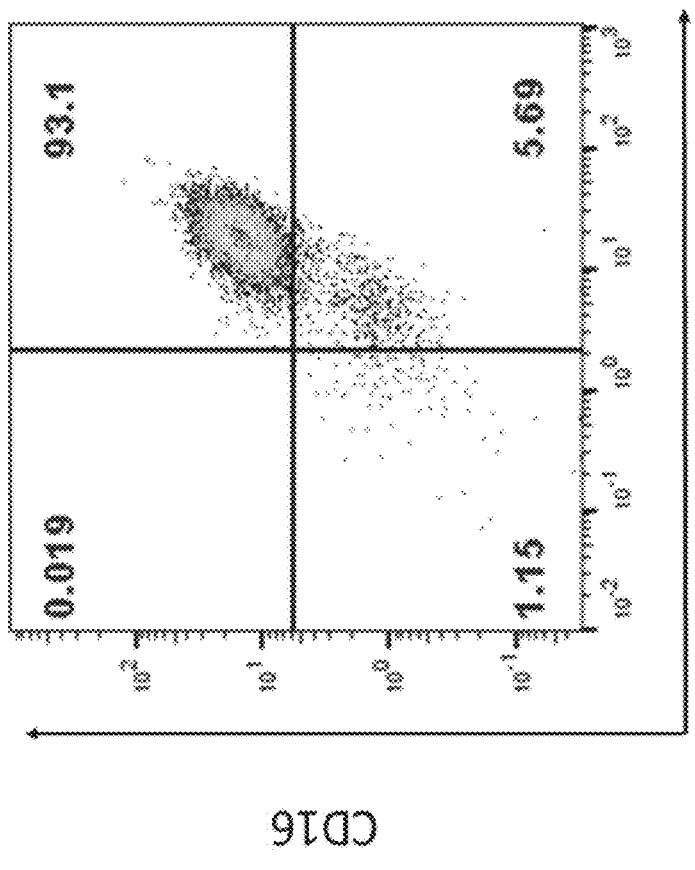
FIG. 27 shows exemplary results for expression of CD16 and CD33.CAR.
Figure 28:
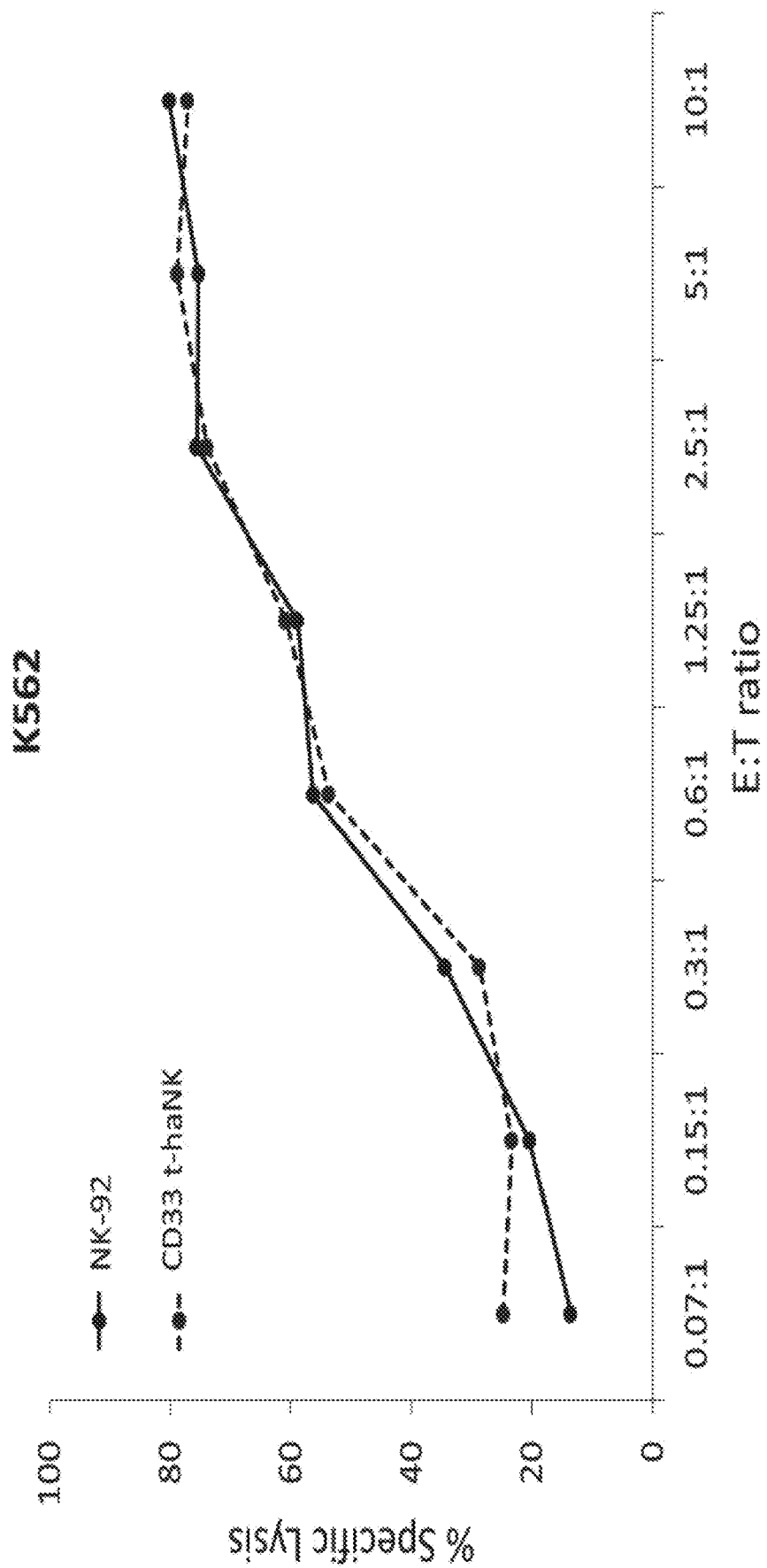
FIG. 28 shows exemplary results for natural cytotoxicity of CD33.CAR-t-haNK cells against K562 cells.
Figure 29:
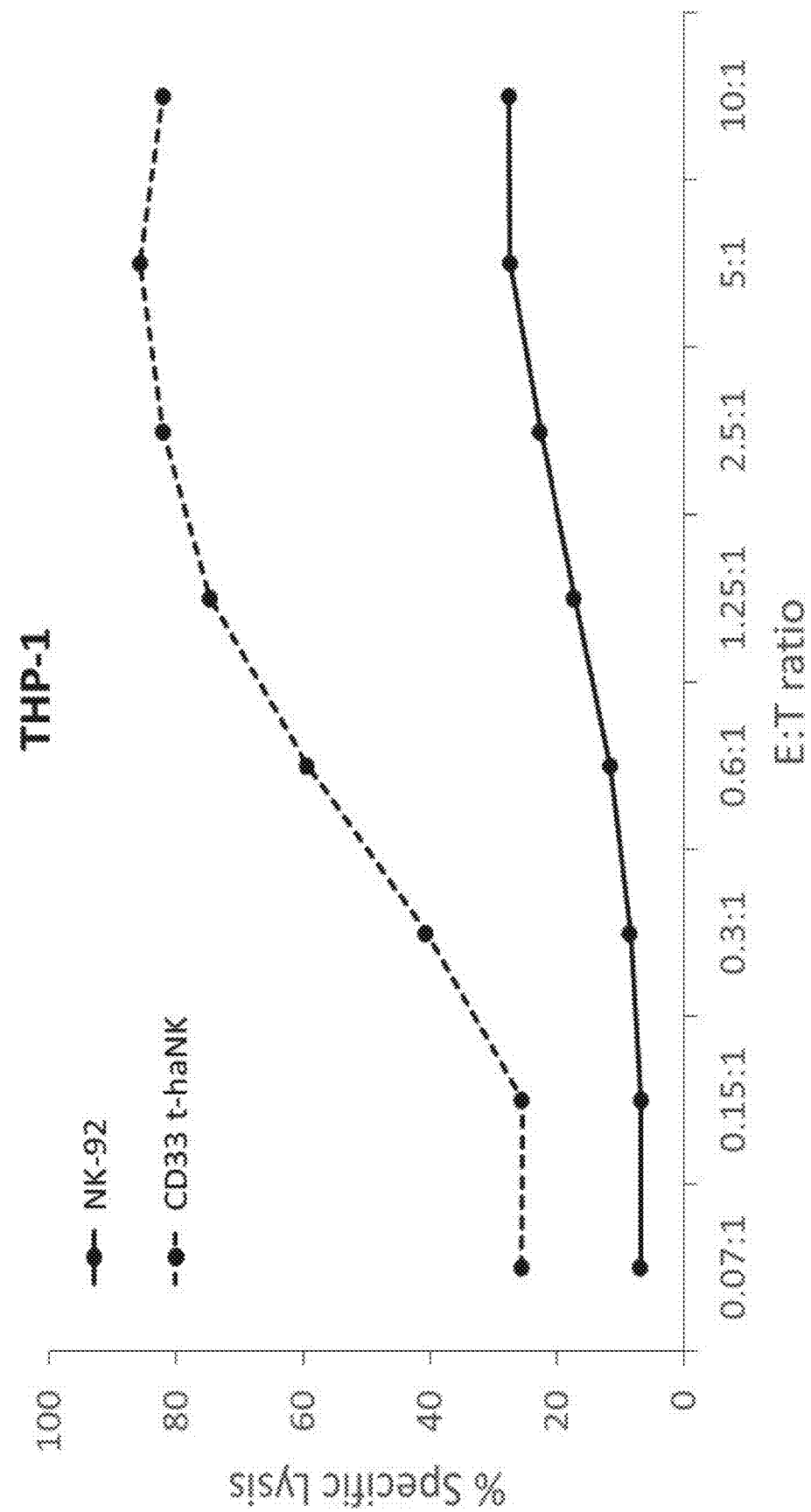
FIG. 29 shows exemplary results for CAR mediated cytotoxicity of CD33.CAR-t-haNK cells against THP-1 cells.
Figure 30:
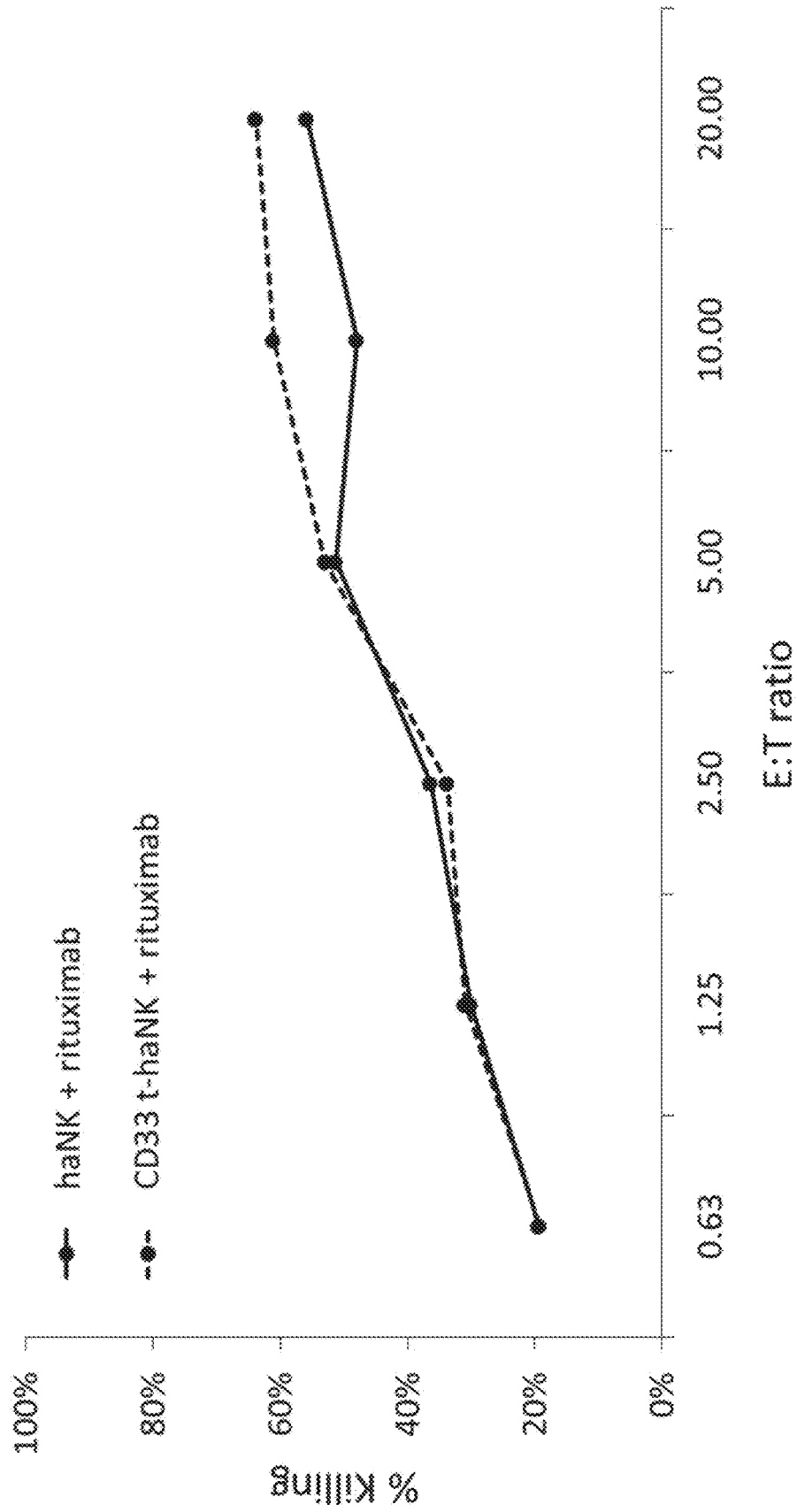
FIG. 30 shows exemplary results for ADCC of CD33.CAR-t-haNK cells.

Functionality of the so constructed CD33.CAR-t-haNK cells was tested against THP-1 cells using a standard cytotoxicity assay and exemplary results are shown in FIG. 11. As can be readily seen from the data, the CD33.CAR-t-haNK cells expressing the CAR with the FcεRIγ signaling domain exhibited significant cytotoxicity against the THP-1 target cells. Further data depicting strong expression of the CD33CAR in NK-92 cells are presented in FIG. 27. Natural cytotoxicity of the CD33.CAR-t-haNK cells against K562 cells is shown in FIG. 28, and FIG. 29 depicts results for CAR mediated cytotoxicity against THP-1 cells. FIG. 30 shows further results for ADCC of CD33.CAR-t-haNK cells against SUP-B15 CD19$^{KO}$/CD20$^{+}$ with rituximab.

Example 14: gp120-CAR with FcεRIγ Signaling Domain

In this example, the inventors constructed a 1$^{st}$ generation CARs with a FcεRIγ signaling domain that included an anti-gp120 scFv coupled to a CD8 hinge, that in turn was coupled to a CD28 transmembrane domain, which was coupled to a FcεRIγ signaling domain. The so constructed gp120-CAR had a nucleic acid sequence of SEQ ID NO:44 and an amino acid sequence of SEQ ID NO:61.

Figure 53:
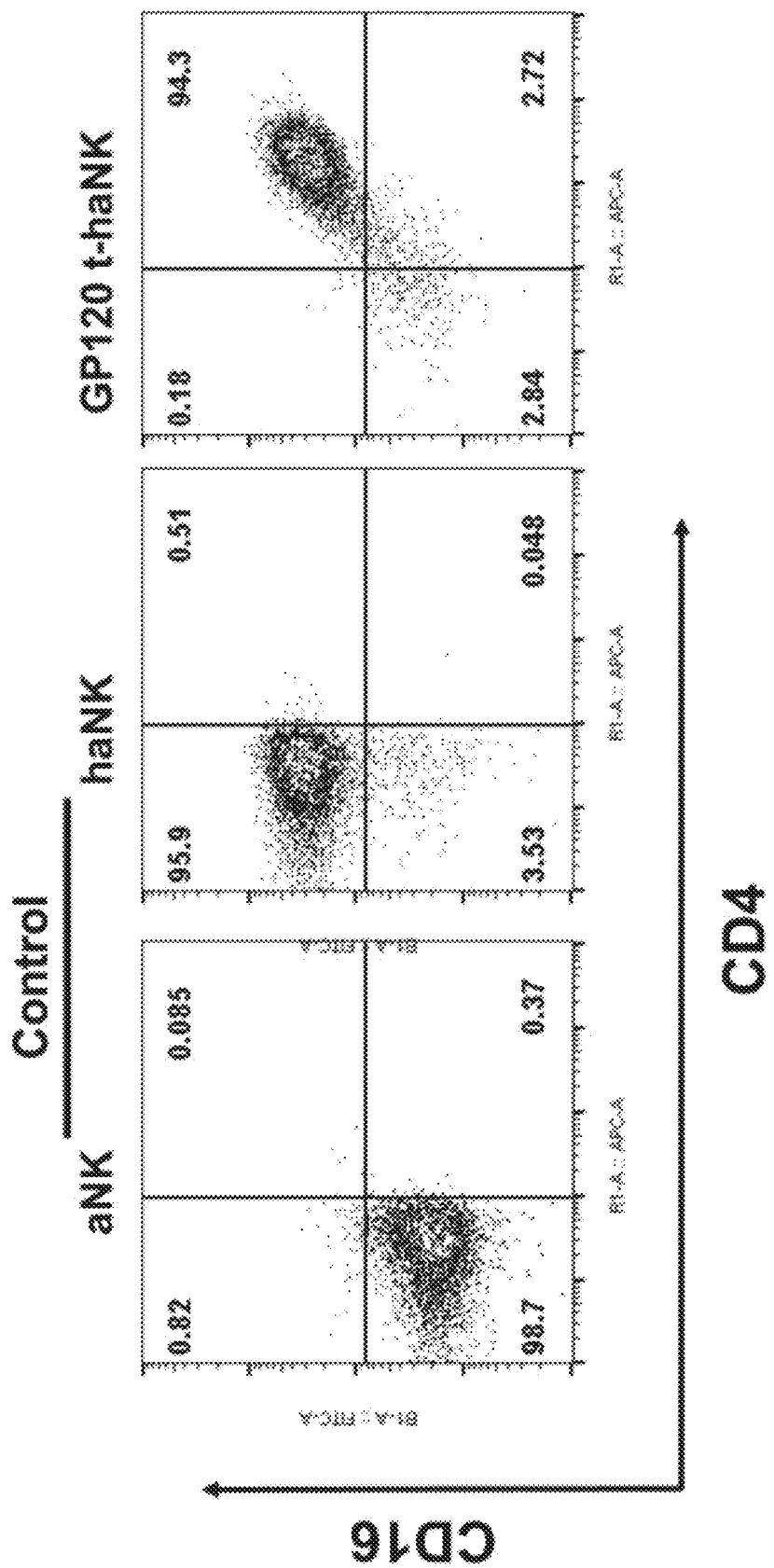
FIG. 53 shows exemplary results for expression of CD16 and gp120.CAR.
Figure 54:
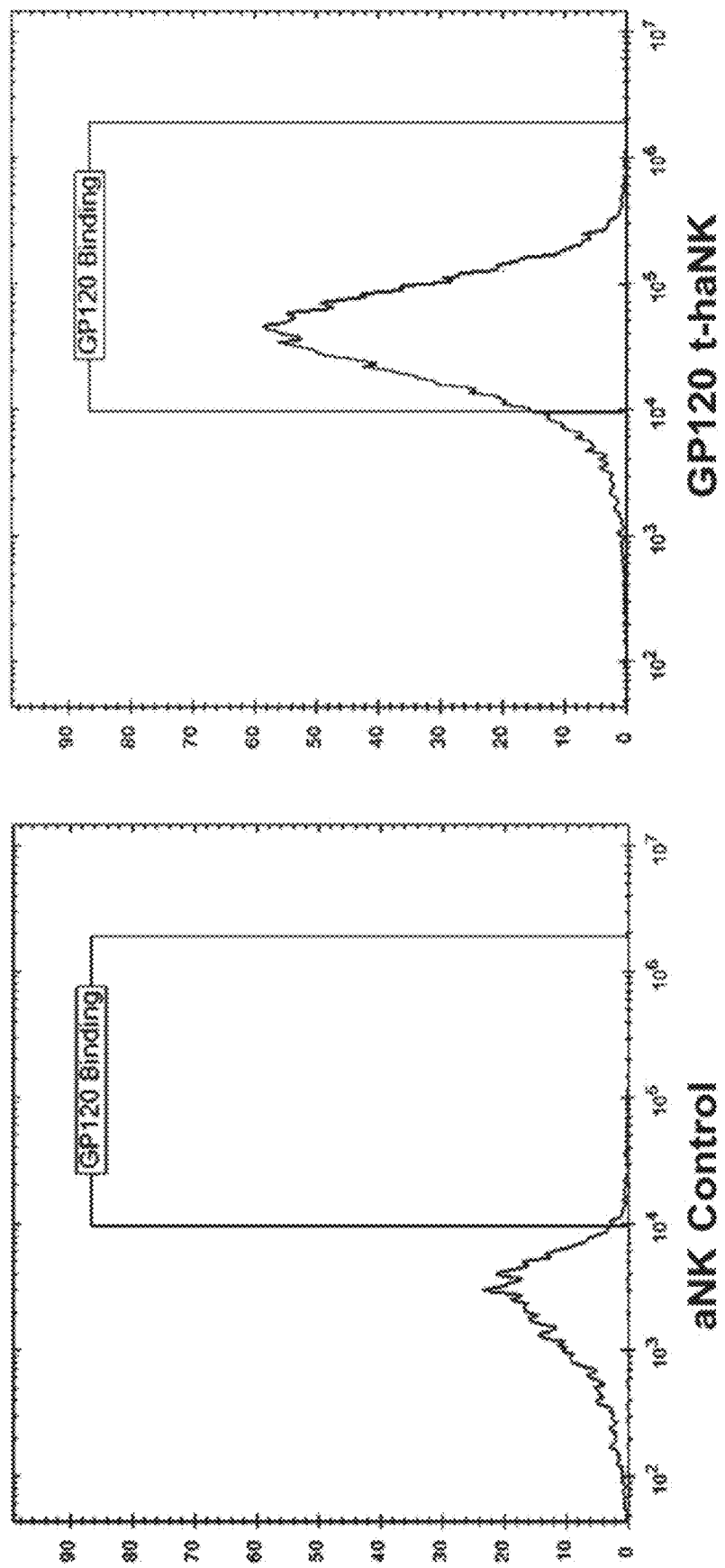
FIG. 54 shows exemplary results for GP120 binding of gp120.CAR-t-haNK cells.
Figure 55:
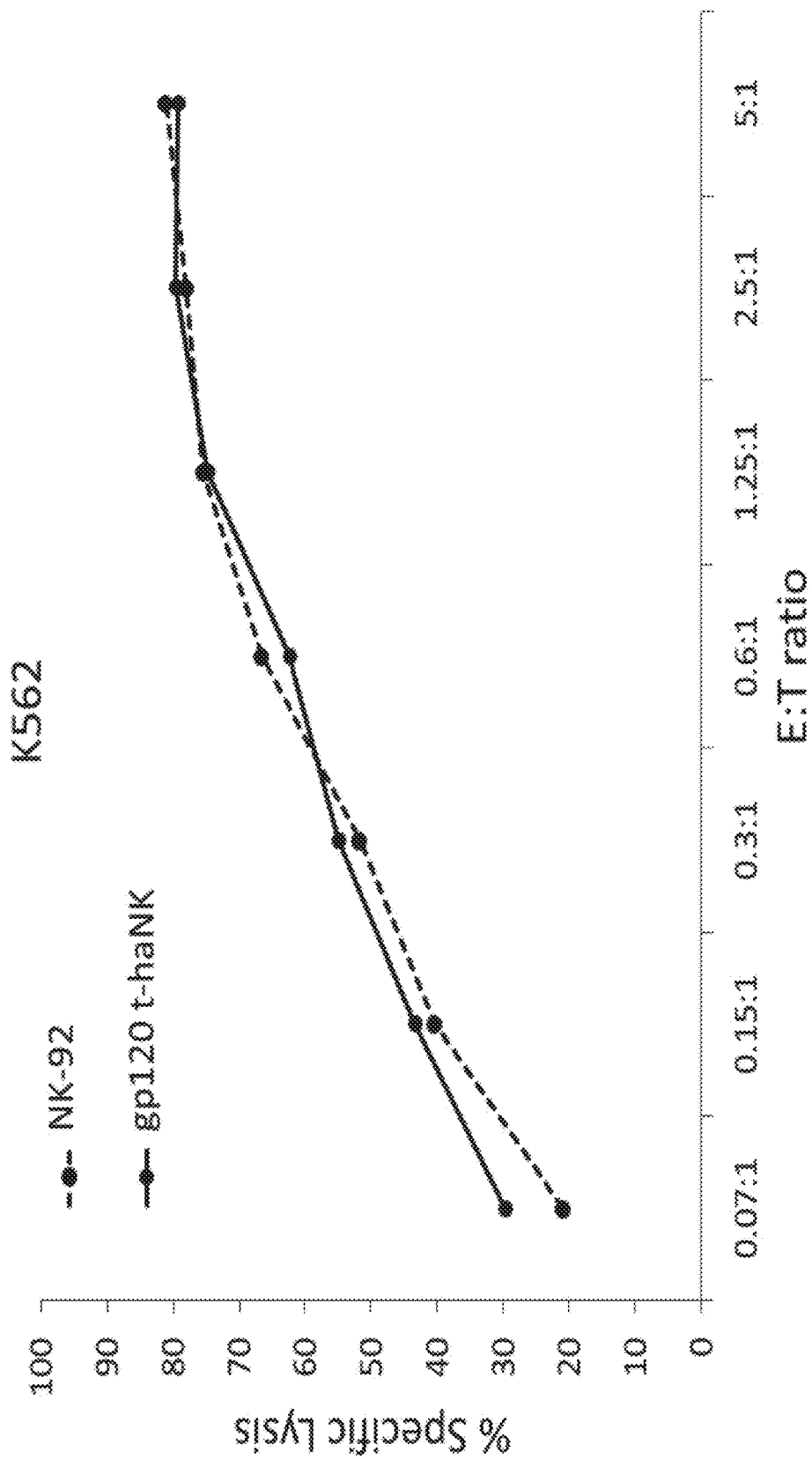
FIG. 55 shows exemplary results for natural cytotoxicity of gp120.CAR-t-haNK cells against K562 cells.
Figure 56:
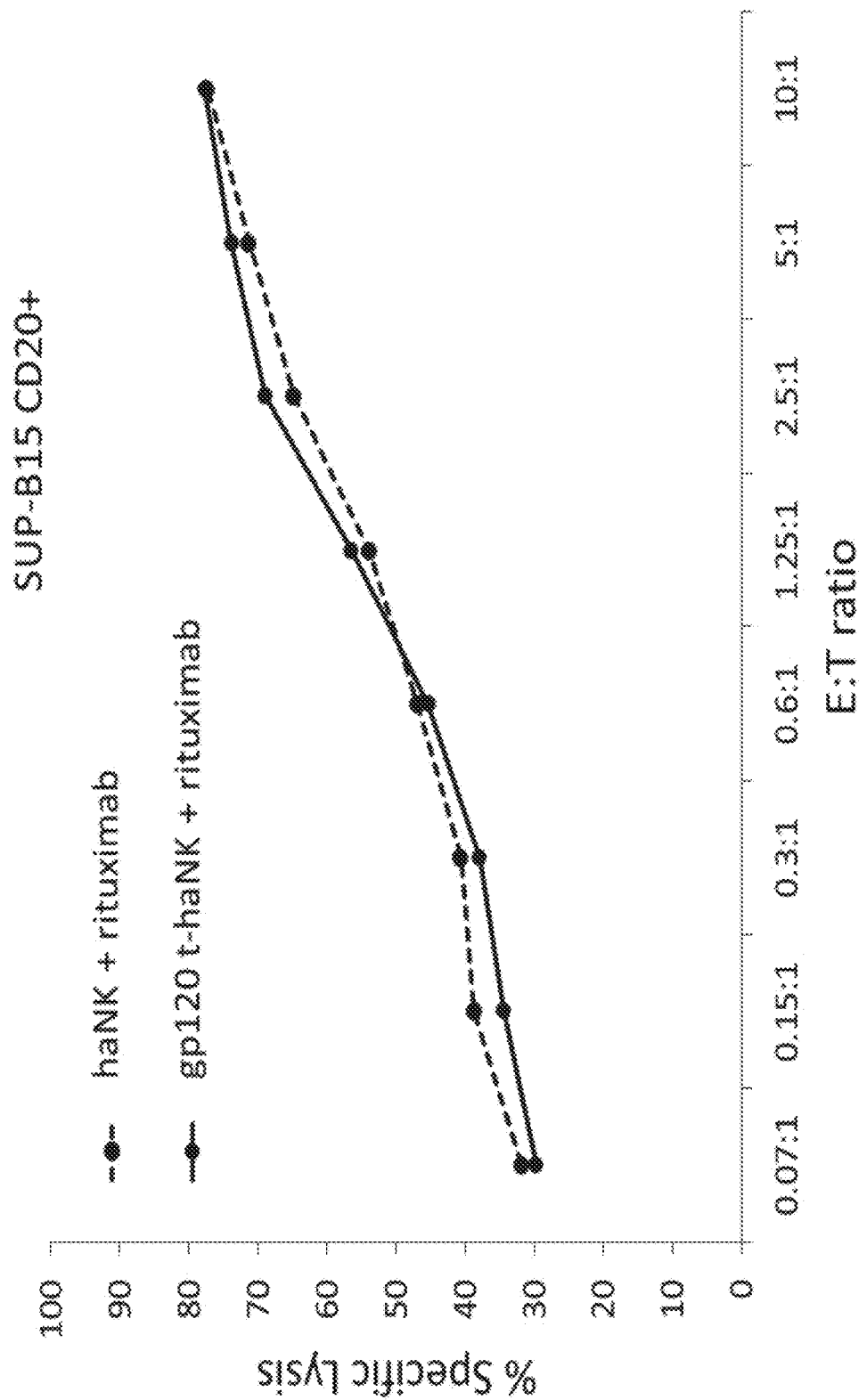
FIG. 56 shows exemplary results for ADCC of gp120.CAR-t-haNK cells.

The inventors further demonstrated that so generated cells expressed significant quantities of CD16 and gp120CAR as can be seen from FIG. 53. Binding of GP120 to the gp120CAR was shown as demonstrated in FIG. 54 versus non-recombinant aNK cells as negative control. Natural cytotoxicity of the so generated cells is shown in FIG. 55, while corresponding ADCC data are shown in FIG. 56.

Example 15: B7-H4-CAR with FcεRIγ Signaling Domain

In this example, the inventors constructed a 1$^{st}$ generation CARs with a FcεRIγ signaling domain that included an anti-B7-H4 scFv coupled to a CD8 hinge, that in turn was coupled to a CD28 transmembrane domain, which was coupled to a FcεRIγ signaling domain. The so constructed B7-H4-CAR had a nucleic acid sequence of SEQ ID NO:45 and an amino acid sequence of SEQ ID NO:62.

Example 16: BCMA-CAR with FcεRIγ Signaling Domain

In this example, the inventors constructed a 1$^{st}$ generation CARs with a FcεRIγ signaling domain that included an anti-BCMA scFv coupled to a CD8 hinge, that in turn was coupled to a CD28 transmembrane domain, which was coupled to a FcεRIγ signaling domain. The so constructed BCMA-CAR had a nucleic acid sequence of SEQ ID NO:46 and an amino acid sequence of SEQ ID NO:63.

Figure 50:
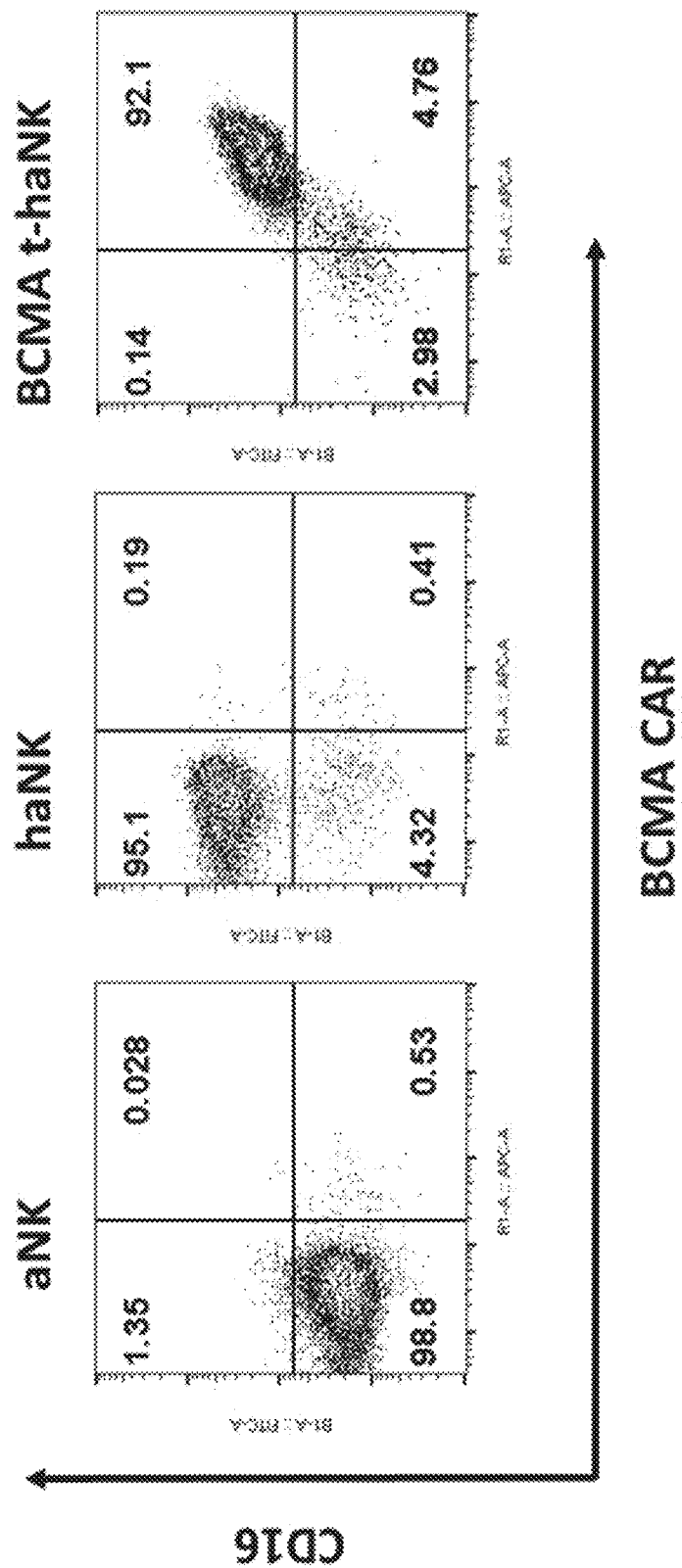
FIG. 50 shows exemplary results for CD16 and BCMA.CAR expression.
Figure 51:
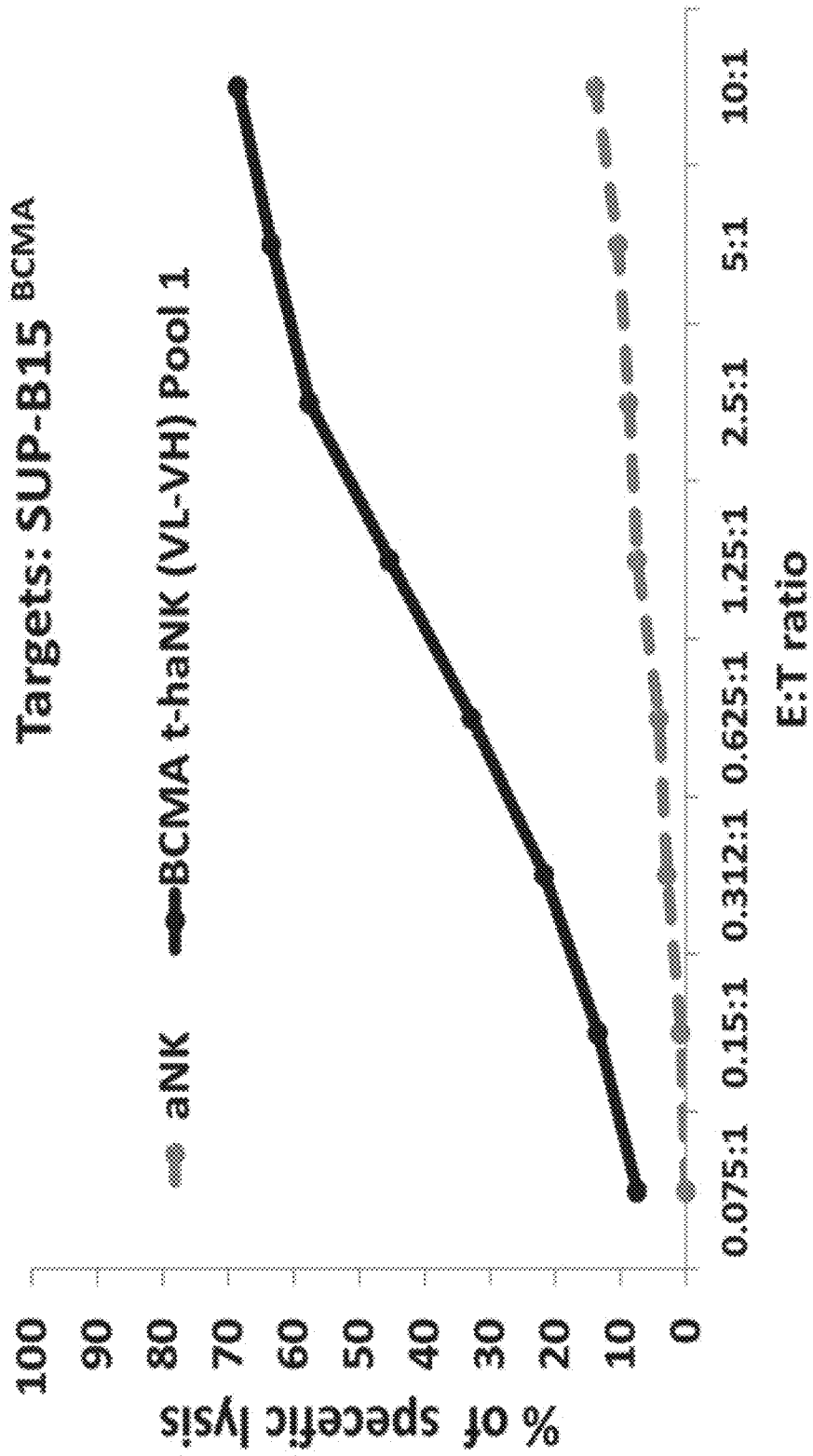
FIG. 51 shows exemplary results for CAR mediated cytotoxicity of BCMA.CAR-t-haNK cells.
Figure 52:
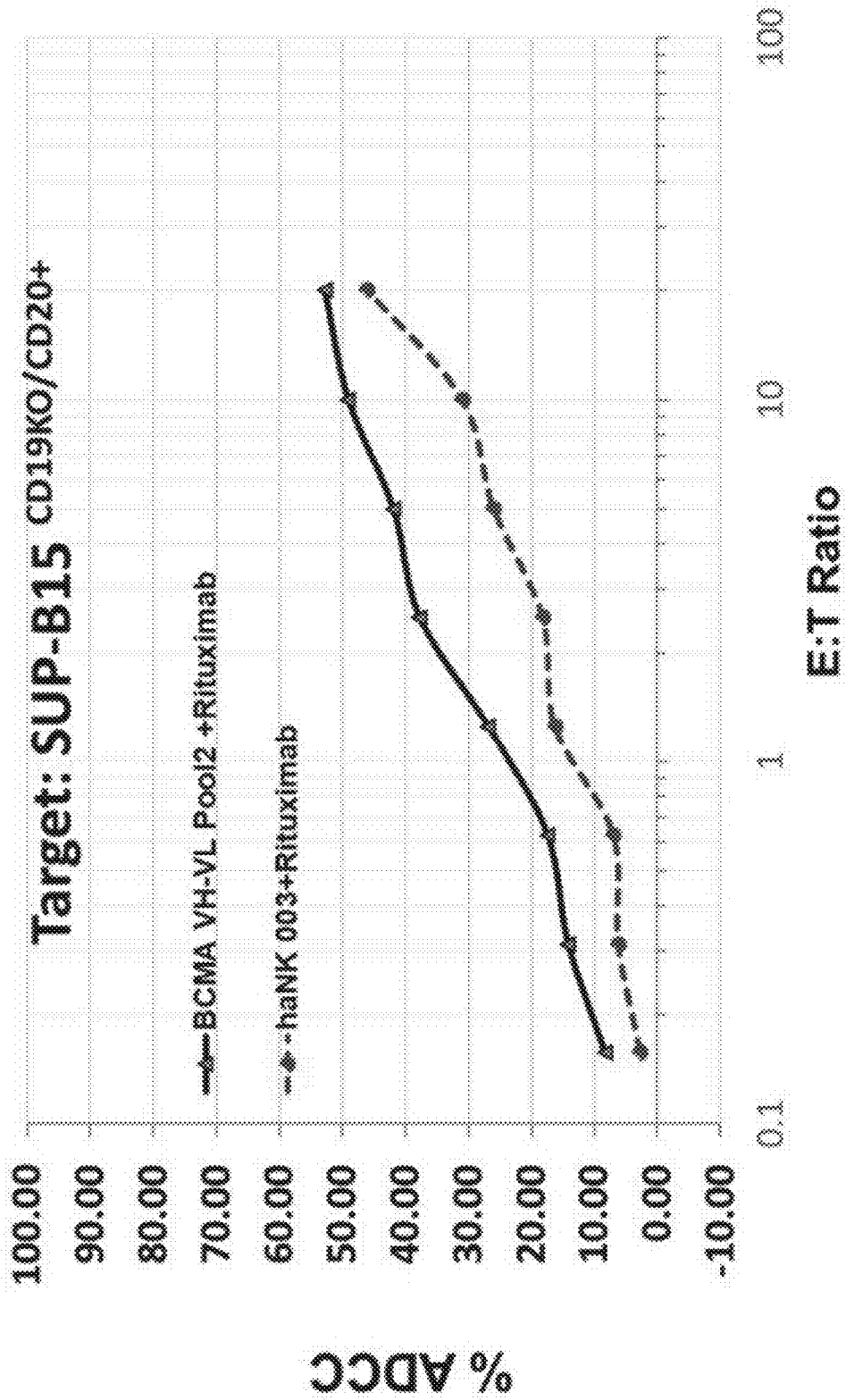
FIG. 52 shows exemplary results for ADCC of BCMA.CAR-t-haNK cells.

BCMA expression was confirmed as is shown in the exemplary results of FIG. 50, and CAR mediated cytotoxicity was demonstrated against target cells as is shown in FIG. 51. Similarly, as can be seen from the results in FIG. 52, recombinant cells had significant ADCC using rituximab as antibody against the target cells.

Example 17: GD2-CAR with FcεRIγ Signaling Domain

In this example, the inventors constructed a 1$^{st}$ generation CARs with a FcεRIγ signaling domain that included an anti-GD2 scFv coupled to a CD8 hinge, that in turn was coupled to a CD28 transmembrane domain, which was coupled to a FcεRIγ signaling domain. The so constructed GD2-CAR had a nucleic acid sequence of SEQ ID NO:47 and an amino acid sequence of SEQ ID NO:64.

Example 18: FAP-CAR with FcεRIγ Signaling Domain

Figure 57:
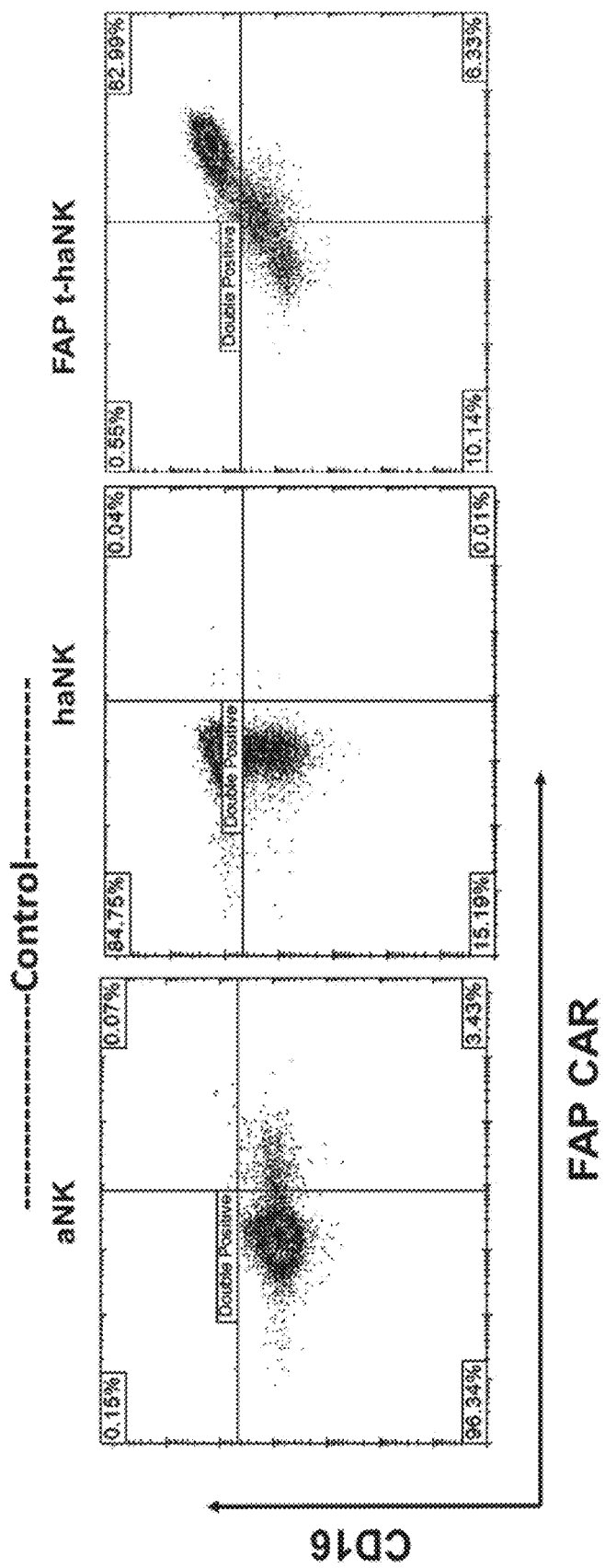
FIG. 57 shows exemplary results for CD16 and FAP.CAR expression.
Figure 58:
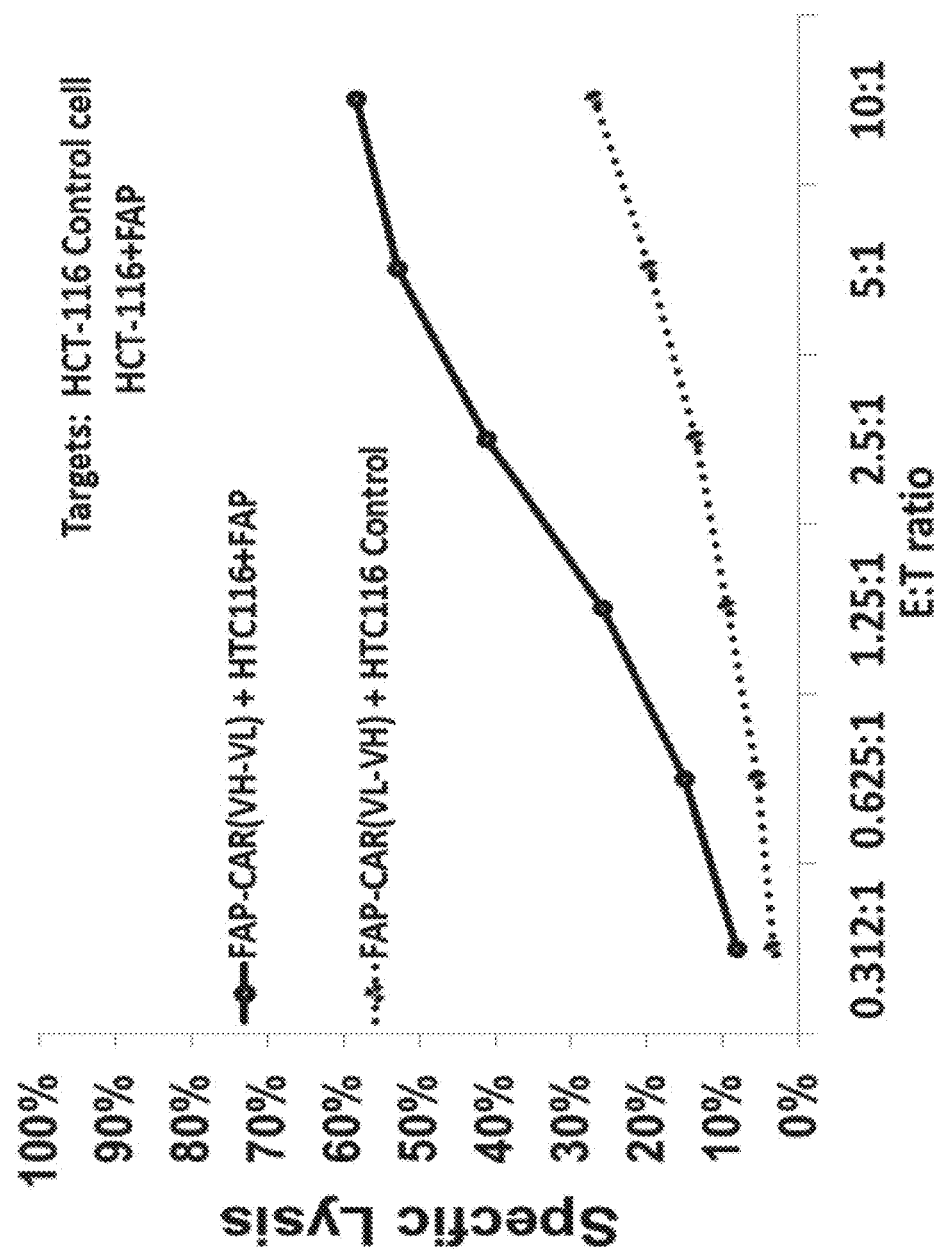
FIG. 58 shows exemplary results for CAR mediated cytotoxicity of FAP.CAR-t-haNK cells.

In this example, the inventors constructed a 1$^{st}$ generation CARs with a FcεRIγ signaling domain that included an anti-FAP scFv coupled to a CD8 hinge, that in turn was coupled to a CD28 transmembrane domain, which was coupled to a FcεRIγ signaling domain. The so constructed FAP-CAR had a nucleic acid sequence of SEQ ID NO:48 and an amino acid sequence of SEQ ID NO:65. Expression of the FAP-CAR is shown in the data of FIG. 57, and FAP.CAR cytotoxicity is demonstrated on target cells in the results of FIG. 58.

Example 19: CSPG-4-CAR with FcεRIγ Signaling Domain

Figure 59:
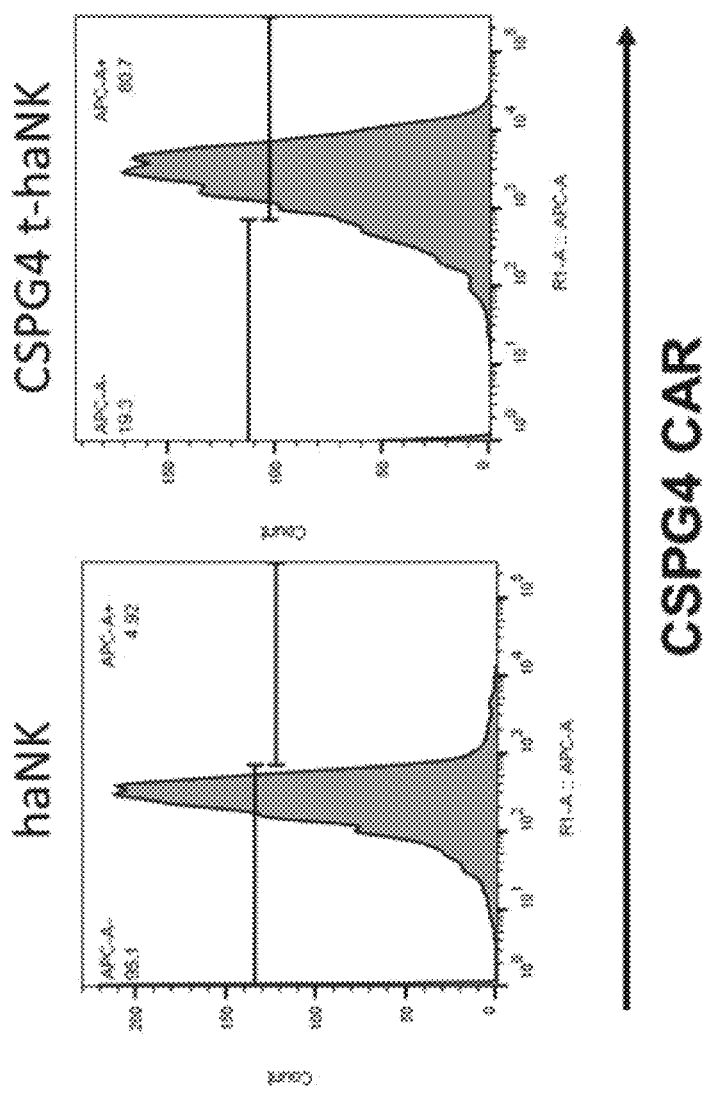
FIG. 59 shows exemplary results for CSPG4 expression in CSPG4.CAR-t-haNK cells.
Figure 60:
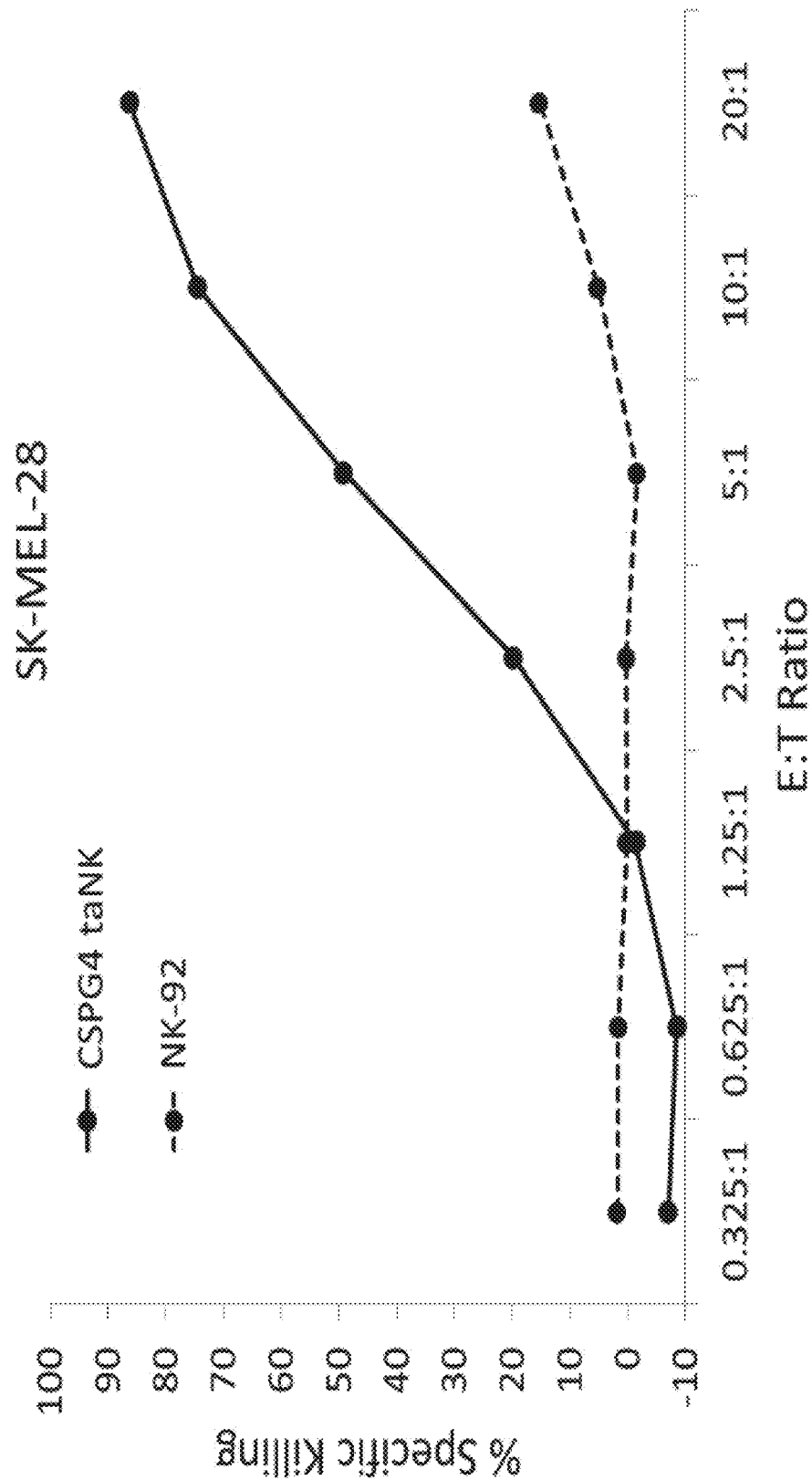
FIG. 60 shows exemplary results for CAR mediated cytotoxicity of CSPG4.CAR-t-haNK cells against SK-MEL-28 cells.

In this example, the inventors constructed a 1$^{st}$ generation CARs with a FcεRIγ signaling domain that included an anti-CSPG-4 scFv coupled to a CD8 hinge, that in turn was coupled to a CD28 transmembrane domain, which was coupled to a FcεRIγ signaling domain. The so constructed CSPG-4-CAR had a nucleic acid sequence of SEQ ID NO:52 and an amino acid sequence of SEQ ID NO:66. Expression of the CSPG-4-CAR was confirmed with FACS analysis and exemplary results are shown in FIG. 59. Thusly constructed cells also exhibited significant cytotoxicity as is shown in the exemplary data of FIG. 60.

Example 20: CD20-CAR with FcεRIγ Signaling Domain

In this example, the inventors constructed a 1$^{st}$ generation CARs with a FcεRIγ signaling domain that included an anti-CD20 scFv coupled to a CD8 hinge, that in turn was coupled to a CD28 transmembrane domain, which was coupled to a FcεRIγ signaling domain. The so constructed CD20-CAR had a nucleic acid sequence of SEQ ID NO:51 and an amino acid sequence of SEQ ID NO:67.

| CAR | FceR1 | | |
|---|---|---|---|
| | CAR | % Identity | binding domain |
| HER2-CAR | SEQ ID NO 54 | 100 | SEQ ID NO 72 |
| CD30-CAR | SEQ ID NO 55 | 100 | SEQ ID NO 73 |
| EGFR-CAR | SEQ ID NO 56 | 100 | SEQ ID NO 74 |
| IGF1R-CAR | SEQ ID NO 57 | 100 | SEQ ID NO 75 |
| CD123-CAR | SEQ ID NO 58 | 100 | SEQ ID NO 76 |
| PD-L1-CAR | SEQ ID NO 59 | 100 | SEQ ID NO 77 |
| CD33-CAR | SEQ ID NO 60 | 100 | SEQ ID NO 78 |
| gp120-CAR | SEQ ID NO 61 | 100 | SEQ ID NO 79 |
| B7-H4-CAR | SEQ ID NO 62 | 100 | SEQ ID NO 80 |
| BCMA-CAR | SEQ ID NO 63 | 100 | SEQ ID NO 81 |
| GD2-CAR | SEQ ID NO 64 | 100 | SEQ ID NO 82 |
| FAP-CAR | SEQ ID NO 65 | 100 | SEQ ID NO 83 |
| CSPG-4-CAR | SEQ ID NO 66 | 100 | SEQ ID NO 84 |
| CD20-CAR | SEQ ID NO 67 | 100 | SEQ ID NO 85 |
| 2nd generation CAR with CD28/CD3zeta | SEQ ID NO 68 | 45.83 | |
| 2nd generation CAR with 4-1BB/CD3zeta signaling domain | SEQ ID NO 69 | 45.83 | |
| 3rd generation CAR with CD28/4-1BB/CD3zeta signaling domain | SEQ ID NO 70 | 45.83 | |
| 3rd generation CAR with 4-1BB/CD3zeta/CD28signaling domain | SEQ ID NO 71 | 45.83 | |

Figure 25:
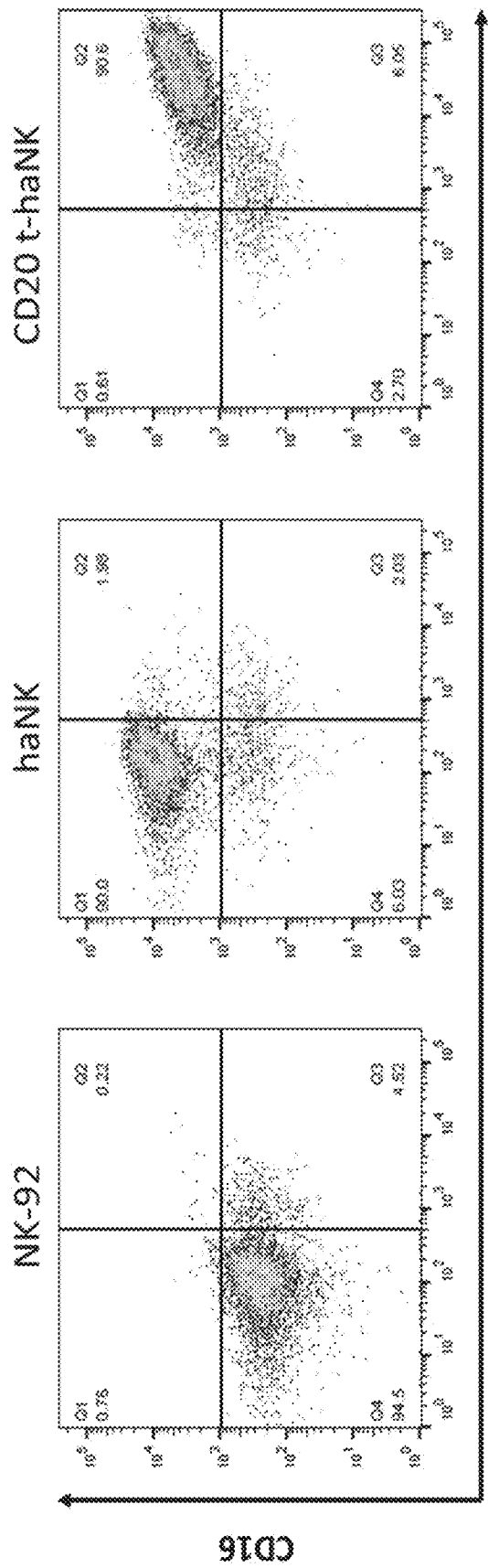
FIG. 25 shows exemplary comparative results for expression of CD16 and CD20.CAR.
Figure 26:
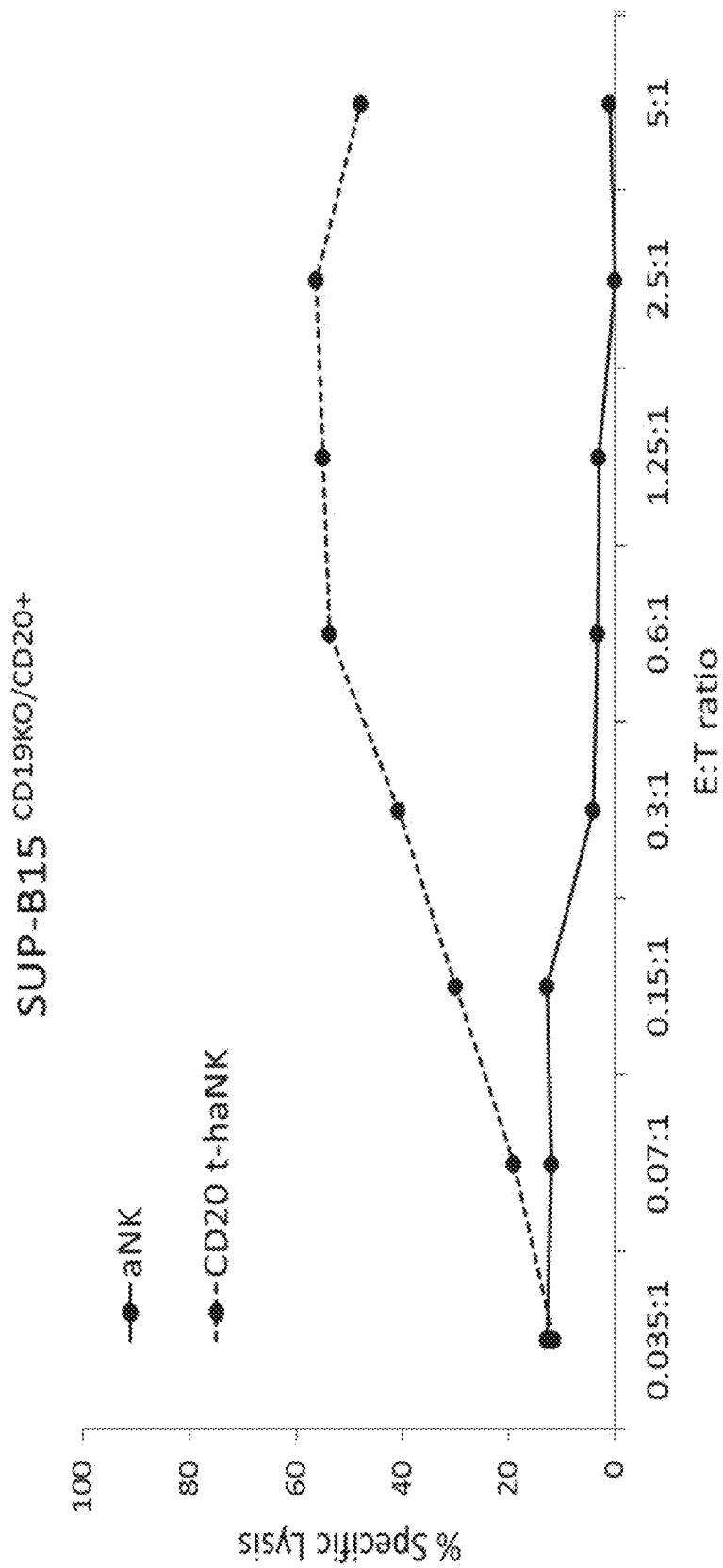
FIG. 26 shows exemplary results for natural cytotoxicity of CD20.CAR-t-haNK cells.

Expression of the CD20 CAR in NK-92 cells is shown in the results of FIG. 25. As can be readily seen, CD20.CAR is expressed strongly in the vast majority of recombinant cells (along with CD16 from the linearized DNA as noted above). FIG. 26 depicts exemplary results for cytotoxicity of the CD20.CAR NK cells against CD20+ target cells.

Example 21: CD19-CAR with FcεRIγ Signaling Domain

In this example, the inventors used the $1^{st}$ generation CARs as described above having a FcεRIγ signaling domain that included an anti-CD19 scFv coupled to a CD8 hinge, that in turn was coupled to a CD28 transmembrane domain, which was coupled to a FcεRIγ signaling domain and transfected NK-92 cells with linearized DNA for functional testing.

Figure 15:
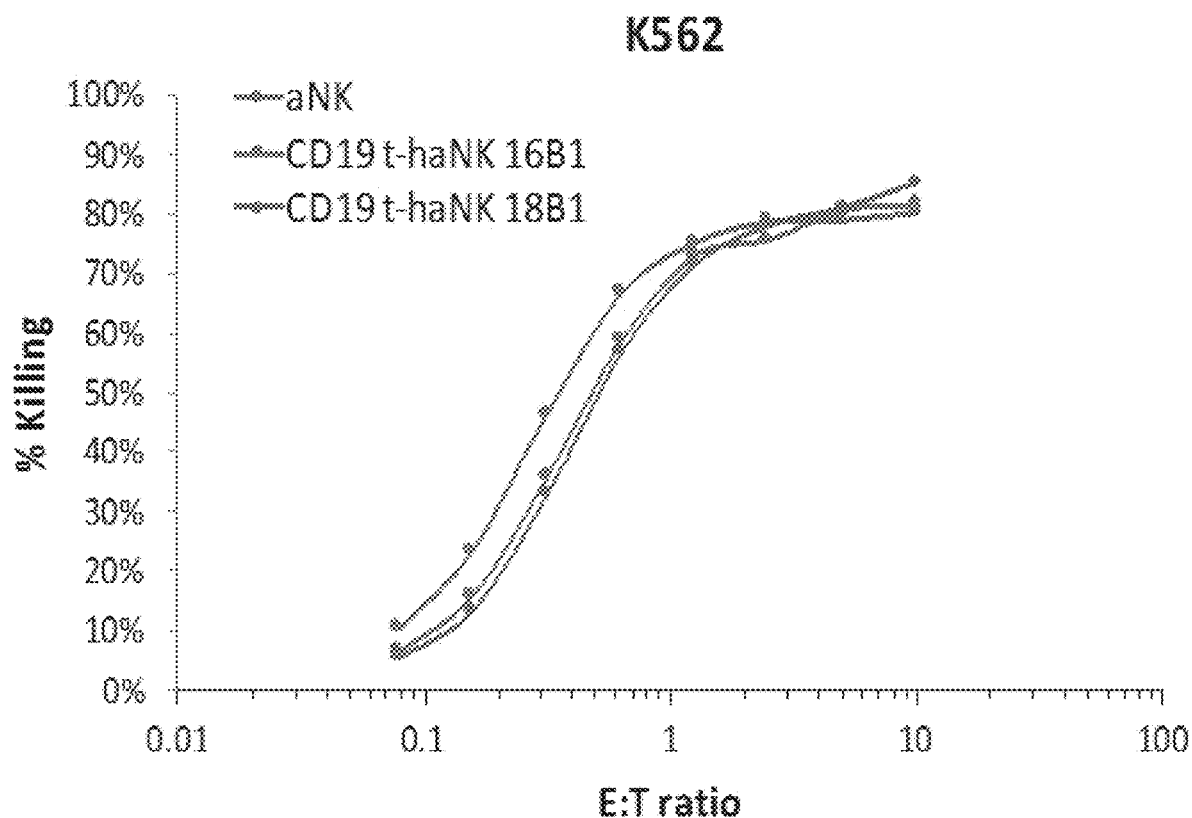
FIG. 15 shows exemplary results for cytotoxicity of CD19.CAR-t-haNK cells against K562 cells.
Figure 16:
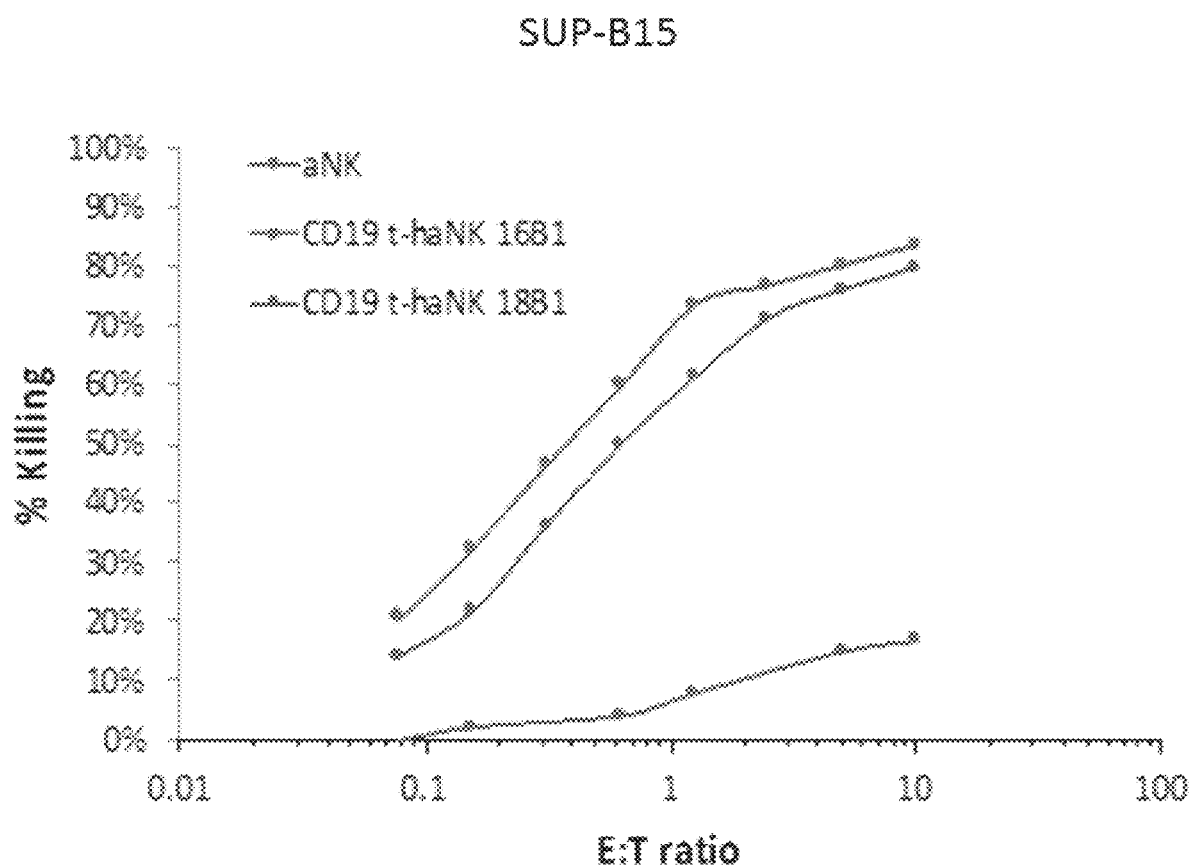
FIG. 16 shows exemplary results for cytotoxicity of CD19.CAR-t-haNK cells against SUP-B15 cells.
Figure 17:
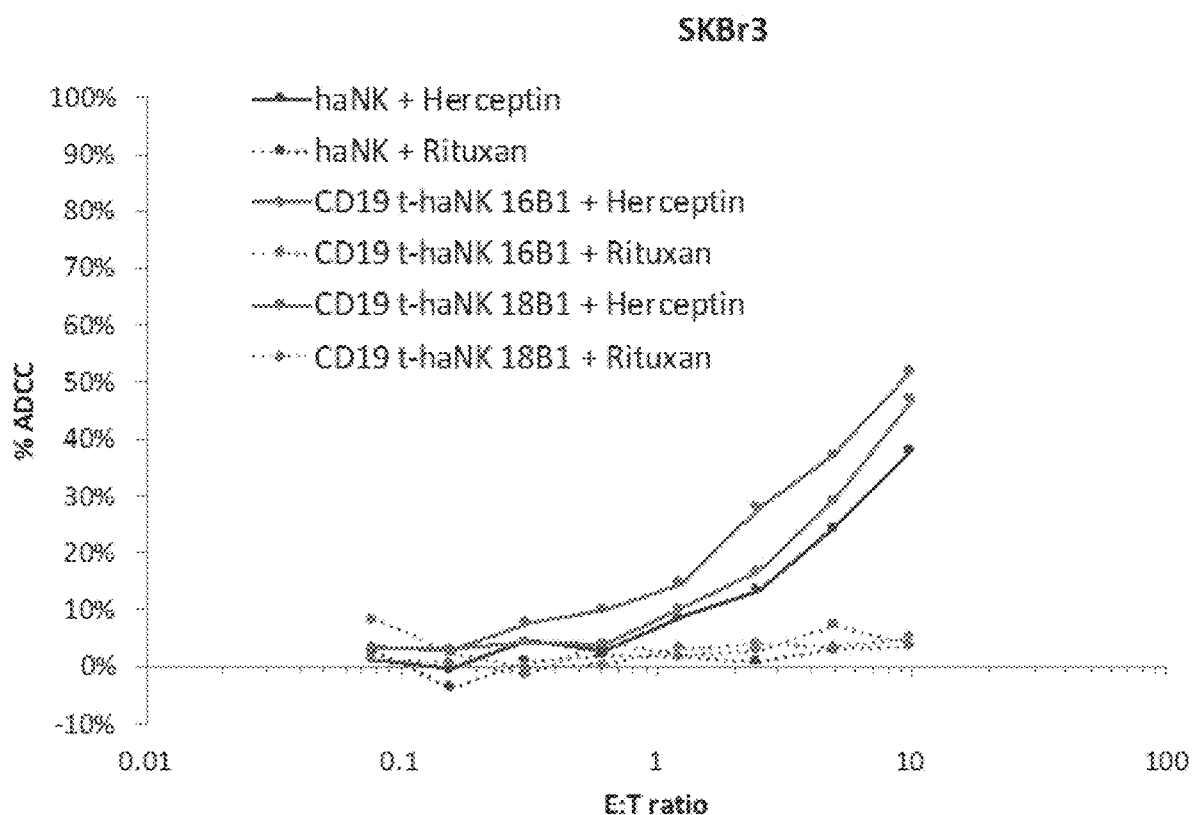
FIG. 17 shows exemplary results for ADCC of CD19.CAR-t-haNK cells against SKBr3 cells.

Functionality of the so constructed CD19.CAR-t-haNK cells was tested against K562 cells for determination of general cytotoxicity using a standard cytotoxicity assay and exemplary results are shown in FIG. 15. As can be readily seen, the CD19.CAR-t-haNK cells expressing the CAR with the FcεRIγ signaling domain exhibited significant cytotoxicity against the K562 target cells. In a further set of experiments, target specific cytotoxicity was determined using SUP-B15 cells in comparison with aNK cells as control, and exemplary results are shown in FIG. 16. Once more, CD19.CAR-t-haNK cells expressing the CAR with the FcεRIγ signaling domain exhibited significant and target specific cytotoxicity. In yet another set of experiments, target specific ADCC was determined using SKBr3 cells using Herceptin and Rituxan as antibodies, and exemplary results are shown in FIG. 17. Again, CD19.CAR-t-haNK cells expressing the CAR with the FcεRIγ signaling domain exhibited significant antibody and target specific ADCC.

Figure 21:
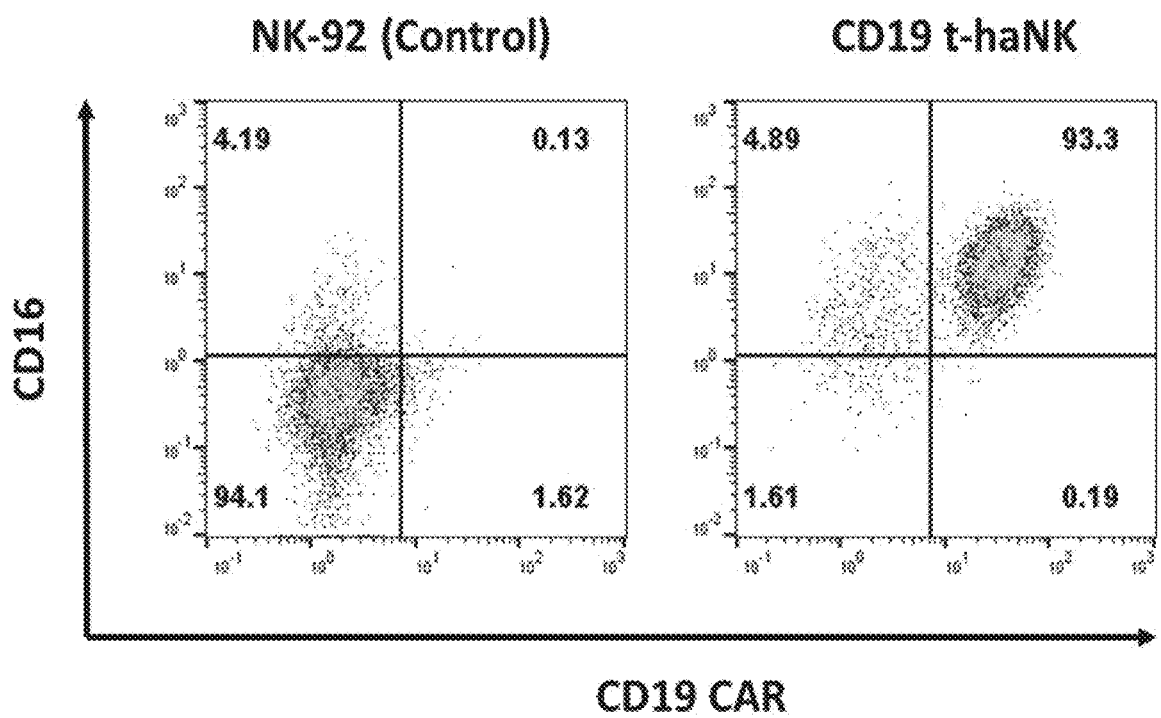
FIG. 21 shows exemplary results expression of CD16 and CD19.CAR.
Figure 22:
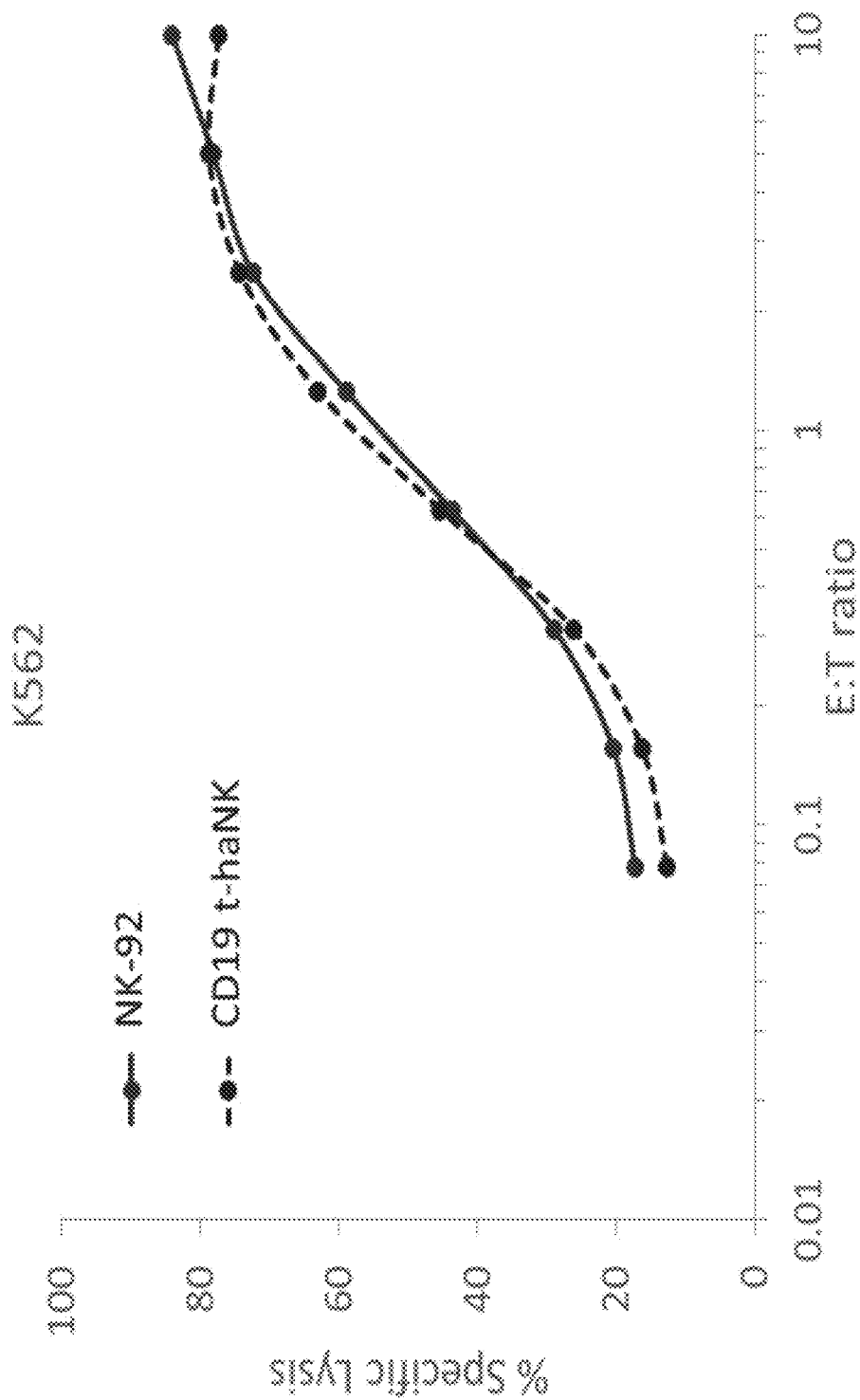
FIG. 22 shows exemplary results for natural cytotoxicity of CD19.CAR-t-haNK cells against K562 cells.
Figure 23:
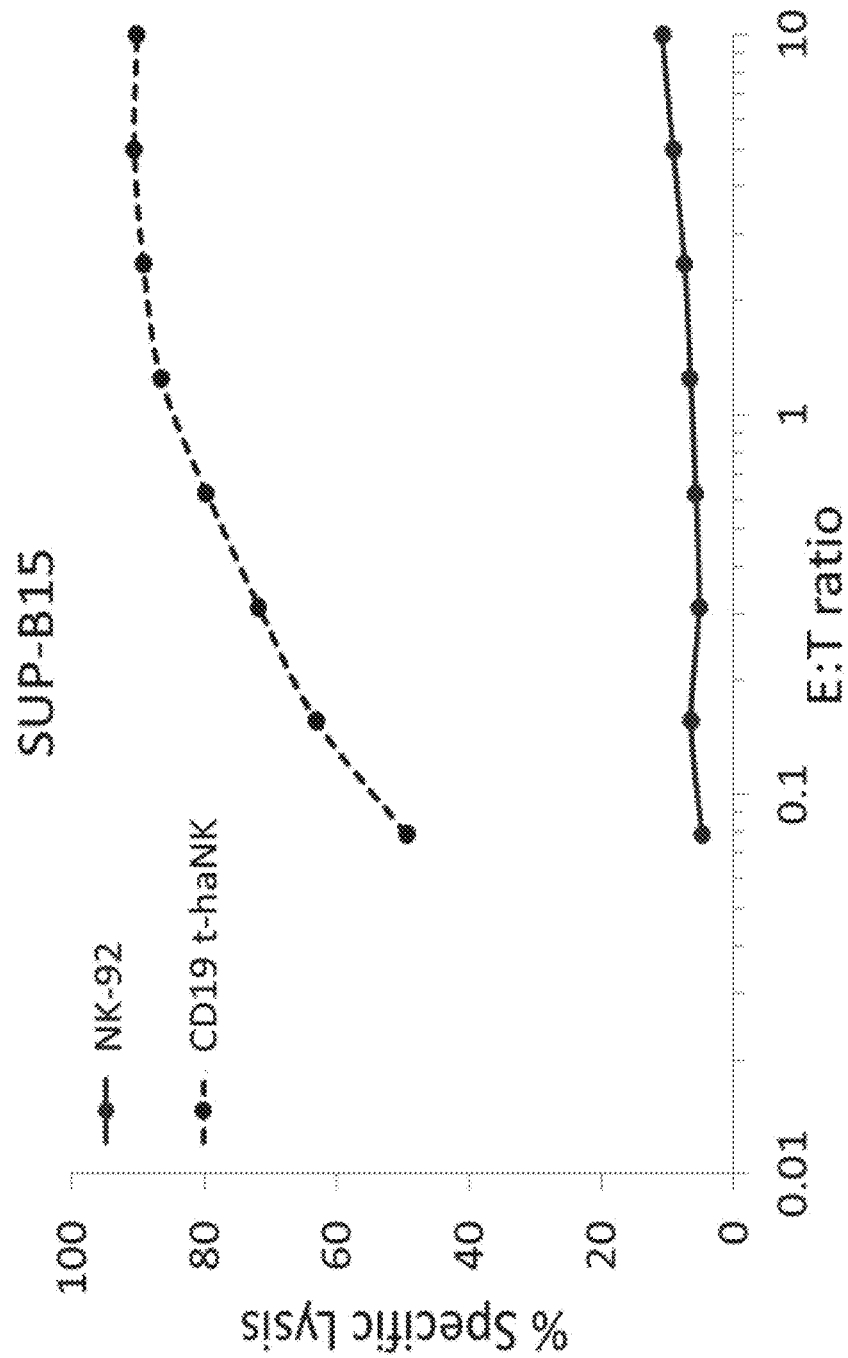
FIG. 23 shows exemplary results for CAR mediated cytotoxicity of CD19.CAR-t-haNK cells against SUP-B15 cells.
Figure 24:
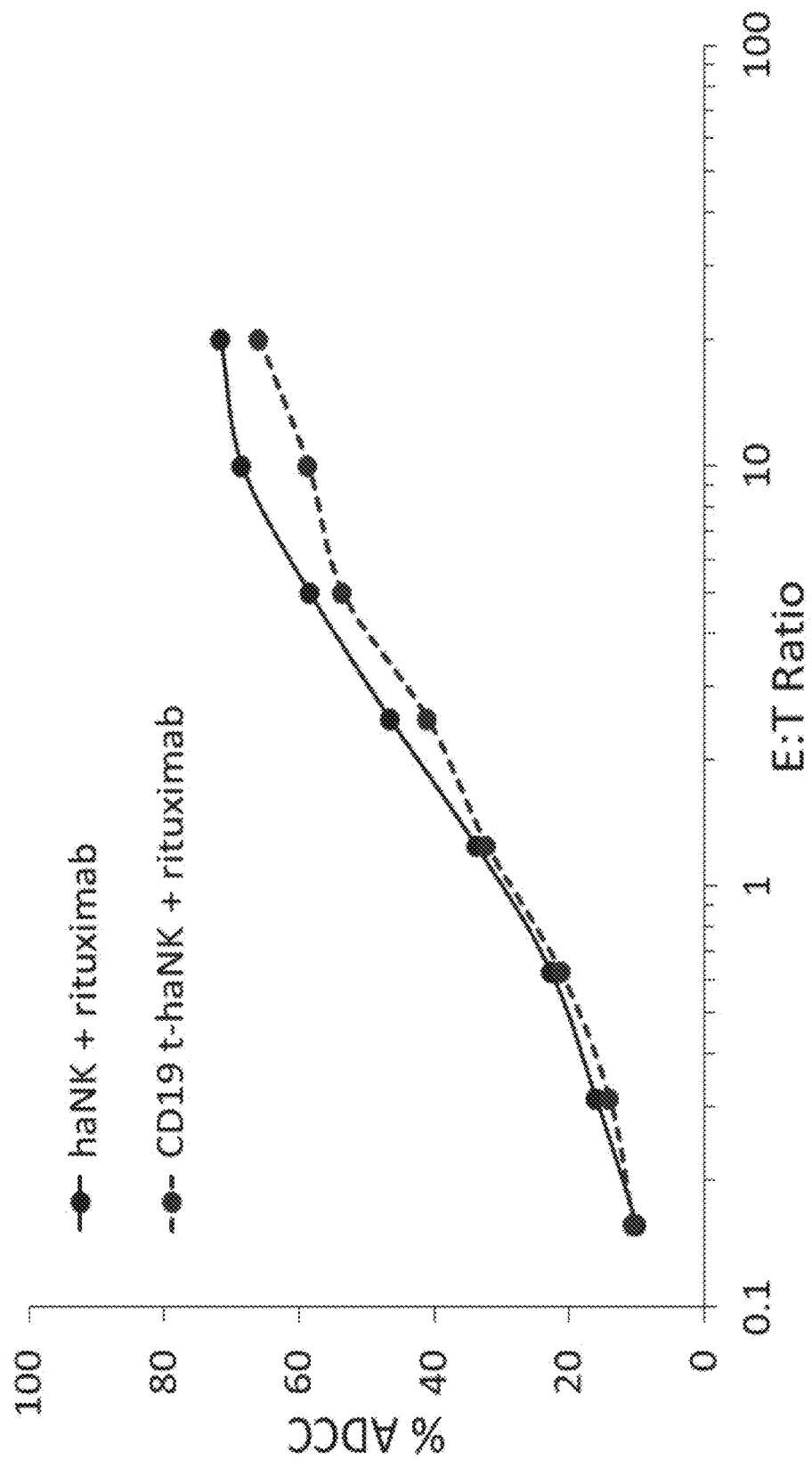
FIG. 24 shows exemplary results for ADCC of CD19.CAR-t-haNK cells.

FIG. 21 exemplarily illustrates CD19.CAR expression from linearized DNA that included a segment encoding CD16 and IL-$2^{ER}$ in NK-92 cells versus control. As can be seen form FIG. 25, the expression was very strong across the vast majority of cells. Additional results for natural cytotoxicity of CD19.CAR t-haNK cells against K562 cells and targeted cytotoxicity against SUP-B15 cells are depicted in FIG. 22 and FIG. 23. Exemplary further results for ADCC of CD19.CAR t-haNK cells against SUP-B15CD19$^{KO}$/CD20+ cells are shown in FIG. 24.

Example 22: Anti-Tumor Activity of PD-L1-Targeting t-haNK Cells in Human Xenograft Models in NSG Mice MDA-MB-231 and HCC827 were used as validated xenograft models that are PDL1 positive, and efficacy of PDL1 t-haNK cells in varied formulations, dosing levels, and dosing routes (IV and IT) was evaluated.

Animals: Animal type: NSG mice (JAX), females, 9-10 weeks old; Number of animals for MDA-MB-231 model: 24 (fresh cells), and for HCC827 model: 24 (fresh cells)+6 (cryopreserved cells). Tumor model used the following cell line: MDA-MB-231 (human breast adenocarcinoma) and HCC827 (human lung adenocarcinoma), Route of inoculation was subcutaneous on both flanks, and average tumor burden upon treatment initiation was for MDA-MB-231 about 100 mm3 and for HCC827 about 75-80 mm3.

Treatment articles: Anti-PD-L1 t-haNK, freshly prepared, irradiated, at a concentration: 5E7 cells/mL or 2E7 cells/mL; Vehicle control was X-VIVO™ 10 medium; Method of administration was IV and IT as noted. Dosage for IV NK dosing was 1E7 cells/dose in 200 μL (Freshly prepared cells), 4E6 cells/dose in 200 μL (Cryopreserved cells); for IT NK dosing (fresh cells only) dose was 2.5E6 cells/tumor/dose in 50 μL. Dosing frequency was Twice a week (M/Th or T/F) for 4 consecutive weeks, and first day of dosing was defined as Day 1.

Study design for MDA-MB-231 is in Table 3 below (This study was ended on Day 27, when some animals in Groups A, C and D had reached combined tumor volume of >2000 mm3)

TABLE 2

| Group | N | Tumor model | Treatment | Fresh or Frozen | NK Cell Dose | NK dosing route | Treatment Regimen | Dosing Volume |
|---|---|---|---|---|---|---|---|---|
| A | 6 | MDA-MB-231 SC, bilateral $1 \times 10^6$ | Vehicle | / | / | IV | BIW × 4 weeks | 200 μL |
| B | 6 | | PD-L1 t-haNK | Fresh | 1E7 | IV | BIW × 4 weeks | 200 μL |
| C | 6 | | Vehicle | / | / | IT | BIW × 4 weeks | 50 μL |
| D | 6 | | PD-L1 t-haNK | Fresh | 2.5E6 | IT | BIW × 4 weeks | 50 μL |

Study design for HCC827 is in Table 4 below (This study was ended on Day 29, when surviving animals were re-purposed and transferred to another study).

TABLE 3

| Group | N | Tumor model | Treatment | Fresh or Frozen | NK Cell Dose | NK dosing route | Treatment Regimen | Dosing Volume |
|---|---|---|---|---|---|---|---|---|
| A | 6 | HCC827 SC, bilateral $1 \times 10^6$ | Vehicle | / | / | IV | BIW × 4 weeks | 200 μL |
| B | 6 | | PD-L1 t-haNK | Fresh | 1E7 | IV | BIW × 4 weeks | 200 μL |
| C | 6 | | Vehicle | / | / | IT | BIW × 4 weeks | 50 μL |
| D | 6 | | PD-L1 t-haNK | Fresh | 2.5E6 | IT | BIW × 4 weeks | 50 μL |
| Pilot | 6 | | PD-L1 t-haNK | Frozen | 4E6 | IV | BIW × 4 weeks | 200 μL |

Results: Freshly prepared PD-L1 t-haNK cells (1E7 cells/dose) led to marked and long-lasting tumor growth inhibition in both MDA-MB-231 and HCC827 models MDA-MB-231: tumor stasis: TGI on Day 16: 84% (peak); TGI on Day 26: 79% (last measurement).

HCC827: tumor regression: TGI on Day 16: 120% (peak); TGI on Day 29: 84% (study end).

Cryopreserved PDL1 t-haNK cells (4E6 cells/dose) also showed statistically significant efficacy in suppressing tumor growth compared to X-VIVO™ 10 media: TGI on Day 26: 60% (peak), and TGI on Day 29: 40% (study end).

Freshly prepared PDL1 t-haNK cells (1E7 cells/dose) also led to significant reduction of metastatic disease burden in the MDA-MB-231 model as shown in Table 5 below.

TABLE 4

| Group | Mouse | Macroscopic lesions found in: | Overall Summary |
|---|---|---|---|
| A (vehicle) | 1 | Liver, lungs | 100% animals developed metastases in multiple organs |
| | 2 | Ax LNs, liver, lungs | |
| | 3 | Ax LN (left), liver, lungs | |
| | 4 | Liver, lungs | |
| | 5 | Ax LNs, spleen, liver, lungs | |
| | 6 | Ax LNs, liver, lungs | |
| B (PD-L1 t-haNK) | 1 | None | 50% developed metastasis; all single-organ findings |
| | 2 | Lungs | |
| | 3 | Ax LNs | |
| | 4 | None | |
| | 5 | Ax LN (left) | |
| | 6 | None | |

The number of visible nodules in liver was in vehicle: 29±9, in the PD-L1 t-haNK group: 0 (P=0.0116 by unpaired 2-tailed t test).

Based on the experiments performed, IV dosing of freshly prepared PD-L1 t-haNK cells at the dosing level of 1E7 cells/dose, twice a week for 4 weeks, showed marked anti-tumor efficacy in both of the subcutaneous xenograft models tested: The treatment resulted in tumor stasis in MDA-MB-231 tumor-bearing mice, with a peak TGI of 84% on Day 16 and an end-of-study TGI of 79% (P<0.0001 for both time points by 2-way ANOVA followed by multiple comparison by Tukey test), and tumor regression in the HCC827 model, with a peak TGI of 120% on Day 16 and an end-of-study TGI of 84% (P<0.0001). IV dosing of cryopreserved PD-L1 t-haNK cells at the dosing level of 4E6 cells/dose, twice a week for 4 weeks, also showed significant therapeutic efficacy in the HCC827 tumor model, reaching a peak TGI of 60% (P<0.0001), and an end-of-study TGI of 40% (P<0.01). IT dosing of freshly prepared PD-L1 t-haNK cells at the dosing level of 2.5E6 cells/dose/tumor, twice a week for 4 weeks, effectively suppressed the growth of HCC827 tumors, resulting in a peak TGI of 70% on Day 20 and an end-of-study TGI of 49% (P<0.001).

Significant adverse reactions were observed for animals that received IV administrations of freshly prepared PD-L1 t-haNK cells (1E7 cells/dose). In contrast to freshly prepared PD-L1 t-haNK cells, cryopreserved cells (dosed at a lower level of 4E6 cells/dose) proved to be safe to the animals after IV administrations. PD-L1 t-haNK cells demonstrated remarkable efficacy in the two subcutaneous tumor models. Cryopreserved cells dosed at the lower 4E6 cells/dose level, also showed significant efficacy in suppressing tumor growth, and proved to be safe for the animals.

Of course, it should be recognized that for all nucleic acid sequences provided herein the corresponding encoded proteins are also expressly contemplated herein. Likewise, for all amino acid sequences, corresponding nucleic acids sequences are also contemplated herein (with any codon usage).

All patent applications, publications, references, and sequence accession numbers cited in the present specification are hereby incorporated by reference in their entirety.

Unless defined otherwise, all technical and scientific terms used herein have the same meaning as commonly understood by one of ordinary skill in the art to which this invention belongs.

In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

It is understood that all numerical values described herein (e.g., pH, temperature, time, concentration, amounts, and molecular weight, including ranges) include normal variation in measurements encountered by one of ordinary skill in the art. Thus, numerical values described herein include variation of +/−0.1 to 10%, for example, +/−0.1%, 0.5%, 1%, 2%, 3%, 4%, 5%, 6%, 7%, 8%, 9%, or 10%. It is to be understood, although not always explicitly stated, that all numerical designations may be preceded by the term "about." Thus, the term about includes variation of +/−0.1 to 10%, for example, +/−0.1%, 0.5%, 1%, 2%, 3%, 4%, 5%, 6%, 7%, 8%, 9%, or 10% of the numerical value. It is also to be understood, although not always explicitly stated, that the reagents described herein are merely exemplary and that equivalents of such are known in the art.

As will be understood by one skilled in the art, for any and all purposes, particularly in terms of providing a written description, all ranges disclosed herein include the end points of the range, and include all values between the end points of the range. All ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

It is also to be understood, although not always explicitly stated, that the reagents described herein are merely exemplary and that equivalents of such are known in the art.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this disclosure.

As used herein, "immunotherapy" refers to the use of NK-92 cells, modified or unmodified, naturally occurring or modified NK cell or T-cell, whether alone or in combination, and which are capable of inducing cytotoxicity when contacting a target cell.

As used herein, "natural killer (NK) cells" are cells of the immune system that kill target cells in the absence of a specific antigenic stimulus, and without restriction according to major histocompatibility complex (MHC) class. Target cells may be tumor cells or cells harboring a virus. NK cells are characterized by the presence of CD56 and the absence of CD3 surface markers.

The term "endogenous NK cells" is used to refer to NK cells derived from a donor (or the patient), as distinguished from the NK-92 cell line. Endogenous NK cells are generally heterogeneous populations of cells within which NK cells have been enriched. Endogenous NK cells may be intended for autologous or allogeneic treatment of a patient.

The term "NK-92" refers to natural killer cells derived from the highly potent unique cell line described in Gong et al. (1994), rights to which are owned by NantKwest (hereafter, "NK-92™ cells"). The immortal NK cell line was originally obtained from a patient having non-Hodgkin's lymphoma. Unless indicated otherwise, the term "NK-92™" is intended to refer to the original NK-92 cell lines as well as NK-92 cell lines that have been modified (e.g., by introduction of exogenous genes). NK-92™ cells and exemplary and non-limiting modifications thereof are described in U.S. Pat. Nos. 7,618,817; 8,034,332; 8,313,943; 9,181,322; 9,150,636; and published U.S. application Ser. No. 10/008,955, all of which are incorporated herein by reference in their entireties, and include wild type NK-92™, NK-92™-CD16, NK-92™-CD16-γ, NK-92™-CD16-ζ, NK-92™-CD16(F176V), NK-92™MI, and NK-92™CI. NK-92 cells are known to persons of ordinary skill in the art, to whom such cells are readily available from NantKwest, Inc. In one embodiment, the term NK-92 refers to the cell line deposited with the American Type Culture Collection (ATCC, 10801 University Boulevard, Manassas, Va. 20110-2209) under Deposit Numbers CRL-2407 (deposited to general depository on Sep. 3, 1998; transferred to patent depository on Apr. 11, 2005 and assigned Deposit No. PTA-6670).

The term "aNK" refers to an unmodified natural killer cells derived from the highly potent unique cell line described in Gong et al. (1994), rights to which are owned by NantKwest (hereafter, "aNK™ cells"). The term "haNK" refers to natural killer cells derived from the highly potent unique cell line described in Gong et al. (1994), rights to which are owned by NantKwest, modified to express CD16 on the cell surface (hereafter, "CD16+NK-92™ cells" or "haNK® cells"). In some embodiments, the CD16+NK-92™ cells comprise a high affinity CD16 receptor on the cell surface. The term "taNK" refers to natural killer cells derived from the highly potent unique cell line described in Gong et al. (1994), rights to which are owned by NantKwest, modified to express a chimeric antigen receptor (hereafter, "CAR-modified NK-92™ cells" or "taNK® cells"). The term "t-haNK" refers to natural killer cells derived from the highly potent unique cell line described in Gong et al. (1994), rights to which are owned by NantkWest, modified to express CD 16 on the cell surface and to express a chimeric antigen receptor (hereafter, "CAR-modified CD16+NK-92™ cells" or "t-haNK™ cells"). In some embodiments, the t-haNK™ cells express a high affinity CD16 receptor on the cell surface.

A "modified NK-92 cell" refers to an NK-92 cell that expresses an exogenous gene or protein, such as an Fc receptor, a CAR, a cytokine (such as IL-2 or IL-15), and/or a suicide gene. In some embodiments, the modified NK-92 cell comprises a vector that encodes for a transgene, such as an Fc receptor, a CAR, a cytokine (such as IL-2 or IL-15), and/or a suicide gene. In one embodiment, the modified NK-92 cell expresses at least one transgenic protein.

As used herein, "non-irradiated NK-92 cells" are NK-92 cells that have not been irradiated. Irradiation renders the cells incapable of growth and proliferation. It is envisioned that the NK-92 cells will be irradiated at the treatment facility or some other point prior to treatment of a patient, since the time between irradiation and infusion should be no longer than four hours in order to preserve optimal activity. Alternatively, NK-92 cells may be prevented from proliferating by another mechanism.

As used herein, "inactivation" of the NK-92 cells renders them incapable of growth. Inactivation may also relate to the death of the NK-92 cells. It is envisioned that the NK-92 cells may be inactivated after they have effectively purged an ex vivo sample of cells related to a pathology in a therapeutic application, or after they have resided within the body of a mammal a sufficient period of time to effectively kill many or all target cells residing within the body. Inactivation may be induced, by way of non-limiting example, by administering an inactivating agent to which the NK-92 cells are sensitive.

As used herein, the terms "cytotoxic" and "cytolytic," when used to describe the activity of effector cells such as NK-92 cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK-92 cells is due to cytolysis.

The term "kill" with respect to a cell/cell population is directed to include any type of manipulation that will lead to the death of that cell/cell population.

The term "Fc receptor" refers to a protein found on the surface of certain cells (e.g., natural killer cells) that contribute to the protective functions of the immune cells by binding to part of an antibody known as the Fc region. Binding of the Fc region of an antibody to the Fc receptor (FcR) of a cell stimulates phagocytic or cytotoxic activity of a cell via antibody-mediated phagocytosis or antibody-dependent cell-mediated cytotoxicity (ADCC). FcRs are classified based on the type of antibody they recognize. For example, Fc-gamma receptors (FCγR) bind to the IgG class of antibodies. FCγRIII-A (also called CD16; SEQ ID NO:34) is a low affinity Fc receptor bind to IgG antibodies and activate ADCC. FCγRIII-A are typically found on NK cells. NK-92 cells do not express FCγRIII-A. Fc-epsilon receptors (FcR) bind to the Fc region of IgE antibodies.

The term "chimeric antigen receptor" (CAR), as used herein, refers to an extracellular antigen-binding domain that is fused to an intracellular signaling domain. CARs can be expressed in T cells or NK cells to increase cytotoxicity. In general, the extracellular antigen-binding domain is a scFv that is specific for an antigen found on a cell of interest. A CAR-expressing NK-92 cell is targeted to cells expressing certain antigens on the cell surface, based on the specificity of the scFv domain. The scFv domain can be engineered to recognize any antigen, including tumor-specific antigens and virus-specific antigens. For example, CD19CAR recognizes CD19, a cell surface marker expressed by some cancers.

The term "tumor-specific antigen" as used herein refers to antigens that are present on a cancer or neoplastic cell but not detectable on a normal cell derived from the same tissue or lineage as the cancer cell. Tumor-specific antigens, as used herein, also refers to tumor-associated antigens, that is, antigens that are expressed at a higher level on a cancer cell as compared to a normal cell derived from the same tissue or lineage as the cancer cell.

The term "virus-specific antigen" as used herein refers to antigens that are present on a virus-infected cell but not detectable on a normal cell derived from the same tissue or lineage as the virus-infected cell. In one embodiment, a virus-specific antigen is a viral protein expressed on the surface of an infected cell.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

As used herein, "percent identity" refers to sequence identity between two peptides or between two nucleic acid molecules. Percent identity can be determined by comparing a position in each sequence which may be aligned for purposes of comparison. When a position in the compared sequence is occupied by the same base or amino acid, then the molecules are identical at that position. Homologous nucleotide sequences include those sequences coding for naturally occurring allelic variants and mutations of the nucleotide sequences set forth herein. Homologous nucleotide sequences include nucleotide sequences encoding for a protein of a mammalian species other than humans. Homologous amino acid sequences include those amino acid sequences which contain conservative amino acid substitutions and which polypeptides have the same binding and/or activity. In some embodiments, a homologous amino acid sequence has no more than 15, nor more than 10, nor more than 5 or no more than 3 conservative amino acid substitutions. In some embodiments, a nucleotide or amino acid sequence has at least 60%, at least 65%, at least 70%, at least 80%, or at least 85% or greater percent identity to a sequence described herein. In some embodiments, a nucleotide or amino acid sequence has at least 90%, 91%, 92%, 93%, 94%, 95%, 96%, 97%, 98% or 99% identity to a sequence described herein. Percent identity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). Algorithms suitable for determining percent sequence identity include the BLAST and BLAST 2.0 algorithms, which are described in Altschul et al. (Nuc. Acids Res. 25:3389-402, 1977), and Altschul et al. (J. Mol. Biol. 215:403-10, 1990), respectively. Software for performing BLAST analyses is publicly available through the National Center for Biotechnology Information (see the internet at ncbi.nlm.nih.gov). The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4.

In some embodiments, a nucleic acid sequence is codon optimized for expression in a particular species, for example, a mouse sequence can be codon optimized for expression in humans (expression of the protein encoded by the codon-optimized nucleic acid sequence). Thus, in some embodiments, a codon-optimized nucleic acid sequence has at least 60%, at least 65%, at least 70%, at least 80%, or at least 85% or greater percent identity to a nucleic acid sequence described herein. In some embodiments, a codon-optimized nucleic acid sequence acid sequence has at least 90%, 91%, 92%, 93%, 94%, 95%, 96%, 97%, 98% or 99% identity to a sequence described herein.

The term "express" refers to the production of a gene product (e.g., a protein). The term "transient" when referring to expression means a polynucleotide is not incorporated into the genome of the cell. The term "stable" when referring to expression means a polynucleotide is incorporated into the genome of the cell, or a positive selection marker (i.e., an exogenous gene expressed by the cell that confers a benefit under certain growth conditions) is utilized to maintain expression of the transgene.

The term "cytokine" or "cytokines" refers to the general class of biological molecules which affect cells of the immune system. Exemplary cytokines include but are not limited to interferons and interleukins (IL) in particular IL-2, IL-12, IL-15, IL-18 and IL-21. In preferred embodiments, the cytokine is IL-2.

As used herein, the term "vector" refers to a non-chromosomal nucleic acid comprising an intact replicon such that the vector may be replicated when placed within a permissive cell, for example by a process of transformation. A vector may replicate in one cell type, such as bacteria, but have limited or no ability to replicate in another cell, such as mammalian cells. Vectors may be viral or non-viral. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In one embodiment, the vector is a viral vector, e.g. adenovirus. Viral vectors are well known in the art.

As used herein, the term "targeted," when referring to protein expression, is intended to include, but is not limited to, directing proteins or polypeptides to appropriate destinations in the cell or outside of it. The targeting is typically achieved through signal peptides or targeting peptides, which are a stretch of amino acid residues in a polypeptide chain. These signal peptides can be located anywhere within a polypeptide sequence, but are often located on the N-terminus. Polypeptides can also be engineered to have a signal peptide on the C-terminus. Signal peptides can direct a polypeptide for extracellular section, location to plasma membrane, golgi, endosomes, endoplasmic reticulum, and other cellular compartments. For example, polypeptides with a particular amino acid sequence on their C-terminus (e.g., KDEL) are retained in the ER lumen or transported back the ER lumen.

As used herein, the term "target," when referring to targeting of a tumor, refers to the ability of NK-92 cells to recognize and kill a tumor cell (i.e., target cell). The term "targeted" in this context refers, for example, to the ability of a CAR expressed by the NK-92 cell to recognize and bind to a cell surface antigen expressed by the tumor.

As used herein, the term "transfect" refers to the insertion of nucleic acid into a cell. Transfection may be performed using any means that allows the nucleic acid to enter the cell. DNA and/or mRNA may be transfected into a cell. Preferably, a transfected cell expresses the gene product (i.e., protein) encoded by the nucleic acid.

The term "suicide gene" refers to a transgene that allows for the negative selection of cells expressing that transgene. A suicide gene is used as a safety system, allowing the cells expressing the gene to be killed by introduction of a selective agent. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene (see also, for example, Yazawa K, Fisher W E, Brunicardi F C: Current progress in suicide gene therapy for cancer. World J. Surg. 2002 July; 26(7):783-9). In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir.

What is claimed is:

1. A genetically modified NK-92 cell, comprising:
   a recombinantly expressed cytokine;
   a recombinantly expressed CD16;
   a membrane bound chimeric antigen receptor (CAR) that comprises a FcεRIγ signaling domain,
   wherein the CAR has at least 90% sequence identity to SEQ ID NO:63, including 100% identity in the binding domain comprised therein, wherein the binding domain comprises SEQ ID NO: 81.

2. The genetically modified NK-92 cell of claim 1, wherein the recombinantly expressed cytokine is IL-2, optionally comprising an endoplasmic retention sequence.

3. The genetically modified NK-92 cell of claim 1, wherein the recombinantly expressed cytokine is IL-15, optionally comprising an endoplasmic retention sequence.

4. The genetically modified NK-92 cell of claim 1, wherein the recombinantly expressed CD16 has at least 80% sequence identity to the amino acid sequence of SEQ ID NO: 35.

5. The genetically modified NK-92 cell of claim 1, wherein the FcεRIγ signaling domain has at least 90% sequence identity to the amino acid sequence of SEQ ID NO:1.

6. The genetically modified NK-92 cell of claim 1, wherein the FcεRIγ signaling domain has an amino acid sequence of SEQ ID NO:1.

7. The genetically modified NK-92 cell of claim 1, wherein the genetically modified NK cell comprises a tricistronic nucleic acid sequence comprising a sequence encoding the recombinantly expressed cytokine, a sequence encoding the recombinantly expressed CD16, and a sequence encoding the recombinantly expressed CAR.

8. The genetically modified NK-92 cell of claim 7, wherein the tricistronic nucleic acid sequence is integrated into the genome of the NK-92 cell.

* * * * *